US012144857B2

(12) United States Patent
Kawaoka et al.

(10) Patent No.: US 12,144,857 B2
(45) Date of Patent: *Nov. 19, 2024

(54) VECTORS FOR ELICITING IMMUNE RESPONSES TO NON-DOMINANT EPITOPES IN THE HEMAGGLUTININ (HA) PROTEIN

(71) Applicant: Wisconsin Alumni Research Foundation (WARF), Madison, WI (US)

(72) Inventors: Yoshihiro Kawaoka, Middleton, WI (US); Gabriele Neumann, Madison, WI (US); Huihui Kong, Madison, WI (US)

(73) Assignee: Wisconsin Alumni Research Foundation (WARF), Madison, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/813,178

(22) Filed: Jul. 18, 2022

(65) Prior Publication Data

US 2023/0190913 A1    Jun. 22, 2023

Related U.S. Application Data

(63) Continuation of application No. 16/545,761, filed on Aug. 20, 2019, now Pat. No. 11,389,523.

(Continued)

(51) Int. Cl.
*A61K 39/145* (2006.01)
*C07K 16/10* (2006.01)
(Continued)

(52) U.S. Cl.
CPC ........ *A61K 39/145* (2013.01); *C07K 16/1018* (2013.01); *C07K 16/34* (2013.01);
(Continued)

(58) Field of Classification Search
None
See application file for complete search history.

(56) References Cited

U.S. PATENT DOCUMENTS

| 4,071,618 A | 1/1978 | Konobe et al. |
| 4,659,569 A | 4/1987 | Mitsuhashi et al. |

(Continued)

FOREIGN PATENT DOCUMENTS

| AU | 2012204138 B2 | 5/2014 |
| AU | 2014202470 | 11/2016 |

(Continued)

OTHER PUBLICATIONS

Li et al. (Nature Microbiology. 2016; 1 (6): 1-10).*

(Continued)

*Primary Examiner* — Shanon A. Foley
(74) *Attorney, Agent, or Firm* — Schwegman Lundberg & Woessner, P.A.

(57) ABSTRACT

Methods of preparing influenza viruses having altered immunodominant epitopes in HA, e.g., having one or more residues in one or more of antigenic sites A-E in HA altered, and viral vectors, e.g., influenza virus VLPs or non-influenza viruses or VLPs thereof expressing or having influenza HAs with altered immunogenicity as a result of altered immunodominant epitopes therein are provided.

14 Claims, 17 Drawing Sheets

Specification includes a Sequence Listing.

Related U.S. Application Data

(60) Provisional application No. 62/719,952, filed on Aug. 20, 2018.

(51) Int. Cl.
*C07K 16/34* (2006.01)
*C12N 15/86* (2006.01)
*A61K 39/00* (2006.01)

(52) U.S. Cl.
CPC ........ *C12N 15/86* (2013.01); *A61K 2039/521* (2013.01); *A61K 2039/5258* (2013.01)

(56) References Cited

U.S. PATENT DOCUMENTS

| | | |
|---|---|---|
| 5,166,057 A | 11/1992 | Palese et al. |
| 5,578,473 A | 11/1996 | Palese et al. |
| 5,716,821 A | 2/1998 | Wertz et al. |
| 5,750,394 A | 5/1998 | Palese et al. |
| 5,786,199 A | 7/1998 | Palese |
| 5,789,229 A | 8/1998 | Wertz et al. |
| 5,820,871 A | 10/1998 | Palese et al. |
| 5,840,520 A | 11/1998 | Clarke et al. |
| 5,854,037 A | 12/1998 | Palese et al. |
| 5,948,410 A | 9/1999 | Van Scharrenburg et al. |
| 5,994,526 A | 11/1999 | Meulewaeter et al. |
| 6,001,634 A | 12/1999 | Palese et al. |
| 6,033,886 A | 3/2000 | Conzelmann |
| 6,037,348 A | 3/2000 | Colacino et al. |
| 6,146,642 A | 11/2000 | Garcia-Sastre et al. |
| 6,169,175 B1 | 1/2001 | Frace et al. |
| 6,194,546 B1 | 2/2001 | Newton et al. |
| 6,270,958 B1 | 8/2001 | Olivo et al. |
| 6,271,011 B1 | 8/2001 | Lee et al. |
| 6,358,733 B1 | 3/2002 | Motwani et al. |
| 6,455,298 B1 | 9/2002 | Groner et al. |
| 6,544,785 B1 | 4/2003 | Palese et al. |
| 6,656,720 B2 | 12/2003 | Groner et al. |
| 6,825,036 B2 | 11/2004 | Makizumi et al. |
| 6,843,996 B1 | 1/2005 | Parkin et al. |
| 6,872,395 B2 | 3/2005 | Kawaoka |
| 6,890,710 B1 | 5/2005 | Palese et al. |
| 6,951,752 B2 | 10/2005 | Reiter et al. |
| 6,951,754 B2 | 10/2005 | Hoffmann |
| 6,974,695 B2 | 12/2005 | Vogels et al. |
| 7,037,707 B2 | 5/2006 | Webster et al. |
| 7,176,021 B2 | 2/2007 | Kawaoka |
| 7,211,378 B2 | 5/2007 | Kawaoka et al. |
| 7,226,774 B2 | 6/2007 | Kawaoka |
| 7,312,064 B2 | 12/2007 | Hoffmann |
| 7,335,356 B2 | 2/2008 | Hart et al. |
| 7,507,411 B2 | 3/2009 | Zhou et al. |
| 7,566,458 B2 | 7/2009 | Yang et al. |
| 7,585,657 B2 | 9/2009 | Kawaoka |
| 7,588,769 B2 | 9/2009 | Kawaoka |
| 7,601,356 B2 | 10/2009 | Jin et al. |
| 7,670,837 B2 | 3/2010 | Schwartz |
| 7,682,618 B2 | 3/2010 | Bavari et al. |
| 7,723,094 B2 | 5/2010 | Kawaoka et al. |
| 7,833,788 B2 | 11/2010 | Pau et al. |
| 7,883,844 B2 | 2/2011 | Nouchi et al. |
| 7,955,833 B2 | 6/2011 | Reiter et al. |
| 7,959,930 B2 | 6/2011 | De Wit et al. |
| 7,968,101 B2 | 6/2011 | Yoshihiro et al. |
| 7,972,843 B2 | 7/2011 | Hoffmann |
| 7,993,924 B2 | 8/2011 | Billeter et al. |
| 8,012,736 B2 | 9/2011 | Hoffman et al. |
| 8,043,856 B2 | 10/2011 | Yoshihiro et al. |
| 8,048,430 B2 | 11/2011 | Yang et al. |
| 8,057,806 B2 | 11/2011 | Kawaoka et al. |
| 8,093,033 B2 | 1/2012 | Kemble et al. |
| 8,114,415 B2 | 2/2012 | Hoffmann et al. |
| 8,119,337 B2 | 2/2012 | Gregersen |
| 8,119,388 B2 | 2/2012 | Schwartz et al. |
| 8,298,805 B2 | 10/2012 | Kawaoka |
| 8,309,099 B2 | 11/2012 | Hoffmann |
| 8,354,114 B2 | 1/2013 | Lu et al. |
| 8,357,376 B2 | 1/2013 | Liu et al. |
| 8,409,843 B2 | 4/2013 | Kemble et al. |
| 8,460,914 B2 | 6/2013 | Gregersen |
| 8,465,960 B2 | 6/2013 | Kawaoka et al. |
| 8,475,806 B2 | 7/2013 | Kawaoka |
| 8,507,247 B2 | 8/2013 | Kawaoka et al. |
| 8,524,497 B2 | 9/2013 | Reiter et al. |
| 8,546,123 B2 | 10/2013 | Lewis |
| 8,574,591 B2 | 11/2013 | Hoffmann et al. |
| 8,574,593 B2 | 11/2013 | Yang et al. |
| 8,580,277 B2 | 11/2013 | Yang et al. |
| 8,591,914 B2 | 11/2013 | Yang et al. |
| 8,597,661 B2 | 12/2013 | Kawaoka et al. |
| 8,679,819 B2 | 3/2014 | Kawaoka |
| 8,877,209 B2 | 11/2014 | Kawaoka et al. |
| 8,900,595 B2 | 12/2014 | Kawaoka et al. |
| 9,101,653 B2 | 8/2015 | Kawaoka et al. |
| 9,109,013 B2 | 8/2015 | Kawaoka et al. |
| 9,222,118 B2 | 12/2015 | Kawaoka et al. |
| 9,254,318 B2 | 2/2016 | Kawaoka et al. |
| 9,284,533 B2 | 3/2016 | Bilsel et al. |
| 9,474,798 B2 | 10/2016 | Watanabe et al. |
| 9,757,446 B2 | 9/2017 | LeFebvre et al. |
| 9,890,363 B2 | 2/2018 | Kawaoka |
| 9,926,535 B2 | 3/2018 | Kawaoka et al. |
| 9,950,057 B2 | 4/2018 | Kawaoka et al. |
| 10,053,671 B2 | 8/2018 | Kawaoka et al. |
| 10,059,925 B2 | 8/2018 | Kawaoka et al. |
| 10,119,124 B2 | 11/2018 | Watanabe et al. |
| 10,130,697 B2 | 11/2018 | Watanabe |
| 10,172,934 B2 | 1/2019 | Kawaoka et al. |
| 10,246,686 B2 | 4/2019 | Kawaoka et al. |
| 10,358,630 B2 | 7/2019 | Kawaoka et al. |
| 10,494,613 B2 | 12/2019 | Kawaoka et al. |
| 10,513,692 B2 | 12/2019 | Kawaoka et al. |
| 10,633,422 B2 | 4/2020 | Kawaoka et al. |
| 10,808,229 B2 | 10/2020 | Kawaoka et al. |
| 11,007,262 B2 | 5/2021 | Watanabe et al. |
| 11,046,934 B2 | 6/2021 | Kawaoka et al. |
| 11,180,737 B2 | 11/2021 | Kawaoka et al. |
| 11,197,925 B2 | 12/2021 | Kawaoka et al. |
| 11,197,926 B2 | 12/2021 | Kawaoka et al. |
| 11,241,492 B2 | 2/2022 | Kawaoka et al. |
| 11,384,339 B2 | 7/2022 | Kawaoka et al. |
| 11,389,523 B2 * | 7/2022 | Kawaoka ............. C07K 14/005 |
| 11,390,649 B2 | 7/2022 | Kawaoka et al. |
| 11,739,303 B2 | 8/2023 | Kawaoka et al. |
| 11,807,872 B2 | 11/2023 | Kawaoka et al. |
| 11,851,648 B2 | 12/2023 | Kawaoka et al. |
| 2002/0010143 A1 | 1/2002 | Barbosa et al. |
| 2002/0164770 A1 | 11/2002 | Hoffmann |
| 2002/0197705 A1 | 12/2002 | Kawaoka |
| 2003/0035814 A1 | 2/2003 | Kawaoka et al. |
| 2003/0044962 A1 | 3/2003 | Makizumi et al. |
| 2003/0073223 A1 | 4/2003 | Groner et al. |
| 2003/0119183 A1 | 6/2003 | Groner |
| 2003/0194694 A1 | 10/2003 | Kawaoka |
| 2003/0215794 A1 | 11/2003 | Kawaoka et al. |
| 2004/0002061 A1 | 1/2004 | Kawaoka |
| 2004/0029251 A1 | 2/2004 | Hoffman et al. |
| 2004/0057967 A1 | 3/2004 | Bavari et al. |
| 2004/0063141 A1 | 4/2004 | Lok |
| 2004/0077086 A1 | 4/2004 | Reiter et al. |
| 2004/0132164 A1 | 7/2004 | Doyle et al. |
| 2004/0142322 A1 | 7/2004 | Malcolm et al. |
| 2004/0219170 A1 | 11/2004 | Kawaoka |
| 2004/0241139 A1 | 12/2004 | Hobom et al. |
| 2004/0242518 A1 | 12/2004 | Chen et al. |
| 2005/0003349 A1 | 1/2005 | Kawaoka |
| 2005/0037487 A1 | 2/2005 | Kawaoka et al. |
| 2005/0095583 A1 | 5/2005 | Pekosz et al. |
| 2005/0118140 A1 | 6/2005 | Vorlop et al. |
| 2005/0158342 A1 | 7/2005 | Kemble et al. |
| 2005/0186563 A1 | 8/2005 | Hoffmann |
| 2005/0202553 A1 | 9/2005 | Groner et al. |
| 2005/0232950 A1 | 10/2005 | Kawaoka |
| 2005/0266023 A1 | 12/2005 | Bavari et al. |

(56) References Cited

U.S. PATENT DOCUMENTS

| | | |
|---|---|---|
| 2005/0266026 A1 | 12/2005 | Hoffmann et al. |
| 2006/0057116 A1 | 3/2006 | Kawaoka et al. |
| 2006/0088909 A1 | 4/2006 | Compans |
| 2006/0099609 A1 | 5/2006 | Bavari et al. |
| 2006/0134138 A1 | 6/2006 | Kawaoka et al. |
| 2006/0166321 A1 | 7/2006 | Kawaoka et al. |
| 2006/0188977 A1 | 8/2006 | Schwartz et al. |
| 2006/0216702 A1 | 9/2006 | Compans et al. |
| 2006/0240515 A1 | 10/2006 | Dimitrov et al. |
| 2006/0246092 A1 | 11/2006 | Neirynck et al. |
| 2007/0141699 A1 | 6/2007 | Kawaoka |
| 2007/0231348 A1 | 10/2007 | Kawaoka et al. |
| 2008/0009031 A1 | 1/2008 | Kawaoka |
| 2008/0187557 A1 | 8/2008 | Sambhara |
| 2008/0233560 A1 | 9/2008 | Hoffmann |
| 2008/0254067 A1 | 10/2008 | Trepanier et al. |
| 2008/0274141 A1 | 11/2008 | Groner et al. |
| 2008/0292658 A1 | 11/2008 | De Wit et al. |
| 2008/0293040 A1 | 11/2008 | Kawaoka et al. |
| 2008/0311148 A1 | 12/2008 | Hoffmann |
| 2008/0311149 A1 | 12/2008 | Hoffmann |
| 2009/0017444 A1 | 1/2009 | Kawaoka et al. |
| 2009/0047728 A1 | 2/2009 | Kawaoka et al. |
| 2009/0074812 A1 | 3/2009 | Watanabe et al. |
| 2009/0081252 A1 | 3/2009 | Gregersen |
| 2009/0181446 A1 | 7/2009 | Nouchi et al. |
| 2009/0311669 A1 | 12/2009 | Kawaoka |
| 2009/0324640 A1 | 12/2009 | Kawaoka et al. |
| 2010/0080825 A1 | 4/2010 | kawaoka et al. |
| 2010/0112000 A1 | 5/2010 | Schwartz |
| 2010/0183671 A1 | 7/2010 | Gregersen et al. |
| 2010/0247572 A1 | 9/2010 | Kawaoka |
| 2010/0267116 A1 | 10/2010 | Kawaoka et al. |
| 2011/0020374 A1 | 1/2011 | Frazer |
| 2011/0027314 A1 | 2/2011 | Broeker |
| 2011/0045022 A1 | 2/2011 | Tsai |
| 2011/0081373 A1 | 4/2011 | Kawaoka et al. |
| 2011/0110978 A1 | 5/2011 | Kawaoka et al. |
| 2011/0159031 A1 | 6/2011 | Falkner et al. |
| 2011/0236417 A1 | 9/2011 | Watanabe et al. |
| 2011/0263554 A1 | 10/2011 | Kawaoka et al. |
| 2011/0300604 A1 | 12/2011 | Kawaoka et al. |
| 2012/0020997 A1 | 1/2012 | Hoffman et al. |
| 2012/0034600 A1 | 2/2012 | Gregersen |
| 2012/0058124 A1 | 3/2012 | Kurosawa et al. |
| 2012/0115206 A1 | 5/2012 | Schwartz et al. |
| 2012/0156241 A1 | 6/2012 | De Wit et al. |
| 2012/0207785 A1 | 8/2012 | Fabry et al. |
| 2012/0251568 A1 | 10/2012 | Garcia-sastre et al. |
| 2013/0095135 A1 | 4/2013 | Collignon et al. |
| 2013/0183741 A1 | 7/2013 | Park et al. |
| 2013/0230552 A1 | 9/2013 | Kawaoka et al. |
| 2013/0243744 A1 | 9/2013 | Betenbaugh |
| 2013/0315929 A1 | 11/2013 | Bock |
| 2013/0316434 A1 | 11/2013 | Reiter et al. |
| 2014/0227310 A1 | 8/2014 | Li et al. |
| 2015/0017205 A1 | 1/2015 | Kawaoka et al. |
| 2015/0166967 A1 | 6/2015 | Kawaoka et al. |
| 2015/0307851 A1 | 10/2015 | Kawaoka et al. |
| 2015/0368621 A1 | 12/2015 | Kawaoka et al. |
| 2016/0024193 A1 | 1/2016 | Ayalon et al. |
| 2016/0024479 A1 | 1/2016 | Kawaoka et al. |
| 2016/0115518 A1 | 4/2016 | Kawaoka et al. |
| 2016/0208223 A1 | 7/2016 | Kawaoka et al. |
| 2016/0215040 A1 | 7/2016 | Kyratsous et al. |
| 2016/0355790 A1 | 12/2016 | Kawaoka et al. |
| 2017/0058265 A1 | 3/2017 | Kawaoka et al. |
| 2017/0067029 A1 | 3/2017 | Kawaoka et al. |
| 2017/0096645 A1 | 4/2017 | Watanabe et al. |
| 2017/0097334 A1 | 4/2017 | Kawaoka et al. |
| 2017/0121391 A1 | 5/2017 | Kawaoka et al. |
| 2017/0258888 A1 | 9/2017 | Kawaoka |
| 2017/0298120 A1 | 10/2017 | Sasisekharan |
| 2017/0354730 A1 | 12/2017 | Kawaoka et al. |
| 2018/0245054 A1 | 8/2018 | Kawaoka et al. |
| 2018/0273588 A1 | 9/2018 | Kawaoka et al. |
| 2018/0340152 A1 | 11/2018 | Kawaoka et al. |
| 2019/0032023 A1 | 1/2019 | Kawaoka et al. |
| 2019/0048324 A1 | 2/2019 | Kawaoka et al. |
| 2019/0117759 A1 | 4/2019 | Wantanabe et al. |
| 2019/0167781 A1 | 6/2019 | Kawaoka et al. |
| 2020/0188506 A1 | 6/2020 | Kawaoka et al. |
| 2020/0237899 A1 | 7/2020 | Kawaoka et al. |
| 2020/0263142 A1 | 8/2020 | Kawaoka et al. |
| 2020/0263143 A1 | 8/2020 | Kawaoka et al. |
| 2020/0291384 A1 | 9/2020 | Kawaoka et al. |
| 2021/0061862 A1 | 3/2021 | Kawaoka et al. |
| 2021/0102178 A1 | 4/2021 | Kawaoka et al. |
| 2021/0121545 A1 | 4/2021 | Knoll et al. |
| 2021/0228708 A1 | 7/2021 | Smith et al. |
| 2021/0246432 A1 | 8/2021 | Kawaoka et al. |
| 2021/0252130 A1 | 8/2021 | Watanabe et al. |
| 2021/0290754 A1 | 9/2021 | Kawaoka et al. |
| 2021/0299249 A1 | 9/2021 | Kawaoka et al. |
| 2022/0025339 A1 | 1/2022 | Kawaoka et al. |
| 2022/0202926 A1 | 6/2022 | Kawaoka et al. |
| 2022/0202927 A1 | 6/2022 | Kawaoka et al. |
| 2022/0241396 A1 | 8/2022 | Kawaoka et al. |
| 2023/0190913 A1* | 6/2023 | Kawaoka ............... C12N 15/86 424/206.1 |
| 2023/0321217 A1 | 10/2023 | Kawaoka et al. |
| 2023/0346911 A1 | 11/2023 | Kawaoka et al. |
| 2024/0010995 A1 | 1/2024 | Kawaoka et al. |
| 2024/0076632 A1 | 3/2024 | Kawaoka et al. |

FOREIGN PATENT DOCUMENTS

| | | |
|---|---|---|
| AU | 2014290203 B2 | 12/2020 |
| AU | 2017221444 B2 | 11/2021 |
| BR | PI0410702 B1 | 4/2022 |
| CA | 2379012 A1 | 1/2001 |
| CA | 2816242 C | 1/2019 |
| CN | 1826407 A | 8/2006 |
| CN | 101472941 A | 7/2009 |
| CN | 1826407 B | 9/2013 |
| CN | 105296356 A | 2/2016 |
| CN | 103540614 B | 2/2018 |
| CN | 109477074 A | 3/2019 |
| CN | 113874496 A | 12/2021 |
| CN | 114929269 A | 8/2022 |
| EP | 0687471 A1 | 12/1995 |
| EP | 0700991 A1 | 3/1996 |
| EP | 0702085 A1 | 3/1996 |
| EP | 0704533 A1 | 4/1996 |
| EP | 1201760 A1 | 5/2002 |
| EP | 2010557 B1 | 2/2014 |
| EP | 1572910 B1 | 12/2015 |
| EP | 1631663 B1 | 8/2016 |
| EP | 2747778 B1 | 12/2017 |
| EP | 3009507 B1 | 6/2020 |
| EP | 2493912 B1 | 7/2020 |
| EP | 3022296 B1 | 12/2022 |
| IL | 171831 A | 5/2015 |
| JP | 07-203958 | 8/1995 |
| JP | 2002536992 A | 11/2002 |
| JP | 2003528570 A | 9/2003 |
| JP | 2004500842 A | 1/2004 |
| JP | 2004531232 A | 10/2004 |
| JP | 2005523698 A | 8/2005 |
| JP | 2005245302 A | 9/2005 |
| JP | 2005535288 A | 11/2005 |
| JP | 2006525815 A | 11/2006 |
| JP | 2007518395 A | 7/2007 |
| JP | 2007525175 A | 9/2007 |
| JP | 2007259758 | 10/2007 |
| JP | 2007529997 A | 11/2007 |
| JP | 2008500041 | 1/2008 |
| JP | 2008520248 A | 6/2008 |
| JP | 2009511084 A | 3/2009 |
| JP | 2009523252 A | 6/2009 |
| JP | 2009532352 A | 9/2009 |
| JP | 2010530248 A | 9/2010 |
| JP | 2011530295 A | 12/2011 |
| JP | 4927290 | 5/2012 |

(56) References Cited

FOREIGN PATENT DOCUMENTS

| | | |
|---|---|---|
| JP | 4927290 B2 | 5/2012 |
| JP | 2013507990 A | 3/2013 |
| JP | 2013511280 A | 4/2013 |
| JP | 2013518059 | 5/2013 |
| JP | 2014039551 A | 3/2014 |
| JP | 2014131516 A | 7/2014 |
| JP | 2015501141 | 1/2015 |
| JP | 2016500007 A | 1/2016 |
| JP | 2016521553 A | 7/2016 |
| JP | 2016144463 A | 8/2016 |
| JP | 2016524915 A | 8/2016 |
| JP | 2016169225 A | 9/2016 |
| JP | 2017527557 A | 9/2017 |
| JP | 2017197555 A | 11/2017 |
| JP | 2018064493 A | 4/2018 |
| JP | 6352974 B2 | 6/2018 |
| JP | 6375329 B2 | 7/2018 |
| JP | 2019510481 A | 4/2019 |
| JP | 2020010711 A | 1/2020 |
| JP | 2020114250 A | 7/2020 |
| JP | 2021500891 A | 1/2021 |
| JP | 2021036878 A | 3/2021 |
| JP | 2021184761 A | 12/2021 |
| JP | 2021533157 A | 12/2021 |
| JP | 2021536228 A | 12/2021 |
| JP | 2022066209 A | 4/2022 |
| JP | 2022522112 A | 4/2022 |
| JP | 2022527235 A | 6/2022 |
| JP | 2022172369 A | 11/2022 |
| JP | 2022551805 A | 12/2022 |
| KR | 101113432 B1 | 2/2012 |
| MX | 285206 | 3/2011 |
| NO | 341506 | 11/2017 |
| WO | WO-9610631 A1 | 4/1996 |
| WO | WO-9610632 A1 | 4/1996 |
| WO | WO-9640955 A1 | 12/1996 |
| WO | WO-9737000 A1 | 10/1997 |
| WO | WO-9802530 A1 | 1/1998 |
| WO | WO-9848834 A1 | 11/1998 |
| WO | WO-9850378 A1 | 11/1998 |
| WO | WO-9928445 A1 | 6/1999 |
| WO | WO-0053786 A1 | 9/2000 |
| WO | WO-0060050 A2 | 10/2000 |
| WO | WO-2000060050 A2 | 10/2000 |
| WO | WO-0060050 A3 | 1/2001 |
| WO | WO-2001004333 A1 | 1/2001 |
| WO | WO-2001025462 A1 | 4/2001 |
| WO | WO-0179273 A2 | 10/2001 |
| WO | WO-2001079273 A2 | 10/2001 |
| WO | WO-0183794 A2 | 11/2001 |
| WO | WO-2001083794 A2 | 11/2001 |
| WO | WO-0210143 A1 | 1/2002 |
| WO | WO-02064757 A2 | 8/2002 |
| WO | WO-02074795 A2 | 9/2002 |
| WO | WO-03068923 A2 | 8/2003 |
| WO | WO-2003068923 A2 | 8/2003 |
| WO | WO-03076462 A1 | 9/2003 |
| WO | WO-2003080846 A1 | 10/2003 |
| WO | WO-03091401 A2 | 11/2003 |
| WO | WO-2003091401 A2 | 11/2003 |
| WO | WO-2004142322 A1 | 7/2004 |
| WO | WO-2004094466 A2 | 11/2004 |
| WO | WO-04112831 A2 | 12/2004 |
| WO | WO-2004112831 A2 | 12/2004 |
| WO | WO-2004112831 A3 | 12/2004 |
| WO | WO-05028658 A2 | 3/2005 |
| WO | WO-05028658 A3 | 3/2005 |
| WO | WO-2005028658 A2 | 3/2005 |
| WO | WO-2005062820 A2 | 7/2005 |
| WO | WO-2006051069 A2 | 5/2006 |
| WO | WO-2007044024 A2 | 4/2007 |
| WO | WO-2007044024 A3 | 4/2007 |
| WO | WO-2007126810 A2 | 11/2007 |
| WO | WO-2007126810 A3 | 11/2007 |
| WO | WO-2007146057 A2 | 12/2007 |
| WO | WO-2007146057 A3 | 12/2007 |
| WO | WO-08156681 A3 | 12/2008 |
| WO | WO-2008147496 A2 | 12/2008 |
| WO | WO-2008147496 A3 | 12/2008 |
| WO | WO-2008156681 A2 | 12/2008 |
| WO | WO-2008156778 A2 | 12/2008 |
| WO | WO-2008156778 A3 | 12/2008 |
| WO | WO-2008157583 A1 | 12/2008 |
| WO | WO-09008921 A3 | 1/2009 |
| WO | WO-09008921 A9 | 1/2009 |
| WO | WO-2009007244 A2 | 1/2009 |
| WO | WO-2009008921 A2 | 1/2009 |
| WO | WO-2009014919 A2 | 1/2009 |
| WO | WO-2008156778 A9 | 2/2009 |
| WO | WO-09128867 A2 | 10/2009 |
| WO | WO-2009152181 A1 | 12/2009 |
| WO | WO-2009128867 A3 | 3/2010 |
| WO | WO-2010053573 A2 | 5/2010 |
| WO | WO-2010053573 A3 | 7/2010 |
| WO | WO-2011014645 A1 | 2/2011 |
| WO | WO-2011056591 A1 | 5/2011 |
| WO | WO-2011087839 A1 | 7/2011 |
| WO | WO-2011126370 A1 | 10/2011 |
| WO | WO-2011130627 A2 | 10/2011 |
| WO | WO-2012045882 A2 | 4/2012 |
| WO | WO-2012177924 A2 | 12/2012 |
| WO | WO-2013032942 A1 | 3/2013 |
| WO | WO-2013032942 A9 | 3/2013 |
| WO | WO-2013034069 A1 | 3/2013 |
| WO | WO-2013087945 A2 | 6/2013 |
| WO | WO-2013148302 A1 | 10/2013 |
| WO | WO-2014195920 A2 | 12/2014 |
| WO | WO-2015009743 A1 | 1/2015 |
| WO | WO-2015134488 A1 | 9/2015 |
| WO | WO-2015142671 A2 | 9/2015 |
| WO | WO-2015196150 A2 | 12/2015 |
| WO | WO-2015196150 A3 | 12/2015 |
| WO | WO-2016144933 A1 | 9/2016 |
| WO | WO-2016207853 A2 | 12/2016 |
| WO | WO-2017007839 A1 | 1/2017 |
| WO | WO-2017040203 A1 | 3/2017 |
| WO | WO-2017136575 A1 | 8/2017 |
| WO | WO-2017143236 A1 | 8/2017 |
| WO | WO-2019084310 A1 | 5/2019 |
| WO | WO-2019241579 A1 | 12/2019 |
| WO | WO-2020033527 A2 | 2/2020 |
| WO | WO-2020041311 A1 | 2/2020 |
| WO | 2020061443 | 3/2020 |
| WO | WO-2020/033527 A3 | 3/2020 |
| WO | WO-2020163804 A1 | 8/2020 |
| WO | WO-2020167432 A2 | 8/2020 |
| WO | WO-2020223699 A1 | 11/2020 |
| WO | WO-2020167432 A3 | 12/2020 |
| WO | WO-2020264141 A1 | 12/2020 |
| WO | WO-2021041624 A2 | 3/2021 |
| WO | WO-2021041624 A3 | 5/2021 |
| WO | WO-2021150874 A1 | 7/2021 |
| WO | WO-2021195410 A1 | 9/2021 |
| WO | WO-2021242597 A1 | 12/2021 |
| WO | 2022245888 | 11/2022 |
| WO | 2023125889 | 7/2023 |
| WO | 2023164556 | 8/2023 |
| WO | WO-2024015510 A1 | 1/2024 |

OTHER PUBLICATIONS

Nara et al. (PLoS Biology. 2010; 8 (12): e1000571).*
Burke et al. (PLoS One. 2014; 9 (11): e112302).*
Li et al. (Nature Microbiology. 2016; 1 (6): Supplementary Infiormation).*
"U.S. Appl. No. 16/545,761, Final Office Action mailed Oct. 20. 2021", 10 pgs.
"U.S. Appl. No. 16/545,761, Non Final Office Action mailed Feb. 11, 2021", 12 pgs.
"U.S. Appl. No. 16/545,761, Notice of Allowance mailed Mar. 9, 2022", 6 pgs.
"U.S. Appl. No. 16/545,761, Preliminary Amendment filed Feb. 7, 2020", 9 pgs.

(56) References Cited

OTHER PUBLICATIONS

"U.S. Appl. No. 16/545,761, PTO Response to Rule 312 Communication mailed May 13, 2022", 2 pgs.
"U.S. Appl. No. 16/545,761, Response filed Feb. 16, 2022 to Final Office Action mailed Oct. 20, 2021", 10 pgs.
"U.S. Appl. No. 16/545,761, Response filed Jun. 30, 2021 to Non Final Office Action mailed Feb. 11, 2021", 13 pgs.
"International Application Serial No. PCT/US2019/047263, International Search Report mailed Dec. 20, 2019", 5 pgs.
"International Application Serial No. PCT/US2019/047263, Written Opinion mailed Dec. 20, 2019", 6 pgs.
Broecker, Felix, et al., "A mosaic hemagglutinin-based influenza virus vaccine candidate protects mice from challenge with divergent H3N2 strains", npj Vaccines (2019) 31, www.nature.com/npjvaccines Published in partnership with the Sealy Center for Vaccine Development, (Jul. 19, 2019), 9 pages.
Broecker, Felix, et al., "Immunodominance of Antigenic Site B in the Hemagglutinin of the Current H3N2 In?uenza Virus in Humans and Mice", Journal of Virology, 92(20): e01100-18, (Oct. 2018), 1-13.
Cho, Alice, et al., "Implications of Broadly Neutralizing Antibodies in the Development of a Universal Influenza Vaccine", Current Opinion in Virology, vol. 17, (Apr. 1, 2016), 110-115.
Giles, Brendan Michael, "Development of Broadly Reactive Vaccine for Highly Pathogenic H5N1 Influenza", Retrieved from the Internet: URL<http//search.proquest.com/docview/928138363>, (Jan. 1, 2011).
Li, et al., "", Nature Microbiology, 1 (6), (2016), 1-10.
Nara, et al., "", PLoS Biology, 8 (12), (2010), e1000571.
Popova, Lyubov, et al., "Immunodominance of Antigenic Site B over Site of Hemagglutinin of Recent H3N2 Influenza Viruses", PLOS ONE, vol. 7 No. 7, (Jul. 25, 2012), e41895.
Sun, Weina, et al., "Development of Influenza B Universal Vaccine Candidates Usingthe "Mosaic" Hemagglutinin Approach", American Society for Microbiology, Journal of Virology, Vaccines and Antiviral Aoents, vol. 93, Issue 12, (Jun. 2019), 1-17.
"U.S. Appl. No. 17/004,583, Notice of Allowance mailed May 15, 2023", 7 pgs.
"U.S. Appl. No. 17/212,836, Response filed May 16, 2023 to Non Final Office Action mailed Feb. 16, 2023", 7 pgs.
"U.S. Appl. No. 16/785,449, Response filed May 22, 2023 to Final Office Action mailed Mar. 22, 2023", 9 pgs.
"U.S. Appl. No. 16/785,449, Advisory Action mailed Jun. 7, 2023", 17 pgs.
"U.S. Appl. No. 16/785,449, Response filed Jul. 13, 2023 to Advisory Action mailed Jun. 7, 2023", 12 pgs.
"U.S. Appl. No. 17/004,583, Notice of Allowability mailed Aug. 1, 2023", 2 pgs.
"U.S. Appl. No. 16/785,449, Notice of Allowance mailed Aug. 7, 2023", 14 pgs.
"U.S. Appl. No. 18/173,535, Preliminary Amendment filed Jun. 26, 2023", 16 pgs.
"U.S. Appl. No. 17/212,836, Final Office Action mailed Jun. 22, 2023", 15 pgs.
"U.S. Appl. No. 18/365,082, Preliminary Amendment filed Aug. 3, 2023", 4 pgs.
Abdoli, Mohsen, "Intranasal administration of cold-adapted live-attenuated SARS-CoV-2 candidate vaccine confers protection against SARS-CoV-2", Virus Research 319 198857, (2022), 10 pgs.
Faizuloev, Evgeny, "Cold-adapted SARS-CoV-2 variants with different sensitivity exhibit an attenuated phenotype and confer protective immunity", Science Direct Vaccine 41 892-902, (2023), 12 pgs.
Lu, Shan, "The SARS-CoV-2 nucleocapsid phosphoprotein forms mutually exclusive condensates with RNA and the membrane-associated M protein", nature communications 12:502, (2021), 15 pgs.
Plescia, Caroline B, "SARS-CoV-2 viral budding and entry can be modeled using BSL-2 level virus-like particles", JBC Research Article, (Nov. 19, 2020), 10 pgs.
Seo, Sang Heui, "Cold-Adapted Live Attenuated SARS-COV-2 Vaccine Completely Protects Human ACE2 Transgenic Mice from SARS-Cov-2 Infection", Vaccines 2020 8, 584, (Oct. 3, 2020), 17 pgs.
Swann, Heather, "Minimal system for assembly of SARS CoV 2 virus like particles", Scientific Reports 10:21877 nature portfolio, (2020), 1-5.
Zhang, Zhikuan, "Structure of SARS-CoV-2 membrane protein essential for virus assembly", nature communications 13:4399, (Aug. 5, 2022), 12 pgs.
U.S. Appl. No. 16/545,761 U.S. Pat. No. 11,389,523, filed Aug. 23, 2019, Vectors for Eliciting Immune Responses to Non-Dominant Epitopes in the Hemagglutinin (HA) Protein.
U.S. Appl. No. 16/785,449, filed Feb. 7, 2020, Humanized Cell Line.
U.S. Appl. No. 17/004,583, filed Aug. 27, 2020, Recombinant Influenza Viruses With Stabilized HA for Replication in Eggs.
U.S. Appl. No. 17/155,625, filed Jan. 22, 2021, Recombinant Influenza Viruses With Stabilized NA.
U.S. Appl. No. 17/936,194, filed Sep. 28, 2022, Compositions Comprising Complexes Displaying Antigens and Methods of Using the Compositions.
U.S. Appl. No. 17/212,836, filed Mar. 25, 2021, Recombinant Multivalent Influenza Viruses.
U.S. Appl. No. 18/173,535, filed Feb. 23, 2023, Broadly Protective Influenza B Virus Vaccines.
"U.S. Appl. No. 17/212,836, Response filed Aug. 22, 2023 to Final Office Action mailed Jun. 22, 2023", 7 pgs.
"U.S. Appl. No. 17/212,836, Advisory Action mailed Aug. 29, 2023", 3 pgs.
"International Application Serial No. PCT US2023 063136, International Search Report mailed Sep. 8, 2023", 6 pgs.
"International Application Serial No. PCT US2023 063136, Written Opinion mailed Sep. 8, 2023", 7 pgs.
"U.S. Appl. No. 16/785,449, Corrected Notice ofAllowability mailed Sep. 11, 2023", 10 pgs.
"Japanese Application Serial No. 2021-536228, Notification of Reasons for Rejection mailed Aug. 22, 2023", W English Translation, 13 pgs.
"International Application Serial No. PCT US2023 027622, International Search Report mailed Nov. 7, 2023", 5 pgs.
"International Application Serial No. PCT US2023 027622, Written Opinion mailed Nov. 7, 2023", 6 pgs.
"U.S. Appl. No. 16/785,449, Corrected Notice ofAllowability mailed Nov. 8, 2023", 10 pgs.
"U.S. Appl. No. 16/785,449, Corrected Notice ofAllowability mailed Nov. 17, 2023", 10 pgs.
Liu, Shufeng, "Stable Cell Clones Harboring Self-Replicating SARS-CoV-2 RNAs for Drug Screen", Journal of Virology, vol. 96, No. 6, [Online] Retrieved from the internet:https: www.ncbi.nlm.nih.gov pmc articles PMC8941906 pdf jvi.02216-21.pdf, (Mar. 23, 2022), 13 pgs.
Netland, Jason, "Immunization with an attenuated severe acute respiratory syndrome coronavirus deleted in E protein protects against lethal respiratory disease", Virolog, vol. 399, No. 1, (Jan. 27, 2010), 9 pgs.
Zhang, Xianwen, "A trans-complementation system for SARS-CoV-2 recapitulates authentic viral replication without virulence", Cell, Elsevier, Amsterdam NL, vol. 184, No. 8, (Feb. 23, 2021), 24 pgs.
Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.
Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.
Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.
Result 17, NCBI Blast nucleotide search of SEQ ID No. 2, database "nr", (Jul. 18, 2006), 3 pgs.
Result 7, NCBI Blast nucleotide search of SEQ ID No. 1, database "nr", (Jul. 18, 2006), 3 pgs.

(56) References Cited

OTHER PUBLICATIONS

FLUMIST™ Package Insert Template, [Online]. Retrieved from the Internet: http://www.fda.gov/downloads/BiologicsBloodVaccines!Vaccines/ApprovedProductzs/UCM294307.pdf, (Mar. 1, 2012), 26 pgs.

"1.A.32 The Type B Influenza Virus NB Channel (NB-C) Family", Transport Protein Database, (University of California, San diego, the Sailer Laboratory Bioinformatics Group) [Online}. http://www.web.archive.org/web/200301311055254/http://tcdb.ucsd.edu/tcdb/tcfamilybrowse.php?tcname=1.A.32, (Archived Jan. 31, 2003), 1 pg.

"U.S. Appl. No. 10/855,975 Response filed Aug. 28, 2007 to Final Office Action mailed Jun. 28, 2007", 16 pgs.

"2018-19 ACIP Background—Immunogenicity, Efficacy, and Effectiveness of Influenza Vaccines", [online]. [archived on Dec. 3, 2018]. Retrieved from the Internet: <URL: https://web.archive.org/web/20181203190316/https://www.cdc.gov/flu/professionals/acip/2018-2019/background/immunogenicity.htm>, (updated Aug. 23, 2018), 5 pgs.

"Final O.A Jun. 28, 2007", 5 pgs.

"Application Serial No. 04809419.7, Office Action Mailed Sep. 9, 2009", 3 pgs.

"U.S. Appl. No. 09/834,095, Advisory Action mailed Jan. 8, 2004", 3 pgs.

"U.S. Appl. No. 09/834,095, Final Office Action mailed Aug. 26, 2003", 12 pgs.

"U.S. Appl. No. 09/834,095, Non-Final Office Action mailed Nov. 4, 2002", 12 pgs.

"U.S. Appl. No. 09/834,095, Notice of Allowance mailed Sep. 27, 2004", 13 pgs.

"U.S. Appl. No. 09/834,095, Office Action mailed Apr. 20, 2004", 11 pgs.

"U.S. Appl. No. 09/834,095, Response filed Feb. 4, 2003 to Office Action mailed Nov. 4, 2002", 14 pgs.

"U.S. Appl. No. 09/834,095, Response filed Jun. 12, 2003 to Restriction Requirement mailed Apr. 22, 2003", 2 pgs.

"U.S. Appl. No. 09/834,095, Response filed Jun. 18, 2004 to Office Action mailed Apr. 20, 2004", 11 pgs.

"U.S. Appl. No. 09/834,095, Response filed Aug. 1, 2002 to Restriction Requirement mailed Jul. 1, 2002", 3 pgs.

"U.S. Appl. No. 09/834,095, Response filed Nov. 26, 2003 to Final Office Action mailed Aug. 26, 2003", 10 pgs.

"U.S. Appl. No. 09/834,095, Restriction Requirement mailed Apr. 22, 2003", 5 pgs.

"U.S. Appl. No. 09/834,095, Restriction Requirement mailed Jul. 1, 2002", 9 pgs.

"U.S. Appl. No. 09/834,095, Supplemental Amendment filed Aug. 4, 2004", 7 pgs.

"U.S. Appl. No. 10/081,170, Advisory Action mailed Sep. 27, 2004", 3 pgs.

"U.S. Appl. No. 10/081,170, Final Office Action mailed Apr. 12, 2006", 7 pgs.

"U.S. Appl. No. 10/081,170, Final Office Action mailed Jul. 13, 2004", 8 pgs.

"U.S. Appl. No. 10/081,170, Non Final Office Action mailed Jan. 15, 2004", 9 pgs.

"U.S. Appl. No. 10/081,170, Non final Office Action mailed Feb. 8, 2005", 9 pgs.

"U.S. Appl. No. 10/081,170, Non Final Office Action mailed Aug. 24, 2005", 9 pgs.

"U.S. Appl. No. 10/081,170, Notice of Allowance mailed Sep. 18, 2006", 8 Pgs.

"U.S. Appl. No. 10/081,170, Preliminary Amendment filed May 20, 2003", 2 pgs.

"U.S. Appl. No. 10/081,170, Preliminary Amendment filed Jun. 6, 2002", 1 pg.

"U.S. Appl. No. 10/081,170, Response filed Jan. 24, 2006 to Non Final Office Action mailed Aug. 24, 2005", 11 pgs.

"U.S. Appl. No. 10/081,170, Response filed Apr. 12, 2004 to Non Final Office Action mailed Jan. 15, 2004", 12 pgs.

"U.S. Appl. No. 10/081,170, Response filed Jun. 8, 2005 to Non Final Office Action mailed Feb. 8, 2005", 11 pgs.

"U.S. Appl. No. 10/081,170, Response filed Aug. 17, 2006 to Final Office Action mailed Apr. 12, 2006", 9 pgs.

"U.S. Appl. No. 10/081,170, Response filed Sep. 13, 2004 to Final Office Action mailed Jul. 13, 2004", 10 pgs.

"U.S. Appl. No. 10/081,170, Response filed Oct. 10, 2003 to Restriction Requirement mailed Sep. 10, 2003", 3 pgs.

"U.S. Appl. No. 10/081,170, Restriction Requirement mailed Sep. 10, 2003", 4 pgs.

"U.S. Appl. No. 10/353,856, Final Office Action mailed Jun. 1, 2006", 10 pgs.

"U.S. Appl. No. 10/353,856, Non-Final Office Action mailed Sep. 30, 2005", 9 pgs.

"U.S. Appl. No. 10/353,856, Non-Final Office Action mailed Dec. 16, 2004", 11 pgs.

"U.S. Appl. No. 10/353,856, Notice of Allowance mailed Oct. 18, 2006", 9 pgs.

"U.S. Appl. No. 10/353,856, Preliminary Amendment filed May 20, 2003", 2 pgs.

"U.S. Appl. No. 10/353,856, PTO Response to 312 Amendment mailed Mar. 8, 2007", 2 pgs.

"U.S. Appl. No. 10/353,856, Response filed Feb. 28, 2006 to Non-Final Office Action mailed Sep. 30, 2005", 10 pgs.

"U.S. Appl. No. 10/353,856, Response filed Apr. 7, 2005 to Non-Final Office Action mailed Dec. 16, 2004", 10 pgs.

"U.S. Appl. No. 10/353,856, Response filed Aug. 17, 2006 to Final Office Action mailed Jun. 1, 2006", 11 pgs.

"U.S. Appl. No. 10/353,856, Response filed Oct. 8, 2004 to Restriction Requirement mailed Sep. 10, 2004", 2 pgs.

"U.S. Appl. No. 10/353,856, Restriction Requirement mailed Sep. 10, 2004", 5 pgs.

"U.S. Appl. No. 10/353,856, Supplemental Amendment filed Jan. 1, 2007", 4 pgs.

"U.S. Appl. No. 10/353,856, Supplemental Preliminary Amendment filed Jun. 23, 2003", 4 pgs.

"U.S. Appl. No. 10/827,995, Final Office Action mailed Nov. 15, 2006", 10 pgs.

"U.S. Appl. No. 10/827,995, Non-Final Office Action mailed Jun. 2, 2006", 15 pgs.

"U.S. Appl. No. 10/827,995, Non-Final Office Action mailed Oct. 25, 2007", 7 pgs.

"U.S. Appl. No. 10/827,995, Notice of Allowance mailed Feb. 17, 2009", 9 pgs.

"U.S. Appl. No. 10/827,995, Notice of Allowance mailed Jul. 2, 2008", 9 pgs.

"U.S. Appl. No. 10/827,995, Notice of Allowance mailed Oct. 17, 2008", 7 pgs.

"U.S. Appl. No. 10/827,995, Notice of Non-Compliant Amendment Jul. 25, 2007", 4 pgs.

"U.S. Appl. No. 10/827,995, Proposed Examiner's Amendment mailed Jun. 5, 2008", 6 pgs.

"U.S. Appl. No. 10/827,995, Response filed Mar. 3, 2008 to Office Action mailed Oct. 25, 2007", 10 pgs.

"U.S. Appl. No. 10/827,995, Response filed May 14, 2007 Final Office Action mailed Nov. 15, 2006", 16 pgs.

"U.S. Appl. No. 10/827,995, Response filed Aug. 13, 2007 to Notice of Non-Compliant Amendment Jul. 25, 2007", 16 pgs.

"U.S. Appl. No. 10/827,995, Response filed Aug. 17, 2006 Non-Final Office Action mailed Jun. 2, 2006", 15 pgs.

"U.S. Appl. No. 10/855,875, Response filed May 17, 2012 to Non Final Office Action mailed Mar. 15, 2012", 15 pgs.

"U.S. Appl. No. 10/855,875, Final Office Action mailed Mar. 11, 2008", FOAR, 20 Pgs.

"U.S. Appl. No. 10/855,875, Final Office Action mailed Aug. 2, 2006", 34 pgs.

"U.S. Appl. No. 10/855,875, Final Office Action mailed Dec. 10, 2010", 15 pgs.

"U.S. Appl. No. 10/855,875, Non Final Office Action mailed Mar. 15, 2012", 15 pgs.

"U.S. Appl. No. 10/855,875, Non-Final Office Action mailed Feb. 19, 2010", 7 pgs.

(56) References Cited

OTHER PUBLICATIONS

"U.S. Appl. No. 10/855,875, Non-Final Office Action mailed May 3, 2007", 13 pgs.
"U.S. Appl. No. 10/855,875, Non-Final Office Action mailed Aug. 7, 2009", 32 pgs.
"U.S. Appl. No. 10/855,875, Non-Final Office Action mailed Nov. 6, 2008", 12 pgs.
"U.S. Appl. No. 10/855,875, Non-Final Office Action mailed Nov. 30, 2005", 13 pgs.
"U.S. Appl. No. 10/855,875, Notice of Allowance mailed Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action mailed Aug. 2, 2007", 14 pgs.
"U.S. Appl. No. 10/855,875, Response filed Mar. 18, 2011 to Final Office Action mailed Dec. 10, 2010", 15 pgs.
"U.S. Appl. No. 10/855,875, Response filed Aug. 17, 2010 to Non Final Office Action mailed Feb. 19, 2010", 20 pgs.
"U.S. Appl. No. 10/855,875, Response filed Dec. 7, 2009 to Non Final Office Action mailed Aug. 7, 2009", 15 pgs.
"U.S. Appl. No. 10/855,875, Response filed Mar. 31, 2009 to Non Final Office Action mailed Nov. 6, 2008", 14 pgs.
"U.S. Appl. No. 10/855,875, Response filed May 1, 2006 to Non-Final Office Action mailed Nov. 30, 2005", 13 pgs.
"U.S. Appl. No. 10/855,875, Response filed Aug. 18, 2008 to final Office Action mailed Mar. 11, 2008", 15 pgs.
"U.S. Appl. No. 10/855,875, Response filed Sep. 20, 2005 to Restriction Requirement mailed Jul. 26, 2005", 4 pgs.
"U.S. Appl. No. 10/855,875, Restriction Requirement mailed Dec. 23, 2011", 9 pgs.
"U.S. Appl. No. 10/855,875, Restriction Requirement mailed Jul. 26, 2005", 9 pgs.
"U.S. Appl. No. 10/855,975, Advisory Action mailed Sep. 6, 2006", 3 pgs.
"U.S. Appl. No. 10/855,975, Advisory Action mailed Sep. 13, 2007", 3 pgs.
"U.S. Appl. No. 10/855,975, Advisory Action mailed Dec. 24, 2008", 4 pgs.
"U.S. Appl. No. 10/855,975, Final Office Action mailed May 17, 2006", 7 pgs.
"U.S. Appl. No. 10/855,975, Final Office Action mailed Jun. 28, 2007", 7 pgs.
"U.S. Appl. No. 10/855,975, Final Office Action mailed Aug. 7, 2008", 5 pgs.
"U.S. Appl. No. 10/855,975, Non-Final Office Action mailed Jan. 4, 2008", 10 pgs.
"U.S. Appl. No. 10/855,975, Non-Final Office Action mailed Jan. 19, 2007", 7 pgs.
"U.S. Appl. No. 10/855,975, Non-Final Office Action mailed May 29, 2009", 5 pgs.
"U.S. Appl. No. 10/855,975, Non-Final Office Action mailed Nov. 30, 2005", 11 pgs.
"U.S. Appl. No. 10/855,975, Notice of Allowance mailed Dec. 16, 2009", 19 pgs.
"U.S. Appl. No. 10/855,975, Response filed Jan. 29, 2009 to Advisory Action mailed Dec. 24, 2008", 15 pgs.
"U.S. Appl. No. 10/855,975, Response filed Feb. 28, 2006 to Non-Final Office Action mailed Nov. 30, 2005", 15 pgs.
"U.S. Appl. No. 10/855,975, Response filed Apr. 3, 2008 to Non Final Office Action mailed Jan. 4, 2008", 16 pgs.
"U.S. Appl. No. 10/855,975, Response filed Apr. 19, 2007 to Non-Final Office Action mailed Jan. 19, 2007", 16 pgs.
"U.S. Appl. No. 10/855,975, Response filed Aug. 13, 2009 to Non Final Office Action mailed May 29, 2009", 19 pgs.
"U.S. Appl. No. 10/855,975, Response filed Aug. 17, 2006 to Final Office Action mailed May 17, 2006", 13 pgs.
"U.S. Appl. No. 10/855,975, Response filed aug. 28, 2007 to Final Office Action mailed Jun. 28, 2007", 15 pgs.
"U.S. Appl. No. 10/855,975, Response filed Sep. 28, 2005 to Restriction Requirement mailed Jul. 12, 2005", 3 pgs.
"U.S. Appl. No. 10/855,975, Response filed Dec. 11, 2008 to Final Office Action mailed Aug. 7, 2008", 14 pgs.
"U.S. Appl. No. 10/855,975, Restriction Requirement mailed Jul. 12, 2005", 8 pgs.
"U.S. Appl. No. 10/855,975, Response filed Nov. 2, 2007 to Office Action mailed May 3, 2007", 16 pgs.
"U.S. Appl. No. 11/043,768, Non-Final Office Action mailed Sep. 27, 2010", 8 pgs.
"U.S. Appl. No. 11/043,768, Final Office Action mailed Jun. 27, 2008", 8 pgs.
"U.S. Appl. No. 11/043,768, Non-Final Office Action mailed Feb. 23, 2010", 6 pgs.
"U.S. Appl. No. 11/043,768, Non-Final Office Action mailed Feb. 23, 2009", 7 pgs.
"U.S. Appl. No. 11/043,768, Non-Final Office Action mailed Nov. 28, 2007", 9 pgs.
"U.S. Appl. No. 11/043,768, Notice of Allowance mailed Jun. 29, 2011", 12 pgs.
"U.S. Appl. No. 11/043,768, Response filed May 2, 2011 to Final Office Action mailed Feb. 3, 2011", 11 pgs.
"U.S. Appl. No. 11/043,768, Response filed Jun. 15, 2010 to Non Final Office Action mailed Feb. 23, 2010", 9 pgs.
"U.S. Appl. No. 11/043,768, Response filed Jun. 23, 2009 to Non-Final Office Action mailed Feb. 23, 2009", 9 pgs.
"U.S. Appl. No. 11/043,768, Response filed Sep. 13, 2007 to Restriction Requirement mailed Mar. 13, 2007", 10 pgs.
"U.S. Appl. No. 11/043,768, Response filed Oct. 26, 2010 to Non Final Office Action mailed Sep. 27, 2010", 11 pgs.
"U.S. Appl. No. 11/043,768, Response filed Dec. 12, 2008 to Final Office Action mailed Jun. 27, 2008", 9 pgs.
"U.S. Appl. No. 11/043,768, Response filed Mar. 10, 2008 to Office Action mailed Nov. 28, 2007", 12 pgs.
"U.S. Appl. No. 11/043,768, Restriction Requirement mailed Mar. 13, 2007", 9 pgs.
"U.S. Appl. No. 11/043,768, Final Office Action mailed Feb. 3, 2011", 10 pgs.
"U.S. Appl. No. 11/283,498, Non Final Office Action mailed Sep. 3, 2009", 5 pgs.
"U.S. Appl. No. 11/283,498, Non Final Office Action mailed Jul. 9, 2007", 7 pgs.
"U.S. Appl. No. 11/283,498, Non-Final Office Action mailed Jan. 23, 2008", 20 pgs.
"U.S. Appl. No. 11/283,498, Non-Final Office Action mailed Apr. 29, 2010", 10 pgs.
"U.S. Appl. No. 11/283,498, Notice of Allowance mailed Feb. 23, 2011", 9 pgs.
"U.S. Appl. No. 11/283,498, Response filed Jan. 4, 2010 to Non Final Office Action mailed Sep. 3, 2009", 12 pgs.
"U.S. Appl. No. 11/283,498, Response filed Oct. 28, 2010 to Non Final Office Action mailed Apr. 29, 2010", 13 pgs.
"U.S. Appl. No. 11/283,498, Response filed Nov. 7, 2007 to Office Action mailed Jul. 9, 2007", 17 pgs.
"U.S. Appl. No. 11/283,498, Response filed Apr. 16, 2007 to Restriction Requirement mailed Oct. 16, 2006", 17 pgs.
"U.S. Appl. No. 11/283,498, Response filed Jul. 22, 2008 to Non Final Office Action mailed Jan. 23, 2008", 12 pgs.
"U.S. Appl. No. 11/283,498, Restriction Requirement mailed Oct. 16, 2006", 6 pgs.
"U.S. Appl. No. 11/283,498, Supplemental Amendment Response to Non Final Office Action mailed Oct. 28, 2010", 11 pgs.
"U.S. Appl. No. 11/509,249, Final Office Action mailed Jun. 12, 2008", 5 pgs.
"U.S. Appl. No. 11/509,249, Final Office Action with Restriction Requirement mailed Aug. 24, 2007", 8 pgs.
"U.S. Appl. No. 11/509,249, Notice of Allowance mailed Apr. 9, 2009", 7 pgs.
"U.S. Appl. No. 11/509,249, Notice of Allowance mailed Nov. 17, 2008", 4 pgs.
"U.S. Appl. No. 11/509,249, Response filed Feb. 20, 2008 to Non Final Office Action mailed Aug. 24, 2007", 11 pgs.

(56) References Cited

OTHER PUBLICATIONS

"U.S. Appl. No. 11/509,249, Response filed Oct. 6, 2008 to Office Action mailed Jun. 12, 2008", 5 pgs.
"U.S. Appl. No. 11/644,179 , Response filed Oct. 21, 2013 to Final Office Action mailed May 21, 2013", 8 pgs.
"U.S. Appl. No. 11/644,179, Final Office Action mailed May 21, 2013", 11 pgs.
"U.S. Appl. No. 11/644,179, Final Office Action mailed Jul. 2, 2010", 8 pgs.
"U.S. Appl. No. 11/644,179, Non Final Office Action mailed Nov. 29, 2012", 19 pgs.
"U.S. Appl. No. 11/644,179, Non Final Office Action mailed Dec. 8, 2009", 7 pgs.
"U.S. Appl. No. 11/644,179, Notice of Allowance mailed Nov. 1, 2013", 11 pgs.
"U.S. Appl. No. 11/644,179, Preliminary Amendment filed Dec. 22, 2006", 5 pgs.
"U.S. Appl. No. 11/644,179, Response filed Jan. 30, 2008 to Restriction Requirement mailed Oct. 30, 2007", 5 pgs.
"U.S. Appl. No. 11/644,179, Response filed Apr. 8, 2010 to Non Final Office Action mailed Dec. 8, 2009", 8 pgs.
"U.S. Appl. No. 11/644,179, Response filed Aug. 17, 2010 to Final Office Action mailed Jul. 2, 2010", 8 pgs.
"U.S. Appl. No. 11/644,179, Restriction Requirement mailed Oct. 30, 2007", 7 pgs.
"U.S. Appl. No. 11/644,179, Supplemental Preliminary Amendment filed Feb. 6, 2008", 6 pgs.
"U.S. Appl. No. 11/644,179, Response filed Feb. 20, 2013 to Non Final Office Action mailed Nov. 29, 2012", 10 pgs.
"U.S. Appl. No. 11/654,863, Final Office Action mailed Jul. 17, 2017", 11 pgs.
"U.S. Appl. No. 11/654,863, Restriction Requirement mailed Sep. 3, 2010", 5 pgs.
"U.S. Appl. No. 11/654,863, Appeal Brief filed Apr. 30, 2014", 22 pgs.
"U.S. Appl. No. 11/654,863, Appeal Decision mailed Aug. 3, 2016", 11 pgs.
"U.S. Appl. No. 11/654,863, Decision on Pre-Appeal Brief Request mailed Dec. 5, 2013", 2 pgs.
"U.S. Appl. No. 11/654,863, Declaration of Dr. Heinz Feldman dated Jan. 9, 2018", 2 pgs.
"U.S. Appl. No. 11/654,863, Declaration of Yoshihiro Kawaoka dated Apr. 18, 2012", 2 pgs.
"U.S. Appl. No. 11/654,863, Examiner's Answer to Appeal Brief mailed Jun. 18, 2014", 10 pgs.
"U.S. Appl. No. 11/654,863, Final Office Action mailed Jul. 11, 2013", 9 pgs.
"U.S. Appl. No. 11/654,863, Final Office Action mailed Sep. 12, 2018", 12 pgs.
"U.S. Appl. No. 11/654,863, Final Office Action mailed Oct. 25, 2011", 9 pgs.
"U.S. Appl. No. 11/654,863, Non Final Office Action mailed Feb. 11, 2013", 10 pgs.
"U.S. Appl. No. 11/654,863, Non Final Office Action mailed Mar. 29, 2018", 12 pgs.
"U.S. Appl. No. 11/654,863, Non Final Office Action mailed Jun. 27, 2011", 9 pgs.
"U.S. Appl. No. 11/654,863, Non Final Office Action mailed Dec. 2, 2010", 8 pgs.
"U.S. Appl. No. 11/654,863, Non Final Office Action mailed Dec. 21, 2016", 14 pgs.
"U.S. Appl. No. 11/654,863, Pre-Appeal Brief Request filed Nov. 11, 2013", 5 pgs.
"U.S. Appl. No. 11/654,863, Preliminary Amendment filed May 7, 2007", 15 pgs.
"U.S. Appl. No. 11/654,863, Reply Brief filed Aug. 18, 2014", 6 pgs.
"U.S. Appl. No. 11/654,863, Response filed Jan. 17, 2018 to Final Office Action mailed Jul. 17, 2017", 9 pgs.
"U.S. Appl. No. 11/654,863, Response filed Apr. 18, 2012 to Final Office Action mailed Oct. 25, 2011", 8 pgs.
"U.S. Appl. No. 11/654,863, Response filed Jun. 2, 2011 to Non Final Office Action mailed Dec. 2, 2010", 6 pgs.
"U.S. Appl. No. 11/654,863, Response filed Jun. 7, 2013 to Non Final Office Action mailed Feb. 11, 2013", 10 pgs.
"U.S. Appl. No. 11/654,863, Response filed Jun. 21, 2017 to Non Final Office Action mailed Dec. 21, 2016", 11 pgs.
"U.S. Appl. No. 11/654,863, Response filed Jul. 9, 2018 to Non Final Office Action mailed Mar. 29, 2018", 10 pgs.
"U.S. Appl. No. 11/654,863, Response filed Sep. 28, 2010 to Restriction Requirement mailed Sep. 3, 2010", 6 pgs.
"U.S. Appl. No. 11/654,863, Response filed Oct. 6, 2011 to Non Final Office Action mailed Jun. 27, 2011", 9 pgs.
"U.S. Appl. No. 11/729,557, Advisory Action mailed May 9, 2011", 3 pgs.
"U.S. Appl. No. 11/729,557, Advisory Action mailed Dec. 24, 2014", 3 pgs.
"U.S. Appl. No. 11/729,557, Final Office Action mailed Feb. 2, 2011", 14 pgs.
"U.S. Appl. No. 11/729,557, Final Office Action mailed Aug. 20, 2009", 13 Pgs.
"U.S. Appl. No. 11/729,557, Final Office Action mailed Sep. 12, 2014", 14 pgs.
"U.S. Appl. No. 11/729,557, Non final Office Action mailed Feb. 18, 2015", 13 pgs.
"U.S. Appl. No. 11/729,557, Non Final Office Action mailed Feb. 26, 2014", 16 pgs.
"U.S. Appl. No. 11/729,557, Non-Final Office Action mailed Jan. 30, 2009", 20 pgs.
"U.S. Appl. No. 11/729,557, Non-Final Office Action mailed Feb. 22, 2010", 16 pgs.
"U.S. Appl. No. 11/729,557, Non-Final Office Action mailed Aug. 23, 2010", 15 pgs.
"U.S. Appl. No. 11/729,557, Notice of Allowance mailed Sep. 30, 2015", 11 pgs.
"U.S. Appl. No. 11/729,557, Response filed Jun. 22, 2010 to Non Final Office Action mailed Feb. 22, 2010", 33 pgs.
"U.S. Appl. No. 11/729,557, Response filed Apr. 27, 2011 to Final Office Action mailed Feb. 2, 2011", 14 pgs.
"U.S. Appl. No. 11/729,557, Response filed Apr. 30, 2009 to Non Final Office Action mailed Jan. 30, 2009", 18 pgs.
"U.S. Appl. No. 11/729,557, Response filed May 22, 2014 to Non Final Office Action mailed Feb. 26, 2014", 13 pgs.
"U.S. Appl. No. 11/729,557, Response filed May 28, 2008 to Restriction Requirement mailed Nov. 28, 2007", 13 pgs.
"U.S. Appl. No. 11/729,557,Response filed Jun. 22, 2010 to Non Final Office Action mailed Feb. 22, 2010", 16 pgs.
"U.S. Appl. No. 11/729,557, Response filed Jun. 22, 2015 to non Final Office Action mailed Feb. 18, 2015", 13 pgs.
"U.S. Appl. No. 11/729,557, Response filed Oct. 28, 2010 to Non Final Office Action mailed Aug. 23, 2010", 13 pgs.
"U.S. Appl. No. 11/729,557, Response filed Dec. 1, 2009 to Final Office Action mailed Aug. 26, 2009", 16 pgs.
"U.S. Appl. No. 11/729,557, Response filed Dec. 11, 2014 to Final Office Action mailed Sep. 12, 2014", 15 pgs.
"U.S. Appl. No. 11/729,557, Restriction Requirement mailed Nov. 28, 2007", 9 pgs.
"U.S. Appl. No. 11/810,956, Advisory Action mailed Mar. 22, 2010", 8 pgs.
"U.S. Appl. No. 11/810,956, Non-Final Office Action mailed Aug. 11, 2009", 9 pgs.
"U.S. Appl. No. 11/810,956, Response filed Jan. 11, 2010 to Non Final Office Action mailed Aug. 11, 2009", 8 pgs.
"U.S. Appl. No. 11/810,956, Response filed Apr. 23, 2009 to Restriction Requirement mailed Mar. 23, 2009", 6 pgs.
"U.S. Appl. No. 11/810,956, Restriction Requirement mailed Mar. 23, 2009", 6 pgs.
"U.S. Appl. No. 12/058,389, Advisory Action mailed Jan. 2, 2013", 2 pgs.
"U.S. Appl. No. 12/058,389, Final Office Action mailed Jan. 22, 2010", 8 pgs.

(56) References Cited

OTHER PUBLICATIONS

"U.S. Appl. No. 12/058,389, Final Office Action mailed Nov. 14, 2012", 7 pgs.
"U.S. Appl. No. 12/058,389, Non Final Office Action mailed Aug. 10, 2012", 5 pgs.
"U.S. Appl. No. 12/058,389, Non Final Office Action mailed Dec. 8, 2011", 8 pgs.
"U.S. Appl. No. 12/058,389, Non-Final Office Action mailed Apr. 13, 2009", 12 pgs.
"U.S. Appl. No. 12/058,389, Notice of Allowability mailed Mar. 22, 2013", 8 pgs.
"U.S. Appl. No. 12/058,389, Notice of Allowance mailed Feb. 20, 2013", 9 pgs.
"U.S. Appl. No. 12/058,389, Preliminary Amendment filed Jun. 23, 2008", 7 pgs.
"U.S. Appl. No. 12/058,389, Response filed Nov. 6, 2012 to Non Final Office Action mailed Aug. 10, 2012", 7 pgs.
"U.S. Appl. No. 12/058,389, Response filed Feb. 6, 2009 to Restriction Requirement mailed Dec. 3, 2008", 7 pgs.
"U.S. Appl. No. 12/058,389, Response filed Apr. 10, 2012 to Non Final Office Action mailed Dec. 8, 2011", 7 pgs.
"U.S. Appl. No. 12/058,389, Response filed Jun. 16, 2010 to Final Office Action mailed Jan. 22, 2010", 6 pgs.
"U.S. Appl. No. 12/058,389, Response filed Oct. 13, 2009 to Non Final Office Action mailed Apr. 13, 2009", 9 pgs.
"U.S. Appl. No. 12/058,389, Response filed Dec. 18, 2012 to Non Final Office Action mailed Nov. 14, 2012", 7 pgs.
"U.S. Appl. No. 12/058,389, Restriction Requirement mailed Dec. 3, 2008", 7 pgs.
"U.S. Appl. No. 12/113,690, Final Office Action mailed Apr. 15, 2011", 10 pgs.
"U.S. Appl. No. 12/113,690, Non-Final Office Action mailed Nov. 10, 2010", 11 pgs.
"U.S. Appl. No. 12/113,690, Notice of Allowability mailed Aug. 19, 2013", 9 pgs.
"U.S. Appl. No. 12/113,690, Notice of Allowance mailed Jul. 18, 2013", 14 pgs.
"U.S. Appl. No. 12/113,690, Preliminary Amendment filed Jul. 31, 2008", 14 pgs.
"U.S. Appl. No. 12/113,690, Response filed Jun. 23, 2011 to Final Office Action mailed Apr. 15, 2011", 17 pgs.
"U.S. Appl. No. 12/113,690, Response filed Aug. 5, 2010 to Restriction Requirement mailed Apr. 6, 2010", 14 pgs.
"U.S. Appl. No. 12/113,690, Response filed Dec. 22, 2010 to Non Final Office Action mailed Nov. 10, 2010", 19 pgs.
"U.S. Appl. No. 12/113,690, Restriction Requirement mailed Apr. 6, 2010", 10 pgs.
"U.S. Appl. No. 12/139,183, Non Final Office Action mailed Jan. 6, 2011", 12 pgs.
"U.S. Appl. No. 12/139,183, Non-Final Office Action mailed Jan. 4, 2010", 6 pgs.
"U.S. Appl. No. 12/139,183, Non-Final Office Action mailed Jul. 13, 2010", 15 pgs.
"U.S. Appl. No. 12/139,183, Notice of Allowance mailed Jun. 27, 2011", 11 pgs.
"U.S. Appl. No. 12/139,183, Preliminary Amendment filed Sep. 11, 2008", 17 pgs.
"U.S. Appl. No. 12/139,183, Response filed Mar. 22, 2011 to Non Final Office Action mailed Jan. 6, 2011", 21 pgs.
"U.S. Appl. No. 12/139,183, Response filed Apr. 12, 2010 to Non Final Office Action mailed Jan. 4, 2010", 17 pgs.
"U.S. Appl. No. 12/139,183, Response filed Aug. 18, 2009 to Restriction Requirement mailed Jul. 24, 2009", 16 pgs.
"U.S. Appl. No. 12/139,183, Response filed Sep. 21, 2010 to Non Final Office Action mailed Jul. 13, 2010", 21 pgs.
"U.S. Appl. No. 12/139,183, Restriction Requirement mailed Jul. 24, 2009", 12 pgs.
"U.S. Appl. No. 12/214,414, Advisory Action mailed Feb. 2, 2016", 5 pgs.
"U.S. Appl. No. 12/214,414, Advisory Action mailed Apr. 15, 2015", 6 pgs.
"U.S. Appl. No. 12/214,414, Advisory Action mailed Oct. 21, 2011", 5 pgs.
"U.S. Appl. No. 12/214,414, Examiner Interview Summary mailed Dec. 11, 2015", 3 pgs.
"U.S. Appl. No. 12/214,414, Final Office Action mailed Jan. 20, 2015", 28 pgs.
"U.S. Appl. No. 12/214,414, Final Office Action mailed Aug. 2, 2011", 7 pgs.
"U.S. Appl. No. 12/214,414, Final Office Action mailed Nov. 18, 2015", 17 pgs.
"U.S. Appl. No. 12/214,414, Non Final Office Action mailed Jun. 12, 2014", 28 pgs.
"U.S. Appl. No. 12/214,414, Non Final Office Action mailed Dec. 10, 2010", 6 pgs.
"U.S. Appl. No. 12/214,414, Non-Final Office Action mailed Mar. 2, 2010", 9 pgs.
"U.S. Appl. No. 12/214,414, Notice of Allowance mailed Jun. 7, 2016", 18 pgs.
"U.S. Appl. No. 12/214,414, Response filed Jan. 19, 2016 to Final Office Action mailed Nov. 18, 2015", 14 pgs.
"U.S. Appl. No. 12/214,414, Response filed Feb. 18, 2016 to Final Office Action mailed Nov. 18, 2015", 14 pgs.
"U.S. Appl. No. 12/214,414, Response filed Mar. 26, 2015 to Final Office Action mailed Jan. 20, 2015", 13 pgs.
"U.S. Appl. No. 12/214,414, Response filed May 3, 2011 to Non Final Office Action mailed Dec. 10, 2010", 12 pgs.
"U.S. Appl. No. 12/214,414, Response filed Jul. 20, 2015 to Advisory Action mailed Apr. 15, 2015", 14 pgs.
"U.S. Appl. No. 12/214,414, Response filed Aug. 31, 2010 to Non Final Office Action mailed Mar. 2, 2010", 11 pgs.
"U.S. Appl. No. 12/214,414, Response filed Oct. 3, 2011 to Non Final Office Action mailed Aug. 2, 2011", 9 pgs.
"U.S. Appl. No. 12/214,414, Response filed Oct. 14, 2014 to Non final Office Action mailed Jun. 12, 2014", 16 pgs.
"U.S. Appl. No. 12/214,414, Response filed Dec. 21, 2011 to Advisory Action mailed Oct. 21, 2011", 10 pgs.
"U.S. Appl. No. 12/245,296, Final Office Action mailed Jul. 11, 2013", 15 pgs.
"U.S. Appl. No. 12/245,296, Final Office Action mailed Dec. 17, 2010", 16 pgs.
"U.S. Appl. No. 12/245,296, Non Final Office Action mailed Mar. 25, 2013", 14 pgs.
"U.S. Appl. No. 12/245,296, Non-Final Office Action mailed Jun. 1, 2010", 13 pgs.
"U.S. Appl. No. 12/245,296, Notice of Allowance mailed Aug. 1, 2014", 10 pgs.
"U.S. Appl. No. 12/245,296, Preliminary Amendment mailed Jan. 18, 2009", 14 pgs.
"U.S. Appl. No. 12/245,296, Response filed Jan. 8, 2013 to Final Office Action mailed Jul. 11, 2013", 10 pgs.
"U.S. Appl. No. 12/245,296, Response filed Apr. 8, 2010 to Restriction Requirement mailed Mar. 9, 2010", 6 pgs.
"U.S. Appl. No. 12/245,296, Response filed May 17, 2011 to Final Office Action mailed Dec. 17, 2010", 10 pgs.
"U.S. Appl. No. 12/245,296, Response filed Jun. 7, 2013 to Non Final Office Action mailed Mar. 25, 2013", 9 pgs.
"U.S. Appl. No. 12/245,296, Response filed Oct. 1, 2010 to Non Final Office Action mailed Jun. 1, 2010", 12 pgs.
"U.S. Appl. No. 12/245,296, Restriction Requirement mailed Mar. 9, 2010", 6 pgs.
"U.S. Appl. No. 12/467,492, Restriction Requirement mailed Nov. 22, 2010", 6 pgs.
"U.S. Appl. No. 12/470,287 , Response filed Jan. 23, 2012 to Non Final Office Action mailed Jul. 22, 2011", 13 pgs.
"U.S. Appl. No. 12/470,287 , Response filed May 31, 2012 to Final Office Action mailed Apr. 3, 2012", 14 pgs.
"U.S. Appl. No. 12/470,287, Corrected Notice of Allowability mailed Sep. 11, 2012", 2 pgs.
"U.S. Appl. No. 12/470,287, Final Office Action mailed Apr. 3, 2012", 7 pgs.

(56) References Cited

OTHER PUBLICATIONS

"U.S. Appl. No. 12/470,287, Non Final Office Action mailed Jul. 22, 2011", 9 pgs.
"U.S. Appl. No. 12/470,287, Notice of Allowance mailed Jun. 19, 2012", 5 pgs.
"U.S. Appl. No. 12/470,287, Response filed Apr. 28, 2011 to Restriction Requirement mailed Dec. 29, 2010", 8 pgs.
"U.S. Appl. No. 12/470,287, Restriction Requirement mailed Dec. 29, 2010", 6 pgs.
"U.S. Appl. No. 12/854,578 , Response filed Oct. 1, 2012 to Non Final Office Action mailed Jun. 29, 2012", 10 pgs.
"U.S. Appl. No. 12/854,578, Final Office Action mailed Nov. 29, 2012", 8 pgs.
"U.S. Appl. No. 12/854,578, Non Final Office Action mailed Jun. 29, 2012", 8 pgs.
"U.S. Appl. No. 12/854,578, Notice of Allowance mailed Apr. 10, 2013", 6 pgs.
"U.S. Appl. No. 12/854,578, PTO Response to 312 Amendment mailed Jul. 18, 2013", 2 pgs.
"U.S. Appl. No. 12/854,578, Response filed Feb. 28, 2013 to Final Office Action mailed Nov. 29, 2012", 8 pgs.
"U.S. Appl. No. 12/854,578, Restriction Requirement mailed Apr. 6, 2012", 6 pgs.
"U.S. Appl. No. 12/912,411, Advisory Action mailed Feb. 5, 2014", 3 pgs.
"U.S. Appl. No. 12/912,411, Examiner Interview Summary mailed Feb. 11, 2014", 2 pgs.
"U.S. Appl. No. 12/912,411, Final Office Action mailed Jan. 14, 2015", 10 pgs.
"U.S. Appl. No. 12/912,411, Final Office Action mailed Oct. 25, 2013", 11 pgs.
"U.S. Appl. No. 12/912,411, Non Final Office Action mailed Jun. 7, 2013", 8 pgs.
"U.S. Appl. No. 12/912,411, Non Final Office Action mailed Sep. 24, 2014", 11 pgs.
"U.S. Appl. No. 12/912,411, Notice of Allowability mailed May 20, 2015", 7 pgs.
"U.S. Appl. No. 12/912,411, Notice of Allowance mailed Apr. 8, 2015", 11 pgs.
"U.S. Appl. No. 12/912,411, Response filed Jan. 27, 2014 to Final Office Action mailed Oct. 25, 2014", 11 pgs.
"U.S. Appl. No. 12/912,411, Response filed Feb. 18, 2013 to Restriction Requirement mailed Oct. 17, 2012", 9 pgs.
"U.S. Appl. No. 12/912,411, Response filed Feb. 25, 2014 to Final Office Action mailed Oct. 25, 2013", 11 pgs.
"U.S. Appl. No. 12/912,411, Response filed Mar. 16, 2015 to Final Office Action mailed Jan. 14, 2015", 9 pgs.
"U.S. Appl. No. 12/912,411, Response filed Oct. 7, 2013 to Non Final Office Action mailed Jun. 7, 2013", 10 pgs.
"U.S. Appl. No. 12/912,411, Response filed Dec. 31, 2014 to Non Final Office Action mailed Sep. 24, 2014", 12 pgs.
"U.S. Appl. No. 12/912,411, Restriction Requirement mailed Oct. 17, 2012", 9 pgs.
"U.S. Appl. No. 13/070,110 Response filed Feb. 14, 2017 to Final Office Action mailed Sep. 14, 2016", 8 pgs.
"U.S. Appl. No. 13/070,110, Advisory Action mailed Mar. 3, 2017", 5 pgs.
"U.S. Appl. No. 13/070,110, Examiner Interview Summary mailed Jan. 16, 2016", 3 pgs.
"U.S. Appl. No. 13/070,110, Final Office Action mailed Apr. 3, 2015", 18 pgs.
"U.S. Appl. No. 13/070,110, Final Office Action mailed Jun. 12, 2013", 7 pgs.
"U.S. Appl. No. 13/070,110, Final Office Action mailed Sep. 14, 2016", 12 pgs.
"U.S. Appl. No. 13/070,110, Non Final Office Action mailed Jul. 21, 2017", 14 pgs.
"U.S. Appl. No. 13/070,110, Non Final Office Action mailed Oct. 2, 2014", 24 pgs.
"U.S. Appl. No. 13/070,110, Non Final Office Action mailed Dec. 11, 2015", 19 pgs.
"U.S. Appl. No. 13/070,110, Non Final Office Action mailed Dec. 21, 2012", 7 pgs.
"U.S. Appl. No. 13/070,110, Notice of Allowance mailed Mar. 26, 2018", 6 pgs.
"U.S. Appl. No. 13/070,110, Notice of Allowance mailed Jul. 20, 2018", 7 pgs.
"U.S. Appl. No. 13/070,110, Preliminary Amendment filed Jun. 6, 2011", 4 pgs.
"U.S. Appl. No. 13/070,110, PTO Response to Rule 312 Communication mailed Aug. 15, 2018", 2 pgs.
"U.S. Appl. No. 13/070,110, Response filed Jan. 22, 2018 to Non Final Office Action mailed Jul. 21, 2017", 10 pgs.
"U.S. Appl. No. 13/070,110, Response filed Mar. 22, 2013 to Non Final Office Action mailed Dec. 21, 2012", 8 pgs.
"U.S. Appl. No. 13/070,110, Response filed May 27, 2016 to Non Final Office Action mailed Dec. 11, 2015", 13 pgs.
"U.S. Appl. No. 13/070,110, Response filed Jun. 20, 2017 to Advisory Action mailed Mar. 3, 2017", 13 pgs.
"U.S. Appl. No. 13/070,110, Response filed Sep. 3, 2014 to Restriction Requirement mailed Jul. 8, 2014", 7 pgs.
"U.S. Appl. No. 13/070,110, Response filed Oct. 2, 2015 to Final Office Action mailed Apr. 3, 2015", 11 pgs.
"U.S. Appl. No. 13/070,110, Response filed Nov. 12, 2013 to Final Office Action mailed Jun. 12, 2013", 9 pgs.
"U.S. Appl. No. 13/070,110, Response filed Dec. 30, 2014 to Non Final Office Action mailed Oct. 2, 2014", 13 pgs.
"U.S. Appl. No. 13/070,110, Restriction Requirement mailed Jul. 8, 2014", 7 pgs.
"U.S. Appl. No. 13/113,244, Final Office Action mailed Feb. 27, 2014", 8 pgs.
"U.S. Appl. No. 13/113,244, Non Final Office Action mailed Jul. 5, 2013", 6 pgs.
"U.S. Appl. No. 13/113,244, Non Final Office Action mailed Oct. 1, 2012", 7 pgs.
"U.S. Appl. No. 13/113,244, Notice of Allowance mailed Jun. 30, 2014", 9 pgs.
"U.S. Appl. No. 13/113,244, Preliminary Amendment filed Aug. 11, 2011", 4 pgs.
"U.S. Appl. No. 13/113,244, Response filed Jan. 30, 2012 to Restriction Requirement mailed Oct. 31, 2011", 10 pgs.
"U.S. Appl. No. 13/113,244, Response filed Feb. 20, 2013 to Non Final Office Action mailed Oct. 1, 2012", 12 pgs.
"U.S. Appl. No. 13/113,244, Response filed Jun. 13, 2014 to Final Office Action mailed Feb. 27, 2014", 6 pgs.
"U.S. Appl. No. 13/113,244, Response filed Oct. 31, 2013 to Non Final Office Action mailed Jul. 5, 2013", 12 pgs.
"U.S. Appl. No. 13/113,244, Restriction Requirement mailed Oct. 31, 2011", 8 pgs.
"U.S. Appl. No. 13/127,951, Advisory Action mailed Jul. 16, 2014", 3 pgs.
"U.S. Appl. No. 13/127,951, Final Office Action mailed Apr. 9, 2014", 23 pgs.
"U.S. Appl. No. 13/127,951, Non Final Office Action mailed Sep. 26, 2013", 18 pgs.
"U.S. Appl. No. 13/127,951, Notice of Allowance mailed Jul. 20, 2015", 7 pgs.
"U.S. Appl. No. 13/127,951, Preliminary Amendment filed May 5, 2011", 7 pgs.
"U.S. Appl. No. 13/127,951, PTO Response to Rule 312 Communication mailed Oct. 23, 2015", 2 pgs.
"U.S. Appl. No. 13/127,951, Response filed Mar. 18, 2014 to Non Final Office Action mailed Sep. 26, 2013", 14 pgs.
"U.S. Appl. No. 13/127,951, Response filed Jul. 7, 2014 to Final Office Action mailed Apr. 9, 2014", 10 pgs.
"U.S. Appl. No. 13/127,951, Response filed Aug. 30, 2013 to Restriction Requirement mailed Apr. 30, 2013", Aug. 30, 2013.
"U.S. Appl. No. 13/127,951, Response filed Oct. 9, 2014 to Advisory Action mailed Jul. 16, 2014", 10 pgs.
"U.S. Appl. No. 13/127,951, Restriction Requirement mailed Apr. 30, 2013", 15 pgs.

(56) References Cited

OTHER PUBLICATIONS

"U.S. Appl. No. 13/594,611, Final Office Action mailed Aug. 15, 2014", 7 pgs.
"U.S. Appl. No. 13/594,611, Non Final Office Action mailed Apr. 24, 2014", 9 pgs.
"U.S. Appl. No. 13/594,611, Notice of Allowance mailed Jan. 13, 2015", 7 pgs.
"U.S. Appl. No. 13/594,611, PTO Response to Rule 312 Communication mailed Apr. 16, 2015", 2 pgs.
"U.S. Appl. No. 13/594,611, Response filed Feb. 25, 2014 to Restriction Requirement mailed Jan. 27, 2014", 8 pgs.
"U.S. Appl. No. 13/594,611, Response filed Jul. 7, 2014 to Non Final Office Action mailed Apr. 24, 2014", 9 pgs.
"U.S. Appl. No. 13/594,611, Response filed Dec. 15, 2014 to Final Office Action mailed Aug. 15, 2014", 10 pgs.
"U.S. Appl. No. 13/594,611, Restriction Requirement mailed Jan. 27, 2014", 8 pgs.
"U.S. Appl. No. 14/332,121, Non Final Office Action mailed May 16, 2016", 9 pgs.
"U.S. Appl. No. 14/332,121, Notice of Allowance mailed Feb. 15, 2017", 10 pgs.
"U.S. Appl. No. 14/332,121, Notice of Allowance mailed Jun. 15, 2017", 8 pgs.
"U.S. Appl. No. 14/332,121, Notice of Allowance mailed Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement mailed Jul. 30, 2015", 9 pgs.
"U.S. Appl. No. 14/332,121, Response filed Sep. 7, 2017 to Notice of Allowability mailed Jun. 15, 2017", 8 pgs.
"U.S. Appl. No. 14/332,121, Response filed Oct. 11, 2016 to Non Final Office Action mailed May 16, 2016", 9 pgs.
"U.S. Appl. No. 14/332,121, Restriction Requirement mailed Jul. 30, 2015", 9 pgs.
"U.S. Appl. No. 14/332,121, Supplemental Amendment filed Jan. 23, 2017", 10 pgs.
"U.S. Appl. No. 14/528,997, Advisory Action mailed Aug. 9, 2017", 3 pgs.
"U.S. Appl. No. 14/528,997, Final Office Action mailed Feb. 10, 2017", 9 pgs.
"U.S. Appl. No. 14/528,997, Non Final Office Action mailed Jun. 16, 2016", 12 pgs.
"U.S. Appl. No. 14/528,997, Non Final Office Action mailed Jun. 29, 2018", 7 pgs.
"U.S. Appl. No. 14/528,997, Notice of Allowance mailed Mar. 8, 2019", 7 pgs.
"U.S. Appl. No. 14/528,997, PTO Response to Rule 312 Communication mailed Jun. 19, 2019", 2 pgs.
"U.S. Appl. No. 14/528,997, Response filed Mar. 16, 2016 to Restriction Requirement mailed Sep. 16, 2015", 11 pgs.
"U.S. Appl. No. 14/528,997, Response filed Jul. 27, 2017 to Final Office Action mailed Feb. 10, 2017", 11 pgs.
"U.S. Appl. No. 14/528,997, Response filed Oct. 10, 2016 to Non Final Office Action mailed Jun. 16, 2016", 12 pgs.
"U.S. Appl. No. 14/528,997, Response filed Nov. 16, 2018 to Non Final Office Action mailed Jun. 29, 2018", 11 pgs.
"U.S. Appl. No. 14/528,997, Restriction Requirement mailed Sep. 16, 2015", 8 pgs.
"U.S. Appl. No. 14/699,213, Advisory Action mailed Mar. 7, 2018", 3 pgs.
"U.S. Appl. No. 14/699,213, Final Office Action mailed Dec. 1, 2017", 11 pgs.
"U.S. Appl. No. 14/699,213, Non Final Office Action mailed Jun. 2, 2017", 12 pgs.
"U.S. Appl. No. 14/699,213, Non-Final Office Action mailed Jan. 11, 2019", 10 pgs.
"U.S. Appl. No. 14/699,213, Notice of Allowance mailed Jul. 30, 2019", 8 pgs.
"U.S. Appl. No. 14/699,213, Preliminary Amendment filed Apr. 30, 2015", 8 pgs.
"U.S. Appl. No. 14/699,213, PTO Response to Rule 312 Communication mailed Nov. 19, 2019", 2 pgs.
"U.S. Appl. No. 14/699,213, Response filed Feb. 15, 2017 to Restriction Requirement mailed Aug. 15, 2016", 9 pgs.
"U.S. Appl. No. 14/699,213, Response filed Feb. 27, 2018 to Final Office Action mailed Dec. 1, 2017", 34 pgs.
"U.S. Appl. No. 14/699,213, Response filed Aug. 22, 2017 to Non Final Office Action mailed Jun. 2, 2017", 12 pgs.
"U.S. Appl. No. 14/699,213, Response filed Apr. 11, 2019 to Non-Final Office Action mailed Jan. 11, 2019", 13 pgs.
"U.S. Appl. No. 14/699,213, Restriction Requirement mailed Aug. 15, 2016", 10 pgs.
"U.S. Appl. No. 14/745,236, Advisory Action mailed Nov. 15, 2017", 2 pgs.
"U.S. Appl. No. 14/745,236, Final Office Action mailed Aug. 25, 2017", 16 pgs.
"U.S. Appl. No. 14/745,236, Non Final Office Action mailed Feb. 2, 2017", 14 pgs.
"U.S. Appl. No. 14/745,236, Notice of Allowability mailed Jul. 5, 2018", 4 pgs.
"U.S. Appl. No. 14/745,236, Notice of Allowance mailed Feb. 5, 2018", 9 pgs.
"U.S. Appl. No. 14/745,236, PTO Response to Rule 312 Communication mailed Jul. 10, 2018", 2 pgs.
"U.S. Appl. No. 14/745,236, Response filed May 2, 2017 to Non Final Office Action mailed Feb. 2, 2017", 10 pgs.
"U.S. Appl. No. 14/745,236, Response filed Nov. 6, 2017 to Final Office Action mailed Aug. 25, 2017", 12 pgs.
"U.S. Appl. No. 14/745,236, Response filed Dec. 14, 2017 to Final Office Action mailed Aug. 25, 2017", 12 pgs.
"U.S. Appl. No. 14/745,236, Response filed Dec. 23, 2016 to Restriction Requirement mailed Sep. 23, 2016", 8 pgs.
"U.S. Appl. No. 14/745,236, Restriction Requirement mailed Sep. 23, 2016", 8 pgs.
"U.S. Appl. No. 14/816,807, Non Final Office Action mailed Oct. 3, 2017", 7 pgs.
"U.S. Appl. No. 14/816,807, Notice of Allowance mailed Apr. 20, 2018", 8 pgs.
"U.S. Appl. No. 14/816,807, Preliminary Amendment filed Aug. 11, 2015", 8 pgs.
"U.S. Appl. No. 14/816,807, PTO Response to Rule 312 Communication mailed Jul. 6, 2018", 2 pgs.
"U.S. Appl. No. 14/816,807, Response filed Jan. 3, 2018 to Non Final Office Action mailed Oct. 3, 2017", 8 pgs.
"U.S. Appl. No. 14/816,807, Response filed May 1, 2017 to Restriction Requirement mailed Nov. 1, 2016", 9 pgs.
"U.S. Appl. No. 14/816,807, Restriction Requirement mailed Nov. 1, 2016", 8 pgs.
"U.S. Appl. No. 14/919,431, Preliminary Amendment filed Jan. 4, 2016", 8 pgs.
"U.S. Appl. No. 15/000,851, Non Final Office Action mailed Jan. 26, 2017", 15 pgs.
"U.S. Appl. No. 15/000,851, Notice of Allowance mailed Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action mailed Jan. 26, 2017", 16 pgs.
"U.S. Appl. No. 15/000,851, Response filed Oct. 12, 2016 to Restriction Requirement mailed May 12, 2016", 11 pgs.
"U.S. Appl. No. 15/000,851, Restriction Requirement mailed May 12, 2016", 6 pgs.
"U.S. Appl. No. 15/000,851, Supplemental Amendment filed Apr. 4, 2016", 10 pgs.
"U.S. Appl. No. 15/170,556, Final Office Action mailed Jul. 30, 2019", 6 pgs.
"U.S. Appl. No. 15/170,556, Non Final Office Action mailed Feb. 8, 2019", 11 pgs.
"U.S. Appl. No. 15/170,556, Non Final Office Action mailed Jul. 27, 2018", 10 pgs.

(56) References Cited

OTHER PUBLICATIONS

"U.S. Appl. No. 15/170,556, Notice of Allowability mailed Jan. 29, 2020", 4 pgs.
"U.S. Appl. No. 15/170,556, Notice of Allowance mailed Nov. 27, 2019", 8 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement mailed Feb. 16, 2018", 8 pgs.
"U.S. Appl. No. 15/170,556, Response filed Oct. 29, 2018 to Non Final Office Action mailed Jul. 27, 2018", 9 pgs.
"U.S. Appl. No. 15/170,556, Response filed Nov. 18, 2019 to Final Office Action mailed Jul. 30, 2019", 8 pgs.
"U.S. Appl. No. 15/170,556, Response filed Apr. 15, 2019 to Non Final Office Action mailed Feb. 8, 2019", 9 pgs.
"U.S. Appl. No. 15/170,556, Restriction Requirement mailed Feb. 16, 2018", 7 pgs.
"U.S. Appl. No. 15/170,556. PTO Response to Rule 312 Communication mailed Apr. 3, 2020", 2 pgs.
"U.S. Appl. No. 15/203,581, Examiners Interview Summary mailed Sep. 11, 2017", 1 pg.
"U.S. Appl. No. 15/203,581, Notice of Allowance mailed Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication mailed Dec. 27, 2017", 2 pgs.
"U.S. Appl. No. 15/203,581, Response filed Aug. 15, 2017 to Restriction Requirement mailed Jun. 16, 2017", 8 pgs.
"U.S. Appl. No. 15/203,581, Restriction Requirement mailed Jun. 16, 2017", 8 pgs.
"U.S. Appl. No. 15/204,381, Advisory Action mailed Feb. 7, 2019", 3 pgs.
"U.S. Appl. No. 15/204,381, Advisory Action mailed Aug. 25, 2020", 3 pgs.
"U.S. Appl. No. 15/204,381, Final Office Action mailed Feb. 27, 2020", 21 pgs.
"U.S. Appl. No. 15/204,381, Final Office Action mailed Jul. 9, 2021", 14 pgs.
"U.S. Appl. No. 15/204,381, Final Office Action mailed Sep. 21, 2018", 10 pgs.
"U.S. Appl. No. 15/204,381, Non Final Office Action mailed Feb. 23, 2018", 10 pgs.
"U.S. Appl. No. 15/204,381, Non Final Office Action mailed Jun. 13, 2019", 23 pgs.
"U.S. Appl. No. 15/204,381, Non Final Office Action mailed Oct. 6, 2020", 15 pgs.
"U.S. Appl. No. 15/204,381, Preliminary Amendment filed Oct. 25, 2016", 74 pgs.
"U.S. Appl. No. 15/204,381, Response filed Jan. 2, 2019 to Final Office Action mailed Sep. 21, 2018", 6 pgs.
"U.S. Appl. No. 15/204,381, Response filed Jan. 19, 2018 to Restriction Requirement mailed Oct. 13, 2017", 6 pgs.
"U.S. Appl. No. 15/204,381, Response filed Apr. 6, 2021 to Non Final Office Action mailed Oct. 6, 2020", 12 pgs.
"U.S. Appl. No. 15/204,381, Response filed May 30, 2018 to Non Final Office Action mailed Feb. 23, 2018", 9 pgs.
"U.S. Appl. No. 15/204,381, Response filed Jul. 27, 2020 to Final Office Action mailed Feb. 27, 2020", 11 pgs.
"U.S. Appl. No. 15/204,381, Response filed Aug. 27, 2020 to Advisory Action mailed Aug. 25, 2020", 2 pgs.
"U.S. Appl. No. 15/204,381, Response Filed Nov. 14, 2019 to Non Final Office Action mailed Jun. 13, 2019", 9 pgs.
"U.S. Appl. No. 15/204,381, Response Filed Mar. 21, 2019 to Advisory Action mailed Feb. 7, 2019", 7 pgs.
"U.S. Appl. No. 15/204,381, Restriction Requirement mailed Oct. 13, 2017", 10 pgs.
"U.S. Appl. No. 15/227,147, Preliminary Amendment filed Oct. 10, 2016", 7 pgs.

"U.S. Appl. No. 15/227,147, Restriction Requirement mailed Jan. 19, 2017", 14 pgs.
"U.S. Appl. No. 15/247,006, Response filed Jun. 4, 2019 to Final Office Action mailed Feb. 4, 2019", 7 pgs.
"U.S. Appl. No. 15/247,006, Examiner Invetview Summary mailed Nov. 27, 2017", 4 pgs.
"U.S. Appl. No. 15/247,006, Final Office Action mailed Feb. 4, 2019", 8 pgs.
"U.S. Appl. No. 15/247,006, Non Final Office Action mailed Apr. 20, 2018", 7 pgs.
"U.S. Appl. No. 15/247,006, Non Final Office Action mailed Sep. 8, 2017", 8 pgs.
"U.S. Appl. No. 15/247,006, Notice of Allowance mailed Jun. 24, 2019", 7 pgs.
"U.S. Appl. No. 15/247,006, Notice of Allowance mailed Oct. 8, 2019", 7 pgs.
"U.S. Appl. No. 15/247,006, Preliminary Amendment filed Nov. 22, 2016", 3 pgs.
"U.S. Appl. No. 15/247,006, Response filed May 3, 2017 to Restriction Requirement mailed Mar. 17, 2017", 12 pgs.
"U.S. Appl. No. 15/247,006, Response filed Oct. 22, 2018 to Non Final Office Action mailed Apr. 20, 2018", 14 pgs.
"U.S. Appl. No. 15/247,006, Response filed Dec. 7, 2017 to Non Final Office Action mailed Sep. 8, 2017", 13 pgs.
"U.S. Appl. No. 15/247,006, Restriction Requirement mailed Mar. 17, 2017", 9 pgs.
"U.S. Appl. No. 15/292,595, Non Final Office Action mailed Sep. 25, 2017", 13 pgs.
"U.S. Appl. No. 15/292,595, Notice of Allowance mailed Feb. 28, 2018", 9 pgs.
"U.S. Appl. No. 15/292,595, Notice of Allowance mailed Jun. 20, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action mailed Sep. 25, 2017", 9 pgs.
"U.S. Appl. No. 15/436,245, Corrected Notice of Allowability mailed Nov. 10, 2021", 2 pgs.
"U.S. Appl. No. 15/436,245, Final Office Action mailed Mar. 24, 2021", 9 pgs.
"U.S. Appl. No. 15/436,245, Final Office Action mailed Nov. 18, 2019", 9 pgs.
"U.S. Appl. No. 15/436,245, Non Final Office Action mailed Apr. 19, 2019", 9 pgs.
"U.S. Appl. No. 15/436,245, Non Final Office Action mailed Sep. 4, 2020", 9 pgs.
"U.S. Appl. No. 15/436,245, Notice of Allowance mailed Aug. 3, 2021", 9 pgs.
"U.S. Appl. No. 15/436,245, Preliminary Amendment filed May 5, 2017", 3 pgs.
"U.S. Appl. No. 15/436,245, PTO Response to Rule 312 Communication mailed Oct. 27, 2021", 2 pgs.
"U.S. Appl. No. 15/436,245, Response filed Apr. 27, 2020 to Final Office Action mailed Nov. 18, 2019", 10 pgs.
"U.S. Appl. No. 15/436,245, Response filed Jun. 24, 2021 to Final Office Action mailed Mar. 24, 2021", 11 pgs.
"U.S. Appl. No. 15/436,245, Response filed Dec. 4, 2020 to Non Final Office Action mailed Sep. 4, 2020", 12 pgs.
"U.S. Appl. No. 15/436,245, Response filed Jul. 29, 2019 to Non-Final Office Action mailed Apr. 19, 2019", 11 pgs.
"U.S. Appl. No. 15/436,245, Restriction Requirement mailed Oct. 11, 2018", 9 pgs.
"U.S. Appl. No. 15/436,245, Supplemental Amendment filed Jul. 19, 2021", 10 pgs.
"U.S. Appl. No. 15/593,039, Non Final Office Action mailed Feb. 6, 2018", 8 pgs.
"U.S. Appl. No. 15/593,039, Notice of Allowance mailed Jul. 11, 2018", 5 pgs.
"U.S. Appl. No. 15/593,039, Preliminary Amendment filed Jul. 25, 2017", 7 pgs.
"U.S. Appl. No. 15/593,039, PTO Response to Rule 312 Communication mailed Oct. 9, 2018", 2 pgs.

(56) References Cited

OTHER PUBLICATIONS

"U.S. Appl. No. 15/593,039, Response filed Apr. 30, 2018 to Non Final Office Action mailed Feb. 4, 2018", 8 pgs.
"U.S. Appl. No. 15/593,039, Response filed Dec. 18, 2017 to Restriction Requirement mailed Oct. 18, 2017", 8 pgs.
"U.S. Appl. No. 15/593,039, Restriction Requirement mailed Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Notice of Allowance mailed Nov. 15, 2018", 7 pgs.
"U.S. Appl. No. 15/865,364, Preliminary Amendment filed Apr. 10, 2018", 10 pgs.
"U.S. Appl. No. 15/905,454, Preliminary Amendment filed Nov. 2, 2018", 5 pgs.
"U.S. Appl. No. 15/905,454, Restriction Requirement mailed Jan. 3, 2019", 6 pgs.
"U.S. Appl. No. 15/915,486, Supplemental Preliminary Amendment filed Mar. 12, 2019", 5 pgs.
"U.S. Appl. No. 15/915,486, Advisory Action mailed Jun. 28, 2021", 7 pgs.
"U.S. Appl. No. 15/915,486, Advisory Action mailed Jul. 13, 2020", 3 pgs.
"U.S. Appl. No. 15/915,486, Final Office Action mailed Jan. 11, 2022", 9 pgs.
"U.S. Appl. No. 15/915,486, Final Office Action mailed Jan. 27, 2020", 8 pgs.
"U.S. Appl. No. 15/915,486, Final Office Action mailed Feb. 1, 2021", 8 pgs.
"U.S. Appl. No. 15/915,486, Non Final Office Action mailed Sep. 2, 2021", 8 pgs.
"U.S. Appl. No. 15/915,486, Non Final Office Action mailed Sep. 15, 2020", 10 pgs.
"U.S. Appl. No. 15/915,486, Non Final Office Action mailed Oct. 24, 2019", 10 pgs.
"U.S. Appl. No. 15/915,486, Response filed Jan. 3, 2020 to Non Final Office Action mailed Oct. 24, 2019", 8 pgs.
"U.S. Appl. No. 15/915,486, Response filed Jun. 1, 2021 to Final Office Action mailed Feb. 1, 2021", 10 pgs.
"U.S. Appl. No. 15/915,486, Response filed Jun. 23, 2020 to Final Office Action mailed Jan. 27, 2020", 7 pgs.
"U.S. Appl. No. 15/915,486, Response filed Jul. 27, 2021 to Advisory Action mailed Jun. 28, 2021", 10 pgs.
"U.S. Appl. No. 15/915,486, Response filed Nov. 30, 2021 to Non Final Office Action mailed Sep. 2, 2021", 6 pgs.
"U.S. Appl. No. 15/915,486, Response filed Dec. 21, 2020 to Non Final Office Action mailed Sep. 15, 2020", 7 pgs.
"U.S. Appl. No. 15/915,486, Restriction Requirement mailed Aug. 5, 2019", 9 pgs.
"U.S. Appl. No. 15/966,092, Interview Summary mailed Mar. 2, 2021", 2 pgs.
"U.S. Appl. No. 15/966,092, Non Final Office Action mailed Jun. 26, 2020", 22 pgs.
"U.S. Appl. No. 15/966,092, Notice of Allowance mailed Feb. 11, 2021", 5 pgs.
"U.S. Appl. No. 15/966,092, Response filed Oct. 26, 2020 to Non Final Office Action mailed Jun. 26, 2020", 9 pgs.
"U.S. Appl. No. 16/046,250, Non Final Office Action mailed Mar. 6, 2020", 10 pgs.
"U.S. Appl. No. 16/046,250, Notice of Allowance mailed Jun. 15, 2020", 9 pgs.
"U.S. Appl. No. 16/046,250, Response filed Jun. 3, 2020 to Non Final Office Action mailed Mar. 6, 2020", 10 pgs.
"U.S. Appl. No. 16/046,250, Response filed Oct. 25, 2019 to Restriction Requirement mailed Jul. 25, 2019", 9 pgs.
"U.S. Appl. No. 16/046,250, Restriction Requirement mailed Jul. 25, 2019", 7 pgs.
"U.S. Appl. No. 16/170,321, Advisory Action mailed Feb. 23, 2021", 3 pgs.
"U.S. Appl. No. 16/170,321, Corrected Notice of Allowability mailed Sep. 29, 2021", 2 pgs.
"U.S. Appl. No. 16/170,321, Final Office Action mailed Dec. 14, 2020", 13 pgs.
"U.S. Appl. No. 16/170,321, Non Final Office Action mailed Apr. 13, 2020", 13 pgs.
"U.S. Appl. No. 16/170,321, Notice of Allowance mailed Aug. 4, 2021", 10 pgs.
"U.S. Appl. No. 16/170,321, PTO Response to Rule 312 Communication mailed Sep. 1, 2021", 2 pgs.
"U.S. Appl. No. 16/170,321, Response filed Jan. 24, 2020 to Restriction Requirement mailed Nov. 27, 2019", 9 pgs.
"U.S. Appl. No. 16/170,321, Response filed Jan. 26, 2021 to Final Office Action mailed Dec. 14, 2020", 9 pgs.
"U.S. Appl. No. 16/170,321, Response filed Mar. 9, 2021 to Advisory Action mailed Feb. 23, 2021", 9 pgs.
"U.S. Appl. No. 16/170,321, Response filed Sep. 11, 2020 to Non Final Office Action mailed Apr. 13, 2020", 9 pgs.
"U.S. Appl. No. 16/170,321, Restriction Requirement mailed Nov. 27, 2019", 10 pgs.
"U.S. Appl. No. 16/173,605, Preliminary Amendment Filed Nov. 18, 2019", 5 pgs.
"U.S. Appl. No. 16/173,605, Final Office Action mailed Jul. 27, 2020", 7 pgs.
"U.S. Appl. No. 16/173,605, Non Final Office Action mailed Mar. 13, 2020", 10 pgs.
"U.S. Appl. No. 16/173,605, Notice of Allowance mailed Jan. 31, 2021", 6 pgs.
"U.S. Appl. No. 16/173,605, Response filed Jul. 13, 2020 to Non Final Office Action mailed Mar. 13, 2020", 13 pgs.
"U.S. Appl. No. 16/173,605, Response filed Dec. 21, 2020 to Final Office Action mailed Jul. 27, 2020", 7 pgs.
"U.S. Appl. No. 16/547,262, Non Final Office Action mailed Mar. 31, 2021", 13 pgs.
"U.S. Appl. No. 16/547,262, Notice of Allowance mailed Jul. 22, 2021", 7 pgs.
"U.S. Appl. No. 16/547,262, Response filed Jun. 30, 2021 to Non Final Office Action mailed Mar. 31, 2021", 12 pgs.
"U.S. Appl. No. 16/547,262, Response filed Dec. 17, 2020 to Restriction Requirement mailed Jul. 17, 2020", 12 pgs.
"U.S. Appl. No. 16/547,262, Restriction Requirement mailed Jul. 17, 2020", 6 pgs.
"U.S. Appl. No. 16/694,748, Non Final Office Action mailed Nov. 9, 2021", 6 pgs.
"U.S. Appl. No. 16/694,748, Notice of Allowance mailed Mar. 3, 2022", 9 pgs.
"U.S. Appl. No. 16/694,748, Preliminary Amendment filed May 8, 2020", 7 pgs.
"U.S. Appl. No. 16/694,748, Response filed Feb. 9, 2022 to Non Final Office Action mailed Nov. 9, 2021", 7 pgs.
"U.S. Appl. No. 16/694,748, Response filed Jul. 27, 2021 to Restriction Requirement mailed Jan. 27, 2021", 8 pgs.
"U.S. Appl. No. 16/694,748, Restriction Requirement mailed Jan. 27, 2021", 9 pgs.
"U.S. Appl. No. 16/749,910, Notice of Allowance mailed Sep. 22, 2021", 10 pgs.
"U.S. Appl. No. 16/749,910, Response filed Jun. 17, 2021 to Restriction Requirement mailed Apr. 19, 2021", 11 pgs.
"U.S. Appl. No. 16/749,910, Restriction Requirement mailed Apr. 19, 2021", 9 pgs.
"U.S. Appl. No. 16/785,449, Final Office Action mailed Mar. 18, 2022", 12 pgs.
"U.S. Appl. No. 16/785,449, Non Final Office Action mailed Jul. 21, 2021", 9 pgs.
"U.S. Appl. No. 16/785,449, Non Final Office Action mailed Sep. 22, 2022", 13 pgs.
"U.S. Appl. No. 16/785,449, Response filed Jan. 20, 2023 to Non Final Office Action mailed Sep. 22, 2022", 8 pgs.
"U.S. Appl. No. 16/785,449, Response filed Jun. 27, 2022 to Final Office Action mailed Mar. 18, 2022", 7 pgs.
"U.S. Appl. No. 16/785,449, Response filed Jul. 2, 2021 to Restriction Requirement mailed Jun. 21, 2021", 6 pgs.

(56) References Cited

OTHER PUBLICATIONS

"U.S. Appl. No. 16/785,449, Response filed Dec. 17, 2021 to Non Final Office Action mailed Jul. 21, 2021", 8 pgs.
"U.S. Appl. No. 16/785,449, Restriction Requirement mailed Jun. 21, 2021", 8 pgs.
"U.S. Appl. No. 16/785,449, Final Office Action mailed Mar. 22, 2023", 16 pgs.
"U.S. Appl. No. 16/865,194, Notice of Allowance mailed Mar. 3, 2022", 9 pgs.
"U.S. Appl. No. 16/865,194, Response filed Dec. 20, 2021 to Restriction Requirement mailed Oct. 20, 2021", 11 pgs.
"U.S. Appl. No. 16/865,194, Restriction Requirement mailed Oct. 20, 2021", 7 pgs.
"U.S. Appl. No. 17/004,583, 312 Amendment filed Mar. 16, 2023", 7 pgs.
"U.S. Appl. No. 17/004,583, Advisory Action mailed Aug. 30, 2022", 2 pgs.
"U.S. Appl. No. 17/004,583, Final Office Action mailed Jun. 9, 2022", 6 pgs.
"U.S. Appl. No. 17/004,583, Non Final Office Action mailed Feb. 24, 2022", 5 pgs.
"U.S. Appl. No. 17/004,583, Non Final Office Action mailed Sep. 29, 2022", 8 pgs.
"U.S. Appl. No. 17/004,583, Notice of Allowability mailed Feb. 10, 2023", 4 pgs.
"U.S. Appl. No. 17/004,583, Notice of Allowance mailed Feb. 1, 2023", 10 pgs.
"U.S. Appl. No. 17/004,583, Preliminary Amendment filed Dec. 21, 2020", 6 pgs.
"U.S. Appl. No. 17/004,583, PTO Response to Rule 312 Communication mailed Feb. 23, 2023", 4 pgs.
"U.S. Appl. No. 17/004,583, PTO Response to Rule 312 Communication mailed Apr. 6, 2023", 3 pgs.
"U.S. Appl. No. 17/004,583, Response filed Jan. 31, 2022 to Restriction Requirement mailed Nov. 24, 2021", 7 pgs.
"U.S. Appl. No. 17/004,583, Response filed May 24, 2022 to Non Final Office Action mailed Feb. 24, 2022", 9 pgs.
"U.S. Appl. No. 17/004,583, Response filed Aug. 9, 2022 to Final Office Action mailed Jun. 9, 2022", 9 pgs.
"U.S. Appl. No. 17/004,583, Response filed Sep. 8, 2022 to Advisory Action mailed Aug. 30, 2022", 15 pgs.
"U.S. Appl. No. 17/004,583, Response filed Dec. 29, 2022 to Non Final Office Action mailed Sep. 29, 2022", 8 pgs.
"U.S. Appl. No. 17/004,583, Restriction Requirement mailed Nov. 24, 2021", 10 pgs.
"U.S. Appl. No. 17/004,583, Supplemental Amendment filed Mar. 28, 2023", 6 pgs.
"U.S. Appl. No. 17/155,625, Advisory Action mailed Jan. 20, 2023", 3 pgs.
"U.S. Appl. No. 17/155,625, Final Office Action mailed Sep. 28, 2022", 18 pgs.
"U.S. Appl. No. 17/155,625, Non Final Office Action mailed May 26, 2022", 10 pgs.
"U.S. Appl. No. 17/155,625, Notice of Allowance mailed Apr. 12, 2023", 11 pgs.
"U.S. Appl. No. 17/155,625, Response filed Feb. 28, 2023 to Advisory Action mailed Jan. 20, 2023", 8 pgs.
"U.S. Appl. No. 17/155,625, Response filed May 2, 2022 to Restriction Requirement mailed Mar. 3, 2022", 7 pgs.
"U.S. Appl. No. 17/155,625, Response filed Aug. 9, 2022 to Non Final Office Action mailed May 26, 2022", 8 pgs.
"U.S. Appl. No. 17/155,625, Response filed Dec. 28, 2022 to Final Office Action mailed Sep. 28, 2022", 3 pgs.
"U.S. Appl. No. 17/155,625, Restriction Requirement mailed Mar. 3, 2022", 9 pgs.
"U.S. Appl. No. 17/212,836, Non Final Office Action mailed Feb. 16, 2023", 12 pgs.
"U.S. Appl. No. 17/212,836, Response filed Oct. 19, 2022 to Restriction Requirement mailed Aug. 19, 2022", 6 pgs.
"U.S. Appl. No. 17/212,836, Restriction Requirement mailed Aug. 19, 2022", 7 pgs.
"U.S. Appl. No. 17/229,001, Preliminary Amendment filed Apr. 26, 2021", 7 pgs.
"U.S. Appl. No. 17/352,845, Non Final Office Action mailed Dec. 16, 2022", 15 pgs.
"U.S. Appl. No. 17/578,939, Preliminary Amendment filed Apr. 14, 2022", 9 pgs.
"U.S. Appl. No. 14/528,997, Preliminary Amendment filed Dec. 8, 2014", 3 pgs.
"U.S. Appl. No. 14/919,431, Restriction Requirement mailed Feb. 3, 2016", 18 pgs.
"Australian Application Serial No. 2001255336, Examiner's First Report mailed Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2003219745, Examiner's First Report mailed Feb. 14, 2007", 2 pgs.
"Australian Application Serial No. 2003219745, Response filed Mar. 14, 2008 to Examiner's First Report mailed Feb. 14, 2007", 24 pgs.
"Australian Application Serial No. 2004249133, First Examiner's Report mailed May 5, 2008", 4 pgs.
"Australian Application Serial No. 2004249133, Response filed Mar. 30, 2009 to First Examiner's Report mailed May 5, 2008", 30 pgs.
"Australian Application Serial No. 2004274860, Office Action mailed May 21, 2008", 2 pgs.
"Australian Application Serial No. 2007245192, Office Action mailed Aug. 25, 2011", 2 pgs.
"Australian Application Serial No. 2007245192, Response filed Feb. 28, 2012 to Office Action mailed Aug. 25, 2011", 22 pgs.
"Australian Application Serial No. 2008203186, First Examiner Report mailed Jan. 28, 2011", 2 pgs.
"Australian Application Serial No. 2008203186, Office Action Received mailed Sep. 16. 2010", 1 page.
"Australian Application Serial No. 2008203186, Response filed Mar. 28, 2011 to First Examiner Report mailed Jan. 28, 2011", 53 pgs.
"Australian Application Serial No. 2008203186, Response filed Aug. 29, 2011 to Official Action dated Apr. 13, 2011", 20 pgs.
"Australian Application Serial No. 2012204138, First Examiner Report mailed Jul. 16, 2013", 4 pgs.
"Australian Application Serial No. 2012204138, Response filed Dec. 24, 2013 to First Examiner Report mailed Jul. 16, 2013", 21 pgs.
"Australian Application Serial No. 2014202470, First Examiner Report mailed Jul. 20, 2015", 2 pgs.
"Australian Application Serial No. 2014202470, Response filed Jul. 4, 2016 to Subsequent Examiners Report mailed Feb. 1, 2016", 3 pgs.
"Australian Application Serial No. 2014202470, Response filed Jul. 20, 2016 to Subsequent Examiners Report mailed Jul. 19, 2016", 15 pgs.
"Australian Application Serial No. 2014202470, Response filed Dec. 1, 2015 to First Examiner Report mailed Jul. 20, 2015", 22 pgs.
"Australian Application Serial No. 2014202470, Subsequent Examiners Report mailed Feb. 1, 2016", 2 pgs.
"Australian Application Serial No. 2014202470, Subsequent Examiners Report mailed Jul. 19, 2016", 3 pgs.
"Australian Application Serial No. 2014290203, First Examination Report mailed Oct. 10, 2019", 4 pgs.
"Australian Application Serial No. 2014290203, Response filed Mar. 13, 2020 to First Examination Report mailed Oct. 10, 2019", 16 pgs.
"Australian Application Serial No. 2014290203, Response filed Jun. 24, 2020 to Subsequent Examiners Report mailed Mar. 23, 2020", 16 pgs.
"Australian Application Serial No. 2014290203, Response filed Sep. 29, 2020 to Subsequent Examiners Report mailed Jul. 21, 2020", 25 pgs.

(56) References Cited

OTHER PUBLICATIONS

"Australian Application Serial No. 2014290203, Response filed Dec. 9, 2020 to Subsequent Examiners Report mailed Oct. 6, 2020", 14 pgs.
"Australian Application Serial No. 2014290203, Subsequent Examiners Report mailed Mar. 23, 2020", 6 pgs.
"Australian Application Serial No. 2014290203, Subsequent Examiners Report mailed Jul. 21, 2020", 5 pgs.
"Australian Application Serial No. 2014290203, Subsequent Examiners Report mailed Oct. 6, 2020", 4 pgs.
"Australian Application Serial No. 2017221444, First Examination Report mailed Jul. 8, 2020", 6 pgs.
"Australian Application Serial No. 2017221444, Fourth Examiners Report mailed Jun. 29, 2021", 3 pgs.
"Australian Application Serial No. 2017221444, Response filed Jan. 25, 2021 to Subsequent Examiners Report mailed Nov. 27, 2020", 18 pgs.
"Australian Application Serial No. 2017221444, Response filed Jun. 2, 2021 to Subsequent Examiners Report mailed Feb. 24, 2021", 20 pgs.
"Australian Application Serial No. 2017221444, Response filed Jul. 6, 2021 to Fourth Examiners Report mailed Jun. 29, 2021", 7 pgs.
"Australian Application Serial No. 2017221444, Response filed Nov. 13, 2020 to First Examination Report mailed Jul. 8, 2020", 13 pgs.
"Australian Application Serial No. 2017221444, Subsequent Examiners Report mailed Feb. 24, 2021", 4 pgs.
"Australian Application Serial No. 2017221444, Subsequent Examiners Report mailed Nov. 27, 2020", 4 pgs.
"Australian Application Serial No. 2021201844, First Examination Report filed Sep. 29, 2022", 3 pgs.
"Australian Application Serial No. 2021201844, Voluntary Amendment filed Dec. 6, 2021", 17 pgs.
"Australian Application Serial No.2008203186, Subsequent Examiner Report mailed Apr. 13, 2011", 2 pgs.
"Avian Inluenza", Queensland Government—Department of Primary Industries, (Observed Feb. 22, 2003), 2 pgs.
"Avian Inluenza", http://www.iah.bbsrc.ac.uk/reports/1997/ainf.html, (Observed Feb. 22, 2003), 2 pgs.
"Brazil Application Serial No. PI 0410702-0, Office Action mailed Oct. 6, 2020", (w/ English Translation), 9 pgs.
"Brazil Application Serial No. PI 0410702-0, Response filed Dec. 14, 2020 to Office Action mailed Oct. 6, 2020", (w/ English Translation of Claims), 42 pgs.
"Brazil Application Serial No. PI0307679-2, Office Action mailed May 16, 2017", 2 pgs.
"Brazil Application Serial No. PI0307679-2, Response filed Jul. 13, 2017 to Office Action mailed May 16, 2017", 9 pgs.
"Brazilian Application Serial No. PI 0307679-2, Office Action published in Patent Gazette No. 1871 of Nov. 14, 2006", 2 pgs.
"Brazilian Application Serial No. PI 0307679-2, Petition filed Jan. 10, 2007 in response to publication dated Nov. 14, 2006", 6 pgs.
"Brazilian Application Serial No. PI 0410702-0, Office Action mailed Nov. 1, 2019", (w/ English Translation), 6 pgs.
"Brazilian Application Serial No. PI 0410702-0, Response filed Feb. 6, 2020 to Office Action mailed Nov. 1, 2019", (w/ English Translation of Claims), 92 pgs.
"Brazilian Application Serial No. PI0307679-2, Final Office Action mailed Jul. 7, 2020", w/o English Translation, 6 pgs.
"Brazilian Application Serial No. PI0307679-2, Office Action mailed May 13, 2019", (w/ English Translation), 17 pgs.
"Brazilian Application Serial No. PI0307679-2, Office Action mailed Oct. 3, 2019", (w/ English Translation), 6 pgs.
"Brazilian Application Serial No. PI0307679-2, Office Action mailed Dec. 20, 2016", 2 pgs.
"Brazilian Application Serial No. PI0307679-2, Response filed Feb. 1, 2017 to Office Action mailed Dec. 20, 2016", 6 pgs.
"Brazilian Application Serial No. PI0307679-2, Response filed Aug. 16, 2019 to Office Action mailed May 13, 2019", (w/ English Translation of Claims), 29 pgs.
"Brazilian Application Serial No. PI0307679-2, Response filed Dec. 11, 2019 to Office Action mailed Oct. 3, 2019", w/ English Claims, 59 pgs.
"Brazilian Application Serial No. PI0410702-0, Office Action mailed Feb. 23, 2012", w/ English Translation, 4 pgs.
"Brazilian Application Serial No. PI0410702-0, Office Action mailed Apr. 1, 2020", (w/ English Summary), 6 pgs.
"Brazilian Application Serial No. PI0410702-0, Response filed May 7, 2012 to Office Action mailed Feb. 23, 2012", w/ English Claims, 11 pgs.
"Brazilian Application Serial No. PI0410702-0, Response filed Aug. 28, 2020 to Office Action mailed Apr. 1, 2020", (w/ English Translation of Claims), 86 pgs.
"Canadian Application Serial No. 11/509,249, Response filed May 16, 2011 to Office Acttion mailed Nov. 18, 2010", 15 pgs.
"Canadian Application Serial No. 2,406,180, Office Action mailed Sep. 9, 2008", 5 pgs.
"Canadian Application Serial No. 2,406,180, Office Action mailed Nov. 10, 2011", 3 pgs.
"Canadian Application Serial No. 2,406,180, Office Action mailed Nov. 23, 2009", 3 pgs.
"Canadian Application Serial No. 2,406,180, Office Action mailed Dec. 10, 2010", 2 Pgs.
"Canadian Application Serial No. 2,406,180, Response filed Jan. 26, 2009 to Official Action mailed Sep. 9, 2008", 22 pgs.
"Canadian Application Serial No. 2,406,180, Response filed May 7, 2012 to Office Action mailed Nov. 10, 2011", 11 pgs.
"Canadian Application Serial No. 2,406,180, Response filed May 21, 2010 to Office action mailed Nov. 23, 2009", 13 pgs.
"Canadian Application Serial No. 2,406,180, Response filed Jun. 14, 2011 to Office Action mailed Dec. 1, 2010", 10 pgs.
"Canadian Application Serial No. 2,406,180, Response mailed Jun. 10, 2011 to Office Action mailed Dec. 10, 2010", 10 pgs.
"Canadian Application Serial No. 2,492,097, Office Action mailed Jan. 10, 2012", 4 pgs.
"Canadian Application Serial No. 2,492,097, Office Action mailed Apr. 24, 2008", 3 pgs.
"Canadian Application Serial No. 2,492,097, Office Action mailed Jul. 31, 2009", 3 pgs.
"Canadian Application Serial No. 2,492,097, Response filed Jan. 29, 2010 to Office Action mailed Jul. 31, 2009", 13 pgs.
"Canadian Application Serial No. 2,492,097, Response filed May 2, 2012 to Office Action mailed Jan. 10, 2012", 12 pgs.
"Canadian Application Serial No. 2,492,097, Response filed Oct. 23, 2008 to Office Action mailed Apr. 24, 2008", 14 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action mailed Jun. 6, 2011", 2 pgs.
"Canadian Application Serial No. 2,522,081, Office Action mailed Aug. 30, 2010", 2 pgs.
"Canadian Application Serial No. 2,522,081, Office Action mailed Oct. 8, 2009", 6 pgs.
"Canadian Application Serial No. 2,522,081, Response filed Feb. 28, 2011 to Office Action mailed Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action mailed Jun. 6, 2011", 11 pgs.
"Canadian Application Serial No. 2,525,953, Amendment and Response filed Feb. 1, 2017 to Office Action mailed Aug. 1, 2016", 28 pgs.
"Canadian Application Serial No. 2,525,953, Non Final Office Action mailed Mar. 30, 2022", 4 pgs.
"Canadian Application Serial No. 2,525,953, Office Action mailed Jan. 21, 2016", 6 pgs.
"Canadian Application Serial No. 2,525,953, Office Action mailed Jan. 29, 2020", 4 pgs.
"Canadian Application Serial No. 2,525,953, Office Action mailed Apr. 28, 2021", 7 pgs.
"Canadian Application Serial No. 2,525,953, Office Action mailed Jul. 31, 2012", 4 pgs.

(56) References Cited

OTHER PUBLICATIONS

"Canadian Application Serial No. 2,525,953, Office Action mailed Aug. 1, 2016", 6 pgs.
"Canadian Application Serial No. 2,525,953, Office Action mailed Aug. 16, 2013", 3 pgs.
"Canadian Application Serial No. 2,525,953, Office Action mailed Oct. 3, 2017", 4 pgs.
"Canadian Application Serial No. 2,525,953, Office Action mailed Nov. 2, 2018", 6 pgs.
"Canadian Application Serial No. 2,525,953, Office Action mailed Nov. 6, 2014", 3 pgs.
"Canadian Application Serial No. 2,525,953, Office Action mailed Jun. 22, 2011", 4 pgs.
"Canadian Application Serial No. 2,525,953, Office Action received Jun. 22, 2011", 4 pgs.
"Canadian Application Serial No. 2,525,953, Response filed Jan. 31, 2013 to Office Action mailed Jul. 31, 2012", 11 pgs.
"Canadian Application Serial No. 2,525,953, Response filed Feb. 1, 2017 to Office Action mailed Aug. 1, 2016", 28 pgs.
"Canadian Application Serial No. 2,525,953, Response filed Feb. 14, 2014 to Office Action mailed Aug. 16, 2013", 16 pgs.
"Canadian Application Serial No. 2,525,953, Response filed Apr. 3, 2018 to Office Action mailed Oct. 3, 2017", 46 pgs.
"Canadian Application Serial No. 2,525,953, Response filed May 1, 2015 to Office Action mailed Nov. 6, 2014", 23 pgs.
"Canadian Application Serial No. 2,525,953, Response filed May 2, 2019 to Office Action mailed Nov. 2, 2018", 31 pgs.
"Canadian Application Serial No. 2,525,953, Response filed May 25, 2020 to Office Action mailed Jan. 29, 2020", 35 pgs.
"Canadian Application Serial No. 2,525,953, Response filed Jul. 11, 2016 to Office Action mailed Jan. 21, 2016", 21 pgs.
"Canadian Application Serial No. 2,525,953, Response filed Aug. 26, 2021 to Office Action mailed Apr. 28, 2021", 16 pgs.
"Canadian Application Serial No. 2,525,953, Response filed Dec. 22, 2011 to Office Action mailed Jun. 22, 2011", 17 pgs.
"Canadian Application Serial No. 2,647,985 , Response filed Sep. 30, 2013 to Office Action mailed May 15, 2013", 20 pgs.
"Canadian Application Serial No. 2,647,985, Office Action mailed May 15, 2013", 3 pgs.
"Canadian Application Serial No. 2,816,242, Office Action mailed Jun. 16, 2014", 3 pgs.
"Canadian Application Serial No. 2,816,242, Office Action mailed Jul. 12, 2017", 4 pgs.
"Canadian Application Serial No. 2,816,242, Office Action mailed Sep. 16, 2016", 4 pgs.
"Canadian Application Serial No. 2,816,242, Office Action mailed Oct. 5, 2015", 6 pgs.
"Canadian Application Serial No. 2,816,242, Response filed Jan. 3, 2018 to Office Action mailed Jul. 12, 2017", 13 pgs.
"Canadian Application Serial No. 2,816,242, Response filed Mar. 10, 2017 to Office Action mailed Sep. 16, 2016", 18 pgs.
"Canadian Application Serial No. 2,816,242, Response filed Apr. 5, 2016 to Office Action mailed Oct. 5, 2015", 13 pgs.
"Canadian Application Serial No. 2,816,242, Response filed Dec. 16, 2014 to Office Action mailed Jun. 16, 2014", 9 pgs.
"Canadian Application Serial No. 2492097, Office Action mailed Nov. 18, 2010", 4 pgs.
"Canadian Application Serial No. 3,014,435, Office Action mailed Oct. 26, 2021", 4 pgs.
"Canadian Application Serial No. 3,014,435, Office Action mailed Nov. 6, 2020", 5 pgs.
"Canadian Application Serial No. 3,014,435, Office Action mailed Nov. 13, 2019", 4 pgs.
"Canadian Application Serial No. 3,014,435, Response filed Feb. 25, 2022 to Office Action mailed Oct. 26, 2021", 15 pgs.
"Canadian Application Serial No. 3,014,435, Response filed Mar. 5, 2021 to Office Action mailed Nov. 6, 2020", 20 pgs.
"Canadian Application Serial No. 3,014,435, Response filed Mar. 13, 2020 to Office Action mailed Nov. 13, 2019", 18 pgs.

"Chinese Application Serial No. 202080048487.4, Voluntary Amendment filed Dec. 5, 2022", w/ English Claims, 33 pgs.
"Chinese Application Serial No. 03808356.6, Office Action mailed Sep. 5, 2008", (English Translation), 6 pgs.
"Chinese Application Serial No. 03808356.6, Office Action", (w/ English Translation of Office Action), 8 pgs.
"Chinese Application Serial No. 03808356.6, Reexamination Notice mailed Nov. 26, 2012", (w/ English Translation), 9 pgs.
"Chinese Application Serial No. 03808356.6, Response filed Mar. 11, 2013 to Office Action mailed Nov. 26, 2012", (w/ English Translation of Amended Claims), 9 pgs.
"Chinese Application Serial No. 03808356.6, Response filed Mar. 16, 2009 to Office Action mailed Sep. 5, 2008", (w/ English Translation of Claims), 8 pgs.
"Chinese Application Serial No. 03808356.6, Response filed Oct. 14, 2011 to Office Action mailed Jul. 11, 2011", (w/ English Translation of Amended Claims), 25 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action mailed Mar. 1, 2010", (w/ English Translation of Claims), 16 pgs.
"Chinese Application Serial No. 200480017037.X, Response filed Aug. 4, 2009 to Second Office Action mailed Mar. 20, 2009", (w/ English Translation of Amended Claims), 15 pgs.
"Chinese Application Serial No. 200480017037.X, Second Office Action mailed Mar. 20, 2009", (English Translation), 7 pgs.
"Chinese Application Serial No. 200480017037.X, Third Office Action mailed Mar. 1, 2010", (w/ English Translation), 9 pgs.
"Chinese Application Serial No. 200480021259.9 Office Action Sep. 11, 2009", (English Translation), 7 pgs.
"Chinese Application Serial No. 200480021259.9 Response filed Aug. 20, 2010 to Office Acton mailed May 6, 2010", (w/ English Translation of Claims), 26 pgs.
"Chinese Application Serial No. 200480021259.9, First Office Action issued on Aug. 24, 2007", (w/ English Translation), 9 pgs.
"Chinese Application Serial No. 200480021259.9, Notice of Reexamination mailed Jul. 3, 2012", (w/ English Translation), 10 pgs.
"Chinese Application Serial No. 200480021259.9, Office Action mailed Jan. 11, 2011", (w/ English Translation), 15 pgs.
"Chinese Application Serial No. 200480021259.9, Office Action mailed May 6, 2010", (w/ English Translation), 12 pgs.
"Chinese Application Serial No. 200480021259.9, Office Action mailed Jul. 3, 2012", (w/ English Translation), 10 pgs.
"Chinese Application Serial No. 200480021259.9, Reexamination Decision mailed Mar. 25, 2013", (w/ English Translation), 17 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offlice Action issued on Aug. 24, 2007", (w/ English Translation of Claims), 13 pgs.
"Chinese Application Serial No. 200480021259.9, Response filed Oct. 16, 2012 to Office Action mailed Jul. 3, 2012", (w/ English Translation of Claims), 13 pgs.
"Chinese Application Serial No. 200480022014, First Office Action mailed Aug. 24, 2007", w/English Translation, 6 pgs.
"Chinese Application Serial No. 200580046922.5, Office Action mailed Jul. 24, 2009", 12 pgs.
"Chinese Application Serial No. 200780020095.1, Decision on Rejection mailed Jul. 22, 2013", (w/ English Translation), 11 pgs.
"Chinese Application Serial No. 200780020095.1, First Office Action mailed Jun. 24, 2011", (w/ English Translation), 13 pgs.
"Chinese Application Serial No. 200780020095.1, Office Action mailed Jan. 29, 2013", (w/ English Translation), 10 pgs.
"Chinese Application Serial No. 200780020095.1, Office Action mailed Mar. 5, 2015", (w/ English Translation), 12 pgs.
"Chinese Application Serial No. 200780020095.1, Office Action mailed Apr. 26, 2016", (w/ English Summary), 4 pgs.

(56) References Cited

OTHER PUBLICATIONS

"Chinese Application Serial No. 200780020095.1, Office Action mailed May 3, 2012", (w/ English Translation), 10 pgs.
"Chinese Application Serial No. 200780020095.1, Office Action mailed Nov. 2, 2016", (w/ English Translation), 11 pgs.
"Chinese Application Serial No. 200780020095.1, Response filed Jan. 6, 2017 to Office Action mailed Nov. 2, 2016", (w/ English Translation of Claims), 15 pgs.
"Chinese Application Serial No. 200780020095.1, Response filed Jun. 9, 2013 to Office Action mailed Jan. 29, 2013", (w/ English Translation of Claims), 10 pgs.
"Chinese Application Serial No. 200780020095.1, Response filed Jun. 23, 2015 to Office Action mailed Mar. 5, 2015", (w/ English Translation of Claims), 16 pgs.
"Chinese Application Serial No. 200780020095.1, Response filed Jun. 30, 2016 to Office Action mailed Apr. 26, 2016", (w/ English Translation of Claims), 22 pgs.
"Chinese Application Serial No. 200780020095.1, Response filed Sep. 17, 2012 to Office Action mailed May 3, 2012", (w/ English Translation of Claims), 17 pgs.
"Chinese Application Serial No. 200780020095.1, Response filed Nov. 5, 2013 to to Decision on Rejection mailed Jul. 22, 2013", (w/ English Translation of Claims), 12 pgs.
"Chinese Application Serial No. 200780020095.1, Response filed Nov. 8, 2011 to Office Action mailed Jun. 24, 2011", (w/ English Translation of Amended Claims), 20 pgs.
"Chinese Application Serial No. 201310400039.8, Notice of Reexamination mailed Aug. 26, 2016", (w/ English Translation), 7 pgs.
"Chinese Application Serial No. 201310400039.8, Office Action mailed Feb. 12, 2015", (w/ English Translation), 10 pgs.
"Chinese Application Serial No. 201310400039.8, Office Action mailed Feb. 15, 2016", (w/ English Translation), 12 pgs.
"Chinese Application Serial No. 201310400039.8, Office Action mailed Apr. 1, 2017", (English Translation), 10 pgs.
"Chinese Application Serial No. 201310400039.8, Office Action mailed Aug. 7, 2015", (w/ English Translation), 10 pgs.
"Chinese Application Serial No. 201310400039.8, Office Action mailed Aug. 21, 2014", (w/ English Translation), 13 pgs.
"Chinese Application Serial No. 201310400039.8, Office Action Response mailed Jun. 16, 2017", W/ English Claims, 8 pgs.
"Chinese Application Serial No. 201310400039.8, Response filed Jan. 4, 2015 to Office Action mailed Aug. 21, 2014", (w/ English Translation of Claims), 10 pgs.
"Chinese Application Serial No. 201310400039.8, Response filed Apr. 27, 2015 to Office Action mailed Feb. 12, 2015", (w/ English Translation of Claims), 16 pgs.
"Chinese Application Serial No. 201310400039.8, Response filed Jun. 1, 2016 to Office Action mailed Feb. 15, 2016", (w/ English Translation of Claims), 9 pgs.
"Chinese Application Serial No. 201310400039.8, Response filed Oct. 10, 2016 to Notice of Reexamination mailed Aug. 26, 2016", (w/ English Translation of Claims), 12 pgs.
"Chinese Application Serial No. 201310400039.8, Response filed Oct. 20, 2015 to Office Action mailed Aug. 7, 2015", (w/ English Translation of Claims), 11 pgs.
"Chinese Application Serial No. 201310400039.8, Response filed Aug. 14, 2017 to Office Action Response mailed Jun. 16, 2017", W/ English Claims, 11 pgs.
"Chinese Application Serial No. 201310400039.8, Response filed Aug. 7, 2017 to Office Action Response mailed Jun. 16, 2017", W/ English Claims, 10 pgs.
"Chinese Application Serial No. 201780024821.0, Office Action mailed Jun. 15, 2022", (w/ English Translation), 6 pgs.
"Chinese Application Serial No. 201780024821.0, Office Action mailed Nov. 30, 2021", (w/ English Translation), 21 pgs.
"Chinese Application Serial No. 201780024821.0, Response filed Apr. 12, 2022 to Office Action mailed Nov. 30, 2021", (w/ English Translation of Claims), 17 pgs.
"Chinese Application Serial No. 201780024821.0, Response filed Aug. 30, 2022 to Office Action mailed Jun. 15, 2022", w/ English Claims, 18 pgs.
"Chinese Application Serial No. 201780024821.0, Response to Examiner Telephone Interview filed Sep. 26, 2022", w/ English Claims, 10 pgs.
"Chinese Application Serial No. 202080048487.4, Notification to Make Rectification mailed Jan. 18, 2022", w/o English Translation, 1 pg.
"Chinese Application Serial No. 202080048487.4, Notification to Make Rectification mailed May 26, 2022", w/o English translation, 1 pg.
"Chinese Application Serial No.200480021259.9, Office Action mailed May 8, 2009", (w/ English Translation), 6 pgs.
"Confirmed Cases of Avian Influenza A(H5N1)", World Health Organization, (Jan. 28 2004), 1 pg.
"Declaration of Anne Koch Ballard dated Oct. 6, 2011", 1 pg.
"Eurasian Application No. 200501890, Notice of Allowance mailed Jun. 23, 2009", 1 pg.
"Eurasian Application Serial No. 200501890, Office Action mailed Mar. 23, 2007", (w English Translation), 2 pgs.
"Eurasian Application Serial No. 200501890, Office Action mailed Sep. 4, 2008", (English Translation), 1 pg.
"Eurasian Application Serial No. 200501890, Office Action mailed Dec. 17, 2007", (w/ English Translation), 6 pgs.
"Eurasian Application Serial No. 200501890, Response filed Mar. 26, 2008 to Office Action mailed Dec. 17, 2007", (w/ English Translation of Claims), 15 pgs.
"Eurasian Application Serial No. 200501890, Response filed Jun. 14, 2007 to Office Action mailed Mar. 23, 2007", (w/ English Translation of Claims), 11 pgs.
"Eurasian Application Serial No. 200501890, Response filed Dec. 17, 2008 to Office Action mailed Sep. 4, 2008", (w/ English Translation of Claims), 14 pgs.
"Eurasian Application Serial No. 200701097,Office Action mailed Sep. 4, 2008", OAR-MISC, 2 pgs.
"Eurasion Application Serial No. 200701097, Office Action mailed Jun. 16, 2009", 3 pgs.
"European Application 04750333.9, Communication dated Oct. 12, 2006", 6 pgs.
"European Application 04750333.9, Communication dated Dec. 8, 202006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication Oct. 12, 2006", 4 pgs.
"European Application Serial 17709236.8 , Response filed Apr. 26, 2019 to Communication Pursuant to Rules 161(1) and 162 EPC mailed Oct. 19, 2018", 9 pgs.
"European Application Serial No. 03716017.3, Office Action mailed Aug. 23, 2012", 4 pgs.
"European Application Serial No. 01928486.8 Office Action mailed Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action mailed Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication mailed Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action mailed Oct. 1, 2009", 11 pgs.
"European Application Serial No. 02724994.5, Office Action mailed Mar. 27, 2009", 2 pgs.

(56) References Cited

OTHER PUBLICATIONS

"European Application Serial No. 03716017.3, Communication and Supplementary European Search Report mailed Jan. 2, 2008", 8 pgs.
"European Application Serial No. 03716017.3, Communication mailed May 23, 2006", 3 pgs.
"European Application Serial No. 03716017.3, Communication mailed Jul. 26, 2006", 2 pgs.
"European Application Serial No. 03716017.3, Communication mailed Oct. 20, 2008", 7 pgs.
"European Application Serial No. 03716017.3, Further Written Submissions filed Mar. 19, 2015", 45 pgs.
"European Application Serial No. 03716017.3, Office Action mailed Jul. 27, 2010", 4 pgs.
"European Application Serial No. 03716017.3, Response filed Feb. 14, 2011 to Office Action mailed Jul. 27, 2010", 12 pgs.
"European Application Serial No. 03716017.3, Response filed Feb. 27, 2015 to Summons mailed Nov. 3, 2014", 29 pgs.
"European Application Serial No. 03716017.3, Response filed Mar. 4, 2013 to Examination Notification Art. 94(3) mailed Aug. 23, 2012", 19 pgs.
"European Application Serial No. 03716017.3, Response filed Mar. 24, 2015 to Office Action mailed Nov. 3, 2014", 38 pgs.
"European Application Serial No. 03716017.3, Response filed Jul. 28, 2006 to Communication mailed May 23, 2006", 5 pgs.
"European Application Serial No. 03716017.3, Response filed Aug. 19, 2009 to Communication mailed Oct. 20, 2008", 17 pgs.
"European Application Serial No. 03716017.3, Response filed Sep. 28, 2015", 13 pgs.
"European Application Serial No. 03716017.3, Result of Consultation mailed Mar. 17, 2015", 5 pgs.
"European Application Serial No. 03716017.3, Summons to Attend Oral proceedings mailed Nov. 3, 2014", 5 pgs.
"European Application Serial No. 04750333.9, Office Action mailed Jan. 22, 2009", 5 pgs.
"European Application Serial No. 04750333.9, Response filed Oct. 21, 2008 to Communication mailed Apr. 11, 2008", 15 pgs.
"European Application Serial No. 04750333.9, Response filed Nov. 17, 2009 to Communication mailed Jan. 22, 2009", 17 pgs.
"European Application Serial No. 04750333.9, Summons to Attend Oral Proceedings mailed Aug. 3, 2011", 13 pgs.
"European Application Serial No. 04776133.3, Communication mailed Mar. 30, 2006", 3 pgs.
"European Application Serial No. 04776133.3, Examination Notification Art. 94(3) mailed Jul. 28, 2015", 4 pgs.
"European Application Serial No. 04776133.3, Examination Notification Art. 94(3) mailed Nov. 25, 2013", 5 pgs.
"European Application Serial No. 04776133.3, Office Action mailed Jan. 5, 2010", 4 pgs.
"European Application Serial No. 04776133.3, Response filed Jan. 25, 2007 to Communication mailed Mar. 30, 2006", 20 pgs.
"European Application Serial No. 04776133.3, Response filed Apr. 30, 2014 to Examination Notification Art. 94(3) mailed Nov. 25, 2013", 12 pgs.
"European Application Serial No. 04776133.3, Response filed Jul. 15, 2010 to Office Action mailed Jan. 5, 2010", 9 pgs.
"European Application Serial No. 04776133.3, Response filed Sep. 18, 2015 to Examination Notification Art. 94(3) mailed Jul. 28, 2015", 47 pgs.
"European Application Serial No. 04809419.7, Communication mailed Apr. 3, 2007", 3 pgs.
"European Application Serial No. 04809419.7. Response filed Oct. 19, 2007 to Communication mailed Apr. 3, 2007", 20 pgs.
"European Application Serial No. 07754132.4, Office Action mailed Apr. 28, 2009", 4 pgs.
"European Application Serial No. 07754132.4, Office Action mailed Sep. 5, 2011", 5 pgs.
"European Application Serial No. 07754132.4, Office Action mailed Nov. 2, 2012", 4 pgs.
"European Application Serial No. 07754132.4, Response filed Feb. 5, 2010 to Office Action mailed Apr. 28, 2009", 15 pgs.
"European Application Serial No. 07754132.4, Response filed Mar. 15, 2012 to Office Action mailed Sep. 5, 2011", 21 pgs.
"European Application Serial No. 07754132.4, Response filed May 10, 2013 to Office Action mailed Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC mailed Apr. 14, 2018", 7 pgs.
"European Application Serial No. 10777154.5, Communication Pursuant to Article 94(3) EPC mailed Jun. 11, 2019", 3 pgs.
"European Application Serial No. 10777154.5, Communication Pursuant to Article 94(3) EPC mailed Oct. 12, 2017", 7 pgs.
"European Application Serial No. 10777154.5, Examination Notification Art. 94(3) mailed Oct. 6, 2014", 7 pgs.
"European Application Serial No. 10777154.5, Office Action mailed May 2, 2016", 6 pgs.
"European Application Serial No. 10777154.5, Office Action mailed Jul. 4, 2012", 2 pgs.
"European Application Serial No. 10777154.5, Response field May 13, 2019 to Summons to Attend Oral Proceedings mailed Jan. 7, 2019", 35 pgs.
"European Application Serial No. 10777154.5, Response field Jun. 4, 2019 to Summons to Attend Oral Proceedings mailed Jan. 7, 2019", 9 pgs.
"European Application Serial No. 10777154.5, Response filed Jan. 14, 2013 to Office Action mailed Jul. 4, 2012", 12 pgs.
"European Application Serial No. 10777154.5, Response filed Feb. 21, 2018 to Communication Pursuant to Article 94(3) EPC mailed Oct. 12, 2017", 12 pgs.
"European Application Serial No. 10777154.5, Response filed Jul. 29, 2019 to Communication Pursuant to Article 94(3) EPC mailed Jun. 11, 2019", 57 pgs.
"European Application Serial No. 10777154.5, Response filed Sep. 7, 2018 to Communication Pursuant to Article 94(3) EPC mailed Apr. 4, 2018", 18 pgs.
"European Application Serial No. 10777154.5, Response filed Sep. 8, 2016 to Office Action mailed May 2, 2016", 69 pgs.
"European Application Serial No. 10777154.5, Summons to Attend Oral Proceedings mailed Jan. 7, 2019", 5 pgs.
"European Application Serial No. 12761841.1, Communication pursuant to Article 94(3) EPC mailed Dec. 23, 2016", 6 pgs.
"European Application Serial No. 12761841.1, Response filed Feb. 23, 2017 to Communication pursuant to Article 94(3) EPC mailed Dec. 23, 2016", 9 pgs.
"European Application Serial No. 12761841.1, Voluntary Amendment filed Dec. 1, 2014", 5 pgs.
"European Application Serial No. 14745060.5, Communication Pursuant to Article 94(3) EPC mailed Feb. 6, 2018", 5 pgs.
"European Application Serial No. 14745060.5, Communication Pursuant to Article 94(3) EPC mailed Mar. 12, 2020", 4 pgs.
"European Application Serial No. 14745060.5, Communication Pursuant to Article 94(3) EPC mailed Jul. 18, 2019", 5 pgs.
"European Application Serial No. 14745060.5, Communication Pursuant to Article 94(3) EPC mailed Sep. 15, 2021", 4 pgs.
"European Application Serial No. 14745060.5, Communication Pursuant to Article 94(3) EPC mailed Sep. 18, 2018", 4 pgs.
"European Application Serial No. 14745060.5, Communication Pursuant to Article 94(3) EPC mailed Nov. 9, 2020", 4 pgs.
"European Application Serial No. 14745060.5, Office Action mailed Feb. 23, 2016", 2 pgs.
"European Application Serial No. 14745060.5, Response filed Jan. 5, 2022 to Communication Pursuant to Article 94(3) EPC mailed Sep. 15, 2021", 78 pgs.
"European Application Serial No. 14745060.5, Response filed Jan. 28, 2020 to Communication Pursuant to Article 94(3) EPC mailed Jul. 18, 2019", 9 pgs.
"European Application Serial No. 14745060.5, Response filed Mar. 27, 2019 to Communication Pursuant to Article 94(3) EPC mailed Sep. 18, 2018", 13 pgs.

(56) References Cited

OTHER PUBLICATIONS

"European Application Serial No. 14745060.5, Response filed May 12, 2021 to Communication Pursuant to Article 94(3) EPC mailed Nov. 9, 2020", 12 pgs.
"European Application Serial No. 14745060.5, Response filed Jun. 15, 2018 to Communication Pursuant to Article 94(3) EPC mailed Feb. 6, 2018", 14 pgs.
"European Application Serial No. 14745060.5, Response filed Jul. 17, 2020 to Communication Pursuant to Article 94(3) EPC mailed Mar. 12, 2020", 52 pgs.
"European Application Serial No. 14745060.5, Response filed Dec. 22, 2016 to Communication pursuant to Rules 161(1) and 162 EPC mailed Feb. 23, 2016", 6 pgs.
"European Application Serial No. 15197386.4, Communication Pursuant to Article 94(3) EPC mailed Feb. 21, 2018", 5 pgs.
"European Application Serial No. 15197386.4, Communication Pursuant to Article 94(3) EPC mailed Apr. 21, 2017", 5 pgs.
"European Application Serial No. 15197386.4, Communication Pursuant to Article 94(3) EPC mailed Jun. 19, 2019", 4 pgs.
"European Application Serial No. 15197386.4, extended European Search Report mailed Feb. 26, 2016", 11 pgs.
"European Application Serial No. 15197386.4, Response filed Jul. 3, 2018 to Communication Pursuant to Article 94(3) EPC mailed Feb. 21, 2018", 7 pgs.
"European Application Serial No. 15197386.4, Response filed Aug. 27, 2019 to Communication Pursuant to Article 94(3) EPC mailed Jun. 19, 2019", 61 pgs.
"European Application Serial No. 15197386.4, Response filed Oct. 20, 2016 to Extended European Search Report mailed Feb. 26, 2016", 4 pgs.
"European Application Serial No. 15197386.4, Response filed Oct. 31, 2017 to Communication Pursuant to Article 94(3) EPC mailed Apr. 21, 2017", 5 pgs.
"European Application Serial No. 16778485.9, Communication Pursuant to Article 94(3) EPC mailed Feb. 18, 2022", 4 pgs.
"European Application Serial No. 16778485.9, Communication Pursuant to Article 94(3) EPC mailed May 25, 2020", 5 pgs.
"European Application Serial No. 16778485.9, Communication Pursuant to Article 94(3) EPC mailed Aug. 22, 2019", 5 pgs.
"European Application Serial No. 16778485.9, Office Action mailed Apr. 30, 2018", 3 pgs.
"European Application Serial No. 16778485.9, Response filed Aug. 9, 2022 to Communication Pursuant to Article 94(3) EPC mailed Feb. 18, 2022", 14 pgs.
"European Application Serial No. 16778485.9, Response filed Oct. 5, 2020 to Communication Pursuant to Article 94(3) EPC mailed May 25, 2020", 14 pgs.
"European Application Serial No. 16778485.9, Response filed Nov. 8, 2018 to Office Action mailed Apr. 30, 2018", 18 pgs.
"European Application Serial No. 16778485.9, Response filed Dec. 19, 2019 to Communication Pursuant to Article 94(3) EPC mailed Aug. 22, 2019", 20 pgs.
"European Application Serial No. 17709236.8, Communication Pursuant to Article 94(3) EPC mailed Jun. 8, 2022", 6 pgs.
"European Application Serial No. 17709236.8, Communication Pursuant to Article 94(3) EPC mailed Jul. 6, 2021", 10 pgs.
"European Application Serial No. 17709236.8, Response filed Jan. 17, 2022 to Communication Pursuant to Article 94(3) EPC mailed Jul. 6, 2021", 13 pgs.
"European Application Serial No. 17709236.8, Response filed Oct. 11, 2022 to Communication Pursuant to Article 94(3) EPC mailed Jun. 8, 2022", 65 pgs.
"European Application Serial No. 18800815.5, Response to Communication pursuant to Rules 161(1) and 162 EPC filed Dec. 15, 2020", 14 pgs.
"European Application Serial No. 19778696.5, Response to Communication persuant to Rules 161 and 162 filed Oct. 15, 2021", 39 pgs.

"European Application Serial No. 20714015.3, Response to Communication persuant to Rules 161 and 162 filed Apr. 7, 2022", 10 pgs.
"European Application Serial No. 20731609.2, Response to Communication persuant to Rules 161 and 162 filed Mar. 16, 2022", 17 pgs.
"European Application Serial No. 20768781.5, Response to Communication pursuant to Rules 161 and 162 filed Oct. 17, 2022", 17 pgs.
"Evaluation of Medicines for human Use", EMEA/CPMP/BWP/2289/01, London The European Agency for the Evaluation of Medicinal Products, Committee for Proprietary Medicinal Products (CPMP), (Feb. 20, 2003), 14.
"FLUZONE Influenza Virus Vaccine", Sanofi Aventis Pasteur, Swiftwater, (Jul. 2005), 12 pgs.
"Gen Bank Accession AFP82914", matrix protein 1 [Influenza A virus (A/reassortant/IVR-148(Brisbane/59/2007 x Texas/1/1977) (H1N1))], (2012), 2 pgs.
"Gen Bank Accession JX414012", Influenza A virus (A/reassortant/IVR-148(Brisbane/59/2007 x Texas/1/1977)(H1 N1)) segment 7 matrix protein 2 (M2) and matrix protein 1 (M1) genes, complete cds, (2012), 2 pgs.
"Gen Bank Accessions QHU79173", surface glycoprotein [Severe acute respiratory syndrome coronavirus 2], (Mar. 17, 2020), 3 pgs.
"Genbank", CY002484.1, (2005), 2 pgs.
"Genbank Accession # AAA43733, Neuraminidase Protein of Influenza B/Beijing/1/87 virus,", (1993), 4 pg.
"Genbank Accession # AAU94753, Neuraminidase Protein of Influenza B/Aichi/5/88 virus,", (2004), 7 pgs.
"Genbank Accession # ABA02233, Neuraminidase Protein of Influenza B/Perth/211/2001 virus", (2006), 3 pgs.
"Genbank Accession #,", neuraminidase influenza virus B/memphis/20/96,, (1999), 3 pgs.
"GFP antibody (ab6556) datasheet", (r) abcam. [online], [retrieved on Dec. 5, 2004]. Retrieved from the Internet: <URL: http://www.abcam.com/index.html?datasheet=6556>, (2004), 5 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"https://www.abcam.com/gfp-antibody-ab6556", [online]. [accessed on Dec. 5, 2004]. Retrieved from the Internet: http://www.abcam.com/index.html?datasheet=6556, (Dec. 5, 2004), 5 pgs.
"Indian Application Serial No. 02082/KOLNP/2005, Examination Report mailed Mar. 17, 2008", 1 pg.
"Indian Application Serial No. 02082/KOLNP/2005, Examination Report mailed Dec. 28, 2007", 1 pg.
"Indian Application Serial No. 02082/KOLNP/2005, First Examination Report mailed Jan. 25, 2007", 9 pgs.
"Indian Application Serial No. 02082/KOLNP/2005, Response filed Jan. 22, 2008 to Examination Report mailed Dec. 28, 2007", 13 pgs.
"Indian Application Serial No. 02082/KOLNP/2005, Response filed Jun. 1, 2008 to Examination Report mailed Mar. 17, 2008", 3 pgs.
"Indian Application Serial No. 02082/KOLNP/2005, Response filed Nov. 19, 2007 to First Examination Report mailed Jan. 25, 2007", 26 pgs.
"Indian Application Serial No. 1026/KOLNP/2009, First Examiner Report mailed Mar. 13, 2014", 2 pgs.
"Indian Application Serial No. 2272/KOLNP/2005, First Examination Report mailed Mar. 17, 2008", 10 pgs.
"Indian Application Serial No. 2272/KOLNP/2005, Response filed Mar. 16, 2009 to Subsequent Examination Report mailed Mar. 6, 2009", 12 pgs.
"Indian Application Serial No. 2272/KOLNP/2005, Response filed Oct. 11, 2008 to First Examination Report mailed Mar. 17, 2008", 27 pgs.
"Indian Application Serial No. 2272/KOLNP/2005, Subsequent Examination Report mailed Mar. 6, 2009", 1 pg.
"Indian Application Serial No. 2388/KOLNP/2005, First Examination Report mailed Mar. 28, 2007", 10 pgs.

(56) References Cited

OTHER PUBLICATIONS

"Influenza B/Ann Arbor/1/66 (cold-adapted) nonstructural protein (seg 8) RNA, complete cds", GenBank Accession M20224, (Aug. 2, 1993), 2 pgs.
"Influenza B/lee/40, neuraminidase & nb (seg 6) ma", Database EM_VI E.B.I. Hinxton U.K., (Jun., 13, 1985), 10 pgs.
"Influenza virus A/CHR/ 157/83 genomic RNA for haemagglutinin", (2012), 2 pgs.
"International Application No. PCT/US2004/016680, International Search Report", (Feb. 2, 2005), 7 pgs.
"International Application Serial No. PCT/US2021/033365, International Search Report mailed Sep. 24, 2021", 6 pgs.
"International Application Serial No. PCT/US2021/033365, Written Opinion mailed Sep. 24, 2021", 6 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report mailed Oct. 15, 2002", 13 pgs.
"International Application Serial No. PCT/US01/11963, International Search Report mailed May 7, 2002", 5 pgs.
"International Application Serial No. PCT/US01/11963, Written Opinion mailed Jun. 14, 2002", 2 pgs.
"International Application Serial No. PCT/US01/11963, Written Opinion mailed Aug. 7, 2002", 6 pgs.
"International Application Serial No. PCT/US02/05455, International Preliminary Examination Report dated Aug. 17, 2004", 4 pgs.
"International Application Serial No. PCT/US02/05455, International Search Report mailed Mar. 25, 2003", 3 pgs.
"International Application Serial No. PCT/US03/04233, International Search Report mailed Dec. 16, 2005", 7 pgs.
"International Application Serial No. PCT/US2004/012050, International Search Report mailed Feb. 2, 2005", 8 pgs.
"International Application Serial No. PCT/US2004/012050, Written Opinion mailed Feb. 2, 2005", 12 pgs.
"International Application Serial No. PCT/US2004/016649, International Preliminary Report on Patentability mailed Dec. 15, 2005", 7 pgs.
"International Application Serial No. PCT/US2004/016649, International Search Report mailed Apr. 18, 2005", 6 pgs.
"International Application Serial No. PCT/US2004/016680, International Preliminary Report on Patentability mailed Dec. 15, 2005", 11 pgs.
"International Application Serial No. PCT/US2005/041991, International Search Report mailed Jun. 4, 2007", 5 pgs.
"International Application Serial No. PCT/US2005/041991, Written Opinion mailed Jun. 4, 2007", 6 pgs.
"International Application Serial No. PCT/US2007/007562, International Preliminary Report on Patentability mailed Oct. 9, 2008", 5 pgs.
"International Application Serial No. PCT/US2007/007562, International Search Report mailed Jan. 14, 2008", 8 pgs.
"International Application Serial No. PCT/US2007/007562, Written Opinion mailed Jan. 14, 2008", 9 pgs.
"International Application Serial No. PCT/US2007/013407, International Search Report mailed Oct. 24, 2008", 10 pgs.
"International Application Serial No. PCT/US2007/013407, Written Opinion mailed Oct. 24, 2008", 14 pgs.
"International Application Serial No. PCT/US2008/004125, International Search Report mailed Feb. 20, 2009", 6 pgs.
"International Application Serial No. PCT/US2008/004125, Written Opinion mailed Feb. 20, 2009", 8 pgs.
"International Application Serial No. PCT/US2008/005641, International Preliminary Report on Patentability dated Nov. 10, 2009", 9 pgs.
"International Application Serial No. PCT/US2008/005641, International Search Report mailed Feb. 4, 2009", 6 pgs.
"International Application Serial No. PCT/US2008/005641, Written Opinion mailed Feb. 4, 2009", 8 pgs.
"International Application Serial No. PCT/US2008/007417, International Search Report mailed Jan. 30, 2009", 20 pgs.
"International Application Serial No. PCT/US2008/007417, Written Opinion mailed Jan. 30, 2009", 10 pgs.
"International Application Serial No. PCT/US2008/007582, International Preliminary Report on Patentability mailed Jan. 7, 2010", 9 pgs.
"International Application Serial No. PCT/US2008/007582, International Search Report and Written Opinion mailed Feb. 18, 2009", 16 pgs.
"International Application Serial No. PCT/US2009/000056, International Search Report mailed Feb. 9, 2010", 3 pgs.
"International Application Serial No. PCT/US2009/000056, Written Opinion mailed Feb. 9, 2010", 5 pgs.
"International Application Serial No. PCT/US2009/006019, International Preliminary Report on Patentability mailed may 19, 2011", 8 pgs.
"International Application Serial No. PCT/US2009/006019, Invitation to Pay Additional Fee mailed Apr. 6, 2010", 8 pgs.
"International Application Serial No. PCT/US2009/006019, Search Report mailed Jun. 10, 2010", 7 Pgs.
"International Application Serial No. PCT/US2009/006019, Written Opinion mailed Jun. 10, 2010", 6 pgs.
"International Application Serial No. PCT/US2010/054128, Preliminary Report on Patentability mailed May 10, 2012", 10 pgs.
"International Application Serial No. PCT/US2010/054128, Search Report mailed Feb. 23, 2011", 6 pgs.
"International Application Serial No. PCT/US2010/054128, Written Opinion mailed Feb. 23, 2011", 8 pgs.
"International Application Serial No. PCT/US2012/052368, International Preliminary Report on Patentability mailed Mar. 13, 2014", 8 pgs.
"International Application Serial No. PCT/US2012/052368, International Search Report mailed Dec. 3, 2012", 4 pgs.
"International Application Serial No. PCT/US2012/052368, Written Opinion mailed Dec. 3, 2012", 6 pgs.
"International Application Serial No. PCT/US2014/046731, International Preliminary Report on Patentability mailed Jan. 28, 2016", 12 pgs.
"International Application Serial No. PCT/US2014/046731, International Search Report mailed Nov. 25, 2014", 9 pgs.
"International Application Serial No. PCT/US2014/046731, Written Opinion mailed Nov. 25, 2014", 10 pgs.
"International Application Serial No. PCT/US2015/036803, International Preliminary Report on Patentability mailed Dec. 29, 2016", 10 pgs.
"International Application Serial No. PCT/US2015/036803, International Search Report mailed Dec. 11, 2015", 8 pgs.
"International Application Serial No. PCT/US2015/036803, Invitation to Pay Add'l Fees and Partial Search Rpt mailed Oct. 2, 2015", 8 pgs.
"International Application Serial No. PCT/US2015/036803, Written Opinion mailed Dec. 11, 2015", 8 pgs.
"International Application Serial No. PCT/US2016/041172, International Preliminary Report on Patentability mailed Jan. 18, 2018", 10 pgs.
"International Application Serial No. PCT/US2016/041172, International Search Report mailed Oct. 27, 2016", 6 pgs.
"International Application Serial No. PCT/US2016/041172, Written Opinion mailed Oct. 27, 2016", 8 pgs.
"International Application Serial No. PCT/US2016/048691, International Preliminary Report on Patentability mailed Mar. 15, 2018", 7 pgs.
"International Application Serial No. PCT/US2016/048691, International Search Report mailed Nov. 22, 2016", 7 pgs.
"International Application Serial No. PCT/US2016/048691, Written Opinion mailed Nov. 22, 2016", 6 pgs.
"International Application Serial No. PCT/US2017/018443, International Preliminary Report on Patentability mailed Aug. 30, 2018", 11 pgs.
"International Application Serial No. PCT/US2017/018443, International Search Report mailed may 22, 2017", 9 pgs.
"International Application Serial No. PCT/US2017/018443, Written Opinion mailed May 22, 2017", 9 pgs.

(56) References Cited

OTHER PUBLICATIONS

"International Application Serial No. PCT/US2018/057576, International Preliminary Report on Patentability mailed May 7, 2020", 12 pgs.
"International Application Serial No. PCT/US2018/057576, International Search Report mailed Mar. 25, 2019", 7 pgs.
"International Application Serial No. PCT/US2018/057576, Invitation to Pay Additional Fees and Partial Search Report mailed Jan. 31, 2019", 16 pgs.
"International Application Serial No. PCT/US2018/057576, Written Opinion mailed Mar. 25, 2019", 10 pgs.
"International Application Serial No. PCT/US2019/037084, International Preliminary Report on Patentability mailed Dec. 24, 2020", 12 pgs.
"International Application Serial No. PCT/US2019/037084, International Search Report mailed Nov. 14, 2019", 10 pgs.
"International Application Serial No. PCT/US2019/037084, Invitation to Pay Add'l Fees and Partial Search Report mailed Sep. 24, 2019", 10 pgs.
"International Application Serial No. PCT/US2019/037084, Written Opinion mailed Nov. 14, 2019", 10 pgs.
"International Application Serial No. PCT/US2019/045476, International Preliminary Report on Patentability mailed Feb. 18, 2021", 13 pgs.
"International Application Serial No. PCT/US2019/045476, International Search Report mailed Feb. 11, 2020", 8 pgs.
"International Application Serial No. PCT/US2019/045476, Invitation to Pay Additional Fees mailed Dec. 17, 2019", 14 pgs.
"International Application Serial No. PCT/US2019/045476, Written Opinion mailed Feb. 11, 2020", 13 pgs.
"International Application Serial No. PCT/US2019/047263, International Preliminary Report on Patentability mailed Mar. 4, 2021", 8 pgs.
"International Application Serial No. PCT/US2020/014659, International Preliminary Report on Patentability mailed Aug. 5, 2021", 12 pgs.
"International Application Serial No. PCT/US2020/014659, International Search Report mailed Nov. 6, 2020", 7 pgs.
"International Application Serial No. PCT/US2020/014659, Invitation to Pay Additional Fees mailed Sep. 16, 2020", 11 pgs.
"International Application Serial No. PCT/US2020/014659, Written Opinion mailed Nov. 6, 2020", 10 pgs.
"International Application Serial No. PCT/US2020/017342, International Preliminary Report on Patentability mailed Aug. 19, 2021", 8 pgs.
"International Application Serial No. PCT/US2020/017342, International Search Report mailed Jun. 26, 2020", 6 pgs.
"International Application Serial No. PCT/US2020/017342, Written Opinion mailed Jun. 26, 2020", 6 pgs.
"International Application Serial No. PCT/US2020/031176, International Preliminary Report on Patentability mailed Nov. 11, 2021", 9 pgs.
"International Application Serial No. PCT/US2020/031176, International Search Report mailed Jul. 22, 2020", 6 pgs.
"International Application Serial No. PCT/US2020/031176, Written Opinion mailed Jul. 22, 2020", 7 pgs.
"International Application Serial No. PCT/US2020/048130, International Preliminary Report on Patentability mailed Mar. 10, 2022", 11 pgs.
"International Application Serial No. PCT/US2020/048130, International Search Report mailed Apr. 20, 2021", 9 pgs.
"International Application Serial No. PCT/US2020/048130, Invitation to Pay Additional Fees mailed Jan. 13, 2021", 7 pgs.
"International Application Serial No. PCT/US2020/048130, Written Opinion mailed Apr. 20, 2021", 9 pgs.
"International Application Serial No. PCT/US2021/014586, International Preliminary Report on Patentability mailed Aug. 4, 2022", 10 pgs.
"International Application Serial No. PCT/US2021/014586, International Search Report mailed May 20, 2021", 7 pgs.
"International Application Serial No. PCT/US2021/014586, Written Opinion mailed May 20, 2021", 8 pgs.
"International Application Serial No. PCT/US2021/024200, International Preliminary Report on Patentability mailed Oct. 6, 2022", 8 pgs.
"International Application Serial No. PCT/US2021/024200, International Search Report mailed Jul. 16, 2021", 6 pgs.
"International Application Serial No. PCT/US2021/024200, Written Opinion mailed Jul. 16, 2021", 6 pgs.
"International Application Serial No. PCT/US2021/033365, International Preliminary Report on Patentability mailed Dec. 8, 2022", 8 pgs.
"Israel Application Serial No. 163,546, Office Action mailed Nov. 12, 2009", w/English Translation, 1 pg.
"Israel Application Serial No. 163,546, Office Action mailed Dec. 26, 2007", w/English Translation, 1 pg.
"Israel Application Serial No. 163,546, Response filed May 9, 2008 to Office Action mailed Dec. 26, 2007", w/English Translation, 2 pgs.
"Israel Application Serial No. 163,546, Response filed Jun. 8, 2010 to Office Action mailed Nov. 12, 2009", w/English Claims, 3 pgs.
"Israel Application Serial No. 163,546, Response filed Aug. 16, 2009 to Substantive Examination Report mailed Feb. 23, 2009", w/English Claims, 4 pgs.
"Israel Application Serial No. 163,546, Response filed Oct. 20, 2010 to Office Action dated Jun. 8, 2010", w/English Claims, 8 pgs.
"Israel Application Serial No. 163,546, Response filed Nov. 27, 2008 to First Examination Report mailed Jul. 28, 2008", w/English Claims, 13 pgs.
"Israel Application Serial No. 163546, Office Action mailed Jun. 8, 2010", w/English Translation, 2 pgs.
"Israel Application Serial No. 183026, Office Action mailed Feb. 9, 2009", w/English Translation, 2 pgs.
"Israel Application Serial No. 238584, Office Action mailed Jul. 24, 2017", w/English Translation, 2 pgs.
"Israel Application Serial No. 238584, Response filed Nov. 21, 2017 to Office Action mailed Jul. 24, 2017", W/English Translation, 2 pgs.
"Israeli Application Serial No. 171831, Notification of Defects mailed Nov. 10, 2008", w/English Translation, 10 pgs.
"Israeli Application Serial No. 163,546, First Examination Report mailed Jul. 28, 2008", (English Translation), 2 pgs.
"Israeli Application Serial No. 163,546, Substantive Examination Report mailed Feb. 23, 2009", w/English Translation, 3 pgs.
"Israeli Application Serial No. 171372, Office Action mailed Feb. 21, 2010", w/English Translation, 2 pgs.
"Israeli Application Serial No. 171372, Office Action mailed Nov. 6, 2008", (Translation), 12 pgs.
"Israeli Application Serial No. 171372, Response filed Nov. 18, 2010 to Office Action mailed Feb. 21, 2010", w/English Translation, 19 pgs.
"Israeli Application Serial No. 171831, Office Action mailed Feb. 21, 2010", w/English Translation, 2 pgs.
"Israeli Application Serial No. 171831, Office Action mailed Apr. 18, 2012", (English Translation), 2 pgs.
"Israeli Application Serial No. 171831, Response filed Jan. 20, 2011 to Office Action mailed Feb. 21, 2010", w/English Translation, 18 pgs.
"Israeli Application Serial No. 171831, Response filed Jun. 24, 2009 to Notification of Defects mailed Nov. 10, 2008", w/English Claims, 10 pgs.
"Israeli Application Serial No. 171831, Response filed Nov. 6, 2012 to Office Action mailed Apr. 18, 2012", w/English Claims, 54 pgs.
"Israeli Application Serial No. 211324, Office Action mailed Sep. 18, 2014", w/English Translation, 5 pgs.
"Israeli Application Serial No. 211324, Office Action mailed Oct. 18, 2015", w/English Translation, 4 pgs.
"Israeli Application Serial No. 211324, Response filed Feb. 16, 2016 to Office Action mailed Oct. 18, 2015", w/English Claims, 4 pgs.
"Israeli Application Serial No. 211324, Response filed Mar. 31, 2015 to Office Action mailed Sep. 8, 2014", w/English Translation, 21 pgs.

(56) References Cited

OTHER PUBLICATIONS

"Israeli Application Serial No. 238584, Notification of Defects in Patent Application mailed Jul. 21, 2019", (w/ English Translation), 5 pgs.
"Israeli Application Serial No. 238584, Office Action mailed Apr. 14, 2016", (English Translation), 3 pgs.
"Israeli Application Serial No. 238584, Office Action mailed Aug. 23, 2018", (w/ English Translation), 6 pgs.
"Israeli Application Serial No. 238584, Response filed Aug. 3, 2016 to Office Action mailed Apr. 14, 2016", (English Translation of Claims), 19 pgs.
"Israeli Application Serial No. 238584, Response filed Nov. 21, 2017 to Office Action mailed Jul. 24, 2017", (Translation), 2 pgs.
"Israeli Application Serial No. 238584, Response filed Nov. 21, 2019 to Notification of Defects in Patent Application mailed Jul. 21, 2019", (w/ English Translation of Claims), 6 pgs.
"Israeli Application Serial No. 238584, Response Filed Dec. 10, 2018 to Office Action mailed Aug. 23, 2018", (w/ English Translation of Claims), 10 pgs.
"Israeli Application Serial No. 171372,Office Action mailed Feb. 20, 2011", (Translation), 2 pgs.
"Japanese Application No. 2001-576868, Office Action mailed May 31, 2011", (w/ English Translation), 5 pgs.
"Japanese Application No. 2001-576868, Response filed Apr. 26, 2011 to Office Action mailed Nov. 2, 2010", (w/ Translation of Amended Claims), 14 pgs.
"Japanese Application Serial No. 2022-144599, Voluntary Amendment filed Nov. 9, 2022", w/ English Claims, 14 pgs.
"Japanese Application Serial No. 2022-544779, Voluntary Amendment filed Sep. 9, 2022", w/ English Claims, 8 pgs.
"Japanese Application Serial No. 2001-576868, Office Action mailed Nov. 2, 2010", w/ English Translation), 10 pgs.
"Japanese Application Serial No. 2001-576868, Response filed Dec. 1, 2011 to Office Action mailed May 3, 2011", (w/ English Translation of Amended Claims), 37 pgs.
"Japanese Application Serial No. 2003-315106, Amended Claims filed Oct. 15, 2009 in Response to Office Action mailed Jun. 24, 2009", (English Translation), 6 pgs.
"Japanese Application Serial No. 2003-315106, Notice of Allowance mailed Jan. 5, 2010", (w/ English Translation), 5 pgs.
"Japanese Application Serial No. 2003-315106, Office Action mailed Jun. 24, 2009", (w/ English Translation), 10 pgs.
"Japanese Application Serial No. 2003-568038, Amendment filed Aug. 19, 2005", (English Translation), 8 pgs.
"Japanese Application Serial No. 2003-568038, Notice of Allowance mailed Nov. 30, 2009", w/out English Translation, 3 pgs.
"Japanese Application Serial No. 2003-568038, Office Action mailed May 15, 2009", (w/ English Translation), 7 pgs.
"Japanese Application Serial No. 2003-568038, Office Action mailed Jul. 10, 2008", (w/ English Translation), 11 pgs.
"Japanese Application Serial No. 2003-568038, Office Action mailed Jul. 21, 2005", w/out English Translation, 3 pgs.
"Japanese Application Serial No. 2003-568038, Request for Examination filed Aug. 19, 2005 in Response to Official Action mailed Jul. 21, 2005", (w/ Partial English Translation of Specification), 8 pgs.
"Japanese Application Serial No. 2003-568038, Response filed Sep. 14, 2009 to Office Action mailed May 15, 2009", (w/ English Translation of Amended Claims), 10 pgs.
"Japanese Application Serial No. 2003-568038, Response filed Dec. 10, 2008 to Office Action mailed Jul. 10, 2008", (w/ English Translation of Amended Claims), 15 pgs.
"Japanese Application Serial No. 2006-513125, Office Action mailed Mar. 9, 2010", (English Translation), 11 pgs.
"Japanese Application Serial No. 2006-513125, Response filed Aug. 30, 2010 to Office Action mailed Mar. 9, 2010", (w/ English Translation of Amended Claims), 60 pgs.
"Japanese Application Serial No. 2006-533439, Decision of Final Rejection mailed Aug. 14, 2012", (w/ English Translation), 5 pgs.
"Japanese Application Serial No. 2006-533439, Office Action mailed Mar. 9, 2010", (w/ English Translations), 20 pgs.
"Japanese Application Serial No. 2006-533439, Office Action mailed Mar. 27, 2012", w/ English Translation, 8 pgs.
"Japanese Application Serial No. 2006-533439, Response filed May 21, 2012 to Office Action mailed Mar. 27, 2012", (w/ English Translation of Amended Claims), 19 pgs.
"Japanese Application Serial No. 2006-533439, Response filed Aug. 3, 2011 to Office Action mailed Feb. 15, 2011", (w/ English Translation of Amended Claims), 18 pgs.
"Japanese Application Serial No. 2006-533439,Office Action mailed Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2008-315106, Office Action mailed Jun. 24, 2009", (w/ English Translation), 10 pgs.
"Japanese Application Serial No. 2008-315106, Response filed Oct. 15, 2009 to Office Action mailed Jun. 24, 2009", w/English Translation, 103 pgs.
"Japanese Application Serial No. 2008-315106, Response filed Oct. 15, 2009 to Office Action mailed Jun. 24, 2009", (w/ English Translation of Amended Claims), 103 pgs.
"Japanese Application Serial No. 2008-315106, Response filed Dec. 3, 2009 to Office Action mailed Jun. 24, 2009", (w/ English Translation of Claims), 9 pgs.
"Japanese Application Serial No. 2009-238781, Office Action mailed Oct. 11, 2011", (w/ English Translation), 3 pgs.
"Japanese Application Serial No. 2009-502945, Examiners Decision of Final Refusal mailed Nov. 12, 2013", (w/ English Translation), 8 pgs.
"Japanese Application Serial No. 2009-502945, Office Action mailed Oct. 23, 2012", (w/ English (Translation), 16 pgs.
"Japanese Application Serial No. 2009-502945, Response filed Apr. 10, 2013 to Office Action mailed Oct. 23, 2012", (w/ English Translation of Claims), 18 pgs.
"Japanese Application Serial No. 2011-111048, Office Action mailed Jun. 25, 2013", (w/ English Translation), 7 pgs.
"Japanese Application Serial No. 2011-111048, Office Action mailed Sep. 18, 2012", (w/ English Translation), 10 pga.
"Japanese Application Serial No. 2011-111048, Response filed Sep. 25, 2012 to Office Action mailed Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2012-273898, Office Action mailed Jun. 10, 2014", (w/ English Translation), 7 pgs.
"Japanese Application Serial No. 2012-273898, Response filed Sep. 4, 2014 to Office Action mailed Jun. 10, 2014", W/ English Claims, 9 pgs.
"Japanese Application Serial No. 2012-536963, Amendment and Argument filed Jun. 26, 2015 to Office Action mailed Jan. 6, 2015", (w/ English Translation of Amended Claims), 12 pgs.
"Japanese Application Serial No. 2012-536963, Examiners Decision of Final Refusal mailed Nov. 17, 2015", (w/ English Translation), 8 pgs.
"Japanese Application Serial No. 2012-536963, Office Action mailed Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2013-198377, Office Action mailed Jan. 6, 2015", (w/ English Translation), 9 pgs.
"Japanese Application Serial No. 2014-049025 Response filed Sep. 4, 2015 to Office Action mailed Jun. 16, 2015", (w/ Amended Claims), 12 pgs.
"Japanese Application Serial No. 2014-049025, Examiners Decision of Final Refusal mailed Feb. 2, 2016", W/ English Translation, 5 pgs.
"Japanese Application Serial No. 2014-049025, Office Action mailed Jun. 16, 2015", (w/ English Translation), 6 pgs.
"Japanese Application Serial No. 2014-527339, Examiners Decision of Final Refusal mailed Feb. 7, 2017", (w/ English Translation), 5 pgs.
"Japanese Application Serial No. 2014-527339, Office Action mailed May 31, 2016", (w/ English Translation), 10 pgs.

(56) References Cited

OTHER PUBLICATIONS

"Japanese Application Serial No. 2014-527339, Response filed Sep. 16, 2016 to Office Action mailed May 31, 2016", (w/ English Translation of Amended Claims), 33 pgs.
"Japanese Application Serial No. 2016-053990, Office Action mailed Jun. 6, 2017", (w/ English Translation), 4 pgs.
"Japanese Application Serial No. 2016-053990, Response filed Dec. 6, 2017 to Office Action mailed Jun. 6, 2017", (w/ English Translation of Amended Claims), 14 pgs.
"Japanese Application Serial No. 2016-110879, Office Action mailed May 30, 2017", (w/ English (Translation), 7 pgs.
"Japanese Application Serial No. 2016-110879, Response filed Nov. 30, 2017 to Office Action mailed May 30, 2017", (w/ English Translation of Claims), 25 pgs.
"Japanese Application Serial No. 2016-527046, Examiners Decision of Final Refusal mailed May 21, 2019", (w/ English Translation), 20 pgs.
"Japanese Application Serial No. 2016-527046, Reasons For Rejection mailed Aug. 14, 2018", (w/ English Translation), 14 pgs.
"Japanese Application Serial No. 2016-527046, Response Filed Dec. 4, 2018 to Reasons for Rejection mailed Aug. 14, 2018", (w/ English Translation of Amended Claims), 18 pgs.
"Japanese Application Serial No. 2017-111526, Office Action mailed May 14, 2019", (w/ English Translation), 6 pgs.
"Japanese Application Serial No. 2017-111526, Office Action mailed Jun. 26, 2018", (w/ English Translation), 5 pgs.
"Japanese Application Serial No. 2017-111526, Response Filed Dec. 21, 2018 to Office Action mailed Jun. 26, 2018", (w/ English Translation of Amended Claims), 7 pgs.
"Japanese Application Serial No. 2018-510751, Examiners Decision of Final Refusal mailed Dec. 17, 2019", w/ English Translation, 10 pgs .
"Japanese Application Serial No. 2018-510751, Notification of Reasons for Refusal mailed Mar. 13, 2019", (w/ English Translation), 14 pgs.
"Japanese Application Serial No. 2018-510751, Response filed Apr. 17, 2020 to Examiners Decision of Final Refusal mailed Dec. 17, 2019", w/ English Claims, 7 pgs.
"Japanese Application Serial No. 2018-510751, Response filed Aug. 9, 2019 to Notification of Reasons for Refusal mailed Mar. 13, 2019", (w/ English Translation of Claims), 24 pgs.
"Japanese Application Serial No. 2018-543688, Notification of Reasons for Rejection mailed Oct. 29, 2019", w/ English Translation, 14 pgs .
"Japanese Application Serial No. 2018-543688, Office Action mailed Jun. 30, 2020", w/ English translation, 11 pgs.
"Japanese Application Serial No. 2018-543688, Response filed Apr. 28, 2020 to Notification of Reasons for Rejection mailed Oct. 29, 2019", w/ English Claims, 12 pgs.
"Japanese Application Serial No. 2019-171818, Examiners Decision of Final Refusal mailed Oct. 5, 2021", (w/ English Translation), 15 pgs.
"Japanese Application Serial No. 2019-171818, Notification of Reasons for Rejection mailed Nov. 10, 2020", (w/ English Translation), 11 pgs.
"Japanese Application Serial No. 2019-171818, Preliminary Examination Report mailed May 10, 2022", (w/ English Translation), 2 pgs.
"Japanese Application Serial No. 2019-171818, Response filed Feb. 4, 2022 to Examiners Decision of Final Refusal mailed Oct. 5, 2021", (w/ English Translation of Claims), 21 pgs.
"Japanese Application Serial No. 2019-171818, Response filed May 10, 2021 to Notification of Reasons for Rejection mailed Nov. 20, 2020", (w/ English Translation of Claims), 12 pgs.
"Japanese Application Serial No. 2019-171818, Response filed Dec. 2, 2022 to Preliminary Examination Report mailed May 10, 2022", w/ English Claims, 44 pgs.
"Japanese Application Serial No. 2019-171818, Trial Brief filed Mar. 30, 2022", (w/ English (Translation), 14 pgs.

"Japanese Application Serial No. 2020-073952, Examiners Decision of Final Refusal mailed Aug. 4, 2022", w/ English translation, 3 pgs.
"Japanese Application Serial No. 2020-073952, Final Notification of Reasons for Refusal mailed Jan. 25, 2022", w/ English Translation, 11 pgs.
"Japanese Application Serial No. 2020-073952, Notification of Reasons for Refusal mailed May 20, 2021", w/o English Translation, 2 pgs.
"Japanese Application Serial No. 2020-073952, Response filed Apr. 20, 2022 to Final Notification of Reasons for Refusal mailed Jan. 25, 2022", w/ English Claims, 40 pgs.
"Japanese Application Serial No. 2020-073952, Response filed Sep. 9, 2021 to Notification of Reasons for Refusal mailed May 20, 2021", w/ English Claims, 27 pgs.
"Japanese Application Serial No. 2020-073952, Response filed Dec. 2, 2022 to Examiners Decision of Final Refusal mailed Aug. 4, 2022", w/ English Claims, 36 pgs.
"Japanese Application Serial No. 2020-182549, Examiners Decision of Final Refusal mailed Jun. 7, 2022", (w/ English Translation), 11 pgs.
"Japanese Application Serial No. 2020-182549, Notification of Reasons for Refusal mailed Nov. 30, 2021", (w/ English Translation), 10 pgs.
"Japanese Application Serial No. 2020-182549, Response filed Feb. 28, 2022 to Notification of Reasons for Refusal mailed Nov. 30, 2021", (w/ English Translation of Claims), 52 pgs.
"Japanese Application Serial No. 2020-182549, Response filed Oct. 6, 2022 to Examiners Decision of Final Refusal mailed Jun. 7, 2022", w/ English Claims, 21 pgs.
"Japanese Application Serial No. 2020-523276, Examiners Decision of Final Refusal mailed May 10, 2022", w/ English Translation, 13 pgs.
"Japanese Application Serial No. 2020-523276, Notification of Reasons for Refusal mailed Jul. 27, 2021", w/ English Translation, 12 pgs .
"Japanese Application Serial No. 2020-523276, Response filed Jan. 12, 2022 to Notification of Reasons for Refusal mailed Jul. 27, 2021", w/ English Claims, 27 pgs.
"Japanese Application Serial No. 2021-146743, Notification of Reasons for Rejection mailed Aug. 17, 2022", w/ English Translation, 3 pgs.
"Japanese Application Serial No. 2021-506434, Notification of Reasons for Refusal mailed May 10, 2022", w/ English translation, 10 pgs.
"Japanese Application Serial No. 2021-506434, Response filed Feb. 18, 2022 to Office Action mailed Dec. 21, 2021", 135 pgs.
"Japanese Application Serial No. 2021-506434, Response filed Nov. 7, 2022 to Notification of Reasons for Refusal mailed May 10, 2022", w/ English Claims, 13 pgs.
"Japanese Application Serial No. 2021-509824, Voluntary Amendment filed Aug. 18, 2022", w/ English Claims, 39 pgs.
"Japanese Application Serial No. 2021-542525, Notification of Reasons for Refusal mailed Dec. 13, 2022", w/ English Translation, 14 pgs.
"Japanese Application Serial No. 2006-513125,Final Office Action mailed Jan. 18, 2011", (English Translation), 4 pgs.
"Korean Application Serial No. 10-2005-7020077, Response filed Apr. 28, 2008 to Examination Report mailed Dec. 28, 2007", (w/ English Translation of Revised Claims), 41 pgs.
"Korean Application Serial No. 10-2004-7012647, Office Action mailed Feb. 26, 2010", (w/ English Translation), 7 pgs.
"Korean Application Serial No. 10-2004-7012647, Response filed Jun. 10, 2010 to Office Action mailed Feb. 26, 2010", (w/ English Translation of Claims), 17 pgs.
"Korean Application Serial No. 10-2005-7020077, Examination Report mailed Dec. 28, 2007", (w/ English Translation), 8 pgs.
"Korean Application Serial No. 10-2005-7020077, Notice of Preliminary Rejection mailed Jun. 28, 2007", (w/ English Translation), 9 pgs.
"Korean Application Serial No. 10-2005-7020077, Response filed Aug. 28, 2007 to Notice of Preliminary Rejection mailed Jun. 28, 2007", (w/ EnglishTranslation), 40 pgs.

(56) References Cited

OTHER PUBLICATIONS

"Korean Application Serial No. 10-2005-7022564, Notice of Preliminary Rejection dated Jul. 25, 2007", W/ English Translation, 5 pgs.
"Korean Application Serial No. 10-2005-7022564, Office Action mailed Aug. 6, 2008", W/ English Translation, 4 pgs.
"Korean Application Serial No. 10-2005-7022564, Response and Amendment filed Dec. 29, 2008 to Office Action mailed Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action mailed Aug. 6, 2008", (w/ English Translation of Claims), 16 pgs.
"Korean Application Serial No. 10-2010-7011520, Office Action mailed Jul. 20, 2010", (w/ English Translation), 6 pgs.
"Korean Application Serial No. 10-2010-7011520, Response filed Oct. 20, 2010 to Office Actiion mailed Jul. 20, 2010", (w/ English Translation of Amended Claims), 30 pgs.
"Korean Application Serial No. 10-2010-7011520, Amended Claims filed May 24, 2011 in Response to Office Action mailed Feb. 24, 2011", (English Translation of Amended Claims), 22 pgs.
"Korean Application Serial No. 10-2010-7011520, Office Action mailed Feb. 24, 2011", (w/ English Translation), 5 pgs.
"Mexican Application No. PA/a/2005/012712 Office Action mailed Jul. 21, 2009", (w/ English Translation), 9 pgs.
"Mexican Application Serial No. MX/a/2009/006341, Office Action mailed Mar. 29, 2012", (English Translation), 1 pg.
"Mexican Application Serial No. MX/a/2009/006341, Response filed Jun. 4, 2012 to Mar. 29, 2012", (w/ English Translation of Amended Claims), 16 pgs.
"Mexican Application Serial No. MX/a/2012/009249 Response filed Sep. 10, 2015 to Office Action mailed May 19, 2015", (w/ English Translation of Claims), 21 pgs.
"Mexican Application Serial No. MX/a/2012/009249, Office Action mailed Feb. 5, 2016", W/ English Claims, 2 pgs.
"Mexican Application Serial No. MX/a/2012/009249, Office Action mailed May 19, 2015", (English Translation), 1 pg.
"Mexican Application Serial No. MX/a/2012/009249, Response filed Mar. 29, 2016 to Office Action mailed Feb. 5, 2016", (English Translation of Claims), 18 pgs.
"Mexican Application Serial No. PA/a/2004/007914, Office Action mailed Feb. 14, 2008", (w/ English Translation), 3 pgs.
"Mexican Application Serial No. PA/a/2004/007914, Office Action mailed Feb. 22, 2008", (English Translation), 3 pgs.
"Mexican Application Serial No. PA/a/2004/007914, Response filed Jun. 11, 2008 to Office Action mailed Feb. 22, 2008", (w/ English Translation of Claims), 68 pgs.
"Mexican Application Serial No. PA/a/2005/011250, Office Action mailed Aug. 23, 2010", W/ English Translation, 4 pgs.
"Mexican Application Serial No. PA/a/2005/011250, Response Filed Dec. 20, 2010 to Office Action mailed Aug. 23, 2010", (w/ English Translation of Claims), 14 pgs.
"Mexican Application Serial No. PA/a/2005/012712 , Office Action Mailed Aug. 11, 2009", (English Translation), 5 pgs.
"Mexican Application Serial No. PA/a/2005/012712 , Response filed Sep. 28, 2009 to Office Action Mailed Jul. 21, 2009", (w/ English Translation of Claims), 24 pgs.
"Mexican Application Serial No. PA/a/2005/012712, Office Action mailed May 12, 2010", (w/ English Translation), 19 pgs.
"Mexican Application Serial No. PA/a/2005/012712, Office Action mailed Jun. 9, 2010", (w/ English Translation), 11 pgs.
"Mexican Application Serial No. PA/a/2005/012712, Office Action mailed Nov. 30, 2009", (w/ English Translation), 14 pgs.
"Mexican Application Serial No. PA/a/2005/012712, Official Action mailed Mar. 5, 2009", (English Translation), 2 pgs.
"Mexican Application Serial No. PA/a/2005/012712, Response filed Feb. 3, 2010 to Office Action mailed Nov. 30, 2009", (w/ English Translation of Amended Claims), 22 pgs.
"Mexican Application Serial No. PA/a/2005/012712, Response filed Sep. 27, 2010 to Office Action mailed May 12, 2010", (w/ English Translation of Claims), 19 pgs.
"Mexico Application Serial No. PA/a/2005/012712, Response filed Jun. 12, 2009 to Official Action mailed Mar. 5, 2009", (w/ English Translation of Claims), 11 pgs.
"Neuraminidase [Influenza A virus (A/Aichi/2/1968 (H3N2))]", GenBank: BAD16642.1, NCBI, [online]. Retrieved from the Internet: <URL: http://www.ncbi.nlm.nih.gov/protein/46401580>, (2008), 3 pgs.
"Neuraminidase [Influenza B virus]", GenBank: CAB71147.1, NCBI, [online]. Retrieved from the Internet: <UrL: http://www.ncbi.nlm.nih.gov/protein/6851026>, (2005), 3 pgs.
"Neuraminidase, partial [Influenza A virus (A/swine/France/WVL13/1995(H1N1))]", GenBank Accession# AC025028, (May 22, 2009), 2 pgs.
"New Zealand Application Serial No. 542935, Examination Report dated Feb. 25, 2008", 2 pgs.
"New Zealand Application Serial No. 542935, Examination Report mailed Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report mailed Feb. 29, 2008", 2 pgs.
"New Zealand Application Serial No. 543446, Examination Report mailed May 12, 2008", 1 pg.
"New Zealand Application Serial No. 543446, Response mailed Mar. 20, 2008 to Examination Report mailed Feb. 29, 2008", 2 pgs.
"New Zealand Application Serial No. 543587, Examination Report mailed Mar. 1, 2007", 1 pg.
"New Zealand Application Serial No. 543587, Examination Report mailed Jul. 7, 2006", 2 pgs.
"New Zealand Application Serial No. 543587, Response filed Aug. 7, 2007 to Examination Reports malled Jul. 7, 2006 and Mar. 1, 2007", 24 pgs.
"New Zealand Application Serial No. 543587, Second Examination Report mailed Feb. 25, 2008", 2 pgs.
"New Zealand Application Serial No. 555245, First Examination Report mailed Aug. 26, 2008", 2 pgs.
"New Zealand Application Serial No. 555245, Subsequent Examiner Report mailed Jul. 3, 2009", 1 pg.
"Nonstructural protein 1 [influenza B virus (B/Hong Kong/330/2001)]", GenBank AAT69443.1, (2006), 1 pg.
"Norway Application Serial No. 20056074, Office Action mailed Jan. 17, 2017", (English Translation), 5 pgs.
"Norway Application Serial No. 20056074, Office Action mailed Apr. 25, 2017", (w English Translation), 3 pgs.
"Norway Application Serial No. 20056074, Office Action Response mailed Apr. 18, 2017", W/ English Claims, 27 Pgs.
"Norway Application Serial No. 20056074, Response filed Jul. 25, 2017 to Office Action mailed Apr. 25, 2017", (w/ English Translation of Amended Claims), 111 pgs.
"Norweigan Application Serial No. 20056074, Office Action mailed Apr. 25, 2017", (Translation), 3 pgs.
"Nucleotide sequences of influenza virus segments 1 and 3 reveal mosaic structure of a small viral RNA segment", Database Uniprot, (Nov. 14, 2001), 2 pgs.
"Nucleotides Sequences of Influenza Virus Segments 1 and 3 Reveal Mosaic Structure of Small Viral RNA Segment", Database UniProt EBI / Accession No. NC_002023, (Jul. 10, 2008), 15 pgs.
"PCT Application Serial No. PCT/US2005/041991, International Preliminary Report on Patentability / Written Opinion mailed Jul. 19, 2007", 8 pgs.
"Polymerase acidic [influenza A virus (A/swine/Shizuoka/120/97(H3N2))]", GenBank AAO15329.1, (2003), 1 pg.
"Polymerase PA [Influenza A virus (A/swine/Yangzhou/1/2008(H9N2))]", GenBank: ADK98493.1, [Online]. Retrieved from the Internet: <URL: https://www/ncbi.nlm.nih.gov/protein/ADK98493.1>, 2 pgs.

(56) References Cited

OTHER PUBLICATIONS

"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
"RecName: Full=Non-structural protein 1; Short=NS1; AltName: Full=NS1 B", GenPept Accesion P08013, NS1 of Influenza B strain B/Yamagata/1/73, (Dec. 9, 2015), 2 pgs.
"RNA World", http://faculty.uca.edu/~benw/biol4415/lecture10a/tsld003.htm, (Observed Feb. 25, 2003), 1 pg.
"Russian Federation Application No. 2005136233, Office Action mailed Dec. 25, 2007", 2 pgs.
"Russian Federation Application No. 2005136233, Response filed May 29, 2008 to Office Action mailed Dec. 25, 2007", (w/ Partial English Translation), 7 pgs.
"Russian Federation Application Serial No. 2005136233, First Office Action mailed Feb. 27, 2007", (w/ English Translation), 5 pgs.
"Russian Federation Application Serial No. 2005136233, Response filed Jun. 14, 2007 to First Office Action mailed Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singapore Application Serial No. 200507467-9, Invitation to Respond to Written Opinion mailed Jun. 19, 2007", 5 pgs.
"Singaporean Application Serial No. 200506858-0, Examination Report mailed Feb. 9, 2007", 4 pgs.
"Singaporean Application Serial No. 200506858-0, Response filed Dec. 22, 2006 to Written Opinion mailed Jul. 26, 2006", 18 pgs.
"Singaporean Application Serial No. 200506858-0, Written Opinion mailed Jul. 26, 2006", 8 pgs.
"Singaporean Application Serial No. 200507468-7, Examination Report mailed Mar. 19, 2008", 5 pgs.
"Singaporean Application Serial No. 200507468-7, Invitation to Respond to Written Opinion mailed Jun. 12, 2007", 6 pgs.
"Singaporean Application Serial No. 200507468-7, Response filed Nov. 7, 2007 to Invitation to Respond to Written Opinion mailed Jun. 12, 2007", 9 pgs.
"ST3GAL6 Gene ID: 478535", ncbi, nlm, [Online]. retrieved from the Internet: <URL: https://www.ncbi.nlm.nih.gov/gene/47853> Sep. 14, 2022, (Aug. 17, 2022), 14 pgs.
"The Influenza Virus: Structure and Replication", Rapid Reference to Influenza. Elsevier Ltd, [Online]. Retrieved from the Internet: http://www. rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainese Application Serial No. 200512619, Response filed Jan. 21, 2010 to Office Action mailed Jun. 17, 2009", W/ English Claims, 14 pgs.
"Ukrainian Application Serial No. 200512619, Office Action mailed Feb. 27, 2009", (w/ English Translation), 21 pgs.
"Ukrainian Application Serial No. 200512619, Office Action mailed Jun. 17, 2009", (w/ English Translation), 4 pgs.
"Ukrainian Application Serial No. 200512619, Response filed Apr. 8, 2009 to Office Action mailed Feb. 27, 2009", (w/ English Translation of Claims), 9 pgs.
Abram, M. E, et al., "Nature, position, and frequency of mutations made in a single cycle of HIV-1 replication", J Virol., 84(19), (Oct., 2010), 9864-78.
Air, Gillian M., et al., "Antigenic, Sequence, and Crystal Variation in Influenza B Neuraminidase", Virology, 177(2), (1990), 578-587.
Air, Gillian M., et al., "Antigenic, Sequence, and Crystal Variation in Influenza B Neuraminidase", Virology vol. 177, (1990), 578-587.

Akarsu, H., et al., "Crystal structure of the M1 protein-binding domain of the influenza A virus nuclear export protein (NEP/NS2).", EMBO J., 22(18), (Sep. 15, 2003), 4646-55.
Albo, C., et al., "The 5' Ends of Thogoto Virus (Orthomyxoviridae) mRNAS Are Homogeneous in both Length and Sequence", Journal of Virology, 70(12), (1996), 9013-9017.
Alonso-Caplen, et al., "Efficient Transcription, Not Translation, Is Dependent on Adenovirus Tripartite Leader Sequences at Late Times of Infection", Journal of Virology, vol. 62, No. 5, 1606-1616, (1988), 11 pgs.
Author Unknown, "New Approaches to Influenza Vaccine", Medscape—Infections in Medicine, http://www.medscape.com/viewarticle/417404_3, (Observed Feb. 26, 2003), 4 pgs.
Avetisyan, G, et al., "Cell-mediated immune responses to influenza vaccination in healthy volunteers and allogeneic stem cell transplant recipients", Bone Marrow Transplant 411-415, (2005), 5 pgs.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bai, B., et al., "Virus-Like Particles of SARS-Like Coronavirus Formed by Membrane Proteins from Different Origins Demonstrate Stimulating Activity in Human Dendritic Cells", PloS One, 3(7): e2685, (2008), 1-12.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Bedford, M. T, et al., "FBP WW domains and the Abl SH3 domain bind to a specific class of proline-rich ligands", EMBO J., 16(9), (May 1, 1997), 2376-83.
Betakova, T., et al., "The NB protein is an integral component of the membrane of influenza B virus.", J Gen Virol., 77 ( Pt 11), (Nov. 1996), 2689-94.
Biere, Barbara, et al., "Differentiation of Influenza B Virus Lineages Yamagata and Victoria by Real-Time PCR", Journal of Clinical Microbiology, vol. 48, No. 4 1425-1427, (2010), 3 pgs.
Bilsel, P., et al., "Mutations in the Cytoplasmic Tail of Influenza A Virus Neuraminidase Affect Incorporation into Virions", Journal of Virology, 67(11), (Nov. 30, 1993), 6762-6767.
Blount, K. F., et al., "The Hammerhead Ribozyme", Biochemical Society Transactions, 30(6), (2002), 1119-1122.
Bourmakina, S. V, et al., "Reverse genetics studies on the Filamentous morphology of influenza A Virus", Journal of General Virology (2003) 84,, (2003), 517-527.
Bowie, et al., "Deciphering the Message in Protein Sequences: Tolerance to Amino Acid Substitutions", Science, 247, (Mar. 1990), 1306-1310.
Bowie, J. U., et al., "Deciphering the Message in Protein Sequences: Tolerance to Amino Acid Substitutions", Science, 247(4948) 1306-1310, (1990), 5 pgs.
Boyer, J. C., et al., "Infectious transcripts and cDNA clones of RNA viruses", Virology, 198(2), (Feb. 1994), 415-426.
Bradfute, S. B., "The Early Clinical Development of Ebola Virus Treatments", Exp. Opin. Invest. Drugs 26(1):, (2017), 5 pgs.

(56) References Cited

OTHER PUBLICATIONS

Bradsher, K., "Cases of New Bird Flue in Hong Kong Prompt Worldwide Alerts", The New York Times web site, (Observed Feb. 22, 2003), 3 pgs.
Bradsher, K., "Man's Death of 'Bird Flu' in Hong Kong Raises Fears", The New York Times web site, (Observed Feb. 22, 2003), 3 pgs.
Brandli, A. W, et al., "A Polarized Epithelial Cell Mutant Deficient in Translocation of UDP-galactose into the Golgi Complex", Journal of Biological Chemistry, 263(31), (Nov. 5, 1988), 16283-16290.
Brands, R., et al., "Influvac: A Safe Madin Darby Canine Kidney (MDCK) Cell Culture-Based Influenza Vaccine", Dev. Biol. Stand., 98, (1999), 93-100.
Brassard, D.L., et al., "Influenza B virus NB glycoprotein is a component of the virion", Virol., 220(2), No Document, (1996), 350-360.
Bridgen, A., et al., "Rescue of a Segmented Negative-Strand RNA Virus Entirely From Cloned Complementary DNAs", Proc. Natl. Acad. Sci. USA, 93, (1996), 15400-15404.
Broecker, Felix, et al., "Extending the Stalk Enhances Inmunogenicity of the Influenza Virus Neuraminidase", Journal of Virology, 93(18), e00840-19, (Sep. 1, 2019), 1-12.
Brooke, C B, "Biological activities of 'noninfectious' influenza A virus particles", Future Virol 9(1) 41-51, (Jan. 2014), 16 pgs.
Brown, E. G., et al., "Genetic analysis of mouse-adapted influenza A virus identifies roles for the NA, PB1, and PB2 genes in virulence", Virus Research, 61(1), (May 1999), 63-76.
Brown, TA, "Studying DNA", Genomes—NCBI Bookshelf, Brown TA. Genomes. 2nd edition. Oxford: Wiley-Liss; 2002, (2002), 26 pgs.
Bruhl, P., et al., "Humoral and Cell-Mediated Immunity to Vero Cell-Derived Influenza Vaccine", Vaccine, 19, (2001), 1149-1158.
Buchholz, U. J., et al., "Generation of Bovine Respiratory Syncytial Virus (BRSV) From DNA: BRSV NS2 is Not Essential for Virus Replication in Tissue Culture, and the Human RSV Leader Region Acts as a Functional BRSV Genome Promoter", Journal of Virology, 73(1), (1999), 251-259.
Bukreyev, A., et al., "Chimeric human parainfluenza virus bearing the Ebola virus glycoprotein as the sole surface protein is immunogenic and highly protective against Ebola virus challenge", Virology, 383(2), (Abstract Only), (2009), 1 pg.
Bukreyev, A., et al. "Recovery of infectious respiratory syncytial virus expressing an additional, foreign gene", Journal of Virology, 70(10), (Oct. 1996), 6634-6641.
Bullido, R., et al., "Influenza A Virus NEP (NS2 protein) Downregulates RNA Synthesis of Model Template RNAs", Journal of Virology, 75(10), (May 2001), 4912-4917.
Bullido, R., et al., "Influenza A virus NEP(NS2 protein) downregulates RNA synthesis of model template RNAs", Journal of Virology, vol. 75 4912-4917, (May 2001), 6 pgs.
Burmeister, W. P., et al., "The 2.2 A resolution crystal structure of influenza B neuraminidase and its complex with sialic acid", The EMBO Journal, 11(1), (1992), 49-56.
Cannon, Joseph G., "Chapter Nineteen—Analog Design", In: Burger's Medicinal Chemistry and Drug Discovery, Fifth Edition, vol. I: Principles and Practice, Wiley-Interscience, (1995), 783-802.
Cao, S., et al., "Characterization of the Nucleocytoplasmic Shuttle of the Matrix Protein of Influenza B Virus", Journal of Virology., 88(13), (Jul. 2014), 7464-7473.
Cardona, C. J., "Avian Influenza", http://www.vetmed.ucdavis.edu/vetex/INF-PO_AvianInfluenzaFS.html, ((Observed Feb. 22, 2003), 3 pgs.
Castrucci, M. R, et al., "Attenuation of Influenza A Virus by Insertion of a Foreign Epitope into the Neuraminidase", Journal of Virology, 66(8), (1992), 4647-4653.
Castrucci, M. R., et al., "Biologic Importance of Neuraminidase Stalk Length in Influenza A Virus", Journal of Virology, 67(2), (1993), 759-764.
Castrucci, M. R, et al., "Protection against Lethal Lymphocytic Choriomeningitis Virus (LCMV) Infection by Immunization of Mice with an Influenza Virus Containing an LCMV Epitope Recognized by Cytotoxic T Lymphocytes", Journal of Virology, 68(6), (1994), 3486-3490.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Catchpole, A P, et al., "Alternative base pairs attenuate influenza A virus when introduced into the duplex region of the conserved viral RNA promoter of either the NS or the PA gene", Journal of General Virology, 84, (2003), 507-515.
Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Chang, M. W., et al., "Analysis of HIV Wild-Type and Mutant Structures via in Silico Docking against Diverse Ligand Libraries", J. Chem. Inf. Model., 47(3), (2007), 1258-1262.
Chen, H, et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.
Chiba, Shiho, et al., "Multivalent nanoparticle-based vaccines protect hamsters against SARS-CoV-2 after a single immunization", Communications Biology, 4: 597, (2021), 1-9.
Chothia, Cyrus, et al., "Canonical Structures for the Hypervariable Regions of Immunoglobulins.", J Mol Biol., 196(4), (1987), 901-917.
Chowrira, B M., et al., "In Vitro and in Vivo Comparision of Hammerhead, Hairpin, and Hepatitis Delta Virus Self-Processing Ribozyme Cassettes", The Journal of Biological Chemistry, 269(41), (1994), 25856-25864.
Chung, C, et al., "Glycoengineering of Chinese Hamster Ovary Cells for Improving Biotherapeutics Efficacies", A dissertation submitted to Johns Hopkins University in conformity with the requirements for the degree of Doctor of Philosophy, Retrieved from the Internet: <https://jscholarship.library.jhu.edu/handle/177>, (2016), 137 pgs.
Claas, E C. J., et al., "Human Influenza A H5N1 Virus Related to a Highly Pathogenic Avian Influenza Virus", The Lancet, 351, (1998), 472-477.
Clarke, D. K., et al., "Rescue of Mumps Virus From cDNA", Journal of Virology, 74(10), (2000), 4831-4838.
Cohen, Alexander A., et al., "Mosaic nanoparticles elicit cross-reactive immune responses to zoonotic coronaviruses in mice", Science, 371(6530), and Supplementary Materials, (2021), 735-741 (30 pgs).
Coleman, P. M., et al., "Sequence and Structure Alignment of Paramyxovirus Hemagglutinin-Neuraminidase with Influenza Virus Neuraminidase", Journal of Virology, 67(6), (1993), 2972-2980.
Collins, P. L., et al., "Chapter 41—Parainfluenza Viruses", In: Fields Virology, edited by Fields, B. N., et al. (3rd Edition, 1996, Lippincott-Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Scl. USA, 92, (1995), 11563-11567.
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K.-K., "Genetic Engineering of Animal RNA Viruses", Trends in Microbiology, 4(10), (1996), 386-393.

(56) References Cited

OTHER PUBLICATIONS

Conzelmann, K.-K., "Genetic manipulation of non-segmented negative-strand RNA viruses", Journal of General Virology, 77(Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
Craven, R. C., et al., "Late Domain Function Identified in the Vesicular Stomatitis Virus M Protein by Use of Rhabdovirus-Retrovirus Chimeras", Journal of Virology, 73(4), (1999), 3359-3365.
Crescenzo-Chaigne, B., et al., "Comparative Analysis of the Ability of the Polymerase Complexes of Influenza Viruses Type A, B and C to Assemble into Functional RNPs that Allow Expression and Replication of Heterotypic Model RNA Templates In Vivo", Virology, 265(2), (1999), 342-353.
Cunningham, Brian C, et al., "High-Resolution Epitope Mapping of hGH-Receptor Interactions by Alanine-Scanning Mutagenesis", Science 244:4908, (1989), 6 pgs.
Da Silva, Diogo V, et al., "Assembly of Subtype 1 Influenza Neuraminidase Is Driven by Both the Transmembrane and Head Domains", Journal of Biological Chemistry, 288(1), (Jan. 1, 2013), 644-653.
Daddario-Dicaprio, K. M, et al., "Cross-protection against Marburg virus strains by using a live, attenuated recombinant vaccine", J Virol., 80(19), (Oct. 2006), 9659-66.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De Filette, Marina, et al., "An influenza A vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Del Guidice, G., et al., "What are the limits of adjuvanticity?", (Abstract), Vaccine, 20(Suppl 1), S38-S41, (2001), 1 pg.
Desheva, J. A, et al., "Characterization of an influenza A H5N2 reassortant as a candidate for live-attenuated and inactivated vaccines against highly pathogenic H5N1 viruses with pandemic potential", Vaccine, 24, (2006), 6859-6866.
Desselberger, Ulrich, et al., "The 3' and 5'-terminal sequences of influenza A, B and C virus RNA segments are highly conserved and show partial inverted complementarity", Gene, 8 (3), (Feb. 1980), 315-328.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dollenmaier, G., et al., "Membrane-Associated Respiratory Syncytial Virus F Protein Expressed From a Human Rhinovirus Type 14 Vector Is Immunogenic", Virology, 281(2), (Mar. 15, 2001), 216-230.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Du, Q., "Ribozyme Enzymology", http://academic.brooklyn.cuny.edu/chem/zhuang/QD/toppage1.htm, (Observed Feb. 25, 2003), 8 pgs.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Duhaut, S., et al., "Approximately 150 Nucleotides from the 5' End of an Influenza A segment 1 Defective Virion RNA Are needed for Genome Stability during passage of Defective Virus in Infected Cells", Virology, 275(2) 278-285 Academic Press, Orlando, US, (Sep. 30, 2000), 8 pgs.
Duhaut, S. D, et al., "Defective segment 1 RNAs that interfere with production of infectious influenza A virus require at least 150 nucleotides of 5' sequence: evidence from a plasmid-driven system", Journal of General Virology 83, (2002), 403-411.
Duhaut, S. D, et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", Virology, 248(2), Academic Press, Orlando, Us, (Sep. 1, 1998), 241-253.
Duhaut, Susan, et al., "Approximately 150 Nucleotides from the 5' End of an Influenza A Segment 1 defective virion RNA are Needed for Genome Stability During Passage of Defective Virus in Infected Cells.", Virology, 275(2), (2000), 278-285.
Dumoulin, Mireille, et al., "Single-domain antibody fragments with high conformational stability", Protein Science, 11, (2002), 500-515.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Dunn, E. F., et al., "Transcription of a recombinant bunyavirus RNA template by transiently expressed bunyavirus proteins", Virology, 211(1), (1995), 133-143.
Durbin, A. P, et al., "Human Parainfluenza Virus Type 3 (PIV3) Expressing the Hemagglutinin Protein of Measles Virus Provides a Potential Method for Immunization Against Measles Virus and PIV3 in Early Infancy", Journal of Virology, 74(15), (Aug. 2000), 6821-6831.
Durbin, A. P., et al., "Recovery of infectious human parainfluenza virus type 3 from cDNA", Virology, 235(2), (Sep. 1, 1997), 323-332.
Dyall, J., et al., ""Identification of inhibitors of Ebola virus with a subgenomic replication system"", Antiviral Research, 70(1), 19th International Conference on Antiviral Research, San Juan, PR (May 7-11, 20006), (May 2006), p. A39.
Elhefnawi, M, et al., "Identification of novel conserved functional motifs across most Influenza A viral strains", Virology Journal, 8:44, (2011), 10 pages.
Elliott, R. M., "Emerging Viruses: The Bunyaviridae", Molecular Medicine, 3(9), (1997), 572-577.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.

(56) References Cited

OTHER PUBLICATIONS

Emerson, S. U., et al., "Both NS and L Proteins Are Required for In Vitro RNA Synthesis by Vesicular Stomatitis virus", Journal of Virology, 15(6), (1975), 1348-1356.
Enami, K., et al., "Influenza virus NS1 protein stimulates translation of the M1 protein", Journal of Virology, 68 1432-1437, (1994), 6 pgs.
Enami, M., "An Influenza Virus Containing Nine Different RNA Segments", Virology, 18591), (1991), 291-298.
Enami, M., et al., "High-Efficiency formation of Influenza Virus Transfectants", Journal of virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Enterlein, S., et al., "Antiviral Strategies Against : Exploring Gene Silencing Mechanisms to Identify Potential Antiviral Targets", Antiviral Research, 70(1), (Abstract 33), 19th International Conference on Antiviral Research, San Juan, PR (May 7-11, 2006), (May 2006), p. A38.
Enterlein, S., et al., "Untersuchungen zur Replikation und Transkription von Marburgund Ebolavirus", [Online]. 2005, Phillips-Universitat Marburg , XP002563470, Retrieved from the Internet: <URL:http://deposit.ddb.de/cgi-bin/dokserv?>idn=977005607&dok_var=d1&dok_ext=pdf&filename=977005607 .pdf> [retrieved on Jan. 15, 2010], (2005), p. 70-p. 84.
Essere, Boris, et al., "Critical role of segment-specific packaging signals in genetic reassortment of influenza A viruses", Proc. Natl. Acad. Sci. USA, 110(40), (2013), E3840-E3848.
Fahey, J. L., et al., "Status of Immune-Based Therapies in HIV Infection and Aids", Clinical and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Feng, L., et al., "The mouse Pol I terminator is more efficient than the hepatitis delta virus ribozyme in generating influenza-virus-like RNAs with precise 3' ends in a plasmid-only-based virus rescue system", Arch Virol., 154(7), (2009), 1151-6.
Fields, S., et al., "Nucleotides Sequences of Influenza Virus Segments 1 and 3 Reveal Mosaic Structure of Small Viral RNA Segment", Cell, 28, (1982), 303-313.
Fischer, W. B, et al., "Viral ion channels: structure and function.", Biochim Biophys Acta., 1561(1), (Mar. 19, 2002), 27-45.
Flandorfer, A., et al., "Chimeric Influenza A Viruses with a Functional Influenza B Virus Neuraminidase or Hemagglutinin", Journal of Virology, 77(17), (2003), 9116-9123.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.
Fodor, E., et al., "Rescue of Influenza A Virus from Recombinant DNA", Journal of Virology, 73(11), XP002151487; ISSN:0022-538X, (Nov. 1999), 9679-9682.
Forbes, Nicole E, et al., "Multifunctional Adaptive NS1 Mutations Are Selected upon Human Influenza Virus Evolution in the Mouse", Plos One, vol. 7, No. 2, (Feb. 21, 2012), 20 pgs.
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fouchier, R. A. M., et al., "Avian Influenze A Virus (H7N7) Associated With Human Conjunctivitis and a Fatal Case of Acute Respiratory Distress Syndrome", Proc. Natl. Acad. Sci. USA, 101(5) 1356-1361, (2004), 6 pgs.
Friers, et al., "Soluble recombinant influenza vaccines", Phil. Trans. R. Soc. Lond. B (2001). vol. 356 1961-1963, (2001), 4 pgs.
Fuji, Y., et al., "Selective incorporation of influenza virus RNA segments into virions", Proc. Natl. Acad. Sci. USA, 100(4) 2002-2007, (2003), 6 pgs.
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Fujii, Y, et al., "The packaging of influenza viral genome", Virus, 52 (1), Uirusu (Japanese Journal Name), (Jun. 2002), 203-206.
Gao, Qinshan, et al., "A Nine-Segment In?uenza A Virus Carrying Subtype H1 and H3 Hemagglutinins", Journal of Virology, 84(16), (Aug. 2010), 8062-8071.
Gao, Qinshan, et al., "A Seven-Segmented Influenza A Virus Expressing the Influenza C Virus Glycoprotein HEF", Journal of Virology, 82(13), (Jul. 2008), 6419-6426.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Garay, R. P, et al., "Cancer relapse under chemotherapy: why TLR2/4 receptor agonists can help", Eur J Pharmacol., 563(1-3), (Jun. 1, 2007), 1-17.
Garcia-Sastre, A., et al., "Genetic Manipulation of Negative-Strand RNA Virus Genomes", Annu. Rev. Microbiol., 47, (1993), 765-790.
Garcia-Sastre, A., et al., "Introduction of Foreign Sequences into the Genome of Influenza A Virus", Dev. Biol. Stand. vol. 82, (1994), 237-246.
Garcia-Sastre, A., et al., "Introduction of Foreign Sequences into the Genome of Influenza A Virus", In: Recombinant Vectors in Vaccine Development. Dev. Biol. Stand., 82, Fred Brown, Editor, (1994), 237-246.
Garcia-Sastre, A., et al., "Introduction of foreign sequences into the genome of influenza A virus.", Dev Biol Stand., 82, (1994), 237-246.
Garcia-Sastre, A., et al., "The cytoplasmic tail of the neuraminidase protein of influenza A virus does not play an important role in the packaging of this protein into viral envelopes", Virus Research, 37(1), (1995), 37-47.
Garcia-Sastre, A., et al., "Use of a mammalian internal ribosomal entry site element for expression of a foreign protein by a transfectant influenza virus.", Journal of Virology, 68(10), (1994), 6254-6261.
Garcia-Sastre, Adolfo, et al., "Use of a Mammalian Internal Ribosomal Entry Site Element for Expression of a Foreign Protein by a Transfectant Influenza Virus", Journal of Virology, 68(10) 6254-6261, (Jun. 30, 1994), 8 pgs.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Garrett, L., "Deadly Ebola, Avian Influenza Re-Emerging", Newsday.com, (Feb. 20, 2003), 3 pgs.
Genbank, "", ABD36884.1, (2007), 2 pgs.
Gerdil, C., "The Annual Production Cycle for Influenza Vaccine", Vaccine, 21 1776-1779, (2003), 4 pgs.
Ghate, Anita A, et al., "Influenza Type B Neuraminidase Can Replace the Function of Type A Neuraminidase", Virology, 264 (2), (Nov., 1999), 265-277.
Giddings, A M, et al., "The matrix protein of HIV-1 is not sufficient for assembly and release of virus-like particles", Virology, 248(1), (1998), 108-16.
Gilleland, H. E, et al., "Chimeric Influenza Virus Incorporating Epitopes of Outer Membrane Protein F as a Vaccine Against Pulmonary Infection with Pseudomonas Aeruginosa", Behring Inst. Mitt. 98, (Feb. 28, 1997), 291-301.
Gomez-Puertas, P., et al., "Influenza Virus Matrix Protein Is the Major Driving Force in Virus Budding", Journal of Virology, 74 11538-11547, (Dec. 1, 2000), 10 pgs.
Gorman, O T, et al., "Evolution of influenza A virus PB2 genes: implications for evolution of the ribonucleoprotein complex and origin of human influenza A virus", J. Virol., 64(10), (Oct. 1990), 4893-4902.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.

(56) References Cited

OTHER PUBLICATIONS

Goto, Hideo, et al., "The Genome-Packaging Signal of the Influenza A Virus Genome Comprises a Genome Incorporation Signal and a Genomne-Bundling Signal", Journal of Virology; vol. 87 No. 21, (Nov. 2013), 11316-11322.

Govorkova, E A, et al., "Replication of Influenza A Viruses in a Green Monkey Kidney Continuous Cell Line (Vero)", J. Infect. Dis. 172(1), (1995), 250-253.

Grambas, S., et al., "Influence of amantadine resistance mutations on the pH regulatory function of the M2 protein of influenza A viruses", Virology, 191(2), (Dec. 1992), 541-549.

Green, R. F., et al., "Glycosylation Does Not Determine Segregation of Viral Envelope Proteins in the Plasma Membrane of Epithelial Cells", J. Cell Biol., 89(2), (1981), 230-239.

Groseth, A., "13. Generation of Recombinant Ebola Viruses Using Reverse Genetics", In: Hoenen T., et al. (eds), Ebolaviruses: Methods and Protocols, Methods in Molecular Biology, vol. 162, (2017), 177-187.

Groseth, A., et al., "RNA Polymerase I-Driven Minigenome System for Ebola Viruses", Journal of Virology, 79(7), (2005), 4425-4433.

Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.

Gubareva, "Molecular mechanisms of influenza virus resistance to neuraminidase inhibitors", Virus Research, vol. 103, (2004), pp. 199-203.

Gunther, S, et al., "Application of real-time PCR for testing antiviral compounds against Lassa virus, SARS coronavirus and Ebola virus in vitro", Antiviral Research, Elsevier BV, NL, vol. 63, No. 3, XP004580000 ISSN: 0166-3542, (Sep. 1, 2004), 209-215.

Hagen, M., et al., "Recombinant Influenza Virus Polymerase: Requirement of both 5' and 3' Viral Ends for Endonuclease Activity", Journal of Virology, 68(3), (1994), 1509-1515.

Hai, Rong, et al., "Influenza B Virus NS1-Truncated Mutants: Live-Attenuated Vaccine Approach", Journal of Virology, 82(21), (2008), 10580-10590 .

Halfmann, P., et al., "Generation of biologically contained Ebola viruses", Proceedings of the National Academy of Sciences of the United States of America 1129-1133, vol. 105, No. 4, XP002563467 ISSN: 1091-6490 the whole document, (Jan. 29, 2008), 6 pgs.

Halfmann, P., et al., "Replication-Deficient Ebolavirus as a Vaccine Candidate", Journal of Virology, vol. 83, No. 8 3810-3815, XP002563468; ISSN: 1098-5514; the whole document, (Apr. 2009), 6 pgs.

Halfmann, Peter J., et al., "Potent neutralization of SARS-CoV-2 including variants of concern by vaccines presenting the receptor-binding domain multivalently from nanoscaffolds", Bioengineering & Translational Medicine, 6(3): e10253, (2021), 8 pgs.

Halperin, S. A., et al., "Safety and Immunogenicity of a Trivalent, Inactivated, Mammalian Cell Culture-Derived Influenza Vaccine in Healthy Adults, Seniors, and Children", Vaccine, 20 1240-1247, (2002), 8 pgs.

Halstead, Scott B., et al., "Dengue Antibody-Dependent Enhancement: Knowns and Unknowns", Microbiology Spectrum, 2(6), (2014), 1-18 .

Harding, Alfred T, et al., "Rationally Designed Influenza Virus Vaccines That Are Antigenically Stable during Growth in Egg", MBIO, vol. 8, No. 3, e00669-17, (Jul. 5, 2017), 1-16.

Harmsen, M. M., et al., "Properties, production, and applications of camelid single-domain antibody fragments", Appl Microbiol Biotechnol,77, (2007), 13-22.

Harty, R. N, et al., "A PPXY Motif within the VP40 Protein of Ebola Virus Interacts Physically and Functionally with a Ubiquitin Ligase: Implications for Filovirus Budding", Proc. Natl. Acad. Sci, 97 (25), (Dec. 5, 2000), 13871-13876.

Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.

Harvey, K. F, et al., "All three WW domains of murine Nedd4 are involved in the regulation of epithelial sodium channels by intracellular Na+.", J Biol Chem., 274(18), (Apr. 30, 1999), 12525-30.

Hatada, E., et al., "Binding of Influenza A Virus NS1 Protein to dsRNA in vitro", Journal of General Virology, 73, (1992), 3325-3329.

Hatakeyama, S., et al., "Dissection and identification of regions required to form pseudoparticles by the interaction between the nucleocapsid (N) and membrane (M) proteins of SARS coronavirus", Virology, 380(1), (2008), 99-108.

Hatakeyama, S., et al., "Emergence of Influenza B Viruses With Reduced Sensitivity to Neuraminidase Inhibitors", Journal of the American Medical Association, 297(13) 1435-1442, (Apr. 4, 2007), 8 pgs.

Hatakeyama, S., et al., "Enhanced Expression of an a2,6-Linked Sialic Acid on MDCK Cells Improves Isolation of Human Influenza Viruses and Evaluation of Their Sensitivity to a Neuraminidase Inhibitor", J Clin Microbiol, 43(8), (2005), 4139-4146.

Hatakeyma, S., et al., "The molecular basis of resistance to anti-influenza drugs", Japanese Journal of Clinical Medicine—Nippon Rinsho, 64(10) 1845-1852, (Oct. 1, 2006), 8 pgs.

Hatta, M., et al., "The NB protein of influenza B virus is not necessary for virus replication in vitro", Journal of Virology, 77(10), (May, 2003), 6050-6054.

Hay, A. J., et al., "The role of the M2 protein in influenza A virus infection", Proceedings of the International Conference on Options for the Control of Influenza, Courchevel, (1992), 281-288.

He, B., et al., "Recovery of infectious SV5 from cloned DNA and expression of a foreign gene", Virology, 237(2), (1997), 249-260.

He, X., et al., "Generation of SARS-CoV-2 reporter replicon for high-throughput antiviral screening and testing", Proc. Natl. Acad. Sci. USA, 118(15): e2025866118, (2021), 8 pgs.

Helenius, A., "Unpacking the Incoming Influenza Virus", Cell, 69, (May 1992), pp. 577-578.

Hevey, Michael, et al., "Marburg virus vaccines based upon alphavirus replicons protect guinea pigs and nonhuman primates", Virology, 251(1), (Nov. 10, 1998), 28-37.

Hickman, Danielle, et al., "An avian live attenuated master backbone for potential use in epidemic and pandemic influenza vaccines", Journal of General Virology, 89(Part 11), (2008), 2682-2690.

Hiromoto, Y., et al., "Phylogenetic Analysis of the Three Polymerase Genes (PB1, PB2 and PA) of Influenza B Virus", Journal of General Virology, 81, (Apr. 2000), 929-937.

Hiti, A. L., et al., "P03470—Neuraminidase", Entrez Protein Database, http://www.ncbi.nlm.nih.gov/entrez/viewer.fcgi?db=protein&val=84028231, (1982), 730-734.

Hiti, A. L., et al., "P03470—Neuraminidase", Entrez Protein Database, [online]. [retrieved on Aug. 30, 2006]. Retrieved from the Internet: <URL: http://www.ncbi.nlm.nih.gov/entrez/viewer.fcgi?db=protein&val=84028231>, (1982), 730-734 (8 pgs.).

Ho, Y., et al., "Assembly of human severe acute respiratory syndrome coronavirus-like particles", Biochem Biophys Res Commun, 318(4), (2004), 833-838.

Hoenen, T., et al., "11. Reverse Genetics Systems for Filoviruses", In: Perez, Daniel (Ed.), Reverse Genetics of RNA Viruses: Methods and Protocols, Methods in Molecular Biology, vol. 1602, (2017), 159-170.

Hoenen, Thomas, et al., "Minigenomes, Transcription and Replication Competent Virus-Like Particles and Beyong: Reverse Genetics Systgems for Filoviruses and other Negative Stranded Hemorrhagic Fever Viruses", Antiviral Res., 91:195, (2011), 30.

Hoffman, E., et al., "Ambisense Approach for the Generation of Influenza A Virus: vRNA and mRNA Synthesis from One Template", Virology 267(2) 310-317, (Feb. 15, 2006), 8 pgs.

Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.

Hoffman, M. A., et al., "An Infectious Clone of Human Parainfluenza Virus Type 3", Journal of Virology, 71(6), (1997), 4272-4277.

(56) References Cited

OTHER PUBLICATIONS

Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Hoffmann, Erich, et al., "A DNA transfection system for generation of influenza A virus from eight plasmids", Proceedings of the National Academy of Sciences, vol. 97, No. 11, (2000), 6108-6113.
Holmes, E. C, et al., "Whole-Genome Analysis of Human Influenza A Virus Reveals Multiple Persistent Lineages and Reassortment Among Recent H3N2 Viruses", PLoS Biology, 3(9) 1579-1589, (2005), 11 pgs.
Holsinger, L. J., et al., "Influenza A Virus M2 Ion Channel Protein: a Structure-Function Analysis", Journal of Virology, 68 (3), (1994), pp. 1551-1563.
Honda, A., et al., "RNA Polymerase of Influenza Virus: Role of NP in RNA Chain Elongation", The Journal of Biochemistry, 104(6), (1988), 1021-1026.
Honda, Ayae, et al., "Differential Roles of Viral RNA and cRNA in Functional Modulation of the Influenza Virus RNA Polymerase", The Journal of Biological Chemistry, 276(33), (2001), 31179-31185.
Horimoto, "Designing Vaccines for Pandemic Influenza", Current Topics Microbiol Immunol 333, (2009), 165-176.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14) 8031-8038, (2003), 11 pgs.
Horimoto, T., et al., "Reverse Genetics Provides Direct Evidence for a Correction of Hemagglutinin Cleavability and Virulence of an Avian Influenza A Virus", Journal of Virology, 68(5), (1994), 3120-3128.
Horimoto, T., et al., "The Development and Characterization of H5 Influenza Virus Vaccines Derived from a 2003 Human Isolate", Vaccine, 24(17) 3669-3676, (2006), 8 pgs.
Hossain, M. J., et al., "Establishment and Characterization of a Madin-Darby Canine Kidney Reporter Cell Line for Influenza A Virus Assays", J Clin Microbiol, 48(7), (2010), 2515-2523.
Hsieh, P.-K., et al., "Assembly of Severe Acute Respiratory Syndrome Coronavirus RNA Packaging Signal into Virus-Like Particles Is Nucleocapsid Dependent", J Virol., 79(22), (2005), 13848-13855.
Huang, T. S, et al., "Determinaton of Influenza Virus Proteins Required for Genome Replication", Jounal of Virology, vol. 64 5669-5673, (1990), 5 pgs.
Huang, T.-S., et al., "Determination of Influenza Virus Proteins Required for Genome Replication", Journal of Virology, 64(11), (1990), 5669-5673.
Huang, Y., et al., "Generation of Synthetic Severe Acute Respiratory Syndrome Coronavirus Pseudoparticles: Implications for Assembly and Vaccine Production", J. Virol,, 78(22), (Nov. 2004), 12557-12565.
Huddleston, J. A., et al., "The Sequence of the Nucleoprotein Gene of Human Influenza A Virus, Strain A/NT/60/68", Nucleic Acids Research, 10(3), (1982), 1029-1038.
Huggins, J., et al., "Antiviral drug therapy of filovirus infections: S-adenosylhomocysteine hydrolase inhibitors inhibit Ebola virus in vitro and in a lethal mouse model.", Journal of Infectious Diseases, vol. 179, NR .(Suppl 1), XP002574255 ISSN: 0022-1899 abstract, (Feb. 1999), 240-247.

Hughes, M. T., et al., "Adaptation of Influenza A Viruses to Cells Expressing Low Levels of Sialic Acid Leads to Loss of Neuraminidase Activity", Journal of Virology, 75(8), (2001), 3766-3770.
Hughes, M. T., et al., "Influenza A Viruses Lacking Sialidase Activity Can Undergo Multiple Cycles of Replication in Cell Culture, Eggs, or Mice", Journal of Virology, 74 (11), (2000), 5206-5212.
Hughes, M. T, et al., "Influenza A Viruses Lacking Sialidase Activity Can Undergo Multiple Cycles of Replication in Cell Culture, Eggs, or Mice", Journal of Virology, 74(11) 5206-212, (2000), 7 pgs.
Huisman, W., et al., "Vaccine-induced enhancement of viral infections", Vaccine, 27(4), (2009), 505-512.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Hurt, A. C, et al., "Identification of a human influenza type B strain with reduced sensitivity to neuraminidase inhibitor drugs", Virus Research, vol. (103), (2004), 205-211.
Hutchinson, Edward C., et al., "Genome packaging in influenza A virus", Journal of General Virology, 91(Pt 2), (2010), 313-328.
Hwang, Jung-Shan, et al., "Expression of Functional Influenza Virus RNA Polymerase in the Methylotrophic Yeast *Pichia pastoris*", Journal of Virology, 74(9), (2000), 4074-4084.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.
Ito, T, et al., "Differences in Sialic Acid-Galactose Linkages in the Chicken Egg Amnion and Allantois Influence Human Influenza Virus Receptor Specificity and Variant Selection", Journal of Virology, 71 (4), (Apr. 1997), 3357-3362.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun. 2006), 5233-40.
Jackson, et al., "Characterization of recombinant influenza B viruses with key neuraminidase inhibitor resistance mutations,", Journal of Antimicrobial Chemotherapy, vol. 55, (2005), 162-169.
Jackson, D., et al., "A reverse genetics approach for recovery of recombinant influenza B viruses entirely from cDNA.", J Virol., 76(22), (Nov. 2002), 11744-7.
Jahrling, P. B., et al., "Ebola Hemorrhagic Fever: Evaluation of Passive Immunotherapy in Nonhuman Primates", J. Infect. Dis. 196, (2007), 4 pgs.
Jang, S.-W., et al., "Deoxygedunin, a Natural Product with Potent Neurotrophic Activity in Mice", PLoS ONE 5(7): e11528, (2010), 1-15.
Jasenosky, Luke D, et al., "Ebola Virus VP40-Induced Particle Formation and Association with the Lipid Bilayer", Journal of Virology, 75 (110, (Jun. 2001), 5205-5214.
Jennings, Philip A., et al., "Does the Higher Order Structure of the Influenza Virus Ribonucleoprotein Guide Sequence Rearrangements in Influenza Viral RNA?", Cell, 34, (Sep. 1983), 619-627.
Jiang, H, et al., "Influenza virus genome C4 promoter/origin attenuates its transcription and replication activity by the low polymerase recognition activity", Virology, 408(2), (2010), 190-196.
Jiang, Y., et al., "Genome wide analysis of protein protein interactions and involvement of viral proteins in SARS CoV 2 replication", Cell Biosci, 11:140, 2021, 16 pgs., (2021), 16 pgs.
Jin, H., et al., "Imparting temperature sensitivity and attenuation in ferrets to A/Puerto Rico/8/34 influenza virus by transferring the genetic signature for temperature sensitivity from cold-adapted A/Ann Arbor/6/60", Journal of Virology, 78(2), (2004), 995-998.
Jin, H., et al., "Influenza virus hemagglutinin and neuraminidase cytoplasmic tails control particle shape", The EMBO Journal, 16(6), (1997), 1236-1247.

(56) References Cited

OTHER PUBLICATIONS

Jin, H., et al., "The influenza virus hemagglutinin cytoplasmic tail is not essential for virus assembly or infectivity", The EMBOL Journal, 13(22), (1994), 5504-5515.

Johnson, David A, et al., "TLR4 Agonists as Vaccine Adjuvants", Vaccine Adjuvants and Delivery Systems, (2007), 131-156.

Johnson, R. F., et al., "Ebola Virus VP35-VP40 Interaction Is Sufficient for Packaging 3E-5E Minigenome RNA into Virus-Like Particles", Journal of Virology, 80(11), (Jun. 2006), 5135-5144.

Ju, X., et al., "A novel cell culture system modeling the SARS-CoV-2 life cycle", PloS Pathogens, 17(3): e1009439, (2021), 23 pgs.

Justice, P. A., et al., "Membrane Vesiculation Function and Exocytosis of Wild-Type and Mutant Matrix Proteins of Vesicular Stomatitis Virus", Journal of Virology, 69(5), (1995), 3156-3160.

Kang, Byoung-Hoon, et al., "Ultrafast and Real-Time Nanoplasmonic On-Chip Polymerase Chain Reaction for Rapid and Quantitative Molecular Diagnostics", ACS Nano, 15(6), (2021), 10194-10202.

Kaplan, G., et al., "In vitro Synthesis of Infectious Poliovirus RNA", Proc. Natl. Acad. Sci. USA, 82, (1985), 8824-8428.

Katinger, D., et al., "Attenuated Influenza Viruses as a Vector for Mucosal Immunization Against HIV-1", Vaccines, 97, Cold Spring Harbor, (1997), 315-319.

Kato, A., et al., "Initiation of Sendai Virus Multiplication From Transfected cDNA or RNA With Negative or Positive Sense", Genes to Cells, 1, (1996), 569-579.

Kawaoka, Y, et al., "Sequence requirements for cleavage activation of influenza virus hemagglutinin expressed in mammalian cells", Proc Natl Acad Sci., 85(2), (1988), 324-328.

Kawaoka, Y., "Identification by siRNA of host proteins involved in Ebolavirus replication", Great Lakes Regional Center of Excellence for Biodefense and Emerging Infectious Diseases Research, [Online]; Retrieved from the Internet: URL:http://www.rcebiodefense.org/girce/docs/2007/Kawaoka.pdf> [retrieved on Jan. 13, 2010] p. 10, under item C,—-& Anonymous: "Index of GLRCE: documents from 2007" Great Lakes Regional Center of Excellence Index, [Online] 2007, XP002563469 Retrieved from the Internet: URL:http://www.rcebiodefense.org/girce/docs/2007/> [retrieved on Jan. 14, 2010]—& Kawaoka Y .:, (2007), pp. 1-19.

Kawaoka, Y., "Mutant Cells With Altered Sialic Acid", U.S. Appl. No. 11/644,179, filed Dec. 22, 2006, 51 pgs.

Kawaoka, Y., "Prevention and Control of Ebola Virus Infection (Ongoing Research)", Great Lakes Regional Center of Excellence (GLRCE) Annual Meeting Schedule, (Abstract), [online] [retrieved on Jan. 14, 2010]. Retrieved from the Internet: <URL:http://www.rcebiodefense.org/glrce/annualmeeting/2007Agenda.pdf>, (Nov. 29, 2007), 4 pgs.

Keitel, W. A., et al., "Chapter 28—Live Cold-Adapted, Reassortant Influenza Vaccines (USA)", In: Textbook of Influenza, Nicoholson, K. G., et al., Editors, Blackwell Science Ltd., (1998), 373-390.

Kijima, H., et al., "Therapeutic Application of Ribozymes", Pharmac. Ther., 68(2), (1995), 247-267.

Kilbourne, E. D, et al., "Related studies of a recombinant influenza-virus vaccine. I. Derivation and characterization of virus and vaccine", J Infect Dis., 124(5), (Nov. 1971), 449-62.

Kim, H., et al., "Cold adaptation generates mutations associated with the growth of influenza B vaccine viruses", Vaccine, 33(43), (2015), 5786-5793.

Kim, Min-Chul, et al., "Supplementation of Influenza Split Vaccines with Conserved M2 Ectodomains Overcomes Strain Specificity and Provides Long-term Cross Protection", Molecular Therapy, 22(7), (2014), 1364-1374.

Kimura, N., et al., "An In Vivo Study of the Replication Origin in the Influenza Virus Complementary RNA", The Journal of Biochemistry, 113(1), (1993), 88-92.

Kimura, N., et al., "Transcription of a Recombinant Influenza Virus RNA in Cells That Can Express the Influenza Virus RNA Polymerase and Nucleoprotein Genes", Journal of General Virology, 73, (1992), 1321-1328.

Kiseleva, I., et al., "Role of individual genes of the A-Leningrad/134/17/57 (H2N2) cold-adapted donor strain in manifestation of the temperature-sensitive phenotype of reassortant influenza A viruses", International Congress Series, vol. 1263, (2004), 547-550.

Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.

Kistner, O., et al., "A Novel Mammalian Cell (Vero) Derived Influenza Virus Vaccine: Development, Characterization and Industrial Scale Production", Wiener Klinische Wochenschrift, 111/5, (1999), 207-214.

Kistner, O., et al., "Development of a mammalian cell (Vero) derived candidate influenza virus vaccine", Vaccine, 16(9-10), (May-Jun. 1998), 960-8.

Kistner, O., et al., "Development of a Vero Cell-Derived Influenza Whole Virus Vaccine", Dev. Biol. Stand., 98, (1999), 101-110.

Kistner, Otfried, et al., "Cell culture (Vero) derived whole virus (H5N1) vaccine based on wild-type virus strain induces cross-protective immune responses", Vaccine, 25(32), (2007), 6028-6036.

Kittel, Christian, et al., "Generation of an Influenza A Virus Vector Expressing Biologically Active Human Interleukin-2 from the NS Gene Segment", Journal of Virology, 79(16), (Aug. 2005), 10672-10677.

Kobayashi, H., et al., "A replication-incompetent influenza virus bearing the HN glycoprotein of human parainfluenza virus as a bivalent vaccine", Vaccine, 31(52), (2013), 6239-6246.

Kobayashi, M., et al., "Reconstitution of Influenza Virus RNA Polymerase From Three Subunits Expressed Using Recombinant Baculovirus System", Virus Research, 22, (1992), 235-245.

Kochendoerfer, G. G, et al., "Total Chemical Synthesis of the Integral Membrane Protein Influenza A Virus M2: Role of its C-Terminal Domain in Tetramer Assembly", Biochemistry 38, (1999), 11905-11913.

Kon, Theone C, et al., "Influenza Vaccine Manufacturing: Effect of Inactivation, Splitting and Site of Manufacturing. Comparison of Influenza Vaccine Production Processes", PLoS ONE, 11(3), e0150700, (Mar. 9, 2016), 19 pgs.

Konarska, M. M., et al., "Structure of RNAs Replicated by the DNA-Dependent T7 RNA Polymerase", Cell, 63(2), (1990), 609-618.

Konduru, K., et al., "Ebola virus glycoprotein Fc fusion protein confers protection against lethal challenge in vaccinated mice", Vaccine, 29(16), (Apr. 5, 2011), 2968-77.

Koopmans, M., et al., "Transmission of H7N7 Avian Influenza Virus to Human Beings During a Large Outbreak in Commercial Poultry Farms in the Netherlands", The Lancet, 363 587-593, (2004), 7 pgs.

Kopecky, S. A, et al., "Matrix protein and another viral component contribute to induction of apoptosis in cells infected with vesicular stomatitis virus", J Virol., 75(24), (Dec. 2001). Abstract Only.

Kovacova, A., et al., "Sequence similarities and evolutionary relationships of influenza virus A hemagglutinins.", Virus Genes, 24(1), (2002), 57-63.

Kovacova, Andrea, et al., "Sequence Similarities and Evolutionary Relationships of Influenza Vrus A Hemagglutinins", Virus Genes, 24(1), (2002), 57-63.

Kovesdi, I., et al., "Adenoviral Vectors for Gene Transfer", Current Opinion in Biotechnology, 8(5), (Oct. 1997), 583-589.

Krystal, M., et al., "Expression of the Three Influenza Virus Polymerase Proteins in a Single Cell Allows Growth Complementation of Viral Mutants", Proc. Natl. Acad. Sci. USA, 83, (1986), 2709-2713.

Krystal, M., "Influenza B/Lee/40, hemagglutinin (seg 4), complete segment.", Database EM_VI E.B.I. Hinxton U.K., (Apr. 25, 1990), 9 pgs.

Kugelman, J. R., et al., "Emergence of Ebola Virus Escape Variants in Infected Nonhuman Primates Treated with the MB-003 Antibody Cocktail", Cell Reports 12, (Sep. 2015), 2111-2120.

Kumar, P. K. R., et al., "Artificial Evolution and Natural Ribozymes", The FASEB Journal, 9, (1995), 1183-1195.

(56) References Cited

OTHER PUBLICATIONS

Kunik, Vered, et al., "Paratome: an online tool for systematic identification of antigen-binding regions in antibodies based on sequence or structure", Nucleic Acids Research, Volume 40, Issue W1, (2012), W521-W524.

Kunkel, T. A., "Rapid and Efficient Site-Specific Mutagenesis Without Phenotypic Selection", Proc. Natl. Acad. Sci. USA, 82, (1985), 488-492.

Kuwahara, Tomoko, et al., "Characterization of cell-derived and egg-passaged influenza A/Saitama/103/2014 (H3N2) strain", The 65th Annual Meeting of the Japanese Society of Virology, (2017), 1 pg.

Kuwahara, Tomoko, et al., "Isolation of an Egg-Adapted Influenza A(H3N2) Virus without Amino Acid Substitutions at the Antigenic Sites of Its Hemagglutinin", Japanese Journal of Infectious Diseases, 71(3), (2018), 234-238.

Lamb, Robert A., et al., "Chapter 20—Paramyxoviridae: The Viruses and Their Replication", In: Fundamental Virology, Fields, B. N., et al., editors, Lippincott-Raven (2nd Edition), (1996), 577-647.

Latham, T, et al., "Formation of Wild-Type and Chimeric Influenza Virus-Like Particles following Simultaneous Expression of Only Four Structural Proteins", Journal of Virology 75 (13), (2001), 6154-6165.

Lawson, N. D., "Recombinant Vesicular Stomatitis Viruses From DNA", Proc. Natl. Acad. Sci. USA, 92(10), (1995), 4477-4481.

Laxman, B., "Noninvasive Real-Time Imaging of Apoptosis", PNAS, 99(26), (2002), 16551-16555.

Lazarovits, Janette, et al., "Endocytosis of Chimeric Influenza Virus Hemaggulutinin Proteins That Lack a Cytoplasmic Recognition Feature for Coated Pits", The Journal of Cell Biology, vol. 134, No. 2, (1996), 339-348.

Le, T., "CaSpeR5, a family of *Drosophila* transgenesis and shuttle vectors with improved multiple cloning sites", Biotechniques, 42(2), (Feb. 2007), 164-166.

Leahy, M. B., et al., "An Endonuclease Switching Mechanism in the Virion RNA and cRNA Promoters of Thogoto Orthomyxovirus", Journal of Virology, 72(3), (1998), 2305-2309.

Leahy, M. B., et al., "In Vitro Polymerase Activity of Thogoto Virus: Evidence for a Unique Cap-Snatching Mechanism in a Tick-Borne Orthomyxovirus", Journal of Virology, 71(11), (1997), 8347-8351.

Leahy, M. B., et al., "Striking Conformational Similarities between the Transcription Promoters of Thogoto and Influenza A Viruses: Evidence for Intrastrand Base Pairing in the 5' Promoter Arm", Journal of Virology, 71(11), (1997), 8352-8356.

Leal, et al., "New challenges in therapeutic vaccines against HIV infection", Expert Review of Vaccines, vol. 16, No. 6, (2017), 587-600.

Lee, C. W, et al., "Generation of reassortant influenza vaccines by reverse genetics that allows utilization of a DIVA (Differentiating Infected from Vaccinated Animals) strategy for the control of avian influenza", Vaccine, vol. 22, (2004), 3175-3181.

Lee, D.-H., et al., "H9N2 avian influenza virus-like particle vaccine provides protective immunity and a strategy for the differentiation of infected from vaccinated animals", Vaccine, vol. 29, (2011), 4003-4007.

Lee, Dong-Hun, et al., "Progress and hurdles in development of influenza virus-like particle vaccines for veterinary use", Korean Vaccine Society, (2014), 133-139.

Lee, Jeffrey E., et al., "Complex of a Protective Antibody with Its Ebola Virus GP Peptide Epitope: Unusual Features of a V?x Light Chain", J. Mol. Biol., 375, (2007), 202-216.

Lee, Jong-Soo, et al., "The Highly Conserved HA2 Protein of the Influenza A Virus Induces a Cross Protective Immune Response", Journal of Virological Methods, 194(1-2), (2013), 280-288.

Lee, M. S, et al., "Genetic and pathogenic characterization of H6NI avian influenza viruses isolated in Taiwan between 1972 and 2005", Avian Diseases, 50(4), (Dec. 2006), 561-571.

Lefranc, Marie-Paule, et al., "IMGT unique numbering for immunoglobulin and T cell receptor variable domains and Ig superfamily V-like domains", Developmental & Comparative Immunology, 27, (2003), 55-77.

Lembo, A, et al., "Administration of a synthetic TLR4 agonist protects mice from pneumonic tularemia.", J Immunol., 180(11), 7574-81.

Levis, R., et al., "Deletion Mapping of Sindbis Virus DI RNAs Derived From cDNAs Defines the Sequences Essential for Replication and Packaging", Cell, 44, (1986), 137-145.

Li, Feng, et al., "Generation of Replication-Competent Recombinant Influenza A Viruses Carrying a Reporter Gene Harbored in the Neuraminidase Segment", Journal of Virology, 84(22), (Nov. 2010), 12075-12081.

Li, Junwei, et al., "Engineering Influenza Viral Vectors", Bioengineered, vol. 4, No. 1, (Jan. 1, 2013), 9-14.

Li, K. S., et al., "Genesis of a highly pathogenic and potentially pandemic H5N1 influenza virus in eastern Asia", Nature, vol. 430, (2004), 209-213 pgs.

Li, K. S, et al., "Genesis of a highly pathogenic and potentially pandemic H5NI influenza virus in eastern Asia", Nature, 430(6996), (Jul. 8, 2004), 209-213.

Li, Qi, et al., "Screening of the high yield influenza B virus on MDCK cell and cloning of its whole genome", (English Abstract), Chinese Journal of Virology, 3, (Sep. 30, 2004), 1 pg.

Li, Qi, et al., "Screening of the high yield influenza B virus on MDCK cell and cloning of its whole genome", International Congress Series 1263, (2004), 610-614.

Li, S., et al., "Electroporation of Influenza Virus Ribonucleoprotein Complexes for Rescue of the Nucleoprotein and Matrix Genes", Virus Research, 37(2), (1995), 153-161.

Li, S., et al., "Influenza A Virus Transfectants with Chimeric Hemagglutinins Containing Epitopes from Different Subtypes", Journal of Virology, 66(1), (1992), 399-404.

Li, S., et al., "Recombinant Influenza A Virus Vaccines for the Pathogenic Human A/Hong Kong/97 (H5N1) Viruses", J Infect Dis., 179(5), (1999), 1132-1138.

Li, Shengqiang, et al., "Influenza A Virus Transfectants with Chimeric Hemagglutinins containing Epitopes from different subtypes", Journal of Virology 399-404, (1992), 6 pgs.

Li, Y, et al., "The I binding specificity of human VH4-34 (VH4-21) encoded antibodies is determined by both VH framework region 1 and complementarity determining region 3", J. Mol. Biol. 256 577-589, (1996), 13 pgs.

Li, Y, et al., "Viral liposomes released from insect cells infected with recombinant baculovirus expressing the matrix protein of vesicular stomatitis virus", Journal of Virology, 67 (7). (1993), 4415-4420.

Lin Y P, et al., "Adaptation of egg-grown and transfectant influenza viruses for growth in mammalian cells: selection of hemagglutinin mutants with elevated pH of membrane fusion", Virology, 233(2), (1997), 402-410.

Lin, Yi Pu, et al., "Adaptation of Egg-Grown and Transfectant Influenza Viruses for Growth in Mammalian Cells: Selection of Hemagglutinin Mutants with Elevated pH of Membrane Fusion", Virology, Vol. 233, Issue 2, (1997), 402-410.

Liu, Bo, et al., "Comparison of three methods in construction fusion gene of influenza A virus Nucleoprotein", (English Abstract), Zhonghua Shi Yan He Lin Chuang Bing Du Xue Za Zhi, 26(1), 70-74, (Feb. 2012), 1 pg.

Liu, C., et al., "Influenza type A virus neuraminidase does not play a role in viral entry, replication, assembly, or budding.", Journal of Virology, 69(2), (1995), 1099-1106.

Liu, C., et al., "Selection and Characterization of a Neuraminidase-Minus Mutant of Influenza Virus and its Rescue by Cloned Neuraminidase Genes", Virology, 194(1), (1993), 403-407.

Liu, Y., et al., "A live-attenuated SARS-CoV-2 vaccine candidate with accessory protein deletions", bioRxiv [online]. [retrieved Jun. 10, 2022]. Retrieved from the Internet: <URL: https://www.biorxiv.org/content/10.1101/2022.02.14.480460v1.full.pdf>, (2022), 44 pgs.

Liu Z, et al., "Fine mapping of the antigen-antibody interaction of scFv215 A recombinant antibody inhibiting RNA polymerase II from *Drosophila melanogaster*", J. Mol. Recog. 12:103-111, (1999), 9 pgs.

(56) References Cited

OTHER PUBLICATIONS

Lobo, Ingrid A., "Predicting Vaccine Effectiveness Using Systems Biology", Nature Education, 8(3):9, [online]. Retrieved from the Internet: <URL: https://www.nature.com/scitable/nated/topicpage/predicting-vaccine-effectiveness-using-systems-biology-132628443>, (2015), 4 pgs.

Longnecker, R., et al., "WW- and SH3-domain interactions with Epstein-Barr virus LMP2A", Exp Cell Res., 257(2), (Jun. 15, 2000), Abstract Only.

Lott, W. B., et al., "A Two-Metal Ion Mechanism Operates in the Hammerhead Ribozyme-Mediated Cleavage of an RNA Substrate", Proc. Natl. Acad. Sci. USA, 95, (1998), 542-547.

Lu, Xiuhua, et al., "Cross-protective immunity in mice induced by live-attenuated or inactivated vaccines against highly pathogenic influenza A (H5N1) viruses", Vaccine, 24(44-46), (2006), 6588-6593.

Lugovtsev, V. Y., et al., "Genetic Composition and Mutational Pattern of Influenza B Viruses Adapted to Replication in Embryonated Eggs", GenBank: AAT69446.1, (2005), 1 pg.

Luo, M., "Inhibitors of Influenza Virus Neuraminidase", Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.

Luytjes, W., "Amplification, Expression, and Packaging of a Foreign Gene by Influenza Virus", Cell, 59(6), (1989), 1107-1113.

Ma, Y.-J., et al., "Cellular micro RNA let-7c inhibits M1 protein expression of the H1N1 influenza A virus in infected human lung epithelial cells", J. Cell. Mol. Med., 16(10), (2012), 2539-2546.

Manicassamy, Balaji, et al., "Analysis of in vivo dynamics of influenza virus infection in mice using a GFP reporter virus", Proc Natl Acad Sci. USA, 107(25), (2010), 11531-11536.

Mansky, L. M, "Retrovirus mutation rates and their role in genetic variation", J Gen Virol., 79 (Pt 6), (Jun. 1998), 1337-45.

Manz, Benjamin, et al., "Disruption of the Viral Polymerase Complex Assembly as a Novel Approach to Attenuate Influenza A Virus", The Journal of Biological Chemistry, 286(10), (2011), 8414-8424.

Mark, A, et al., "Effect of Mutations and Deletions in a Bicistronic mRNA on the Synthesis of Influenza B Virus NB and NA Glycoproteins", Journal of Virology, vol. 77, No. 10, (May 2003). 6050-6054.

Marsh, Glenn A., et al., "Specific Residues of the Influenza A Virus Hemagglutinin Viral RNA Are Important for Efficient Packaging into Budding Virions", Journal of Virology, 81(18), (Sep. 2007), 9727-9736.

Martin, J., et al., "Studies of the Binding Properties of Influenza Hemagglutinin Receptor-Site Mutants", Virology, 241(1), (Feb. 1, 1998), 101-111.

Martinez-Sobrido, L., et al., "Hemagglutinin-Pseudotyped Green Fluorescent Protein-Expressing Influenza Viruses for the Detection of Influenza Virus Neutralizing Antibodies", J Virol., 84(4), (2010), 2157-2163.

Martorelli Di, Genova B., et al., "Intestinal delta-6-desaturase activity determines host range for Toxoplasma sexual reproduction", PLOS Biology, vol. 17, No. 8, E3000364, (Aug. 20, 2019), XP055619380, (Aug. 20, 2019), 1-19.

Masuda, H., et al., "Substitution of Amino Acid Residue in Influenza A Virus Hemagglutinin Affects Recognition of Sialyl-Oligosaccharides Containing N-Glycolylneuraminic Acid", FEBS Letters, 464, (1999), 71-74.

Matrosovich, M, et al., "Overexpression of the [alpha]-2,6-sialyltransferase in MDCK cells increases influenza virus sensitivity to neuraminidase inhibitors", Journal of Virology, The American Society for Microbiology, US, vol. 77, No. 15, (Aug. 1, 2003), 8418-8425.

Matsuoka, et al., "Neuraminidase Stalk Length and Additional Glycosylation of the Hemagglutinin Influence the Virulence of Influenza H5N1 Viruses for Mice", Journal of Virology, vol. 83, No. 9,, (2009), pp. 4704-4708.

Matsuzaki, Y., et al., "Epitope Mapping of the Hemagglutinin Molecule of A/(H1N1)pdm09 Influenza Virus by Using Monoclonal Antibody Escape Mutants", Journal of Virology, 88(21) 12364-12373, (2014), 10 pgs.

Matta, M, et al., "Cell-surface sialoglycoconjugate structures in wild-type and mutant Crithidia fasciculata", Parasitol. Res., 85(4), (1999), 293-299.

Mccown, M F, et al., "The influenza A virus M2 cytoplasmic tail is required for infectious virus production and efficient genome packaging.", J Virol., 79(6), (Mar. 2005), 3595-605.

Mccown, M. F, et al., "Distinct domains of the influenza a virus M2 protein cytoplasmic tail mediate binding to the M1 protein and facilitate infectious virus production.", J Virol., 80(16), (Aug. 2006), 8178-89.

Mccullers, et al., "Multiple Genotypes of Influenza B Virus Circulated between 1979 and 2003,", Journal of Virology, vol. (78), No. (23) 12817-12828, (2004), 13 pgs.

Mccullers, Jonathan A., et al., "A single amino acid change in the C-terminal domain of the matrix protein M1 of influenza B virus confers mouse adaption and virulence", Virology, 336(2) 318-326, (Jun. 5, 2005), 9 pgs.

Mckee, dwight L, et al., "Candidate drugs against SARS-CoV-2 and COVID-19", Pharmacological Research, Academic Press, London, GB, vol. 157, (Apr. 29, 2020), 9 pgs.

Mckimm, J. L., et al., "Mutations in a Conserved Residue in the Influenza Virus Neuraminidase Active Site Decreases Sensitivity to Neu5Ac2en-Derived Inhibitors", Journal of Virology, 72(3), (1998), 2456-2462.

Mcsharry, J. J, et al., "Phenotypic Drug Susceptibility Assay for Influenza Virus Neuraminidase Inhibitors", Clinical and Diagnostic Laboratory Immunology vol. 11, No. 2., (2004), 10 pgs.

Mebatsion, Teshome, et al., "Budding of Rabies Virus Particles in the Absence of the Spike Glycoprotein", Cell, 84(6), (1996), 941-951.

Mebatsion, Teshome, et al., "Matrix Protein of Rabies Virus Is Responsible for the Assembly and Budding of Bullet-Shaped Particles and Interacts with the Transmembrane Spike Glycoprotein G", Journal of Virology, 73 (1), (Jan. 1999), 242/250.

Mena, I., "Rescue of a Synthetic Choramphenicol Acetyltransferase RNA into influenza Virus-Like Particles obtained from recombinant plasmids", Journal of Virology, 70(8), (1996), 5016-5024.

Mena, I., et al., "Synthesis of biologically active influenza virus core proteins using a vaccinia virus- T7 RNA polymerase expression system", Journal of General Virology, 75 2109-2114, (1994), 6 pgs.

Mena, 1., et al., "Synthesis of Biologically Active Influenza Virus Core Proteins Using a Vaccinia Virus-T7 RNA Polymerase Expression System", Journal of General Virology, 75, (1994), 2109-2114.

Mishin, V. P. et al., "Protection afforded by intranasal immunization with the neuraminidase-lacking mutant of influenza A virus in a ferret model", Vaccine, 23(22), (Apr. 22, 2005), 2922-7.

Mitnaul, et al., "The Cytoplasmic Tail of Influenza a Virus Neuraminidase (NA) Affects NA Incorporation into Virons, Viron Morphology, and Virulence in Mice but is not essential for Virus Replication", Journal of Virology, 70 (2), (1996), 873-879.

Mitnaul, L. J., et al., "Balanced Hemagglutinin and Neuraminidase Activities are Critical for Efficient Replication of Influenza A Virus", Journal of Virology, 74 (13), (2000), 6015-6020.

Mittler, E., et al., "Role of the transmembrane domain of marburg virus surface protein GP in assembly of the viral envelope.", J Virol., 81(8), (Apr. 2007), 3942-8.

Miyoshi, H., et al., "Development of Self-Inactivating Lentivirus Vector", Journal of Virology, 72(10), (1998), 8150-8157.

Monto, A. S, et al., "Detection of influenza viruses resistant to neuraminidase inhibitors in global surveillance during the first 3 years of their use", Antimicrobal Agents and Chemotherapy, 50(7) 2395-2402, (2006), 8 pgs.

Monto, Arnold S, et al., "Comparative efficacy of inactivated and live attenuated influenza vaccines.", N Engl J Med., 361(13) 1260-7, (Sep. 24, 2009), 8 pgs.

Morita, S., et al., "Plat-E: an efficient and stable system for transient packaging of retroviruses", Gene Therapy, 7(12), (2000), 1063-1066.

(56) References Cited

OTHER PUBLICATIONS

Moss, B., et al., "New Mammalian Expression Vectors", Nature, 348, (1990), 91-92.

Moyer, S. A., et al., "Assembly and Transcription of Synthetic Vesicular Stomatitis Virus Nucleocapsids", Journal of Virology, 65(5), (1991), 2170-2178.

Muhlberger, E., et al., "Comparision orf the Transcription and Replication Strategies of Marburg Virus and Ebola Virus by Using Artificial Replication Systems", Journal of Virology, 73(3) 2333-2342, (1999), 10 pgs.

Muhlberger, E., et al., "Three of the four nucleocapsid proteins of Marburg virus, NP, VP35, and L, are sufficient to mediate replication and transcription of Marburg virus-specific monocistronic minigenomes", Journal of Virology, 72(11) 8756-8764, (1998), 11 pgs.

Muhlberger, Elke, "Filovirus replication and transcription", Future Virol., 2:205, (2007), 16 pgs.

Murakami, Shin, et al., "Enhanced Growth of Influenza Vaccine Seed Viruses in Vero Cells Mediated by Broadening the Optimal pH Range for Virus Membrane Fusion", J Virol 86(3), (2012), 1405-1410.

Murakami, Shin, et al., "Growth Determinants for H5N1 Influenza Vaccine Seed Viruses in MDCK Cells", Journal of Virology, vol. 82, No. 21, (Nov. 2008), 10502-10509.

Muramoto, Y., et al., "Hierarchy among Viral RNA (vRNA) Segments in Their Role in vRNA Incorporation into Influenza A Virions", J. Virol., 80(5), (2006), 2318-2325.

Muramoto, Yukiko, "Hierarchy among Viral RNA (vRNA) Segments in Their Role in vRNA Incorporation into Influenza A Virions", Journal of Virology, 80(5), (2006), 2318-2325.

Murphy, B. R, et al., "An influenza A live attenuated reassortant virus possessing three temperature-sensitive mutations in the PB2 polymerase gene rapidly loses temperature sensitivity following replication in hamsters", Vaccine, 15(12-13) 1372-8, (1997), 7 pgs.

Murphy, Brian R, et al., "Virulence of Avian Influenza A Viruses for Squirrel Monkeys", Infection and Immunity 37 (3), (Sep. 1982), 1119-1126.

Muster, T., et al., "An Influenza A Virus Containing Influenza B Virus 5' and 3' Noncoding Regions on the Neuraminidase Gene is Attenuated in Mice", Proc. Natl. Acad. Sci. USA, 88, (1991), 5177-5181.

Muyldermans, S, "Nanobodies: Natural single-domain antibodies", Ann. Rev. Biochem. 82, (2013), 1 pg.

Naim, H. Y., et al., "Basis for Selective Incorporation of Glycoproteins into the Influenza Virus Envelope", Journal of Virology, 67(8), (1993), 4831-4841.

Naito, S., et al., "Function and Structure of RNA Polymerase From Vesicular Stomatitis Virus", The Journal of Biological Chemistry, 251(14), (1976), 4307-4314.

Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.

Neirynck, S., "A universal influenza A vaccine based on the extracellular domain of the M2 protein", Nature Medicine, 5 (10), (Oct. 1999), pp. 1157-1163.

Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.

Neumann, G., et al., "A Decade After the Generation of a Negative-Sense RNA Virus From Cloned cDNA-What Have We Learned?", Journal of General Virology, 83(11), (Nov. 2002), 2635-2662.

Neumann, G., et al., "An Improved Reverse Genetics System for Influenza A Virus Generation and Its Implications for Vaccine Production", Proc. Natl. Acad. Sci. USA, 102(46) 16825-16829, (2005), 5 pgs.

Neumann, G., et al., "An improved reverse genetics system for influenza A virus generation and its implications for vaccine production", Proc. Natl. Acad. Sci. USA. 102(46), (2005), 16825-16829.

Neumann, G., et al., "Emergence and pandemic potential of swine-origin H1N1 influenza virus", Nature (London), 459(7249), (Jun. 2009), 931-939 .

Neumann, G., et al., "Generation of influenza A virus from cloned cDNAs—historical perspective and outlook for the new millenium. ", Rev Med Virol., 12(1), XP002314285, (Jan.-Feb. 2002), 13-30.

Neumann, G., et al. "Generation of influenza A viruses entirely from cloned cDNAs", Proc. Natl. Acad. Sci. USA., 96(16), (1999), 9345-9350.

Neumann, G., et al., "Genetic Engineering of Influenza and Other Negative-Strand RNA Viruses Containing Segmented Genomes", Advances in Virus Research, 53, (1999), 265-300.

Neumann, G., et al., "Influenza A virus NS2 protein mediates vRNP nuclear export through NES-independent interaction with hCRM1", The EMBO Journal, 19 (24), (2000), 6751-6758.

Neumann, G., et al., "Mutational analysis of influenza virus promoter elements in vivo", Journal of General virology, 76 1709-1717, (1995), 9 pgs.

Neumann, G., et al., "Nuclear Import and Export of Influenza Virus Nucleoprotein", Journal of Virology, 71(12), (1997), 9690-9700.

Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.

Neumann, G., et al., "Reverse genetics of influenza virus.", Virology, 287(2), (Sep. 1, 2001), 243-50.

Neumann, G., et al., "Reverse Genetics of Influenza Viruses—Applications in Research and Vaccine Design", Monographs in Virology, 27, (2008), 118-133.

Neumann, G., et al., "RNA Polymerase I-Mediated Expression of Influenza Viral RNA Molecules", Virology, 202(1), (1994), 477-479.

Neumann, G., et al., "Synthesis of Influenza Virus: New impetus from an old enzyme, RNA polymerase I", Virus Research 82(1-2), (Jan. 30, 2002), 153-158.

Neumann, Gabriele, "MINIREVIEW Reverse Genetics of Influenza Virus", Virology, vol. 287, (2001), 243-250.

Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.

Nicolson, C., et al., "Generation of Influenza Vaccine Viruses on Vero Cells by Reverse Genetics: an H5N1 Candidate Vaccine Strain Produced Under a Quality System", Vaccine, 23 2943-2952, (2005), 10 pgs.

Niwa, H., et al., "Efficient Selection for High-Expression Transfectants With a Novel Eukaryotic Factor", Gene, 108(2), (1991), 193-199.

Noda, Takeshi, et al., "Three-dimensional analysis of ribonucleoprotein complexes in influenza A virus", Nature Communications, 3, (2012), 1-6.

Odagiri, T., et al., "Nucleotide Sequence of the PA Gene of Influenza A/WSN/33 (H1N1)", Nucleic Acids Research, 18 (3), Department of Virology, (Jan. 9, 1990), 1 pg.

Odagiri, Takato, et al., "Segment-Specific Noncoding Sequences of the In?uenza Virus Genome RNA Are Involved in the Speci?c Competition between Defective Interfering RNA and Its Progenitor RNA Segment at the Virion Assembly Step", Journal of Virology, 71(3), (1997), 2138-2145.

Olivo, P. D, et al., "Detection and quantitation of human respiratory syncytial virus (RSV) using minigenome cDNA and a Sindbis virus replicon: a prototype assay for negative-strand RNA viruses.", Virology, 251(1), (Nov. 10, 1998), 198-205.

Onishi, M., et al., "Applications of retrovirus-mediated expression cloning", Experimental Hematology, 24(2), (1996), 324-329.

Orkin, S. H, et al., "Report and Recommendations of the Panel to Assess the NIH Investment in Research on Gene Therapy", http://www.nih.gov/news/panelrep.html, (Dec. 7, 1995), 37 pgs.

Ozaki, "Generation of High-Yielding Influenza A Viruses in African Green Monkey Kidney (Vero) Cells by Reverse Genetics", J Virol 78(4), (2004), 1851-1857.

Ozaki, H., et al., "Generation of High-Yielding Influenza A Viruses in African Green Money Kidney (Vero) Cells by Reverse Genetiics", Journal of Virology, 78(4) 1851-1857, (2004), 6 pgs.

(56) References Cited

OTHER PUBLICATIONS

Ozawa, M., et al., "An adenovirus vector-mediated reverse genetics system for Influenza A virus generation", Journal of Virology, The American society for Microbiology, US vol. 81(17), XP002471230, ISSN: 0022-538X, (Jun. 27, 2007), 9556-9559.

Ozawa, M., et al., "Replication-incompetent influenza A viruses that stably express a foreign gene", Journal of General Virology, 92(Part 12)., (2011), 2879-2888.

Palache, A. M., et al., "Safety, Reactogenicity and Immunogenicity of Madin Darby Canine Kidney Cell-Derived Inactivated Influenza Subunit Vaccine. A Meta-Analysis of Clinical Studies", Dev. Biol. Stand., 98 133-134 abstract, (1999), 1 pg.

Palese, P., et al., "47. Orthomyxoviridae: The Viruses and Their Replication", In: Fields Virology (5th Edition), (2007), 90 pgs.

Palese, P., "Negative-Strand RNA Viruses: Genetic Engineering and Applications", Proc. Natl. Acad. Sci. USA, 93(21), (1996), 11354-11358.

Park, Eun K., et al., "The M2 Ectodomain is important for its incorporation into influenza A virions", J. of Virology, vol. 72, No. 3, XP002196797, (Mar. 1998), 2449-2455.

Park, K. H., et al., "Rescue of a Foreign Gene by Sendai Virus", Proc. Natl. Acad. Sci. USA, 88, (1991), 5537-5541.

Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.

Pattnaik, A. K., et al., "The Termini of VSV DI Particle RNAs are Sufficient to Signal RNA Encapsidation, Replication, and Budding to Generate Infectious Particles", Virology, 206, (1995), 760-764.

Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.

Peiris, J. S. M., et al., "Re-Emergence of Fatal Human Influenza A Subtype H5N1 Disease", The Lancet, 363 617-619, (2004), 3 pgs.

Pekosz, A., "Commentary—Reverse Genetics of Negative-Strand RNA Viruses: Closing the Circle", Proc. Natl. Acad. Sci. USA, 96, (1999), 8804-8806.

Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.

Pelet, T., et al., "High throughput screening assay for negative single stranded RNA virus polymerese inhibitors", Journal of Virological Methods, 128 29-36, (2005), 8 pgs.

Percy, N., et al., "Expression of a Foreign Protein by Influenza A Virus", Journal of Virology, 68(7), (1994), 4486-4492.

Perdue, M., et al., "Virulence and the Avian Influenza Virus Hemagglutinin Gene", United States Department of Agriculture—Agriculture Research Service, http://www.nps.ars.usda.gov/publications/publications.htm?SEQ_NO_155=106036, (Observed Feb. 22, 2003), 1 pg.

Perez, D. R., et al., "The Matrix 1 Pretein of Influenza A Virus Inhibits the Transcriptase Activity of a Model Influenza Reporter Genome in Vivo", Virology, 249(1), (1998), 52-61.

Perez, Jasmine T., et al., "UNIT 15G.4—Insertion of a GFP Reporter Gene in Influenza Virus", Caurr protoc Microbiol., (2013), 20 pgs.

Peterson, B. C., et al., "Homologous sequences other than insertion elements can serve as recombination sites in plasmid drug resistance gene amplification", Journal of Bacteriology, Oct. 1983 156(1) 177-185, 5 pgs.

Piatti, G., "Identification of immunodominant epitopes in the filamentous Hemagglutinin of Bordatella pertusis", FEMS Immunology and Medical Microbiology, 23(3), (1999), 235-241.

Piller, S.C., et al., "Vpr protein of human immunodeficiency virus type 1 forms cation-selective channels in planar lipid bilayers", PBAS, 93, (1996), 111-1115.

Ping, J., et al., "Development of high-yield influenza B virus vaccine viruses", Proc. Natl. Acad. Sci. USA, 113(51), (Dec. 5, 2016), E8296-E8305.

Ping, Jihui, et al., "Development of high-yield influenza A virus vaccine viruses", Nature Communications, [online]. Retrieved from the Internet: <http://www.nature.eom/article-assets/npg/ncomms/2015/150902/ncomms9148/extref/ncomms9148-s1.pdf>, (Sep. 2, 2015), 50 pgs.

Pinto, L. H., et al., "Influenza Virus M2 Protein Has Ion Channel Activity", Cell, 69, (May 1992), pp. 517-528.

Pittman, Kelly J., et al., "Z-DNA Binding Protein Mediates Host Control of Toxoplasma gondii Infection", Infection and Immunity, 84(10), (Oct. 2016), 3063-3070.

Plant, E P, et al., "Mutations to A/PuertoRico/8/34 PB1 gene improves seasonal reassortant influenza A virus growth kinetics", Vaccine, 31(1), (Dec. 1, 2012), 207-212.

Pleschka, S., et al., "A Plasmid-Based Reverse Genetics System for Influenza A Virus", Journal of Virology, 70(6), (1996), 4188-4192.

Pley, H. W., et al., "Three-Dimensional Structure of a Hammerhead Ribozyme", Nature, 372, (1994), 68-74.

Portela, A., et al., "Replication of orthomyxoviruses", Advances in Virus Research, 54, (1999), 319-348.

Potter, C. W., "Chapter 1—Chronicle of Influenza Pandemics", In: Textbook of Influenza, Nicholson, K. G., et al., Editors, (Blackwell Scientific Publication), (1998), 3-18.

Powell, Robin H., et al., "WRN conditioned media is sufficient for in vitro propagation of intestinal organoids from large farm and small companion animals", Biology Open, vol. 6, No. 5, (Mar. 27, 2017), XP055620505, (Mar. 27, 2017), 698-705.

Preston, Andrew, "Choosing a Cloning Vector", Methods in Molecular Biology, vol. 235, E. coli Plasmid Vectors 19-27, Edited by: N. Casali and A. Preston, (2003), 9 pgs.

Pushko, P., et al., "Replicon-Helper Systems from Attenuated Venezuelan Equine Encephalitis Virus: Expression of Heterologous Genes in Vitro and Immunization against Heterologous Pathogens in Vivo", Virology, 239(2), (Abstract Only), (1997), 1 page.

Puzelli, S., et al., "Changes in the Hemagglutinins and Neuraminidase of Human Influenza B Viruses Isolated in Italy During the Feb. 2001, Mar. 2002, and Apr. 2003 Seasons", Journal of Medical Virology, 74(4) 629-640, (2004), 12 pgs.

Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.

Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.

Racaniello, V. R., et al., "Cloned Poliovirus Complimentary DNA Is Infectious in Mammalian Cells", Science, 214, (1981), 4 pgs.

Radecke, F., et al., "Rescue of Measles Viruses From Cloned DNA", The EMBO Journal, 14(23), (1995), 5773-5784.

Radecke, F., et al., "Reverse Genetics Meets the Nonsegmented Negative-Strand RNA Viruses", Reviews in Medical Virology, 7, (1997), 49-63.

Ramanunninair, Manojkumar, et al., "Molecular Signature of High Yield (Growth) Influenza A Virus Reassortants Prepared as Candidate Vaccine Seeds", PLoS ONE, 8(6): e65955, (2013), 1-16.

Ray, M. K., et al., "A Novel Glycosylation Phenotype Expressed by Lec23, a Chinese Hamster Ovary Mutant Deficient in alpha-Glucosidase I", Journal of Biological Chemistry, 266(34), (1991), 22818-22825.

Rayner, J., et al., "Alphavirus vectors and vaccination", Reviews in Medical Virology, 12, (2002), 279-296.

Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.

Restifo, N. P., et al., "Transfectant Influenza A Viruses are Effective Recombinant Immunogens in the Treatment of Experimental Cancer", Virology, 249(1), (1998), 89-97.

Ricardo-Lax, I., et al., "Replication and single-cycle delivery of SARS-CoV-2 replicons", Science, 374(6571), (2021), 1099-1106 (9 pgs).

Rimmelzwaan, G. F., et al., "Use of GFP-expressing influenza viruses for the detection of influenza virus A/H5N1 neutralizing antibodies", Vaccine, 29(18), (2011), 3424-3430.

(56) References Cited

OTHER PUBLICATIONS

Roberts, A., et al., "Minireview—Recovery of Negative-Strand RNA Viruses From Plasmid DNAs: A Positive Approach Revitalizes a Negative Field", Virology, 247(1), (1998), 1-6.

Robison, C. S, et al., "The Membrane-Proximal Stem Region of Vesicular Stomatitis Virus G Protein Confers Efficient Virus Assembly", Journal of Virology, 74 (5), (Mar. 2000), 2239-2246.

Rodrigues, M., et al., "Influenza and Vaccinia Viruses Expressing Malaria CD8+ T and B Cell Epitopes. Comparison of Their Immunogenicity and Capacity to Induce Protective Immunity", J. Immunol., 153(10), (1994), 4636-4648.

Romanova, J., et al., "Live cold-adapted influenza A vaccine produced in Vero cell line", Virus Research, 103, (2004), 187-193.

Rose, J. K., "Positive Strands to the Rescue Again: A Segmented Negative-Strand RNA Virus Derived From Cloned cDNAs", Proc. Natl. Acad. Sci. USA, 94, (1996), 14998-15000.

Ruigrok, R W, et al., "Characterization of three highly purified influenza virus strains by electron microscopy", J Gen Virol 65 (Pt 4) 799-802, (Apr. 1984), 4 pgs.

Ruigrok, R W, et al., "Structural Characterization and Membrane Binding Properties of the Matrix Protein VP40 of Ebola Virus", Journal of Molecular Biology, 300(1), (2000), 103-112.

Ruiz-Arguello, M. B, et al., "Phosphatidylinositol-Dependent Membrane Fusion Induced by a Putative Fusogenic Sequence of Ebola Virus", Journal of Virology, 72(3), (Mar. 1998), 1775-1781.

Sansom, M. S., et al., "Influenza virus M2 Protein: a molecular modelling study of the ion channel", Protein Engineering, 6 (1), (1993), pp. 65-74.

Saphire, E. O., et al., "Feverish Quest for Ebola Immunotherapy: Straight or Cocktail", Trends Microbial, 24(9), (Sep. 2016), 684-686.

Satterlee, B., "Production of H5N1 avian influenza virus vaccine by plasmid-based reverse genetics technology", Basic Biotechnology eJournal, vol. 4, pp. 93-98, (2008), 93-98 Pgs.

Saunders, Kevin O., et al., "Neutralizing antibody vaccine for pandemic and pre-emergent coronaviruses", Nature, 594, (2021), 553-559 (27 pgs.).

Schares, G., et al., "Oocysts of Neospora caninum, Hammondia heydorni, Toxoplasma gondii and Hammondia hammondi in faeces collected from dogs in Germany", International Journal of Parasitology, vol. 35, No. 14, (Dec. 1, 2005), XP027737007, (Dec. 1, 2005), 1525-1537.

Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.

Schlesinger, S., "RNA Viruses as Vectors for the Expression of Heterologous Proteins", Molecular Biotechnology, 3(2), (1995), 155-165.

Schmidt, Kristina Maria, et al., "Marburg Virus Reverse Genetics Systems", Viruses 2016, 8, 178; doi: 10.3390 / v8060178, www.mdpi.com/journal/viruses, (2016), 17 pgs.

Schnell, M. J., "Infectious Rabies Viruses From Cloned cDNA", The EMBO Journal, 13(18), (1994), 4195-4203.

Schnell, Matthias J, et al., "Requirement for a non-specific glycoprotein cytoplasmic domain sequence to drive efficient budding of vesicular stomatitis virus", EMBO Journal, 17 (5), (1998), 1289-1296.

Schotsaert, M, et al., "Universal M2 ectodomain-based influenza A vaccines: preclinical and clinical developments", Expert Rev Vaccines. Apr. 2009;8(4):, 499-508.

Schultz-Cherry, S., et al., "Influenza Virus NS1 Protein Induces Apoptosis in Cultured Cells", Journal of Virology, 75(17), (2001), 7875-7881.

Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.

Sheridan, Cormac, et al., "Innovators target vaccines for variants and shortages in global South", Nature Biotechnology, 39(4), (Apr. 2021), 393-396.

Shi, Pei-Yong, "Infectious cDNA Clone of the Epidemic West Nile Virus from New York City", Journal of Virology 5847-5856, (Jun. 2002), 10 pgs.

Shimojima, M., et al., "Tyro3 family-mediated cell entry of Ebola and Marburg viruses", J Virol., 80(20), (Oct. 2006), 10109-16.

Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.

Shortridge, K. F., et al., "Characterization of Avian H5N1 Influenza Viruses From Poultry in Hong Kong", Virology, 252 331-342, (1998), 12 pgs.

Sidhu, M. S., et al., "Rescue of Synthetic Measles Virus Minireplicons: Measles Genomic Termini Direct Efficient Expression and Propagation of a Reporter Gene", Virology, 208. (1995), 800-807.

Silvas, J. A., et al., "Contribution of SARS-CoV-2 Accessory Proteins to Viral Pathogenicity in K18 Human ACE2 Transgenic Mice", J Virol, 95(17): e00402-21, (Sep. 2021), 1-14.

Siu, Y. L., et al., "The M, E, and N Structural Proteins of the Severe Acute Respiratory Syndrome Coronavirus Are Required for Efficient Assembly, Trafficking, and Release of Virus-Like Particles", J Virol., 82(22), (2008), 11318-11330.

Skehel, J. J., et al., "On the Mechanism of Inhibition of Influenza Virus Replication by Amantadine Hydrochloride", The Journal of General Virology, 38 (1), (1977), pp. 97-110.

Smatti, Maria K., et al., "Viral-Induced Enhanced Disease Illness", Front Microbiol, vol. 9: Article 2991, (Dec. 2018), 1-19.

Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.

Smura, T, "Surface glycoprotein [Severe acute respiratory syndrome coronavirus 2]", Gen Bank Accessions QH062107, (Feb. 11, 2020), 2 pgs.

Stray, S. J., et al., "Influenza virus infection of desialylated cells", Glycobiology, 10(7), (2000), 649-658.

Strobel, I., et al., "Efficient Expression of the Tumor-Associated Antigen MAGE-3 in Human Dendritic Cells, Using an Avian Influenza Virus Vector", Human Gene Therapy, 11(16), (2000), 2207-2218.

Stroud, Chad K., et al., "Disruption of FADS2 gene in mice impairs male reproduction and causes dermal and intestinal ulceration", Journal of Lipid Research, vol. 50, (2009), 1870-1880.

Subbarao, E. K., et al., "Rescue of an InfluenzaA Virus Wild-Type PB2 Gene and a Mutant Derivative Bearing a Site-Specific Temperature-Sensitive and Attenuating Mutation", Journal of Virology, 67(12), (1993), 7223-7228.

Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.

Subbarao, K., et al., "Characterization of an Avian Influenza A (H5N1) Virus Isolated From a Child With a Fatal Respiratory Illness", Science, 279, (1998), 393-396.

Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.

Sugawara, K., et al., "Development of Vero Cell-Derived Inactivated Japanese Encephalities Vaccine", Biologicals, 30 303-314, (2002), 12 pgs.

Sugrue, R. J., et al., "Specific structural alteration of the influenza haemagglutinin by amantadine", The EMBO Journal, 9 (11), (1990), pp. 3469-3476.

Sugrue, R. J., et al., "Structural Characteristics of the M2 Protein of Influenza A Viruses: Evidence That It Forms a Tetrameric Channel", Virology, 180, (1991), pp. 617-624.

Suguitan, A. L, et al., "Live, Attenuated Influenza A H5N1 Candidate Vaccines Provide Broad Cross-Protection in Mice and Ferrets", PLoS Med., 3(9), (2006), 1541-1555.

(56) References Cited

OTHER PUBLICATIONS

Sunstrom, N. A., et al., "Ion Channels formed by NB, an influenza B virus Protein", J. of Membrane Biology, vol. 150, XP002196654, (Dec. 1996), 127-132.

Sweet, T. M., et al., "Creation of amantadine resistant clones of influenza type A virus using a new transfection procedure.", J Virol Methods., 69(1-2), (Dec. 1997), 103-11.

Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.

Taira, K., et al., "Construction of a novel RNA-transcript-trimming plasmid which can be used both in vitro in place of run-off and (G)-free transcriptions and in vivo as multi-sequences transcription vectors", Nucleic Acids Research, 19(19), (1991), 5125-5130.

Takada, A., et al., "Downregulation of beta1 integrins by Ebola virus glycoprotein: implication for virus entry", Virology, 278(1), (Dec. 2000), Abstract Only.

Takada, Ayato, et al., "A system for functional analysis of Ebola?virus?glycoprotein", Proc. Natl. Acad. Sci. USA, 94(26), (1997), 14764-14769.

Takada, Ayato, et al., "Antibody-dependent enhancement of viral infection: molecular mechanisms and in vivo implications", Rev Med Virol, 13(6), (2003), 387-398.

Takada, Ayato, et al., "Epitopes Required for Antibody-Dependent Enhancement of Ebola Virus Infection", J Infect Dis, 196 (Suppl 2), (2007), S347-S356.

Takada, Ayato, et al., "Identification of Protective Epitopes on Ebola Virus Glycoprotein at the Single Amino Acid Level by Using Recombinant Vesicular Stomatitis Viruses", Journal of Virology, 77(2), (2003), 1069-1074.

Takada, Ayato, et al., "Infectivity-Enhancing Antibodies to Ebola Virus Glycoprotein", Journal of Virology, 75(5), (2001), 2324-2330.

Takada, Ayato, et al., "Protective efficacy of neutralizing antibodies against Ebola virus infection", Vaccine, 25(6), (2007), 993-999.

Takada, Ayato, et al., "The pathogenesis of Ebola hemorrhagic fever", Trends in Microbiology, 9(10), (2001), 506-511.

Takada, Kosuke, et al., "A Humanized MDCK Cell Line for the Efficient Isolation and Propagation of Human Influenza Viruses", Nature Microbiology, Nature Publishing Group UK, London, vol. 4, No. 8, (Apr. 29, 2019), 1268-1273.

Takeda, M., et al., "Influenza a virus M2 ion channel activity is essential for efficient replication in tissue culture.", J Virol., 76(3), (Feb. 2002), 1391-9.

Takeda, T., et al., "Expression of Podocalyxin Inhibits Cell-Cell Adhesion and Modifies Junctional Properties in Madin-Darby Canine Kidney Cells", Molecular Biology of the Cell, 11, (2000), 3219-3232.

Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.

Tan, Tiong Kit, et al., "A COVID-19 vaccine candidate using SpyCatcher multimerization of the SARS-CoV-2 spike protein receptor-binding domain induces potent neutralising antibody responses", Nature Communications, 12: 542, (2021), 1-16.

Tang, et al., "Recombinant adenovirus encoding the HA gene from swine H3N2 influenza virus partially protects mice from challenge with heterologous virus: AIHK/1/68 (H3N2)", Archives of Virology, vol. 147 2125-2141, (2002), 17 pgs.

Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.

Taylor, J., et al., "Newcastle Disease Virus Fusion Protein Expressed in a Fowlpox Virus Recombinant Confers Protection in Chickens", Journal of Virology, 64(4), (1990), 1441-1450.

Terry, G., et al., "The Contruction of Defective Interfering Rubella Virus Particles", Archives of Virology, 145(3), (2000), 625-633.

Tetsutani, K., et al., "Adjuvants in Influenza Vaccines", Vaccine 2012, vol. 30, (2012), 4 pgs.

Thao, Tran Thi Nhu, et al., "Rapid reconstruction of SARS-CoV-2 using a synthetic genomics platform", Nature, vol. 582 561-565, (2020), 24 pgs.

Theriault, S., "The role of reverse genetics systems in determining filovirus pathogenicity", Archives of Virology, Supplementum. 157-177, (2005), 22 pgs.

Thompson, Christine M, et al., "Critical assessment of influenza VLP production in Sf9 and HEK293 expression systems", BMC Biotechnology, 15(1), (May 16, 2015), 12 pgs.

Thompson, W. W., et al., "Mortality Associated With Influenza and Respiratory Syncytial Virus in the United States", JAMA, 289(2) 179-186, (2003), 8 pgs.

Tobler, K, et al., "Effect of cytoplasmic tail truncations on the activity of the M(2) ion channel of influenza A virus", J Virol., 73(12), (Dec. 1999), 9695-9701.

Towner, J S, et al., "Generation of eGFP express ing recombinant Zaire ebolavirus for analysis of early pathogenesis events and high-throughput antiviral drug screening", Virology, Academic Press , Orlando, US , vol. 332, No. 1 20-27, XP004715289 ISSN: 0042-6822 the whole document, (Feb. 5, 2005), 8 pgs.

Treanor, J. J, et al., "The B allele of the NS gene of avian influenza viruses, but not the A allele, attenuates a human influenza a virus for squirrel monkeys", Virology, 171(1), (1989), 1-9.

Uraki, R., et al., "A Bivalent Vacine Based on a PB2-Knockout Influenza Virus Protects Mice From Secondary Pneumoccal Pneumonia", The Journal of Infectious Diseases, 212(12), (2015), 1939-1948.

Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.

Vaishnava, Shipra, et al., "The Antibacterial Lectin Regilly Promotes the Spatial Segregation of Microbiota and Host in the Intestine", Science, 334 255-258, (2011), 4 pgs.

Vanessa, Monteil, et al., "Inhibition of SARS-CoV-2 Infections in Engineered Human Tissues Using Clinical-Grade Soluble Human ACE2", Cell, vol. 181 905-913, Retrieved from the Internet: <URL:https://www.ncbi.nlm.nih.gov/pmc/articles/PMC7181998/pdf/main.pdf>, (Apr. 24, 2020), 17 pgs.

Varner, Chad, "Developing Synthetic Multivalent Cellular Effectors", Thesis, School of Chemical and Biomolecular Engineering, Georgia Institute of Technology, (Aug. 2017), 88 pgs.

Verma, I. M, et al., "Gene Therapy—Promises, Problems and Prospects", Nature, 389, (1997), 239-242.

Via, L. E, et al., "Isolation of restriction fragments from large plasmids recovered from bacteria with multiple plasmids", Biotechniques, 11(4), (Oct. 1991), Abstract Only.

Victor, Sylvia T., et al., "A Replication-Incompetent PB2-Knockout Influenza A Virus Vaccine Vector", Journal of Virology, 2012, 86(8):4123; DOL: 10.1128/JVI.06232-11. Journals.ASM.org;, Downloaded from http://jvi.asm.org/ on Aug. 20, 2012 by Univ. of Wisonsin-Mad, (Feb. 1, 2012), 7.

Victor, Sylvia, et al., "A Replication-Incompetent PB2-Knockout Influenza A Virus Vaccine Vector", Journal of Virology, vol. 86, No. 8, (Apr. 2012), 4123-4128.

Vincke, C, et al., "Introduction to heavy chain antibodies and derived nanobodies", Meth. Mol. Biol. 911, (2012), 13 pgs.

Voeten, J. T, et al., "Characterization of high-growth reassortant influenza A viruses generated in MDCK cells cultured in serum-free medium", Vaccine, vol. 17, (1999), 1942-1950.

Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.

Von Wielink, R., et al., "Mutations in the M-Gene Segment can Substantially Increase Replication Efficiency of NS1 Deletion Influenza A Virus in MCK Cells", Journal of Virology. vol. 86, (2012), 12341-12350.

Waap, Helga, et al., "In vitro Isolation and seroprevalence of in stray cats and pigeons in Lisbon, Portugal", Veterinary Parasitology, vol. 187, No. 3 XP028492469 542-547, (Jan. 17, 2012), 6 pgs.

(56) References Cited

OTHER PUBLICATIONS

Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Walker, W. S, et al., "HEL-Flu: an influenza virus containing the hen egg lysozyme epitope recognized by CD4+ T cells from mice transgenic for an alphabeta TCR", J. Immunol., 159(6), (Sep. 1997), 2563-2566.
Wan, Yushun, et al., "Molecular mechanism for Antibody-Dependent Enhancement of Coronavirus EntrM", Journal of Virology, 94(5): e02015-19, (2019), 1-15.
Wang, et al., "Glycoengineering of CHO Cells to Improve Product Quality", Methods in Molecular Biology book series (MIMB, vol. 1603) 25-44, (May 11, 2017), 256 pgs.
Wang, B., et al., "Construction of Non-infectious SARS-CoV-2 Replicons and Their Application in Drug Evaluation", Virologica Sinica, 36, (2021), 890-900.
Wang, C., et al., "Ion Channel Activity of Influenza A Virus M2 Protein: Characterization of the Amantadine Block", Journal of Virology, 67 (9), (Sep. 1993), pp. 5585-5594.
Wang, Sheng-Fan, et al., "Antibody-dependent SARS coronavirus infection is mediated by antibodies against spike proteins", Biochem Biophys Res Commun, 451 208-214, (2014), 8 pgs.
Wang, Weijia, et al., "Identification of Critical Residues in the Hemagglutinin and Neuraminidase of Influenza Virus H1N1pdm for Vaccine Virus Replication in Embryonated Chicken Eggs", Journal of Virology, 87(8), (2013), 4642-4649.
Wang, Wenlig, et al., "Robust Immunity and Heterologous Protection against Influenza in Mice Elicited by a Novel Recombinant NP-M2e Fusion Protein Expressed in E. coli", PLoS ONE 7(12): e52488, (Dec. 2012), 1-13.
Wanitchang, Asawin, et al., "Characterization of influenza A virus pseudotyped with the spike protein of porcine epidemic diarrhea virus", Archives of Virology, 163(12), (2018), 3255-3264.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Warfield, et al., "", PNAS, vol. 100(26), (2003), pp. 5889-15894.
Watanabe, S., et al., "Ebola virus (EBOV) VP24 inhibits transcription and replication of the EBOV genome", J Infect Dis., 196(Suppl 2), (Nov. 15, 2007), S284-90.
Watanabe, S., et al., "Influenza A Virus Lacking M2 Protein as a Live Attenuated Vaccine", Journal of Virology, 83(11), (2009), 5947-5950.
Watanabe, S., et al., "Production of Novel Ebola Virus-Like Particles from cDNAs: an Alternative to Ebola Virus Generation by Reverse Genetics", Journal of Virology, 78(2). (Jan. 2004), 999-1005.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, T., et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, Tokiko, et al., "Exploitation of Nucleic Acid Packaging Signals to Generate a Novel In?uenza Virus-Based Vector Stably Expressing Two Foreign Genes", Journal of Virology, 77(19), (Oct. 2003), 10575-10583.
Watanabe, Tokiko, et al., "Exploitation of Nucleic Acid Packaging Signals to Generate a Novel Influenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.
Weber, F., et al., "Conserved vRNA end sequences of Thogoto-orthomyxovirus suggest a new panhandle structure", Archives of Virology, 142(5), (1997), 1029-1033.
Weber, F., et al., "Nucleoprotein Viral RNA and mRNA of Thogoto Virus: a Novel "Cap-Stealing" Mechanism in Tick-Borne Othomyxoviruses?", Journal of Virology, 70(12), (1996), 8361-8367.
Webster, R G, et al., "Evolution and molecular epidemiology of H9N2 influenza A viruses from quail in southern China", XP002744257, retrieved from EBI accession No. UNIPROT:A3R6C9 Database accession No. A3R6C9 the whole document, (Apr. 3, 2007), 1 pg.
Wei, Hung-Ju, et al., "Fabrication of influenza virus-like particles using M2 fusion proteins for imaging single viruses and designing vaccines", Vaccine, 29, (2011), 7163-7172.
Wei, Kai, et al., "Influenza A Virus Acquires Enhanced Pathogenicity and Transmissibility after Serial Passages in Swine", Journal of Virology, 88(20), (Oct. 2014), 11981-11994.
Wentworth, D E, et al., "The NIAID Influenza Genome Sequencing Project", XP002744258, retrieved from EBI accession No. UNIPROT:U3S198 Database accession No. U3S198 the whole document, (Dec. 11, 2013), 1 pg.
Whelan, S. P. J., et al., "Efficient Recovery of Infectious Vesicular Stomatitis Virus Entirely from cDNA Clones", Proc. Natl. Acad. Scl. USA, 92, (1995), 8388-8392.
Wiedmer, T., et al., "Identification of three new members of the phospholipid scramblase gene family", Biochim Biophys Acta, 1467(1), (Jul. 31, 2000), Abstract Only.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wills, J. W., et al., "An Assembly Domain of the Rous Sarcoma Virus Gag Protein Required Late in Budding", Journal of Virology, 68(10), (1994), 6605-6618 .
Wilson, et al., "Vaccine Potential of Ebola Virus VP24, VP30, VP35 and VP40 Proteins", Virology 286, (2001), 384-90.
Wilson, Julie A, et al., "Epitopes Involved in Antibody-Mediated Protection from Ebola Virus", Science, 287(5458), (Mar. 2000), 1664-1666.
Winkler, K, et al., "Changing the antigen binding specificity by single point mutations of an anti-p24 (HIV-1) antibody", J. Immunol. 165 4505-4514, (2000), 11 pgs.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wood, J. M., et al., "From Lethal Virus to Life-Saving Vaccine: Developing Inactivated Vaccines for Pandemic Influenza", Nature Reviews Microbiology, 2(10), (2004), 842-847.
Wu, Rui, et al., "A live bivalent influenza vaccine based on a H9N2 virus strain", Vaccine, 28, (2010), 673-680.
Wu, Tai Te, et al., "An Analysis of the Sequences of the Variable Regions of Bence Jones Proteins and Myeloma Light Chains and Their Implications for Anti-body complementarity", J. Exp. Med., 132(2), (1970), 211-250.
Xiang, J, et al., "Modification in framework region I results in a decreased affinity of chimeric anti-Tag72 antibody", Mol. Immunol. 28(1/2), (1991), 141-148.
Xu, Jiayu, et al., "The Cold-Adapted, Temperature-Sensitive SARS-Co V-2 Strain TS11 Is Attenuated in Syrian Hamsters and a Candidate Attenuated Vaccine", Viruses 2023, 15, 95. https://doi.org/10.3390/v15010095, (2023), 23.
Xu, Ruodan, et al., "Construction of SARS-CoV-2 Virus-Like Particles by Mammalian Expression System", Frontiers in Bioengineering and Technology, 8:862, (2020), 1-6.
Xu, X., et al., "Reassortment and evolution of current human influenza A and B viruses", Virus Research, 103, (2004), 55-60.
Yagi, Y., et al., "In silico panning for a non-competitive peptide inhibitor", BMC Bioinformatics, 8(11), (2007), 11 pgs.
Yamamoto, K., et al., "Orientation Dependence in Homologous Recombination", Genetics May 1996; 143(1): 27-36, (1996), 27-36.

(56) References Cited

OTHER PUBLICATIONS

Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.

Yang, P., et al., "Hemagglutinin Specificity and Neuraminidase Coding Capacity of Meuraminidase-Deficient Influenza Viruses", Virology, 229(1), (1997), 155-165.

Yang, Z. Y, et al., "Identification of the Ebola virus glycoprotein as the main viral determinant of vascular cell cytotoxicity and injury", Nat Med., 6(8), (Aug. 2000), Abstract Only.

Yannarell, Dean A., et al., "Factors affecting the yield of cold-adapted influenza virus vaccine", Journal of Virological Methods, vol. 64, 161-169, (1997), 1 pg.

Yasuda, J., "Growth Control of Influenza A Virus by M1 Protein: Analysis of Transfectant Viruses Carrying the Chimeric M Gene", Journal of Virology, 68(12), (1994), 8141-8146.

Yen, H L, et al., "Neuraminidase Inhibitor-Resistant Recombinant A/Vietnam/1203/04 (K5N1) Influenza Viruses Retain Their Replication Efficiency and Pathogenicity In Vitro and In Vivo", Journal of Virology., vol. 81, No. 22, (Nov. 15, 2007), 12418-12426.

Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.

Yip, Ming S., et al., "Antibody-dependent infection of human macrophages by severe acute respiratory syndrome coronavirus", Virology Journal, 11: 82, (2014), 11 pgs.

Yonezawa, A., et al., "Studies of Eboa Virus Glycoprotein-Mediated Entry and Fusion by Using Pseudotyped Human Immunodeficiency Virus Type 1 Virions: Involvement of Cytoskeletal Proteins and Enhancement by Tumor Necrosis Factor Alpha", Journal of Virology, 79(2), (2005), 918-926.

Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.

Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.

Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.

ZAGHOUANI, H., et al., "Cells Expressing an H Chain Ig Gene Carrying a Viral T Cell Epitope are Lysed by Specific Cytolytic T Cells", The Journal of Immunology, 148(11), (1992), 3604-3609.

Zanin, M., et al., "An Amino Acid in the Stalk Domain of N1 Neuraminidase Is Critical for Enzymatic Activity", Journal of Virology, 2017, Vo. 91, No. 2, (Jan. 2017), 12 pgs.

Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.

Zeitlin, L., et al., "Antibody Therapeutics for Ebola Virus Disease", Curr. Opin. Viral. 17:, (2016), 11 pgs.

Zhang, Baoshan, et al., "A platform incorporating trimeric antigens into self-assembling nanoparticles reveals SARS-CoV-2-spike nanoparticles to elicit substantially higher neutralizing responses than spike alone", Scientific Reports 10, Article No. 18149, (2020), 13 pgs.

Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.

Zhang, Q.-Y., et al., "SARS-CoV-2 replicon for high-throughput antiviral screening", J Gen Virol,, 102(5), (2021), 1-4.

Zhang, V. Q, et al., "Easy two-step method for randomizing and cloning gene fragments", Methods Mol Biol., 634, (2010), Abstract Only.

Zhang, Xuming, et al., "Expression of Interferon-γ by a Coronavirus Defective-Interfering RNA Vector and its Effect on Viral Replication, Spread, and Pathogenicity", Medical Institute, University of Southern California School of Medicine, (May 1997), 327-338.

Zhang, Y., et al., "A bacterial artificial chromosome (BAC)-vectored noninfectious replicon of SARS-CoV-2", Antiviral Research, vol. 185, 104974, (Jan. 2021), 1-9.

Zhao, Lili, et al., "New Insights into the Nonconserved Noncoding Region of the Subtype-Determinant Hemagglutinin and Neuraminidase Segments of Influenza A Viruses", Journal of Virology, 88(19) 11493-11503, (Oct. 2014), 11 pgs.

Zhou, Yan, "Membrane-Anchored Incorporation of a Foreign Protein in Recombinant Influenza Virions", Virology 246(1), (1998), 83-94.

Zobel, A., et al., "RNA Polymerase I Catalysed Transcription of Insert Viral cDNA", Nucleic Acids Research, 21(16), (1993), 3607-3614.

"Japanese Application Serial No. 2021-536228, Response filed Feb. 24, 2024 to Notification of Reasons for Rejection mailed Aug. 22, 2023", w/ English claims, 30 pgs.

"European Application Serial No. 19778696.5, Communication Pursuant to Article 94(3) EPC mailed Jun. 3, 2024", 6 pgs.

"U.S. Appl. No. 18/525,460, Preliminary Amendment filed Jun. 7, 2024", 6 pgs.

"U.S. Appl. No. 17/212,836, Non Final Office Action mailed Jun. 13, 2024", 14 pgs.

"Japanese Application Serial No. 2021-509824, Notification of Reasons for Rejection mailed Jun. 4, 2024", W English Translation, 18 pgs.

Giles, Brendan Michael, "Development of a broadly reactive vaccine for highly pathogenic H5N1 influenza", [Online]. Retrieved from the Internet:URL: http: search.proquest.com docview 928138363, (Jan. 11, 2011), 24 pgs.

* cited by examiner

Library generation and screening (C.1.2, C.1.3):
Selection of 100 ID-EpiMut HAs

↓

Reactivity with H3 HA- and stem-specific mAbs (C.1.4):
Selection of 50 ID-EpiMut HAs

↓ ↓

Generation of 50 ID-EpiMut HA/VP40 VLPs decorated with one EpiMut HA each (C.2.1.1)

Generation of 8 ID-EpiMut HA/VP40 VLPs (5 VLPs decorated with 10 EpiMut HAs each, 2 VLPs decorated with 25 EpiMut HAs each, 1 VLP decorated with 50 EpiMut HAs; C.2.1.2)

↓ ↓

Characterization of mouse sera (C.2.1.3): Selection of 30 ID-EpiMut HA/VP40 VLPs (decorated with one EpiMut HA each)

Characterization of mouse sera (C.2.1.3): Elimination of VLPs that do not elicit sera with high amounts of Abs to immune-subdominant epitopes

↓ ↓

Mouse immunization studies (C.2.2); Vaccination Strategies 1-3 (Table 4)

Mouse immunization studies (C.2.2); Vaccination Strategies 4-6 (Table 4)

↓ ↓

Selection of ___ vaccination regimen

↓

Challenge studies in mice (C.2.3): Selection of ___ vaccination regimen

↓

Immunogenicity and protective efficacy in ferrets (C.2.3, C.2.4) for the ___ vaccination regimen

Figure 5.

```
DEFINITION  hemagglutinin, partial [Influenza A virus
            (A/California/7/2004(H3N2))].
ACCESSION   ABH01021

1 qklpgndnst atlclghhav pngtivktit ndqievtnat elvqssstgg icdsphqild
 61 genctlidal lgdpqcdgfq nkkwdlfver skaysncypy dvpdyaslrs lvassgtlef
121 nnesfnwtgv tqngtsssck rrsnnsffsr lnwlthlkfk ypalnvtmpn nekfdklyiw
181 gvhhpgtnnd qislytqasg ritvstkrsq qtvipnigsr prvrdipsri siywtivkpg
241 dillinstgn liaprgyfki rsgkssimrs dapigkcnse citpngsipn dkpfqnvnri
301 tygacpryvk qntlklatgm mvpekqtr DEFINITION  hemagglutinin, partial [Influenza A virus (A/California/7/2004
            (cell-passaged)(H3))].
ACCESSION   ABO37489
  1 qklpgndnst atlclghhav pngtivktit ndqievtnat elvqssstgg icdsphqild
 61 genctlidal lgdpqcdgfq nkkwdlfver skaysncypy dvpdyaslrs lvassgtlef
121 nnesfnwtgv tqngtssack rrsnnsffsr lnwlthlkfk ypalnvtmpn nekfdklyiw
181 gvhhpgtnnd qislyaqasg ritvstkrsq qtvipnigsr prvrdipsri siywtivkpg
241 dillinstgn liaprgyfki rsgkssimrs dapigkcnse citpngsipn dkpfqnvnri
301 tygacpryvk qntlklatgm rnvpekqtrg ifgaiagfie ngwegmvdgw ygfrhqnseg
361 igqaadlkst qaainqingk lnrligktne kfhqiekefs evegriqdle kyvedtkidl
421 wsynaellva lenqhtidlt dsemnklfer tkkqlrenae dmqngcfkiy hkcdnacigs
481 irngtydhdv yrdealnnrf qikgvelksg yk DEFINITION  hemagglutinin, partial [Influenza A virus (A/California/7/2004
            (egg-passaged)(H3))].
ACCESSION   ABO37490

1 qklpgndnst atlclghhav pngtivktit ndqievtnat elvqssstgg icdsphqild
 61 genctlidal lgdpqcdgfq nkkwdlfver skaysncypy dvpdyaslrs lvassgtlef
121 nnesfnwtgv tqngtsssck rrsnnsffsr lnwlthlkfk ypalnvtmpn nekfdklyiw
181 gvhhpgtnnd qislytqasg ritvstkrsq qtvipnigsr prvrdipsri siywtivkpg
241 dillinstgn liaprgyfki rsgkssimrs dapigkcnse citpngsipn dkpfqnvnri
301 tygacpryvk qntlklatgm rnvpekqtrg ifgaiagfie ngwegmvdgw ygfrhqnseg
361 igqaadlkst qaainqingk lnrligktne kfhqiekefs evegriqdle kyvedtkidl
```

Fig. 6A

```
421 wsynaellva lenqhtidlt dsemnklfer tkkqlrenae dmgngcfkiy hkcdnacigs
481 irngtydhdv yrdealnnrf qikgvelksg yk
```

Accession No. ATD11305

```
  1 mktiialsci lclvftqkip gndnstatlc lghhavpngt ivktitndri evtnatelvq
 61 nssigeicds phqildgenc tlidallgdp qcdgfqnkkw dlfvernkay sncypydvpd
121 yaslrslvas sgtlefnnes fnwagvtqng tssscirgsk ssffsrlnwl thlnskypal
181 nvtmpnneqf dklyiwgvhh pgtdkdqisl yaqssgritv stkrsqqavi pnigsrprir
241 dipsrisiyw tivkpgdill instgnliap rgyfkirsgk ssimrsdapi gkcksecitp
301 ngsipndkpf qnvnrityga cpryvkqstl klatgmrnvp erqtrgifga iagfiengwe
361 gmvdgwygfr hqnsegrgqa adlkstqaai dqingklnrl igktnekfhq iekefseveg
421 riqdlekyve dtkidlwsyn aellvalenq htidltdsem nklfektkkq lrenaedmgn
481 gcfkiyhkcd nacigsirng tydhnvyrde alnnrfqikg velksgykdw ilwisfaisc
541 fllcvallgf imwacqkgni rcnici
```

Sequence : gb:KP307984|gi:748112957|UniProtKB:A0A0C4X0C0|Organism:Influenza A virus (A/gyrfalcon/Washington/41088-6/2014(H5N8))|Strain Name:A/gyrfalcon/Washington/41088-6/2014|Protein Name:HA Hemagglutinin|Gene Symbol:HA|Segment:4|Subtype:H5N8|Host:Falcon

```
MEKIVLLLAV ISLVKSDQIC IGYHANNSTK QVDTIMEKNV TVTHAQDILE 050
KTHNGKLCDL NGVKPLILKD CSVAGWLLGN PMCDEFIRVP EWSYIVERAN 100
PANDLCYPGT LNDYEELKHL LSRINHFEKT LIIPRSSWPN HETSLGVSAA 150
CPYQGASSFF RNVVWLIKKN DAYPTIKISY NNTNREDLLI LWGIHHSNNA 200
AEQTNLYKNP DTYVSVGTST LNQRLVPKIA TRSQVNGQSG RMDFFWTILK 250
PNDAIHFESN GNFIAPEYAY KIVKKGDSTI MKSEMEYGHC NTKCQTPIGA 300
INSSMPFHNI HPLTIGECPK YVKSNKLVLA TGLRNSPLPE RRRKRGLFGA 350
IAGFIEGGWQ GMVDGWYGYH HSNEQGSGYA ADKESTQKAI DGVTNKVNSI 400
IDKMNTQFEA VGREFNNLER RIENLNKKME DGFLDVWTYN AELLVLMENE 450
RTLDFHDSNV KNLYDKVRLQ LRDNAKELGN GCFEFYHKCD NECMESVRNG 500
TYDYPKYSEE AILKREEISG VKLESIGTYQ ILSIYSTVAS SLALAIIVAG 550
LSLWMCSNGS LQCRICI                                       567
```

Sequence : gb:KP307984|gi:748112957|UniProtKB:A0A0C4X0C0|Organism:Influenza A virus (A/gyrfalcon/Washington/41088-6/2014(H5N8))|Strain Name:A/gyrfalcon/Washington/41088-6/2014|Protein Name:HA Hemagglutinin|Gene Symbol:HA|Segment:4|Subtype:H5N8|Host:Falcon

```
MEKIVLLLAV  ISLVKSDQIC  IGYHANNSTK  QVDTIMEKNV  TVTHAQDILE  050
KTHNGKLCDL  NGVKPLILKD  CSVAGWLLGN  PMCDEFIRVP  EWSYIVERAN  100
PANDLCYPGT  LNDYEELKHL  LSRINHFEKT  LIIPRSSWPN  HETSLGVSAA  150
CPYQGASSFF  RNVVWLIKKN  DAYPTIKISY  NNTNREDLLI  LWGIHHSNNA  200
AEQTNLYKNP  DTYVSVGTST  LNQRLVPKIA  TRSQVNGQSG  RMDFFWTILK  250
PNDAIHFESN  GNFIAPEYAY  KIVKKGDSTI  MKSEMEYGHC  NTKCQTPIGA  300
INSSMPFHNI  HPLTIGECPK  YVKSNKLVLA  TGLRNSPLRE  RRRKRGLFGA  350
IAGFIEGGWQ  GMVDGWYGYH  HSNEQGSGYA  ADKESTQKAI  DGVTNKVNSI  400
IDKMNTQFEA  VGREFNNLER  RIENLNKKME  DGFLDVWTYN  AELLVLMENE  450
RTLDFHDSNV  KNLYDKVRLQ  LRDNAKELGN  GCFEFYHKCD  NECMESVRNG  500
TYDYPKYSEE  AILKREEISG  VKLESIGTYQ  ILSIYSTVAS  SLALAIIVAG  550
LSLWMCSNGS  LQCRICI                                         567
```

Figure 8

MKANLLVLLCALAAADADTICIGYHANNSTDTVDTVLEKNVTVTH
SVNLLEDSHNGKLCRLKGIAPLQLGKCNIAGWLLGNPECDPLLPVR
SWSYIVETPNSENGICYPGDFIDYEELREQLSSVSSFERFEIFPKESS
WPNHNTNGVTAACSHEGKSSFYRNLLWLTEKEGSYPKLKNSYVNK
KGKEVLVLWGIHHPPNSKEQQNLYQNENAYVSVVTSNYNRRFTPE
IAERPKVRDQAGRMNYYWTLLKPGDTIIFEANGNLIAPMYAFALS
RGFGSGIITSNASMHECNTKCQTPLGAINSSLPYQNIHPVTIGECP
KYVRSAKLRMVTGLRNIPSIQSRGLFGAIAGFIEGGWTGMIDGWY
GYHHQNEQGSGYAADQKSTQNAINGITNKVNTVIEKMNIQFTAV
GKEFNKLEKRMENLNKKVDDGFLDIWTYNAELLVLLENERTLDFH
DSNVKNLYEKVKSQLKNNAKEIGNGCFEFYHKCDNECMESVRNGT
YDYPKYSEESKLNREKVDGVKLESMGIYQILAIYSTVASSLVLLVSL
GAISFWMCSNGSLQCRIC

Figure 9

1 maiiylillf tavrgdqici gyhannstek vdtilernvt vthakdilek thngklckln 61 gipplelgdc siagwllgnp ecdrllsvpe wsyimekenp rdglcypgsf ndyeelkhll 121 ssvkhfekvk ilpkdrwtqh tttggsraca vsgnpsffrn mvwltekgsn ypvakgsynn 181 tsgeqmliiw gvhhpndete qrtlyqnvgt yvsvgtstln krstpeiatr pkvngqggrm 241 efswtlldmw dtinfestgn liapeygfki skrgssgimk tegtlencet kcqtplgain 301 ttlpfhnvhp ltigecpkyv kseklvlatg lrnvpqiesr glfgaiagfi eggwqgmvdg 361 wygyhhsndq gsgyaadkes tqkafdgitn kvnsviekmn tqfeavgkef snlerrlenl 421 nkkmedgfld vwtynaellv lmenertldf hdsnvknlyd kvrmqlrdnv kelgngcfef 481 yhkcddecmn svkngtydyp kyeeesklnr neikgvklss mgvyqilaiy atvagslsla 541 immagisfwm csngslqcri ci

Figure 10

1 maiiylillf tavrgdqici gyhannstek vdtilernvt vthakdilek thngklckln 61 gipplelgdc siagwllgnp ecdrllsvpe wsyimekenp rdglcypgsf ndyeelkhll 121 ssvkhfekvk ilpkdrwtqh tttggsraca vsgnpsffrn mvwltekgsn ypvakgsynn 181 tsgeqmliiw gvhhpndete qrtlyqnvgt yvsvgtstln krstpeiatr pkvngqggrm 241 efswtlldmw dtinfestgn liapeygfki skrgssgimk tegtlencet kcqtplgain 301 ttlpfhnvhp ltigecpkyv kseklvlatg lrnvpqiesr glfgaiagfi eggwqgmvdg 361 wygyhhsndq gsgyaadkes tqkaf

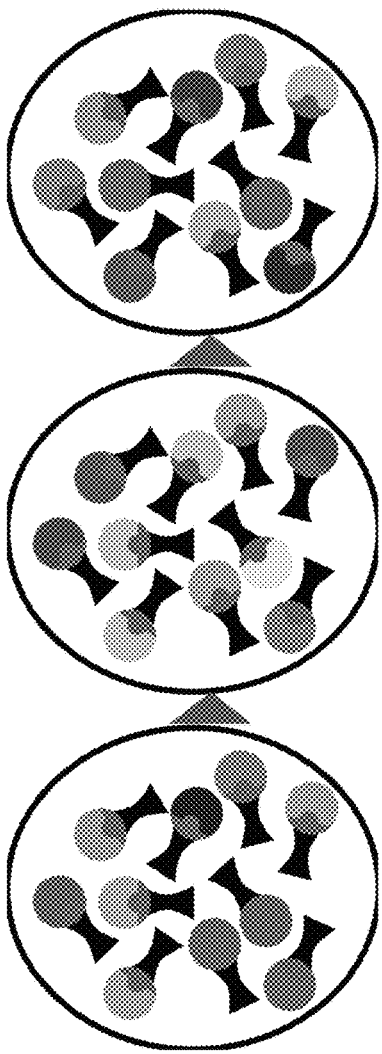
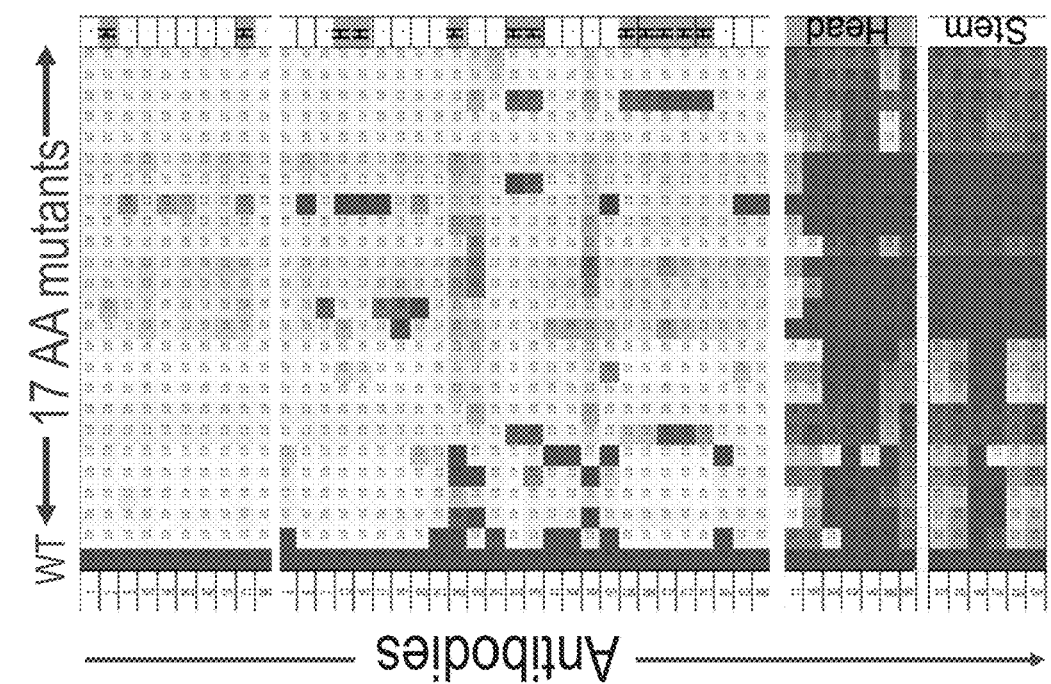
FIGURE 15

Figure 17:
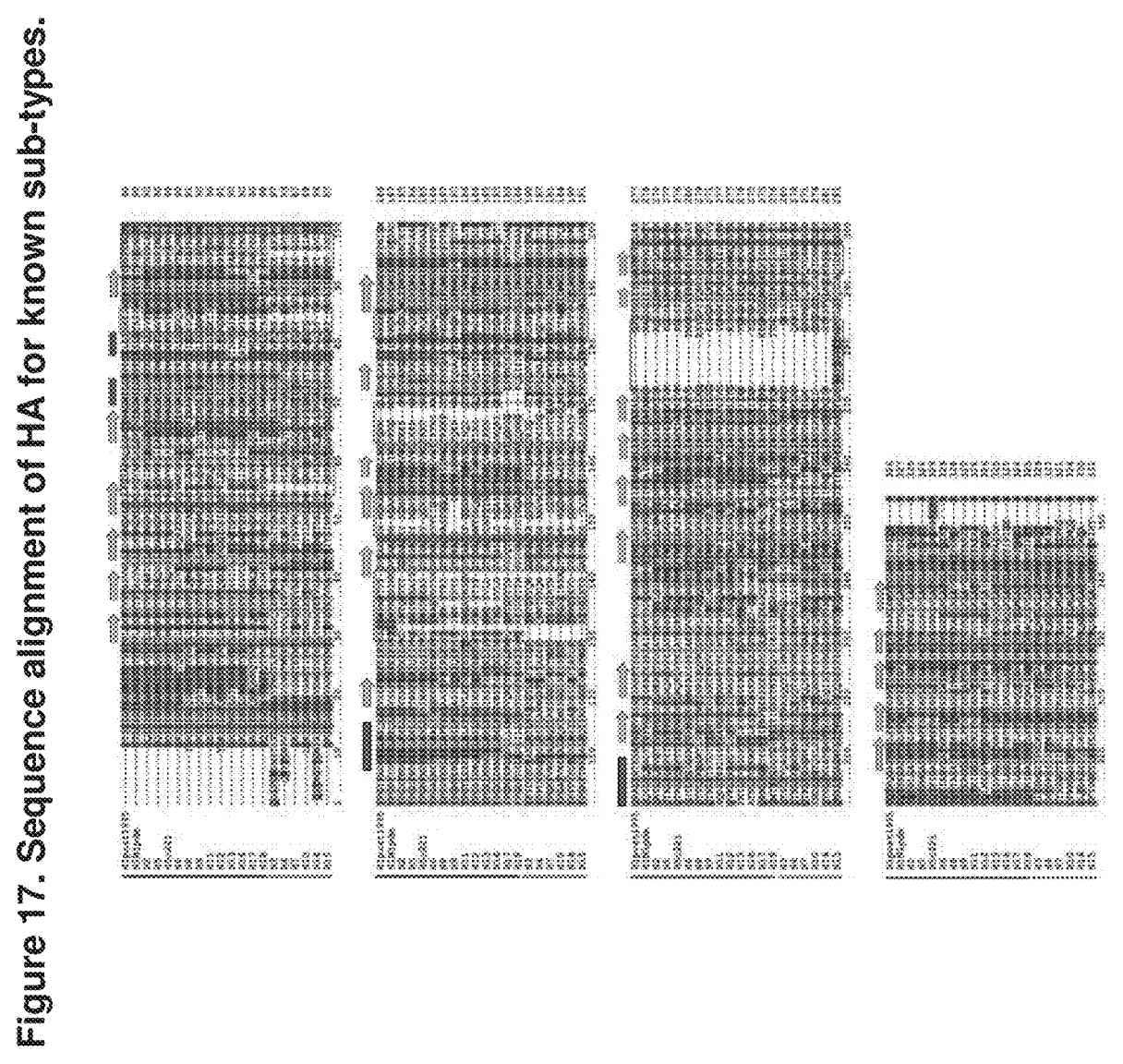

Figure 17. Sequence alignment of HA for known sub-types.

EXEMPLARY ANTIGENIC SITES IN H3 HA

| | |
|---|---|
| 122 | T |
| 124 | G |
| 126 | T |
| 130 | V |
| 131 | T |
| 132 | Q |
| 133 | N |
| 135 | R |
| 137 | N |
| 138 | A |
| 140 | K |
| 142 | G |
| 143 | P |
| 144 | G |
| 145 | S |
| 146 | G |
| 150 | R |
| 152 | N |
| 168 | M |

Fig. 18A

| | |
|---|---|
| 128 | T |
| 129 | G |
| 155 | T |
| 156 | K |
| 157 | S |
| 158 | G |
| 159 | S |
| 160 | T |
| 163 | V |
| 164 | L |
| 165 | N |
| 186 | S |
| 187 | T |
| 188 | N |
| 189 | Q |
| 190 | E |
| 192 | T |
| 193 | S |
| 194 | L |
| 196 | V |
| 197 | Q |
| 198 | A |

Fig. 18B

| | |
|---|---|
| 44 | Q |
| 45 | S |
| 46 | S |
| 47 | S |
| 48 | T |
| 50 | K |
| 51 | I |
| 53 | N |
| 54 | N |
| 273 | P |
| 275 | D |
| 276 | T |
| 278 | I |
| 279 | S |
| 280 | E |
| 294 | F |
| 297 | V |
| 299 | K |
| 300 | I |
| 304 | A |
| 305 | C |
| 307 | K |
| 308 | Y |
| 309 | V |
| 310 | K |
| 311 | Q |
| 312 | N |

Fig. 18C

| | |
|---|---|
| 96 | N |
| 102 | V |
| 103 | P |
| 117 | T |
| 121 | I |
| 167 | T |
| 170 | N |
| 171 | N |
| 172 | D |
| 173 | N |
| 174 | F |
| 175 | D |
| 176 | K |
| 177 | L |
| 179 | I |
| 182 | I |
| 201 | R |
| 203 | T |
| 207 | R |
| 208 | R |
| 209 | S |
| 212 | T |
| 213 | I |
| 214 | I |
| 215 | P |
| 216 | N |
| 217 | I |
| 218 | G |
| 219 | S |
| 226 | L |
| 227 | S |
| 228 | S |
| 229 | R |
| 230 | I |
| 238 | K |
| 240 | G |
| 242 | V |
| 244 | V |
| 246 | N |
| 247 | S |
| 248 | N |

Fig. 18D

| | |
|---|---|
| 57 | R |
| 59 | L |
| 62 | I |
| 63 | D |
| 67 | I |
| 75 | H |
| 78 | V |
| 80 | Q |
| 81 | N |
| 82 | E |
| 83 | T |
| 86 | L |
| 87 | F |
| 88 | V |
| 91 | S |
| 92 | K |
| 109 | R |
| 260 | M |
| 261 | R |
| 262 | T |
| 265 | S |

Fig. 18E

VECTORS FOR ELICITING IMMUNE RESPONSES TO NON-DOMINANT EPITOPES IN THE HEMAGGLUTININ (HA) PROTEIN

CROSS-REFERENCE TO RELATED APPLICATIONS

This application is a continuation of U.S. application Ser. No. 16/545,761, filed Aug. 20, 2019, which claims the benefit of the filing date of U.S. application No. 62/719,952, filed on Aug. 20, 2018, the disclosures of which are incorporated by reference herein.

STATEMENT OF GOVERNMENT RIGHTS

This invention was made with government support under HHSN272201400008C awarded by the National Institutes of Health. The government has certain rights in the invention.

INCORPORATION BY REFERENCE OF SEQUENCE LISTING

A Sequence Listing is provided herewith as an xml file, "2294470.xml" created on Dec. 14, 2022 and having a size of 57,344 bytes. The content of the xml file is incorporated by reference herein in its entirety.

BACKGROUND

Influenza outbreaks in humans are a major public health concern. Annual epidemics (outbreaks of influenza viruses circulating in humans) and sporadic pandemics (outbreaks of novel influenza viruses to which people lack protective immunity) increase morbidity and mortality in human populations and create considerable economic costs. Infections with influenza viruses and vaccination with current vaccines elicit antibodies against highly variable major antigenic epitopes in the head region of the viral surface glycoprotein hemagglutinin (HA). High mutation rates and immune pressure lead to the accumulation of mutations in these epitopes, resulting in viral 'escape' from the antibodies circulating in an individual; hence, the individual becomes infected again. As a consequence of viral 'escape' from immune responses elicited upon infection or vaccination, the vaccine strains must be replaced frequently. Recently, the National Institute of Allergy and Infectious Diseases (NIAID) therefore announced a strategic plan for the development of a 'universal' influenza vaccine that protects against multiple, antigenically diverse strains.

Immunodominance describes the phenomenon whereby strong immune responses are directed towards a subset of antigenic epitopes (i.e., immunodominant antigenic epitopes), while much weaker immune responses are directed against the remaining, immune-subdominant epitopes. The immunodominant epitopes of influenza viruses are located in the highly variable regions of the HA head (i.e., most antibodies elicited after infection or vaccination are directed against these major antigenic epitopes). Immune-subdominant epitopes are located in conserved regions of the HA head and in the conserved HA stem. Antibodies elicited to these subdominant, conserved regions are typically reactive against a broad range of influenza viruses; however, since the epitopes are immune-subdominant, the levels of these broadly reactive antibodies are low.

Several studies have shown that the first exposure to an antigenically unique influenza virus generates relatively high levels of antibodies to immune-subdominant epitopes in the HA stem, in addition to high levels of antibodies to the immunodominant major epitopes in the highly variable regions of the HA head.

Palese and colleagues demonstrated that repeat immunization with chimeric HAs that possess the same stem region but head regions derived from different HA subtypes increased the levels of stem-reactive antibodies compared to repeat vaccination with HAs possessing the same head (Chen et L., 2016; Krammer et al., 2013; Margine et al., 2013; Nachbagauer et al., 2017 and 2015; Krammer et al., 2012 and 2014; Goff et al., 2013).

Despite the promising data obtained with chimeric HAs, this approach has drawbacks: (i) the number of HA subtypes that can be used to swap the head region is limited (and not all combinations of stems and heads are stable); and (ii) the current approach of exchanging the HA head does not exploit the subtype-specific conserved, immune-subdominant epitopes in the head.

Human influenza virus infections pose a considerable burden on individual health, the public health sector, and the global economy. Influenza viruses circulating in humans (i.e., 'seasonal' influenza viruses) typically cause annual epidemics that have resulted in the US alone in 9.2-35.6 million illnesses, 140,000-710,000 hospitalizations, and 12,000-56,000 deaths per year since 2010. Epidemics are caused by influenza viruses of type A and B. Influenza viruses of type A are further divided into subtypes based on the antigenicity of the viral surface glycoproteins HA and neuraminidase (NA). To date, 18 HA (H1-18) and 11 NA (N1-11) subtypes have been identified; based on their phylogenetic relationships, the HAs are categorized into two super-groups (group 1, H1, H2, H5, H6, H8, H9, H11-H13, H16-18; group 2, H3, H4, H7, H10, H14, H15). However, only viruses of the H1N1, H2N2, and H3N2 subtypes have extensively circulated in humans. Global outbreaks (pandemics) are caused by viruses possessing an HA that is antigenically distinct from that of viruses previously circulating in humans, so they encounter immunologically naïve populations, resulting in rapid spread around the globe. Four pandemics have occurred in the last 100 years. The 1918 pandemic was caused by H1N1 viruses, which were replaced by H2N2 viruses in 1957, causing the 'Asian' pandemic. In 1968, H3N2 viruses replaced the H2N2 viruses, causing the 'Hong Kong' pandemic. H1N1 viruses similar to those circulating in the 1950's re-emerged in 1977 and co-circulated with H3N2 viruses until 2009, when the H1N1 viruses were replaced by H1N1 viruses with an antigenically distinct HA (2009 pandemic).

Wild aquatic birds are the natural reservoir of influenza A viruses and harbor influenza viruses of most subtypes. Sporadic transmission of avian influenza viruses to humans can cause severe respiratory disease with high fatality rates. Highly pathogenic avian influenza of the H5 subtype have infected 840 people and caused 454 deaths; human infections with H7N9 viruses (which emerged in 2013) have resulted in 1,625 reported human cases with a case fatality rate of 38% (as of May 24, 2018). These avian influenza viruses do not efficiently transmit among humans and have not (yet) caused a pandemic, although H7N9 viruses transmit via respiratory droplets among ferrets (1-4) (the commonly used animal model for influenza virus transmission studies) and H5 viruses with a small number of mutations can become transmissible among ferrets via respiratory

SUMMARY

Disclosed herein is a method to redirect immune responses in an avian or a mammal from the immunodominant epitopes (which mutate frequently) towards non-dominant (sub-dominant) epitopes, which are more conserved. Immunization with one or more viruses produced by the method produce higher amounts of antibodies targeting the conserved non-dominant epitopes which in turn increases broadly-protective immunity. The method outdilutes immune responses to the immunodominant epitopes, resulting in higher levels of antibodies directed against the conserved, non-dominant epitopes. Influenza vaccines having one or more of the influenza viruses with modified HAs that elicit immune responses to non-dominant epitopes, epitopes that are more conserved than the dominant antigenic epitopes on the hemagglutinin (HA) head of influenza viruses, e.g., human influenza viruses, may provide protection against antigenically drifted viruses. Thus, the need to vaccinate may be extended beyond 1-3 years. The vaccines may include mixtures of different HA proteins, each with mutated, e.g., non-naturally occurring, immunodominant antigenic epitopes, in order to dilute the immune responses to the immunodominant epitopes, thereby boosting the levels of antibodies directed against immune-subdominant epitopes.

As described herein, an influenza virus 'library' (e.g., a mixture of millions of variants) is generated with random mutations at selected positions of the highly variable immunodominant antigenic epitopes in the HA head, e.g., from any of the HA subtypes. For example, in a H3 HA, influenza viruses with up to 17 mutations in the immunodominant antigenic epitopes of HA were prepared and found to be viable. The virus library is incubated with different sera, e.g., ferret and/or human sera, to eliminate variants that are antigenically similar to wild-type virus(es). The individual modified HA sequences (Individual ID-EpiMut HAs) may be cloned, sequenced, and tested for their reactivity with monoclonal antibodies directed against immunodominant or sub-dominant epitopes of HA. ID-EpiMut HAs with high reactivity to antibodies directed against conserved, immune subdominant epitopes and low reactivity to antibodies directed against immunodominant epitopes are then isolated and optionally pooled in a vaccine formulation.

In one embodiment, for immunization studies in mice, the ID-EpiMut HAs are incorporated into virus-like particles (VLPs) composed of the Ebola virus VP40 matrix protein, hence eliminating potential contributions to immunity conferred by other influenza viral proteins. The mouse sera is tested for the levels of antibodies directed against immunodominant or -subdominant epitopes. Vaccination and challenge studies in ferrets are carried out with inactivated influenza vaccines possessing ID-EpiMut HAs. Naïve or pre-exposed animals are vaccinated, the levels of antibodies to immune subdominant epitopes assessed, and animals challenged with homologous and heterologous influenza viruses. ID-EpiMut based vaccines are likely be more cross-protective than vaccines based on wild-type HA.

Thus, the disclosure provides a method to elicit broadly protective antibodies to immune-subdominant epitopes in HA of any subtype. Mixtures of influenza viruses or mixtures of other vectors, e.g., mixtures of isolated nucleic acid including mRNA and DNA encoding the altered HAs, including other viral vectors, e.g., filoviruses, adenoviruses, and the like, or virus-like particles including Ebola VLPs and influenza VLPs, or mixtures of polypeptides having altered influenza hemagglutinins (HAs), altered with a non-naturally occurring immunodominant antigenic head, as a result of substitutions and/or deletions in residues that form the immunodominant epitope, and conserved, immune subdominant epitopes (FIG. 2) provide a vaccine that may elicit high amounts of Abs to the conserved, immune subdominant epitopes in the head and in the stem, resulting in broader protection than that elicited by current vaccines. A composition having an individual recombinant virus, e.g., influenza virus, filovirus, adenovirus, or a VLP thereof, comprising HA having one or more of the altered residues, isolated nucleic acid encoding HA having one or more of the altered residues, or isolated HA having one or more of the altered residues, is envisioned.

In one embodiment, a recombinant influenza virus produced by the method has a HA that has one or more altered residues in one or more immunodominant epitopes of HA (residues in an epitope do not need to be contiguous or in close proximity in the primary amino acid sequence) resulting in altered epitopes that do not, for example, bind antibodies specific for the one or more immunodominant epitopes as efficiently as the (unaltered) immunodominant epitopes in the parental HA, and/or once administered, the HA with the one or more altered residues in the immunodominant epitopes elicit antibodies to conserved, immune subdominant epitopes in the head and/or in the stem of HA. In one embodiment, a recombinant influenza virus produced by the method has 20 or fewer unaltered residues that are part of one or more immunodominant epitopes, e.g., 15, 10, 5, 4, 3, 2, 1 or 0 residues are unaltered in one or more naturally occurring immunodominant epitope, for instance, in a specific parental influenza virus. In one embodiment, a recombinant influenza virus produced by the method has 1 to 10 or 10 to 20 altered immunodominant residues in two or more immunodominant epitopes. In one embodiment, a recombinant influenza virus produced by the method has 10 or fewer, e.g., 5 or 3, unaltered immunodominant residues in one or two immunodominant epitopes. For example, a recombinant influenza H3 virus produced by the method has 5 or fewer immunodominant residues at positions 121, 131, 135, 138, 140, 142, 144, 145, 155, 156, 157, 158, 171, 189, 193, 212, or 225. For example, a recombinant influenza H5 virus produced by the method has 5 or fewer immunodominant residues at positions 119, 123, 125, 126, 127, 129, 138, 140, 141, 151, 152, 153, 154, 155, 156, 185, or 189 in H5.

In one embodiment, a recombinant influenza virus produced by the method has 2 or more residues, e.g., has 2, 3, 4, 5, 6, 7, 8, 9, 10, 11, 12, 13, 14, 15, 16, 17 or more residues, that result in decreased antibody binding with antibodies that recognize immunodominant epitopes. Thus, residues in immunodominant epitopes are replaced (substituted) with residues that, if present in a HA in an influenza virus that infects an animal that has been infected with the HA with the immunodominant epitope, does not result in a memory response (immunological memory) as a result of the substitutions but instead redirects the immune response to subdominant epitopes in the HA head or stem, allowing for a broader immune response, e.g., to a specific HA subtype or a specific clade in a HA subtype. In one embodiment, a recombinant influenza virus produced by the method has 2 to 5, 5 to 10, 10 to 15, 15 to 20, or more substitutions in residues in immunodominant epitopes. In one embodiment, a recombinant influenza virus produced by the method has about 10 to 17 substitutions in residues in immunodominant epitopes. For example, a recombinant influenza H3 virus produced by the method has 2 to 5, 5 to 10, 10 to 15, or 10 to 17 non-dominant residues at a combination of positions 121, 131, 135, 138, 140, 142, 144, 145, 155, 156, 157, 158, 171, 189, 193, 212, or 225. For example, a recombinant influenza H5 virus produced by the method has 2 to 5, 5 to 10, 10 to 15, or 10 to 17 substitutions (to non-dominant residues) at a combination of positions 119, 123, 125, 126, 127, 129, 138, 140, 141, 151, 152, 153, 154, 155, 156, 185, or 189 in H5. In one embodiment, a recombinant influenza virus produced by the method has 1 to 2, 2 to 5, or up to 10 residues deleted, including for example positions 121, 131, 135, 138, 140, 142, 144, 145, 155, 156, 157, 158, 171, 189, 193, 212, or 225 in H3, or positions 119, 123, 125, 126, 127, 129, 138, 140, 141, 151, 152, 153, 154, 155, 156, 185, or 189 in H5, which deletion(s) in HA result in decreased antibody binding with antibodies that recognize immunodominant epitopes In one embodiment, a vaccine comprises a plurality of recombinant influenza viruses having substitutions (or deletions) at immunodominant positions (substitutions to "non-immunodominant residues"). In one embodiment, the vaccine comprises 2 to 5, 5 to 10, 10 to 20, 20 to 30, 30 to 40, or 40 to 50 distinct recombinant influenza viruses having substitutions (or deletions) at immunodominant epitope positions. In one embodiment, the vaccine comprises 2, 3, 4, 5, 6, 7, 8, 9, 10, 11, 12, 13, 14, 15, 16, 17, 18, 19 or 20 distinct recombinant influenza viruses having substitutions at immunodominant epitope positions. In one embodiment, the vaccine comprises 21, 22, 23, 24, 25, 26, 27, 28, 29, 30, 31, 32, 33, 34, 35, 36, 37, 38, 39 or 40 distinct recombinant influenza viruses having substitutions at immunodominant epitope positions.

In one embodiment, combinations of vectors with altered HAs in Tables 1 or 6 are employed in a composition that is administered to a mammal or an avian.

BRIEF DESCRIPTION OF FIGURES

FIG. 5. Flowchart.

FIGS. 6A-6B. Exemplary HA sequences of H3N2 viruses and a H5N8 virus (SEQ ID Nos. 1 and 6-9).

FIG. 7. HA sequence of an exemplary H5 (SEQ ID NO:2).

FIG. 8. HA sequences of an exemplary H1 (SEQ ID NO:3).

FIG. 9. HA sequence of an exemplary H2 (SEQ ID NO:4).

FIG. 10. HA sequence of an exemplary H7 (SEQ ID NO:5).

FIG. 15. Combining sets of 10 independent (distinct) H3 variants with substitutions in immunodominant epitope residues.

FIG. 17. Alignment of HA subtypes (see, e.g., Burke et al., *PLoS One*, 9:e112302 (2014)).

FIGS. 18A-18E. Exemplary antigenic sites in H3 HA.

DETAILED DESCRIPTION

Definitions

Figure 1:
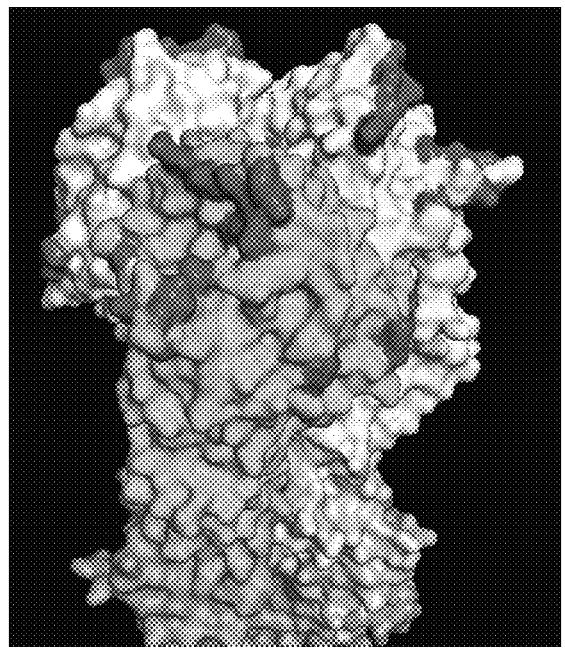
FIG. 1. X-ray structure of a human H3 HA protein. The positions targeted by mutagenesis are show in red.
Figure 2:
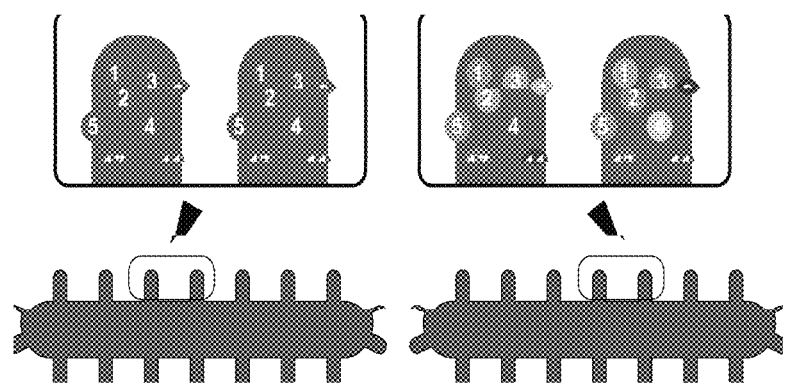
FIG. 2. Ebola VP40-based VLPs possessing wild-type HA (left), or HA with randomized amino acid changes at up to 17 amino acid positions (right).

As used herein, the term "isolated" refers to in vitro preparation and/or isolation of a nucleic acid molecule, e.g., vector or plasmid, peptide or polypeptide (protein), or virus, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or viral segment is from an influenza virus source that is different than a majority of the other influenza viral genes or viral segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information. The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5, N=−4, and a comparison of both strands. For amino acid sequences, the BLASTP program may use as defaults a wordlength (W) of 3, an expectation (E) of 10, and the BLOSUM62 scoring matrix. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Immunodominant HA Epitopes and Methods to Alter Those Epitopes

Both the processes of infection and vaccination with influenza viruses elicit, primarily, antibodies against the immune-dominant epitopes in the 'head' region of the viral hemagglutinin (HA) protein, the major viral antigen. Mutations in the immune-dominant epitopes may confer 'escape' from the antibodies circulating in an individual, so that a person that gained immunity to the previous influenza virus becomes vulnerable to the mutated 'escape variant' virus. Several strategies are being tested to redirect a recipient's immune response from the immune-dominant epitopes (which mutate frequently) in HA towards non-dominant epitopes in HA, which are more conserved. Targeting the conserved non-dominant epitopes should increase broadly-protective immunity.

Infections or vaccinations with influenza viruses elicit neutralizing antibodies that protect against infection with an antigenically closely related virus. Most neutralizing antibodies are directed against highly variable, immunodominant antigenic epitopes in the head of HA. For H3N2 viruses, early studies with antigenic escape mutants against mouse monoclonal antibodies identified five immunodominant antigenic epitopes (A-E) in the head of HA (Wiley et al., 1981 and 1987) (FIG. 1). The high mutation rate of influenza viruses and immune pressure in previously infected and/or vaccinated people result in the accumulation of mutations in these immunodominant antigenic epitopes, causing the antibodies circulating in an individual to no longer neutralize the virus. This so-called 'antigenic drift' is why humans get re-infected with seasonal influenza viruses. Current seasonal influenza vaccine strains are selected based on the antigenic properties of the highly variable immunodominant antigenic epitopes in the HA head. Therefore, the vaccine strain must be replaced for each new cluster or clade of antigenic drift variants. Moreover, antigenic drift may occur between the time the vaccine is selected (February for the northern hemisphere) and the start of the influenza season (fall in the northern hemisphere), rendering the vaccine largely ineffective ('vaccine mismatch').

Most antibodies (Abs) elicited upon influenza virus infection or vaccination are directed against the highly variable, immunodominant antigenic epitopes on the HA head; therefore, they only react with closely related viruses. In 1993, Okuno et al. reported a monoclonal Ab (mAb) that neutralized influenza viruses of two different subtypes. This finding was not fully appreciated at the time, and it was another decade before numerous studies reported mAbs that reacted with multiple HAs of the same subtype, with HAs of another subtype from the same group, with HAs from both groups 1 and 2, or with both influenza A and B virus HAs. Most of these broadly reactive mAbs bind to the HA stem (which anchors HA in the membrane and mediates the pH-induced membrane fusion event in late endosomes that releases the viral genome into the cytosol) (FIG. 1). However, some broadly reactive mAbs interact with conserved regions in the HA head. These mAbs fall into at least two main categories: broadly reactive mAbs that interact with a conserved, immune-subdominant epitope in the center of the receptor-binding site (conserved among most HA subtypes), and broadly reactive mAbs that interact with conserved, immune-subdominant epitopes on the HA head outside the receptor-binding pocket (these epitopes may not be conserved among all subtypes). The conserved, immune-subdominant epitopes evolve at a much slower rate than the immunodominant epitopes, explaining why antibodies that bind to the conserved epitopes react with more diverse strains (compared with antibodies that interact with the major antigenic epitopes). Antibodies directed at the conserved, immune-subdominant epitopes may therefore provide protection against viruses of different antigenic clusters within the same subtype, or against viruses of different subtypes.

Broadly reactive Abs to conserved regions in HA may pave the way for the development of broadly protective influenza vaccines. However, the conserved epitopes are immune-subdominant and Abs to these epitopes are detected at much lower levels than Abs targeting the immunodominant, highly variable major antigenic epitopes in the HA head. Researchers have therefore tried to refocus immune responses from the immunodominant, highly variable major epitopes in the HA head towards the conserved, immune-subdominant epitopes of HA.

A study in the 1980s demonstrated that vaccination with an HA lacking the head region ('headless HA') elicited stem-reactive Abs that reacted with the HA protein of a different subtype (Graves et al., 1983). Removing the HA head appeared to be an appealing strategy to elicit Abs to the conserved stem, and various membrane-anchored or secreted versions of headless HAs have been tested. Some of these studies led to the generation of broadly protective antibodies upon vaccination, but headless HAs are of low stability and may not fold correctly; moreover, they lack the conserved, immune-subdominant epitopes in the HA head.

In 2011, Wilson and colleagues reported that infection with the pandemic 2009 H1N1 virus (an antigenically novel influenza virus that had not circulated in humans prior to 2009) elicited more broadly cross-reactive antibodies against conserved, immune-subdominant epitopes in the HA stem than typically detected after infection or vaccination with a seasonal influenza virus (Wrammert et al., 2011). Others reported similar results. Moreover, vaccination with experimental vaccines to H5 (Ellebedy et al., 2014: Nachbagauer et al., 2014) or H7 viruses (Henry et al., 2016 and 2015; Liu et al., 2017; Krammer et al., 2014; Halliley et al., 2015), neither of which circulate in humans, elicited higher amounts of broadly reactive antibodies to conserved, immune-subdominant epitopes in the HA stem than typically detected after infection or vaccination with a seasonal influenza virus. This effect was strongest after the first encounter with a novel (not previously encountered) HA. For example, the first vaccination with a pandemic 2009 H1N1 vaccine elicited high levels of broadly reactive Abs to immune-subdominant epitopes in the HA stem (Andrews et al., 2015). However, after the second exposure to the pandemic 2009 H1N1 virus, most Abs were directed against immunodominant epitopes in the HA head, and the level of Abs directed against the immune-subdominant stem epitopes declined considerably compared with the levels measured after the first exposure (Andrews et al., 2015). Collectively, these findings indicate that the first encounter with an unique HA elicits appreciable amounts of broadly reactive Abs to conserved, immune-subdominant epitopes. In contrast, repeated infection or vaccination with seasonal influenza viruses (which differ by as little as one or two amino acids in one major antigenic epitope but share the other major epitopes) primarily stimulates (recall) Abs to the immunodominant antigenic epitopes.

Exemplary Methods

The present disclosure relates to influenza vaccines based on a distinct 'outdilution' approach for improving the antigenic response to the non-dominant epitopes. Customized influenza viruses with strategically antigenically-distinct immunodominant epitopes (the residues in the immunodominant epitope are changed to residues that do not react with antibodies that recognize the immunodominant epitope) in the 'head' region of HA are pooled, so that the response of the body is to make small amounts of antibodies to the various antigenically-distinct immunodominant epitopes (also referred to as non-immunodominant epitope residues), whereas the large amount of conserved non-dominant epitopes shared by the entire pool strengthen the response to those non-dominant epitopes and thereby create an immune response that is more likely to prove protection against a range of circulating natural viruses, which can be predicted to share those conserved non-dominant epitopes, also.

In one embodiment, a plurality of positions in HA, e.g., up to 17 positions in H3 HA, that are known or suspected of being associated with an epitope, are randomly mutated. For H3, 60 viable viruses were recovered. Monoclonal antibodies are used to evaluate the antigenicity of the recovered viruses. Many of the viruses bind to a limited number of the tested mAbs, which apparently correspond to non-dominant epitopes. The same approach can be used for a range of subtypes or just one subtype (e.g., H3N2, H5N1, etc.) that makes up the vaccine cocktail. For human seasonal H3N2 viruses, the method resulted in viruses with 'heavily' mutated immunodominant antigenic epitopes, viruses that were viable, functional, and antigenically distinct from the parent virus.

In one embodiment, a pan-H3 vaccine is prepared from the modified HA containing viruses that confers protection against multiple antigenic clusters of seasonal human H3N2 viruses. Since the mixtures of immunodominant antigenic head epitopes that have not been detected in nature, the immune response is focused towards conserved, immune subdominant epitopes. Because the method can generate millions of HA variants with multiple non-naturally occurring mutations in the immunodominant epitopes, viable viruses that possess multiple amino acid changes in their immunodominant epitopes that alter their antigenic properties can be obtained. Unlike other approaches, vaccine candidates are prepared that (i) present non-naturally occurring immunodominant antigenic head epitopes, (ii) preserve the conserved, immune subdominant epitopes in the HA stem and the HA head; and (iii) maintain the structural and functional integrity of HA; as a result, our vaccine candidates should be more cross-protective than vaccines based on a wild-type virus.

Influenza Vaccines

A vaccine of the invention includes at least one of the isolated recombinant influenza viruses having the desired property, e.g., one or more of non-naturally occurring immunodominant antigenic head epitopes and/or conserved, immune subdominant epitopes in the HA stem and the HA head, as well as maintaining the structural and functional integrity of HA, and optionally one or more other isolated viruses including other isolated influenza viruses having the desired property, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition;

and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 µg, e.g., 30 to 100 µg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscamet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition having one of more influenza viruses with the desired properties may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{20}$, e.g., $10^3$-$10^2$, $10^2$-$10^{10}$, $10^5$-$10^{11}$, $10^6$-$10^{15}$, $10^2$-$10^{10}$, or $10^{15}$-$10^{20}$ plaque forming units (PFU)/kg, or any range or value therein. The dose of one viral isolate vaccine, e.g., in an inactivated vaccine, may range from about 0.1 to 1000, e.g., 0.1 to 10 µg, 1 to 20 pig, 30 to 100 µg, 10 to 50 µg, 50 to 200 µg, or 150 to 300 µg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 µg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 µg or any range or value therein, or the amount recommended by the U.S. Public Heath Service (PHS), which is usually 15 µg, per component for older children >3 years of age, and 7.5 µg per component for children <3 years of age. The quantity of NA can also be standardized, however, this glycoprotein can be labile during the processor purification and storage (Kendal et al., 1980; Kerr et al., 1975). Each 0.5-ml dose of vaccine may contain approximately 0.1 to 0.5 billion viral particles, 0.5 to 2 billion viral particles, 1 to 50 billion virus particles, 1 to 10 billion viral particles, 20 to 40 billion viral particles, 1 to 5 billion viral particles, or 40 to 80 billion viral particles.

EXEMPLARY EMBODIMENTS

In one embodiment, a method to prepare a plurality of influenza virus nucleic acid molecules encoding a hemagglutinin (HA) having a reduced number of immunodominant epitopes is provided. The method includes introducing random mutations at a plurality of codons in an isolated parental influenza virus nucleic acid molecule encoding a hemagglutinin having immunodominant epitopes, thereby providing a library of influenza virus nucleic acid molecules encoding a mutant hemagglutinin, wherein the mutations are at codons that encode a residue in an immunodominant epitope in the parental hemagglutinin; introducing the library into cells so as to provide a library of cells that express the mutant hemagglutinins; and identifying nucleic acid molecules encoding a mutant hemagglutinin with a reduced number of immunodominant epitopes as a result of substitutions and/or deletions at residues that form the immunodominant epitopes. In one embodiment, the cells are mammalian cells. In one embodiment, the hemagglutinin (HA) is H1, H2, H3, H5, H6, H7, or H9. In one embodiment, the mutant HA has non-immunodominant residues at two or more of positions 121, 131, 135, 138, 140, 142, 144, 145, 155, 156, 157, 158, 171, 189, 193, 212, or 225 in H3. In one embodiment, the residue in H3 at position 121 is Q, R, I, L, V, S, F, Y or A, position 131 is R, V, S, Q, C, V, Y, D, E, or L, position 135 is Y, K, N, V, W, S, V, or P, position 138 is W, K, I, R, or L, position 140 is L, M, T, S, R K, M, or P, position 142 is N, G, Y, Q, E, H, N, L, or P, position 144 is T, V, G, D, H, L or Q, position 145 is P, R, W or K, position 155 is C, I, R, A, V, S or N, position 156 is P, G, S, T, A, or C, position 157 is D, P, S, G, I, R or T, position 158 is R, V, S, A, K, C, Q, position 171 is T, F, L, E, H, C or R, position 189 is A, P, T, L, A, S, Y, or R, position 193 is Q, R, N, T, E, V, or P, position 212 is V, R, G, S, M, D or E, or position 225 is L, P, C, S, Q, G, Y, or F In one embodiment, the residue in H3 at position 121 is not N, position 131 is not T, position 135 is not T, position 138 is not A, position 140 is not I, position 142 is not R, position 144 is not S, position 145 is not S, position 155 is not T, position 156 is not H, position 157 is not L, position 158 is not N, position 171 is not N, position 189 is not K, position 193 is not F, position 212 is not A, or position 225 is not D. In one embodiment, the residue in H3 at position 121 is N, position 131 is T, position 135 is T, position 138 is A, position 140 is I, position 142 is R, position 144 is S, position 145 is S, position 155 is T, position 156 is H, position 157 is L, position 158 is N, position 171 is N, position 189 is K, position 193 is F, position 212 is A, or position 225 is D. In one embodiment, the mutant HA has non-immunodominant residues at two or more of positions 119, 123, 125, 126, 127, 129, 138, 140, 141, 151, 152, 153, 154, 155, 156, 185, or 189 in H5. In one embodiment, the residue in H5 at position 119 is not R, 123 is not P, 125 is not H, 126 is not E, 127 is not T, 129 is not L, 138 is not Q, 140 is not A, 141 is not S, 151 is not I, 152 is not K, 153 is not K, 154 is not N, 155 is not D, 156 is not A, 185 is not A, or 189 is not N. In one embodiment, the residue in H5 at position 119 is R, position 123 is P, position 125 is H, position 126 is E, position 127 is T, position 129 is L, position 138 is Q, position 140 is A, position 141 is S, position 151 is I, position 152 is K, position 153 is K, position 154 is N, position 155 is D, position 156 is A, position 185 is A, or position 189 is N. In one embodiment, the residue in H5 at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N: position 185 is L, D, N, G, E, F, S, L, Q, P, V, M, R, A, or S; or position 189 is Y, S, L, R, K, G, E, F, D, V, E, I, or H. In one embodiment, 2, 3, 4, 5, 6, 7, 8, 9, 10, 11, 12, 13, 14 15, 16, 17, 18, 19 or 20 of the codons that encode residues that form the immunodominant epitope are mutated. In one embodiment, the mutant HA has 2,3,4,5, 6, 7, 8, 9, 10, 11, 12, 13, 1415, 16, 17, 18, 19 or 20 non-immunodominant epitope residues. In one embodiment, the mutant HA has 10, 11, 12, 13, 14 15, 16, or 17 non-immunodominant epitope residues. In one embodiment, the mutant HA has 1, 2, 3, 4, 5, 6, 7, 8, 9, or 10, immunodominant epitope residues of the parent. In one embodiment, the mutant HA has 1, 2, 3, 4, or 5 immunodominant epitopes of the parent. In one embodiment, the nucleic acid molecules are identified using one or more antibodies that recognize conserved sub-dominant epitopes. In one embodiment, the cells encoding the nucleic acid molecules are identified as those that do not bind one or more antibodies that recognize immunodominant epitopes. In one embodiment, the nucleic acid molecule encoding the mutant hemagglutinin is sequenced.

In one embodiment, a method to prepare an influenza virus encoding a mutant hemagglutinin that has one or more altered residues in one or more immunodominant epitopes relative to a parental influenza virus is provided. The method includes introducing a plurality of mutations at residues that form an immunodominant domain of a HA of a parent influenza virus and isolating or preparing one or more influenza viruses with the mutated HA. In one embodiment, a plurality of mutations is introduced to antigenic sites A and/or B in HA, thereby forming a library of influenza viruses having mutant HAs. Viruses in the library having distinct mutations in antigenic sites A and/or B, e.g., those that have lower reactivity with sera that bind immunodominant epitopes in the parent HA, can be pooled to form a 'pan' HA sub-type specific vaccine. In one embodiment, a mutation is introduced in an H3 HA encoding nucleic acid molecule at two or more of residues 121, 131, 135, 138, 140, 142, 144, 145, 155, 156, 157, 158, 171, 189, 193, 212, or 225, to encode a residue that is not a residue that is part of an immunodominant epitope in the parent virus, and one or more influenza viruses with the mutated H3 HA are prepared. In one embodiment, a mutation is introduced in an H5 HA encoding nucleic acid molecule at two or more of residues 119, 123, 125, 126, 127, 129, 138, 140, 141, 151, 152, 153, 154, 155, 156, 185, or 189, wherein the mutations encode a residue that is not an immunodominant epitope; and to encode a residue that is not a residue that forms an immunodominant epitope for the parent virus, and one or more influenza viruses with the mutated H5 HA are prepared. In one embodiment, the residue in the mutated H3 HA at position 121 is Q, R, I, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F. In one embodiment, the residue in H3 at position 121 is not N, position 131 is not T, position 135 is not T, position 138 is not A, position 140 is not I, position 142 is not R, position 144 is not S, position 145 is not S, position 155 is not T, position 156 is not H, position 157 is not L, position 158 is not N, position 171 is not N, position 189 is not K, position 193 is not F, position 212 is not A, or position 225 is not D. In one embodiment, the residue in H3 at position 121 is N, position 131 is T, position 135 is T, position 138 is A, position 140 is I, position 142 is R, position 144 is S, position 145 is S, position 155 is T, position 156 is H, position 157 is L, position 158 is N, position 171 is N, position 189 is K, position 193 is F, position 212 is A, or position 225 is D. In one embodiment, the residue at position 119 is not R, 123 is not P, 125 is not H, 126 is not E, 127 is not T, 129 is not L, 138 is not Q, 140 is not A, 141 is not S, 151 is not I, 152 is not K, 153 is not K, 154 is not N, 155 is not D, 156 is not A, 185 is not A, or 189 is not N. In one embodiment, the residue at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H. In one embodiment, wherein the mutant HA has 2, 3, 4, 5, 6, 7, 8, 9, 10, 11, 12, 13, 14, 15, 16, or 17 different residues (non-immunodominant epitope residues) at the immunodominant epitope positions of the parent.

In one embodiment, a composition is provided comprising a plurality of distinct recombinant influenza viruses each encoding a hemagglutinin comprising non-immunodominant epitope residues at immunodominant epitope residue sites, e.g., antigenic sites A and/or B. Thus, the distinct recombinant influenza viruses have distinct mutations in antigenic sites A and/or B, e.g., those that have lower reactivity with sera that bind immunodominant epitopes in the parent HA, can be pooled to form a 'pan' HA sub-type specific vaccine. In another embodiment, the composition has a plurality of distinct recombinant influenza viruses each encoding a hemagglutinin comprising non-immunodominant epitope residues at immunodominant epitope residue sites, e.g., antigenic sites A and/or B, where at least two of the plurality encode different subtypes of hemagglutinin. In one embodiment, one of the plurality of influenza viruses comprises a non-immunodominant epitope at two or more of positions 121, 131, 135, 138, 140, 142, 144, 145, 155, 156, 157, 158, 171, 189, 193, 212, or 225 in H3. In one embodiment, one of the plurality of influenza viruses comprises a non-immunodominant epitope residue at two or more of positions 119, 123, 125, 126, 127, 129, 138, 140, 141, 151, 152, 153, 154, 155, 156, 185, or 189 in H5. In one embodiment, the composition has at least 2, 3, 4, 5, 6, 7, 8, 9, or 10 or more distinct recombinant influenza viruses.

Further provided is a method to immunize an animal, comprising: administering an effective amount of a composition comprising a plurality of the viruses described to an animal, e.g., a human, canine, feline, bovine, caprine, ovine, equine, swine, or avian.

In one embodiment, a method to prepare a plurality of influenza virus nucleic acid molecules encoding a hemagglutinin (HA) having one or more altered residues in one or more immunodominant epitopes is provided, comprising: introducing random mutations at a plurality of codons in one or more immunodominant epitopes in an isolated parental influenza virus nucleic acid molecule encoding an influenza virus hemagglutinin having at least two immunodominant epitopes, thereby providing a library of influenza virus nucleic acid molecules encoding a mutant influenza virus hemagglutinin; introducing the library into cells so as to provide a library of cells that express the mutant hemagglutinins; and identifying a mutant hemagglutinin encoded by the library with a reduced number of the immunodominant epitopes relative to the parental hemagglutinin as a result of one or more substitutions and/or deletions at residues that form the one or more immunodominant epitopes. In one embodiment, the mutations are introduced into immunodominant epitope (antigenic site) A, B, or A and B. In one embodiment, the mutations are introduced into immunodominant epitope C, D or E, or any combination thereof. In one embodiment, at least 5, 10, or 20 codons, or any integer between 5 and 20, are mutated. In one embodiment, the mutant hemagglutinin is identified using antibodies or other hemagglutinin binding molecules. In one embodiment, at least one of the antibodies or other hemagglutinin binding molecules binds an immunodominant epitope in the parent hemagglutinin or a different influenza virus of the same HA sub-type. In one embodiment, the method includes contacting one or more members of the library with at least one antibody or other hemagglutinin binding molecule that binds a conserved region in the hemagglutinin stem. In one embodiment, the immunodominant epitope that is mutated corresponds to residues 121 to 146 in H3 HA (site A), residues 156 to 196 in H3 HA (site B), residues 50 to 57 or 275 to 279 in H3 HA (site C), residue 164, residue 182 or residues 208 to 217 in H3 HA (site D) or residues 62 to 83 in H3 HA (site E). In one embodiment, the cells are mammalian cells. In one embodiment, the hemagglutinin (HA) is H1, H2, H3, H5, H6, H7 or H9. In one embodiment the mutant HA has a substitution at two or more of positions 121, 131, 135, 138, 140, 142, 144, 145, 155, 156, 157, 158, 171, 189, 193, 212, or 225, or a deletion at one or more of positions 121, 131, 135, 138, 140, 142, 144, 145, 155, 156, 157, 158, 171, 189, 193, 212, or 225, in H3, or a combination thereof, relative to a parental HA. In one embodiment, the residue in H3 at position 121 is Q, R, I, L, V, S, F, Y or A, position 131 is R, V, S, Q, C, V, Y, D, E, or L, position 135 is Y, K, N, V, W, S, V, or P, position 138 is W, K, I, R, or L, position 140 is L, M, T, S, R K, M, or P, position 142 is N, G, Y, Q, E, H, N, L, or P, position 144 is T, V, G, D, H, L or Q, position 145 is P, R, W or K, position 155 is C, I, R, A, V, S or N, position 156 is P, G, S, T, A, or C, position 157 is D, P, S, G, I, R or T, position 158 is R, V, S, A, K, C, Q, position 171 is T, F, L, E, H, C or R, position 189 is A, P, T, L, A, S, Y, or R, position 193 is Q, R, N, T, E, V, or P, position 212 is V, R, G, S, M, D or E, or position 225 is L, P, C, S, Q, G, Y, or F. In one embodiment, the mutant residue at position 121 is not N, position 131 is not T, position 135 is not T, position 138 is not A, position 140 is not I, position 142 is not R, position 144 is not S, position 145 is not S, position 155 is not T, position 156 is not H, position 157 is not L, position 158 is not N, position 171 is not N, position 189 is not K, position 193 is not F, position 212 is not A, or position 225 is not D. In one embodiment, the non-mutant residue at position 121 is N, position 131 is T, position 135 is T, position 138 is A, position 140 is I, position 142 is R, position 144 is S, position 145 is S, position 155 is T, position 156 is H, position 157 is L, position 158 is N, position 171 is N, position 189 is K, position 193 is F, position 212 is A, or position 225 is D. In one embodiment, the mutant HA has a substitution at two or more of positions 119, 123, 125, 126, 127, 129, 138, 140, 141, 151, 152, 153, 154, 155, 156, 185, or 189, or a deletion in one or more of positions 119, 123, 125, 126, 127, 129, 138, 140, 141, 151, 152, 153, 154, 155, 156, 185, or 18, in H5, or any combination thereof. In one embodiment, the mutant residue at position 119 is not R, 123 is not P, 125 is not H, 126 is not E, 127 is not T, 129 is not L, 138 is not Q, 140 is not A, 141 is not S, 151 is not I, 152 is not K, 153 is not K, 154 is not N, 155 is not D, 156 is not A, 185 is not A, or 189 is not N. In one embodiment, the non-mutant residue at position 119 is R, position 123 is P, position 125 is H, position 126 is E, position 127 is T, position 129 is L, position 138 is Q, position 140 is A, position 141 is S, position 151 is I, position 152 is K, position 153 is K, position 154 is N, position 155 is D, position 156 is A, position 185 is A, or position 189 is N. In one embodiment, the residue at position 119 is L, K, R, S, G, T, E, A, V, F or N; position 123 is L, Y, I, M, N, S, V, K, G, T or R; position 125 is L, D, N, G, W, M, 1, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H. In one embodiment, 2, 3, 4, 5, 6, 7, 8, 9, 10, 11, 12, 13, 14, 15, 16, or 17 of the codons that encode residues that form the immunodominant epitope are mutated. In one embodiment, the mutant HA has 2, 3, 4, 5, 6, 7, 8, 9, 10, 11, 12, 13, 14 15, 16, or 17 substitutions. In one embodiment, the mutant HA has 10, 11, 12, 13, 14 15, 16, or 17 substitutions. In one embodiment, the mutant HA has 1, 2, 3, 4, 5, 6, 7, 8, 9, or 10 residues in the one or more immunodominant epitopes that are not substituted or deleted. In one embodiment, the mutant HA has at least 10, 15, 20, 25, 30, 35, 40 or 45 residues in the immunodominant epitope that are not substituted or deleted. In one embodiment, the nucleic acid molecule encoding the mutant hemagglutinin is sequenced.

In one embodiment, a method to prepare an influenza virus encoding a mutant hemagglutinin with altered immunodominant epitopes relative to a parental influenza virus is provided, comprising: introducing a mutation in a parental H3 HA nucleic acid molecule at two or more codons for residue 121, 131, 135, 138, 140, 142, 144, 145, 155, 156, 157, 158, 171, 189, 193, 212, or 225, wherein the mutation encodes a residue that is not an immunodominant epitope residue in the parent H3 HA; and isolating or preparing one or more influenza viruses with the mutated H3 HA. In one embodiment, the mutated H3 is recognized by antibodies that bind sub-dominant epitopes but not antibodies that bind the immunodominant epitope. In one embodiment, the residue in the mutated H3 HA at position 121 is Q, R, I, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F. In one embodiment, the residue in H3 at position 121 is not N, position 131 is not T, position 135 is not T, position 138 is not A, position 140 is not I, position 142 is not R, position 144 is not S, position 145 is not S, position 155 is not T, position 156 is not H, position 157 is not L, position 158 is not N, position 171 is not N, position 189 is not K, position 193 is not F, position 212 is not A, or position 225 is not D. In one embodiment, the residue in H3 at position 121 is N, position 131 is T, position 135 is T, position 138 is A, position 140 is I, position 142 is R, position 144 is S, position 145 is S, position 155 is T, position 156 is H, position 157 is L, position 158 is N, position 171 is N, position 189 is K, position 193 is F, position 212 is A, or position 225 is D.

In one embodiment, a method to prepare an influenza virus encoding a mutant hemagglutinin with altered immunodominant epitopes relative to a parental influenza virus is provided, comprising: introducing a mutation in a parental H5 HA nucleic acid molecule at two or more codons for residue 119, 123, 125, 126, 127, 129, 138, 140, 141, 151, 152, 153, 154, 155, 156, 185, or 189, wherein the mutation encodes a residue that is not an immunodominant epitope residue in the parent H5HA; and isolating or preparing influenza viruses with the mutated H5 HA. In one embodiment, the mutated H5 is recognized by antibodies that bind sub-dominant epitopes but not antibodies that bind the immunodominant epitope. In one embodiment, the residue at position 119 is not R, 123 is not P, 125 is not H, 126 is not E, 127 is not T, 129 is not L, 138 is not Q, 140 is not A, 141 is not S, 151 is not 1, 152 is not K, 153 is not K, 154 is not N, 155 is not D, 156 is not A, 185 is not A, or 189 is not N. In one embodiment, the residue at position 119 is L, K, R, S, G, T, E, A, V, F or N; position 123 is L, Y, 1, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H. In one embodiment, the mutant HA has 2, 3, 4, 5, 6, 7, 8, 9, 10, 11, 12, 13, 14, 15, 16, or 17 substitutions.

In one embodiment, a composition is provided comprising a plurality of distinct recombinant influenza H3 viruses each encoding a hemagglutinin comprising a plurality of antigenically distinct residues relative to residues that form an immunodominant epitope in a parent virus, wherein each of the plurality of influenza viruses comprises substitutions at two or more of positions 121, 131, 135, 138, 140, 142, 144, 145, 155, 156, 157, 158, 171, 189, 193, 212, or 225, or one or more deletions of positions 121, 131, 135, 138, 140, 142, 144, 145, 155, 156, 157, 158, 171, 189, 193, 212, or 225, in H3, or any combination thereof. In one embodiment, the composition has at least three, four or five distinct viruses with the substitutions. In one embodiment, the composition has five to ten distinct viruses with the substitutions. In one embodiment, the composition has ten to twenty distinct viruses with the substitutions. In one embodiment, each distinct virus has at least one to five substitutions in antigenic site A or site B. In one embodiment, each distinct virus has at least one to ten substitutions in antigenic sites A and B. In one embodiment, each distinct virus has altered binding to antibodies that bind the corresponding parental hemagglutinin.

In one embodiment, a composition is provided comprising a plurality of distinct recombinant influenza H5 viruses each encoding a hemagglutinin comprising antigenically distinct residues relative to residues that form an immunodominant epitope in a parent virus, wherein each of the plurality of influenza viruses comprises a substitution at two or more of positions 119, 123, 125, 126, 127, 129, 138, 140, 141, 151, 152, 153, 154, 155, 156, 185, or 189, or a deletion in one or more of positions 119, 123, 125, 126, 127, 129, 138, 140, 141, 151, 152, 153, 154, 155, 156, 185, or 189, in H5, or any combination thereof. In one embodiment, the composition has at least three, four or five distinct viruses with the substitutions. In one embodiment, the composition has five to ten distinct viruses with the substitutions. In one embodiment, the composition has ten to twenty distinct viruses with the substitutions. In one embodiment, each distinct virus has at least one to five substitutions in antigenic site A or site B. In one embodiment, each distinct virus has at least one to ten substitutions in antigenic sites A and B. In one embodiment, wherein each distinct virus has altered binding to antibodies that bind the corresponding parental virus. In one embodiment, the composition has at least 2, 3, 4, 5, 6, 7, 8, 9, or 10 or more distinct recombinant influenza viruses.

In one embodiment a method to immunize an animal is provided, comprising: administering an effective amount of a composition described herein to an animal.

In one embodiment, an isolated influenza virus is provided comprising a H5 HA wherein the residue at position 119 is L, K, R, S, G, T, E, A, V, F or N; position 123 is L, Y, I, M, N, S, V, K, G, Tor R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, 1, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, I, F, or D; position 153 is R, Q, T, N, S, F, P, V, or K; position 154 L, T, D, R, P, S, or H; position 155 is N, G, K, H, T, L, S, I, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H, or any combination of those residues at those positions.

In one embodiment, a composition is provided comprising a plurality of distinct influenza viruses comprising a H5 HA wherein the residue at position 119 is L, K, R, S, G, T, E, A, V, F or N; position 123 is L, Y, I, M, N, S, V, K, G, T or R; position 125 is L, D, N, G, W, M, I, R, K, F, A, or S; position 126 is S, R, I, G, N, Q, A, N or R; position 127 is V, A, S, M, L, K, F or Y; position 129 is D, S, G, K, W, R, E, V, Q, A, I, or F; position 138 is G, D, E, L, A, M, V, F, R or S; position 140 is T, G, S, R, D, K, Q, E, C, or V; position 141 is R, P, W, K, E, A, M, D, L, or Q; position 151 is T, S, L, Y, K, N, or Q; position 152 is A, P, T, Y, H, E, S, 1, F, or D; position 153 is R, Q, T, N, S, F, P, V, or K; position 154 L, T, D, R, P, S, or H; position 155 is N, G, K, H, T, L, S, 1, P, or Q; position 156 is T, F, R, S, D, P, H, G, A, or N; position 185 is L, D, N, G, E, F, S, L, Q, P, V, M, R, A, or S; or position 189 is Y, S, L, R, K, G, E, F, D, V, E, I, or H, or any combination of those residues at those positions.

In one embodiment, an isolated influenza virus is provided comprising a H3 HA wherein the residue at position 121 is Q, R, I, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F, or any combination of those residues at those positions.

In one embodiment, a composition is provided comprising a plurality of distinct influenza viruses comprising a H3 HA wherein the residue at position 121 is Q, R, I, L, V, S, F, Y, or A, position 131 is R, V, S, Q, C, V, Y, D, E, or L, position 135 is Y, K, N, V, W, G, S, V, or P, position 138 is W, K, I, F, R, or L, position 140 is L, M, T, S, R K, M, Y, or P, position 142 is N, G, Y, Q, E, H, N, or Q, position 144 is T, V, G, D, P, H, L, K, or Q, position 145 is P, D, R, W or N, position 155 is C, I, R, A, V, S, or Q, position 156 is P, G, S, T, A, or C, position 157 is D, P, S, G, I, Q, R or T, position 158 is R, V, S, A K, C, Q, or G, position 171 is T, F, L, E, H, V, or R, position 189 is A, P, T, L, S, Y or R, position 193 is Q, R, N, T, E, V or P, position 212 is V, R, G, S, M, D or E, or position 225 is L, P, C, S, Q, G, Y, or F, or any combination of those residues at those positions.

The invention will be described by the following non-limiting examples.

Example 1

VLPs can be generated by expressing influenza HA together with a single viral matrix protein; hence, the immune responses to the other influenza viral proteins, such as M1 and NA, will not affect the interpretation of the results. VLPs based on the Ebola virus VP40 matrix protein are employed because humans do not possess antibodies to VP40, and Ebola VP40-based VLPs expressing HA are efficiently formed.

17 amino acid positions were identified in human H3 HA proteins that are known or expected to affect antigenicity (e.g., positions 121, 131, 135, 138, 140, 142, 144, 145, 155, 156, 157, 158, 171, 189, 193, 212, and 225; see FIG. 1) and gene 'libraries' were prepared that encode all 20 amino acids at each of the 17 positions (resulting in $20^{17}$ theoretically possible variants) in the genetic background of A/Tokyo/UT-IMS2-1/2014 (a clade 3c.2a virus). Virus libraries possessing the up to '17-amino acid mutant HA' proteins were generated and screened with human sera to identify antigenic escape mutants. It was found that HA proteins with up to 17 amino acid changes in their antigenic epitopes were functional and antigenically distinct from the parental virus.

The '17-amino acid mutant HA' proteins may elicit broadly protective immune responses. Immunization with a mixture of HAs with up to 17 amino acid changes at positions responsible for the immune-dominance of the HA head, are unlikely to induce antibodies to the immune-dominant HA epitopes. Rather, stronger responses may be elicited to non-dominant epitopes, resulting in increased cross-protective immunity compared to current vaccines. The use of such vaccines may overcome immunological imprinting (immune response biased towards the first influenza virus encountered).

Specifically, VLP libraries with randomized sequences at 17 amino acid positions of the HA protein of the A/California/7/2004 (Cal/04) virus, a representative of the 'California/2004' antigenic cluster of human H3 viruses are prepared. As a control, VLPs containing wild-type HA protein are also generated. All VLPs are treated with sialidase to prevent self-aggregation. VLPs containing wild-type or '17-amino acid mutant HA' proteins are tested for their reactivity with monoclonal antibodies to the HA head and stalk (e.g., >20 and >10 monoclonal antibodies that react with the head or stalk, respectively, of Cal/04 virus). Compared with VLPs containing wild-type HA, VLPs containing the '17-amino acid mutant HA' proteins likely show reduced binding to antibodies that interact with the HA head, whereas the level of binding to antibodies that interact with the HA stalk is expected to be similar between the two VLPs.

To test the immunogenicity and protective efficacy of the H3 HA-VLPs against antigenically diverse human H3 viruses, ferrets are immunized twice with Cal/04 H3 HA-VLPs; four weeks after the second immunization, the antibody titers against VLPs containing wild-type HA or '17-amino acid mutant HA' proteins are tested. Ferrets are challenged with homologous Cal/04 virus or with three different human H3 influenza viruses belonging to more recent antigenic clusters (e.g., the 'Perth/2009', 'Victoria/2012', and current 3c.2a1 clades). Virus titers in nasal swabs are tested by using plaque assays. Alternatively, or in addition, ferrets are "pre-immunized" with VLPs containing the HA proteins of the 'Wuhan/1995', 'Sydney/1997', and 'Fujian/2002' cluster (ferrets are immunized sequentially with these VLPs; immunizations will be two weeks apart). After the three sequential 'pre-immunizations', animals are vaccinated with VLPs containing wild-type Cal/04 or '17-amino acid mutant Cal/04 HA' proteins and the animals are challenged as described above in order to establish whether a vaccine that elicits antibodies to non-dominant epitopes can overcome immunogenic imprinting.

Immunization with wild-type virus protects ferrets against infection with homologous virus, but not against infection with antigenic drift variants that belong to different antigenic clades. Ferrets immunized with '17-amino acid mutant' H3 HA-VLPs are better protected than those immunized with the wild-type virus against antigenically drifted human H3N2 influenza viruses which establishes that immunization with '17-amino acid mutant HA' proteins elicits broadly protective antibodies, perhaps because immune responses are 'refocused' towards non-dominant epitopes that are more conserved among human H3 viruses than the major immune-dominant epitopes.

Individual mutants and/or libraries in which fewer amino acid positions are randomized allow for the identification of specific mutant HA proteins that elicit cross-protective immune responses to non-dominant epitopes.

Example 2

Generation and In Vitro Characterization of HAs with Multiple Mutations in Immunodominant Epitopes (ID-EpiMut HAs)

Given that the first exposure to previously unencountered HAs elicits high levels of Abs to conserved, immune-subdominant HA epitopes, mixtures of viruses encoding non-naturally occurring immunodominant head epitopes (i.e., immunodominant epitope-mutated HA, ID-EpiMut HA) are prepared. Each of these variants is an unique HA to the immune system, thereby boosting the levels of cross-protective antibodies to the conserved, immune-subdominant regions in HA.

Experimental Approach. Millions of mutant influenza viruses are generated ('virus libraries'), and variants with the desired properties, such as non-naturally occurring immunodominant head epitopes, are selected.

Generation and screening of virus libraries. Methods to generate influenza virus 'libraries', as well as other viral libraries including Ebola VLP libraries, that is, mixtures of viruses possessing random mutations at arbitrary or predetermined amino acid positions of an influenza viral protein, are available ((Li et al., 2016; Ping et al., 2015 and 2016; Taft et al., 2015). Briefly, mutations at predetermined positions of influenza viral cDNAs are introduced by PCR with degenerate oligonucleotides encoding 'NNN' at the targeted codon, or by commercial gene synthesis. The resulting PCR or gene mixtures are cloned into RNA polymerase I vectors for the transcription of influenza viral RNAs, resulting in so-called 'plasmid libraries'. Following established reverse genetics protocols, eukaryotic cells (e.g., 293T human embryonic fibroblast cells) are transfected with the plasmid library, seven RNA polymerase I plasmids for the transcription of the remaining seven viral RNA segments (the genome of influenza A viruses comprises eight segments of single-stranded RNA), and four protein expression plasmids synthesizing the viral polymerase proteins (PB2, PB1, PA) and nucleoprotein (NP), which are all essential to initiate viral replication and transcription. This approach results in the generation of virus libraries composed of millions of mutants.

While classic experimental approaches test one mutation at a time, the present approach allows the simultaneous testing of millions of mutants. Hence, the approach (i) recapitulates multiple steps of evolution in an experimental setting; (ii) covers a large 'sequence space' (including mutants that have not been isolated in nature; (iii) allows for competition among mutants (a critical aspect in virus evolution); and (iv) eliminates non-viable mutants at the stage of virus library generation. Virus libraries are then screened for different biological features including antigenicity, receptor-binding properties, polymerase activity, and virus titers. The power and versatility of this approach has been shown by modeling the antigenic evolution of seasonal human H1N1 and H3N2 influenza viruses (Li et al., 2016), isolating polymerase mutants that confer efficient replication to avian influenza viruses in mammalian cells (an important feature in the generation of pandemic influenza viruses) (Taft et al., 2016), and by selecting mutations that increase the titers of influenza A and B vaccine viruses (Ping et al., 2015 and 2016).

Generation and screening of H5 HA virus libraries. To better understand the antigenic differences among pandemic H5N1 influenza viruses, random mutations were introduced at 17 amino acid positions that are known or suspected to affect the antigenic properties of these viruses (e.g., amino acid positions 119, 123, 125, 126, 127, 129, 138, 140, 141, 151, 152, 153, 154, 155, 156, 185, and 189; numbers refer to the amino acid position of mature H5 protein after the signal peptide has been removed); these positions cluster in the highly variable, immunodominant major antigenic head epitopes of H5N1 viruses. Chemically synthesized gene libraries were obtained which, theoretically, encode all 20 amino acids at each of the 17 selected positions. Gene libraries were amplified by PCR, the PCR products cloned into an RNA polymerase I vector, and H5N1 virus libraries generated. In general, the size of the virus libraries ranges from ~$10^{-4}$-$10^7$ plaque forming units (pfu)/ml of supernatant derived from transfected cells; they do not, therefore, contain all possible combinations of amino acids at the 17 selected positions (i.e., $20^{17}$ different amino acid combinations).

After generating H5 virus libraries with random mutations at 17 amino acid positions in HA, they were incubated with ferret sera raised against different H5 viruses. During this selection step, mutants with antigenic properties similar to recently circulating H5 viruses will be neutralized. The resulting antigenic escape variants were plaque-purified in Madin-Darby canine kidney (MDCK) cells (a cell line commonly used for influenza virus propagation), and individual viruses were amplified and sequenced to identify the amino acid changes that conferred antigenic escape. After antigenic selection, >50 H5 mutants with 13-17 amino acid differences from the parent virus were isolated (see Table 1 for examples of selected sequences), attesting to the sequence plasticity of the highly variable, immunodominant major antigenic head epitopes. Importantly, most of these mutants are antigenically different from the parent virus as demonstrated by hemagglutination inhibition assays. Likewise, studies with seasonal human H3N2 virus (see Example 1 and Table 1B-C) yielded mutants that possessed multiple amino acid changes in the highly variable, immunodominant antigenic head epitopes and are antigenically distinct from the parent virus. Collectively, these studies establish that seasonal H3N2 and pandemic H5 viruses with up to 17 amino acid mutations in immunodominant antigenic epitopes are viable, replicate efficiently, and are antigenically distinct from the parent virus.

TABLE 1

Sequences of H5 HA proteins with randomized amino acids at the indicated positions HA amino acid positions (H5 Numbering)

| | 119 | 123 | 125 | 126 | 127 | 129 | 138 | 140 | 141 | 151 | 152 | 153 | 154 | 155 | 156 | 185 | 189 |
|---|---|---|---|---|---|---|---|---|---|---|---|---|---|---|---|---|---|
| WT | R | P | H | E | T | L | Q | A | S | I | K | K | N | D | A | A | N |
| 1 | R | L | L | S | V | D | G | T | S | T | A | R | L | N | T | L | Y |
| 2 | L | Y | L | S | V | L | G | G | R | T | P | Q | T | D | F | D | S |
| 3 | L | I | D | R | V | S | D | S | P | S | A | Q | N | G | R | D | L |
| 4 | K | M | N | S | V | G | E | R | P | I | T | T | N | K | A | N | L |
| 5 | R | N | D | S | A | K | L | R | P | T | Y | T | N | H | S | G | R |
| 6 | S | M | G | I | S | K | A | R | S | L | T | N | T | T | D | N | L |
| 7 | R | L | G | S | M | W | M | D | W | Y | H | T | T | L | P | E | R |
| 8 | S | L | L | S | V | R | L | K | K | E | S | D | N | H | F | L |
| 9 | G | S | W | G | L | E | L | R | R | N | S | F | N | S | P | S | Y |
| 10 | G | V | W | N | L | V | L | Q | S | T | S | T | L | I | P | L | K |
| 11 | T | Y | M | S | L | R | V | Q | E | I | P | S | R | D | R | Q | E |
| 12 | E | Y | I | S | L | L | D | R | A | T | A | P | R | P | T | L | G |
| 13 | S | K | R | S | V | L | M | R | E | T | A | V | P | T | G | P | S |
| 14 | A | G | K | Q | L | Q | F | R | A | Q | S | K | R | P | A | S | F |
| 15 | L | G | F | A | M | A | L | R | M | K | P | K | T | P | N | V | D |
| 16 | V | G | S | K | R | R | E | M | I | S | T | S | D | R | L | G |
| 17 | F | S | A | N | A | I | S | F | F | I | F | K | N | Q | T | M | V |
| 18 | R | T | F | G | A | F | A | C | D | T | I | T | H | P | T | R | E |
| 19 | N | R | D | R | F | L | A | V | L | L | P | K | S | D | T | A | I |
| 20 | T | R | S | G | Y | F | M | G | Q | Q | D | Q | S | Q | H | S | H |

TABLE 1B

Sequence of TK/2 17AA (H3) mutants

| Short name | Position (H3 Numbering) | | | | | | | | | | |
|---|---|---|---|---|---|---|---|---|---|---|---|
| | 121 | 131 | 135 | 138 | 140 | 142 | 144 | 145 | 155 | 156 | 157 |
| TK2 | N | T | T | A | I | R | S | S | T | H | L |
| TK2-17AA-mut-1 | Y | V | V | K | W | S | G | P | V | G | V |
| TK2-17AA-mut-2 | M | V | G | D | F | T | D | R | C | A | N |
| TK2-17AA-mut-4 | K | R | G | . | P | D | A | G | M | T | S |
| TK2-17AA-mut-5 | Q | R | Y | K | L | N | T | P | C | P | D |
| TK2-17AA-mut-6 | V | R | R | F | M | N | T | W | V | A | . |
| TK2-17AA-mut-7 | F | G | V | . | K | A | M | L | I | L | S |
| TK2-17AA-mut-9 | V | K | V | T | H | E | R | R | A | S | P |
| TK2-17AA-mut-10 | R | V | K | W | M | G | V | P | I | G | P |
| TK2-17AA-mut-11 | T | G | L | R | C | S | G | R | Y | P | . |
| TK2-17AA-mut-12 | I | . | N | K | T | Y | D | . | R | S | S |
| TK2-17AA-mut-14 | V | M | L | K | T | G | A | W | Q | S | R |
| TK2-17AA-mut-15 | A | K | S | R | N | D | G | V | R | S | R |
| TK2-17AA-mut-16 | V | C | N | I | K | . | P | D | A | A | G |
| TK2-17AA-mut-17 | V | C | L | L | R | F | K | T | I | P | S |
| TK2-17AA-mut-21 | V | R | V | V | V | D | P | R | G | S | C |
| TK2-17AA-mut-22 | S | S | . | K | S | Q | G | . | R | P | I |
| TK2-17AA-mut-23 | V | Q | V | R | R | E | H | . | V | T | . |
| TK2-17AA-mut-24 | L | R | N | T | K | T | N | . | Q | K | R |
| TK2-17AA-mut-25 | R | R | I | V | N | G | T | R | W | P | S |
| TK2-17AA-mut-26 | V | R | Y | K | T | A | E | Q | . | L | W |

TABLE 1B-continued

| Sequence of TK/2 17AA (H3) mutants | | | | | | | | | | |
|---|---|---|---|---|---|---|---|---|---|---|
| TK2-17AA-mut-28 | F | D | S | K | G | N | V | K | P | T | R |
| TK2-17AA-mut-29 | S | R | K | T | N | . | A | P | Q | . | M |
| TK2-17AA-mut-30 | F | V | W | S | M | H | Q | P | Q | G | R |
| TK2-17AA-mut-31 | R | V | V | . | T | A | E | G | S | I | P |
| TK2-17AA-mut-32 | F | D | G | F | . | N | . | W | R | A | S |
| TK2-17AA-mut-34 | I | Y | S | R | Y | . | L | . | S | C | S |
| TK2-17AA-mut-35 | I | M | Q | W | A | V | E | K | E | C | G |
| TK2-17AA-mut-36 | H | G | S | R | K | M | G | E | K | R | K |
| TK2-17AA-mut-37 | R | A | V | R | N | N | K | Q | V | R | I |
| TK2-17AA-mut-38 | I | E | R | G | D | P | P | N | V | G | E |
| TK2-17AA-mut-39 | V | E | A | E | L | A | I | N | S | E | E |
| TK2-17AA-mut-40 | T | I | A | R | C | S | K | P | R | N | R |
| TK2-17AA-mut-41 | V | D | C | S | L | G | Q | F | P | L | R |
| TK2-17AA-mut-43 | V | K | A | Q | M | . | . | K | S | S | A |
| TK2-17AA-mut-44 | I | G | G | R | . | D | . | P | I | P | P |
| TK2-17AA-mut-45 | M | N | S | T | R | H | K | . | C | D | T |
| TK2-17AA-mut-46 | Y | L | Q | T | F | . | G | A | A | C | A |
| TK2-17AA-mut-47 | V | N | L | L | A | T | T | . | K | R | A |
| TK2-17AA-mut-48 | F | R | S | V | V | Q | R | P | D | G | N |
| TK2-17AA-mut-50 | V | C | P | L | W | H | Q | P | G | S | T |
| TK2-17AA-mut-51 | M | K | Y | Q | Y | I | N | H | S | P | F |
| TK2-17AA-mut-53 | T | N | C | R | W | N | K | C | I | . | P |
| TK2-17AA-mut-54 | V | R | N | C | F | N | T | P | L | I | P |
| TK2-17AA-mut-55 | Y | R | P | . | N | K | T | R | N | . | P |
| TK2-17AA-mut-56 | R | . | Q | S | C | Q | T | T | A | P | . |
| TK2-17AA-mut-57 | T | S | D | . | G | N | Y | A | P | F | S |
| TK2-17AA-mut-58 | F | H | M | R | L | N | N | T | R | R | C |
| TK2-17AA-mut-59 | H | R | R | R | M | G | N | D | Y | S | R |
| TK2-17AA-mut-60 | T | Q | S | Q | E | Q | I | R | . | S | K |
| TK2-17AA-mut-61 | V | S | K | D | H | K | A | G | R | D | R |
| TK2-17AA-mut-64 | L | G | A | Q | R | Q | E | A | S | D | R |
| TK2-17AA-mut-65 | F | R | V | . | Q | . | E | P | M | T | T |
| TK2-17AA-mut-66 | Y | E | P | L | L | Q | . | N | . | S | T |
| TK2-17AA-mut-67 | L | E | S | V | R | Y | N | D | R | G | P |
| TK2-17AA-mut-68 | I | S | G | L | R | P | G | V | S | W | D |
| TK2-17AA-mut-70 | W | E | S | W | K | H | R | P | L | T | T |
| TK2-17AA-mut-71 | E | Q | E | L | Q | D | M | A | V | P | Q |
| TK2-17AA-mut-72 | T | R | M | R | Q | N | Y | P | W | I | S |
| TK2-17AA-mut-73 | S | L | S | R | L | E | W | P | G | Q | R |

TABLE 1B-continued

Sequence of TK/2 17AA (H3) mutants

| | | | | | | | | | | |
|---|---|---|---|---|---|---|---|---|---|---|
| TK2-17AA-mut-75 | F | R | N | E | R | N | P | T | I | P | V |
| TK2-17AA-mut-76 | E | R | K | L | L | N | N | G | . | Q | . |
| TK2-17AA-mut-77 | A | L | V | I | P | . | K | . | S | T | Q |
| TK2-17AA-mut-79 | L | G | L | D | D | A | . | P | D | K | P |

| Short name TK2 | Position (H3 Numbering) | | | | | | Note | FFU/50 ul |
|---|---|---|---|---|---|---|---|---|
| | 158 N | 171 N | 189 K | 193 F | 212 A | 225 D | | |
| TK2-17AA-mut-1 | R | D | N | A | Q | K | | 8.05E+04 |
| TK2-17AA-mut-2 | G | R | E | G | N | K | | 1.08E+05 |
| TK2-17AA-mut-4 | P | K | D | G | L | E | | 7.91E+04 |
| TK2-17AA-mut-5 | R | T | A | Q | V | L | | 2.92E+06 |
| TK2-17AA-mut-6 | H | T | I | S | R | P | | 4.46E+04 |
| TK2-17AA-mut-7 | G | . | — | — | S | . | Plus deletion of additional amino acids | 1.85E+05 |
| TK2-17AA-mut-9 | V | R | R | T | I | S | | 1.12E+05 |
| TK2-17AA-mut-10 | V | F | T | R | R | P | | 6.16E+05 |
| TK2-17AA-mut-11 | Q | T | F | A | R | T | | 4.37E+04 |
| TK2-17AA-mut-12 | S | F | A | Q | G | C | | 2.37E+05 |
| TK2-17AA-mut-14 | L | Q | L | R | R | E | | 3.03E+04 |
| TK2-17AA-mut-15 | F | T | E | A | Y | G | | 1.17E+05 |
| TK2-17AA-mut-16 | A | L | A | P | S | S | | 2.34E+05 |
| TK2-17AA-mut-17 | P | Q | N | S | T | S | | 1.91E+04 |
| TK2-17AA-mut-21 | I | I | — | — | — | — | Plus deletion of additional amino acids | 5.51E+04 |
| TK2-17AA-mut-22 | K | E | P | N | V | Q | | 3.59E+05 |
| TK2-17AA-mut-23 | R | H | L | T | M | G | | 1.16E+06 |
| TK2-17AA-mut-24 | F | S | . | T | V | S | | 1.65E+05 |
| TK2-17AA-mut-25 | P | R | S | S | V | R | | 1.11E+05 |
| TK2-17AA-mut-26 | G | R | Y | Q | M | N | | 1.13E+05 |
| TK2-17AA-mut-28 | R | L | S | — | P | S | | 3.79E+04 |
| TK2-17AA-mut-29 | K | F | T | N | F | C | | 8.16E+04 |
| TK2-17AA-mut-30 | C | T | S | E | . | Y | | 3.35E+05 |
| TK2-17AA-mut-31 | M | C | S | G | L | C | | 1.02E+05 |
| TK2-17AA-mut-32 | Q | V | Y | R | V | L | | 6.94E+05 |
| TK2-17AA-mut-34 | . | L | R | V | S | S | | 3.13E+05 |
| TK2-17AA-mut-35 | Q | G | T | S | P | S | | 1.29E+05 |
| TK2-17AA-mut-36 | Q | K | A | K | C | S | | 5.46E+03 |
| TK2-17AA-mut-37 | S | S | G | S | T | A | | 4.05E+04 |
| TK2-17AA-mut-38 | H | R | R | . | S | C | | 1.01E+05 |
| TK2-17AA-mut-39 | C | L | N | S | C | H | | 1.47E+05 |

TABLE 1B-continued

Sequence of TK/2 17AA (H3) mutants

| | | | | | | | | |
|---|---|---|---|---|---|---|---|---|
| TK2-17AA-mut-40 | T | R | V | K | T | V | | 5.09E+04 |
| TK2-17AA-mut-41 | R | L | N | S | W | C | | 4.81E+04 |
| TK2-17AA-mut-43 | I | R | A | M | S | . | | 1.57E+05 |
| TK2-17AA-mut-44 | G | L | E | V | L | . | | 8.63E+04 |
| TK2-17AA-mut-45 | Q | V | S | P | I | P | | 2.33E+05 |
| TK2-17AA-mut-46 | H | T | N | L | F | C | | 4.31E+04 |
| TK2-17AA-mut-47 | R | R | V | P | P | P | | 1.03E+05 |
| TK2-17AA-mut-48 | T | M | T | G | R | M | | 2.04E+05 |
| TK2-17AA-mut-50 | H | T | R | K | R | C | | 3.43E+04 |
| TK2-17AA-mut-51 | R | F | I | D | F | C | | 1.05E+05 |
| TK2-17AA-mut-53 | L | K | H | N | V | Q | | 1.45E+05 |
| TK2-17AA-mut-54 | K | R | H | A | R | L | | 4.86E+04 |
| TK2-17AA-mut-55 | A | T | H | N | E | L | C139Δ | 1.98E+05 |
| TK2-17AA-mut-56 | S | R | G | N | V | S | | 4.18E+04 |
| TK2-17AA-mut-57 | G | L | I | D | V | C | | 3.35E+04 |
| TK2-17AA-mut-58 | G | H | T | K | G | A | | 2.87E+04 |
| TK2-17AA-mut-59 | P | I | L | T | V | A | | 6.80E+04 |
| TK2-17AA-mut-60 | G | I | T | R | L | W | | 7.46E+04 |
| TK2-17AA-mut-61 | K | T | V | K | W | S | G209D | 6.47E+04 |
| TK2-17AA-mut-64 | R | E | R | G | V | M | | 2.31E+05 |
| TK2-17AA-mut-65 | H | T | Q | T | R | F | | 1.95E+05 |
| TK2-17AA-mut-66 | G | R | S | P | D | P | | 3.34E+05 |
| TK2-17AA-mut-67 | P | T | A | R | E | I | | 1.33E+05 |
| TK2-17AA-mut-68 | P | . | N | R | E | T | | 2.79E+05 |
| TK2-17AA-mut-70 | K | V | I | R | L | P | | 6.00E+04 |
| TK2-17AA-mut-71 | G | F | P | M | . | E | | 3.88E+05 |
| TK2-17AA-mut-72 | K | W | E | R | S | P | | 1.25E+04 |
| TK2-17AA-mut-73 | T | L | T | S | R | A | | 2.10E+05 |
| TK2-17AA-mut-75 | S | L | S | A | S | C | | 2.02E+05 |
| TK2-17AA-mut-76 | S | A | S | D | . | A | | 9.73E+04 |
| TK2-17AA-mut-77 | Q | L | R | P | E | F | | 6.92E+05 |
| TK2-17AA-mut-79 | C | R | S | N | R | A | | 1.52E+05 |

'.' Same amino acid as wild-type;
'—' Deletion.

TABLE 1C

Sequence of H3 mutants with deletions

| Virus   | 185 | 186 | 187 | 188 | 189 | 190 | 191 | 192 | 193 | 194 | 195 | 196 | 197 | 198 | 199 | 200 |
|---------|-----|-----|-----|-----|-----|-----|-----|-----|-----|-----|-----|-----|-----|-----|-----|-----|
| Tokyo 2 | P   | G   | T   | D   | K   | D   | Q   | I   | F   | L   | V   | A   | Q   | S   | S   | G   |
| TK2-28  | .   | .   | .   | .   | S   | A   | N   | L   | —   | A   | V   | .   | .   | .   | .   | .   |
| TK2-7   | .   | —   | —   | —   | —   | —   | —   | —   | —   | —   | —   | —   | .   | .   | .   | .   |
| TK2-21  | .   | .   | T   | D   | —   | —   | —   | —   | —   | —   | —   | —   | —   | —   | —   | —   |

| Virus   | 201 | 202 | 203 | 204 | 205 | 206 | 207 | 208 | 209 | 210 | 211 | 212 | 213 | 214 | 215 |
|---------|-----|-----|-----|-----|-----|-----|-----|-----|-----|-----|-----|-----|-----|-----|-----|
| Tokyo 2 | R   | I   | T   | V   | S   | T   | K   | R   | S   | Q   | Q   | A   | V   | I   | P   |
| TK2-28  | .   | .   | .   | .   | .   | .   | .   | .   | .   | .   | .   | P   | .   | .   | .   |
| TK2-7   | .   | .   | .   | .   | .   | .   | .   | .   | .   | .   | .   | S   | .   | .   | .   |
| TK2-21  | .   | K   | N   | H   | .   | I   | Y   | Q   | K   | K   | —   | —   | —   | —   | .   |

'.' Same amino acid as wild-type;
'—' Deletion.

Selection of HA positions for mutagenesis. H3N2 HA variants with non-naturally occurring immunodominant antigenic head epitopes are generated so that vaccination with mixtures of these viruses dilutes the antibody responses to the immunodominant epitopes and focus the immune responses towards more conserved immune-subdominant epitopes in the head and stem regions of HA.

Figures 3A, 3B, 3C, 3D:
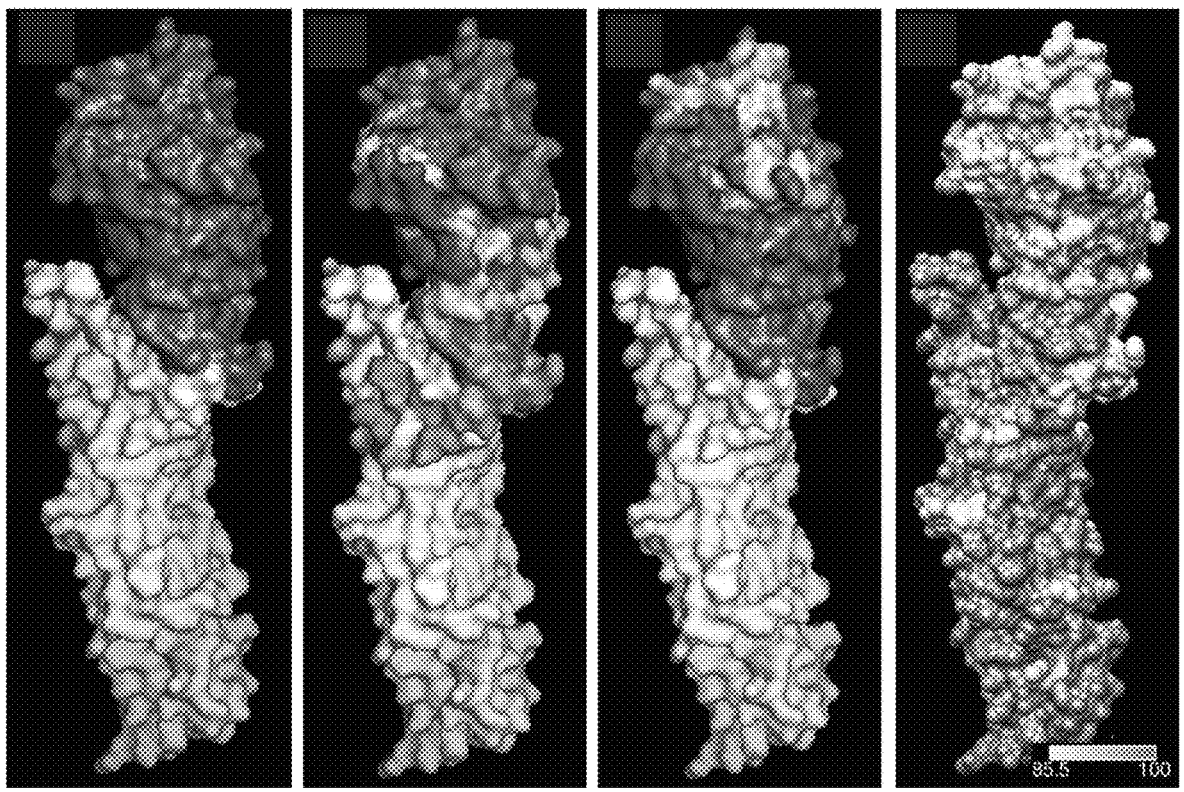
FIGS. 3A-D. Three-dimensional structure of H3 HA (405N). Shown are the head (dark gray) and stem (light gray) regions (A); the five major epitopes A (red), B (blue), C (orange), D (yellow), and E (green) (B); the amino acid positions selected for mutagenesis (wheat), see C.1.2.1 (C); and the sequence conservation of >13,000 unique human H3N2 HA sequences downloaded from the Influenza Research Database (D); the color scale indicates the amino acid sequence conservation at the respective position from 85.5% (gold) to 100% (purple). Shown in magenta is the highly conserved tyrosine residue at position 98 in the receptor-binding pocket.
Figure 4A:
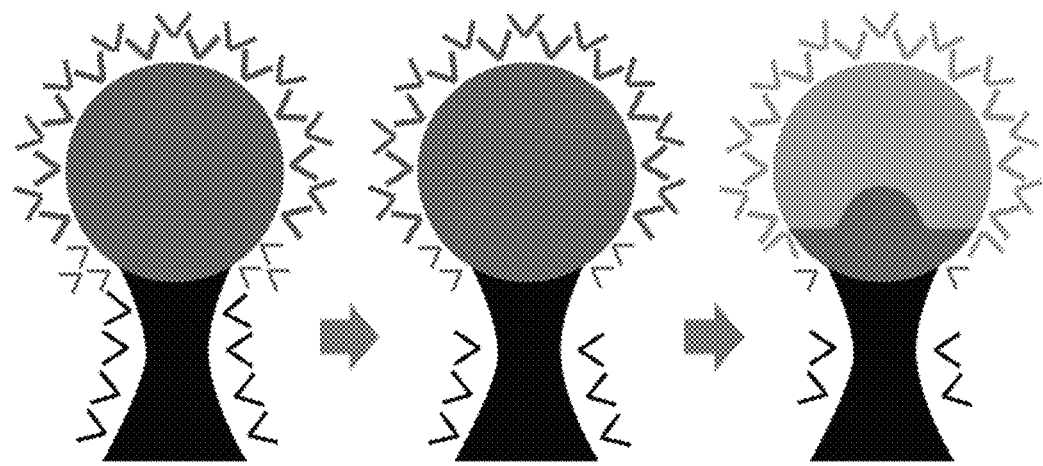
FIGS. 4A-4B. Schematic overview of the proposed strategy to elicit increased amounts of broadly-reactive Abs to immune-subdominant epitopes. (A) Subsequent infections or vaccinations with seasonal influenza viruses result in large amounts of Abs to the highly variable, immunodominant epitopes (shown in blue, dark green, and light green for three consecutive clusters), but consecutively lower amounts of Abs to the immune-subdominant epitopes in the stem (black) and head (dark gray). (B) New concept in which (repeat) immunizations with mixtures of HA proteins (shown here is only one mutant HA) with highly mutated, non-naturally occurring immunodominant antigenic epitopes are used to dilute the immune responses to the immunodominant epitopes, thereby boosting the levels of antibodies directed against immune-subdominant epitopes.
Figure 4B:
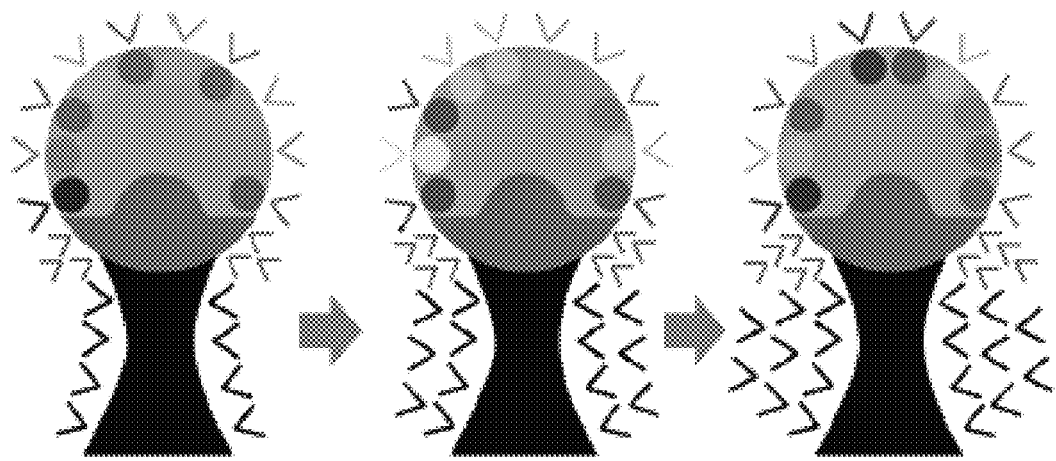
Figure 11:
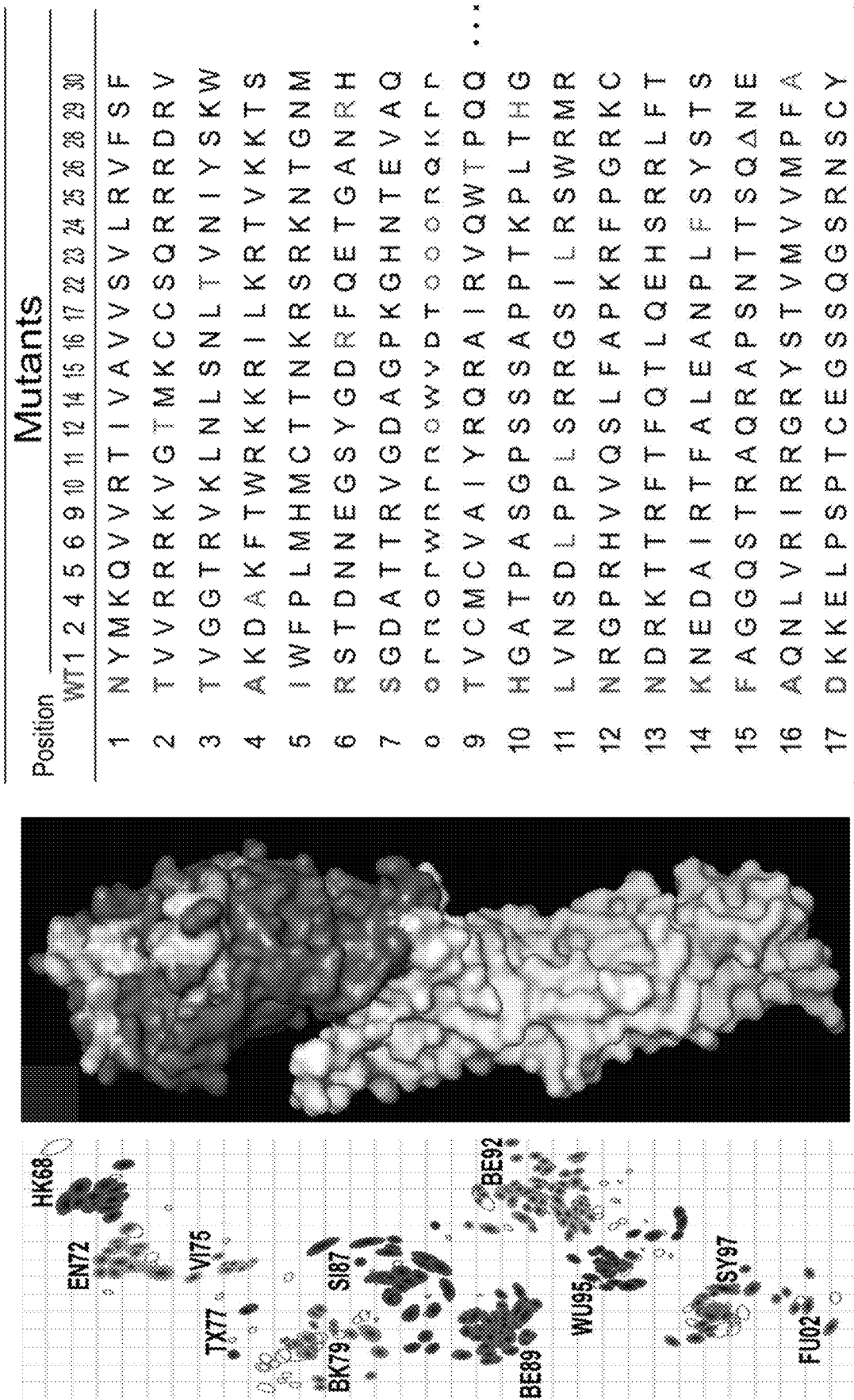
FIG. 11. H3 variants with substitutions in immunodominant epitope residues.
Figure 12:
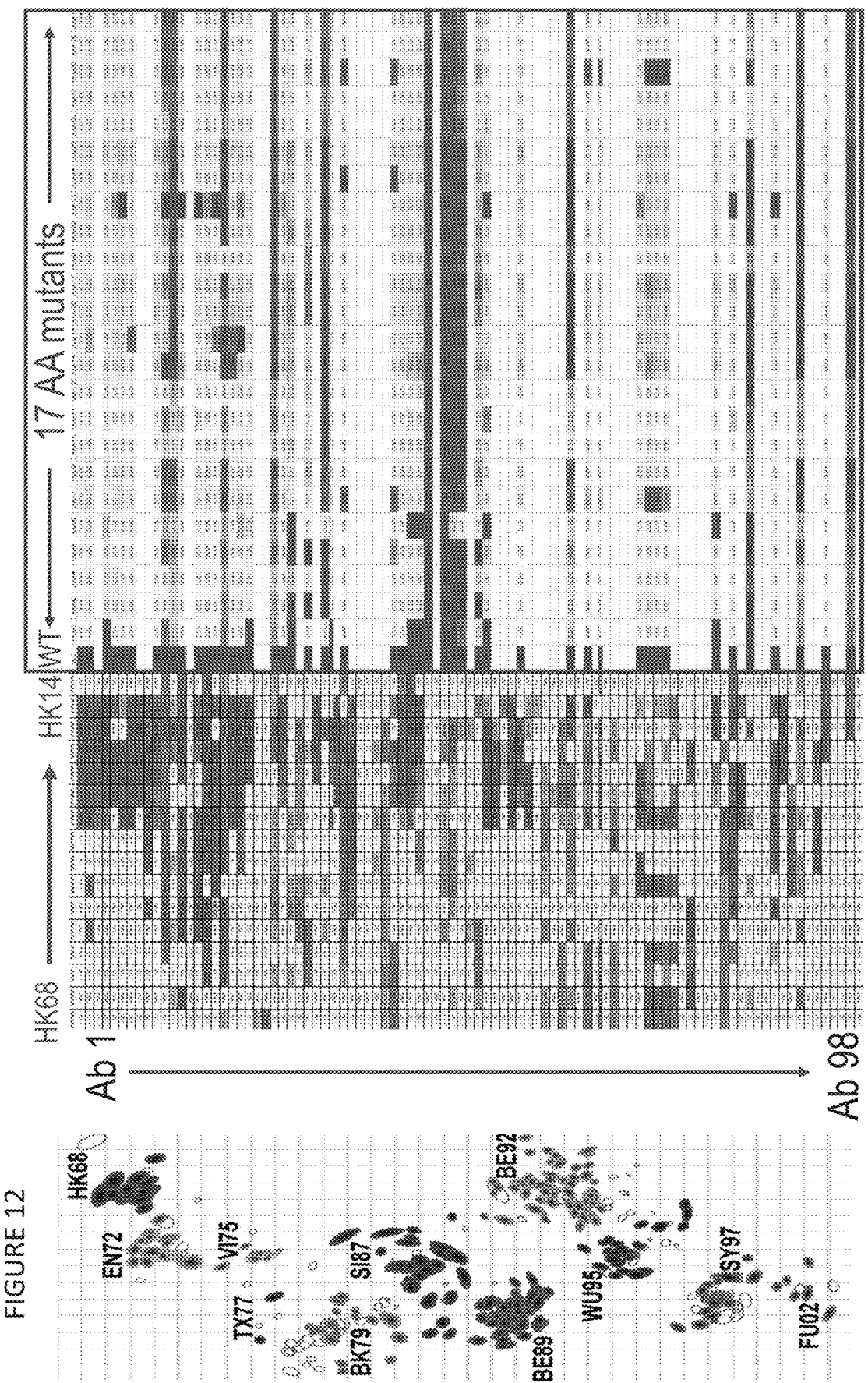
FIG. 12. Antibody reactivities for clusters, wild-type and H3 variants with substitutions in immunodominant epitope residues.
Figure 13:
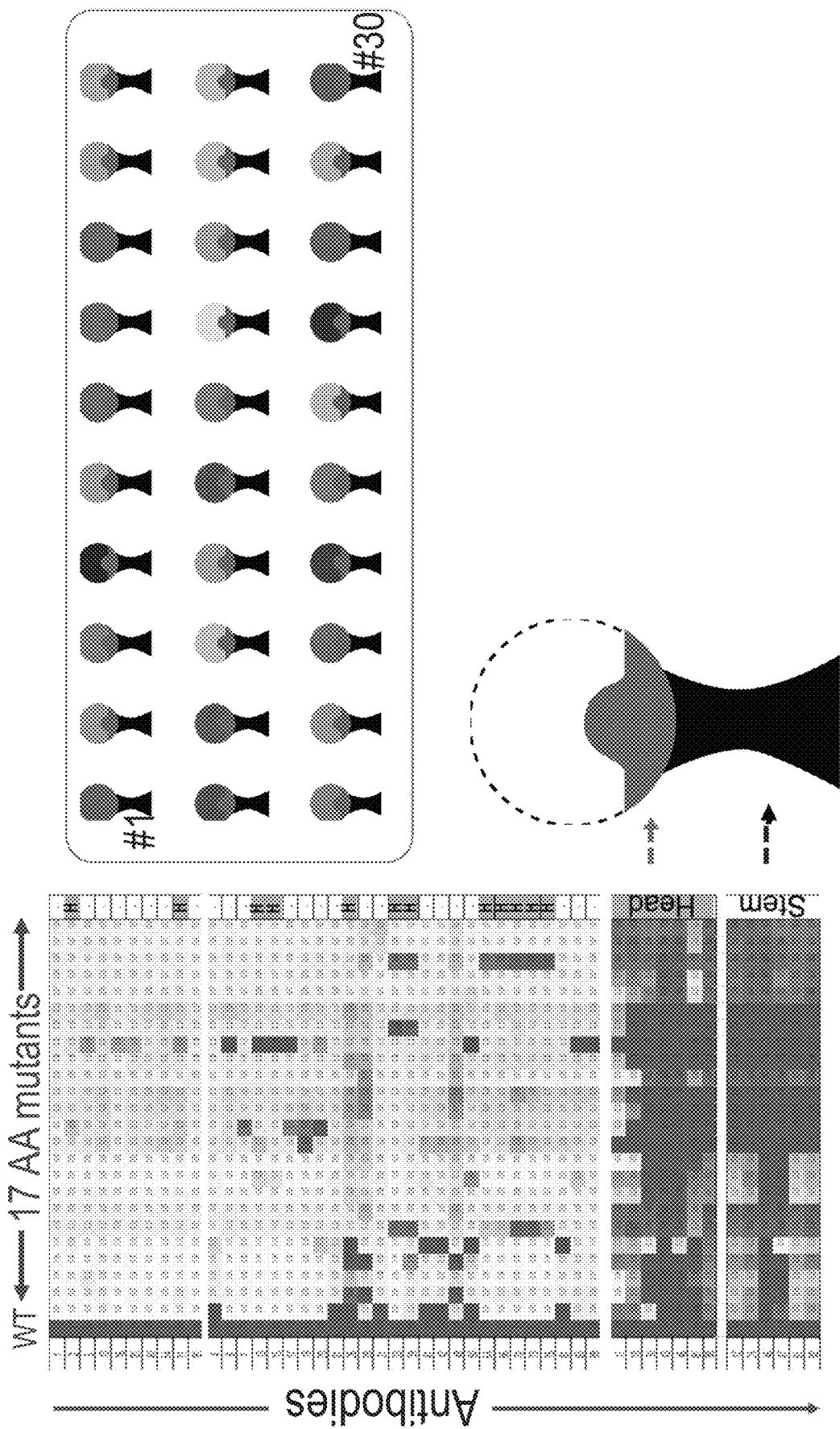
FIG. 13. Antibody reactivities for wild-type and H3 variants with substitutions in immunodominant epitope residues.w FIG. 14. Antibody reactivities for wild-type and selected H3 variants with substitutions in immunodominant epitope residues.
Figure 14:
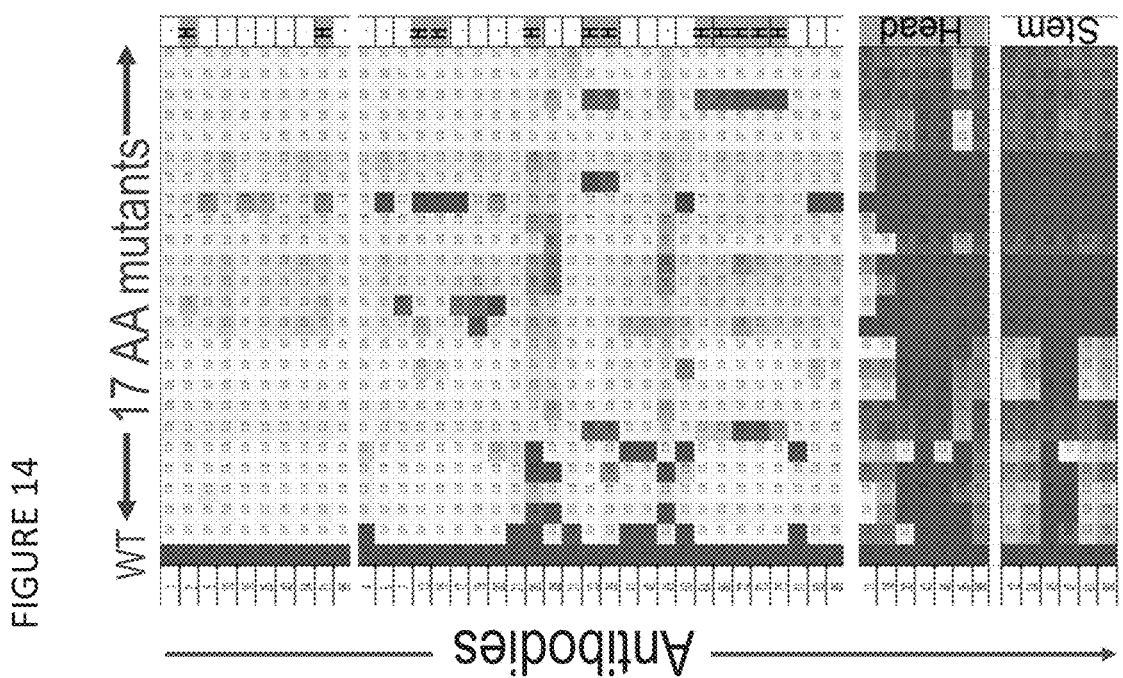
Figure 16:
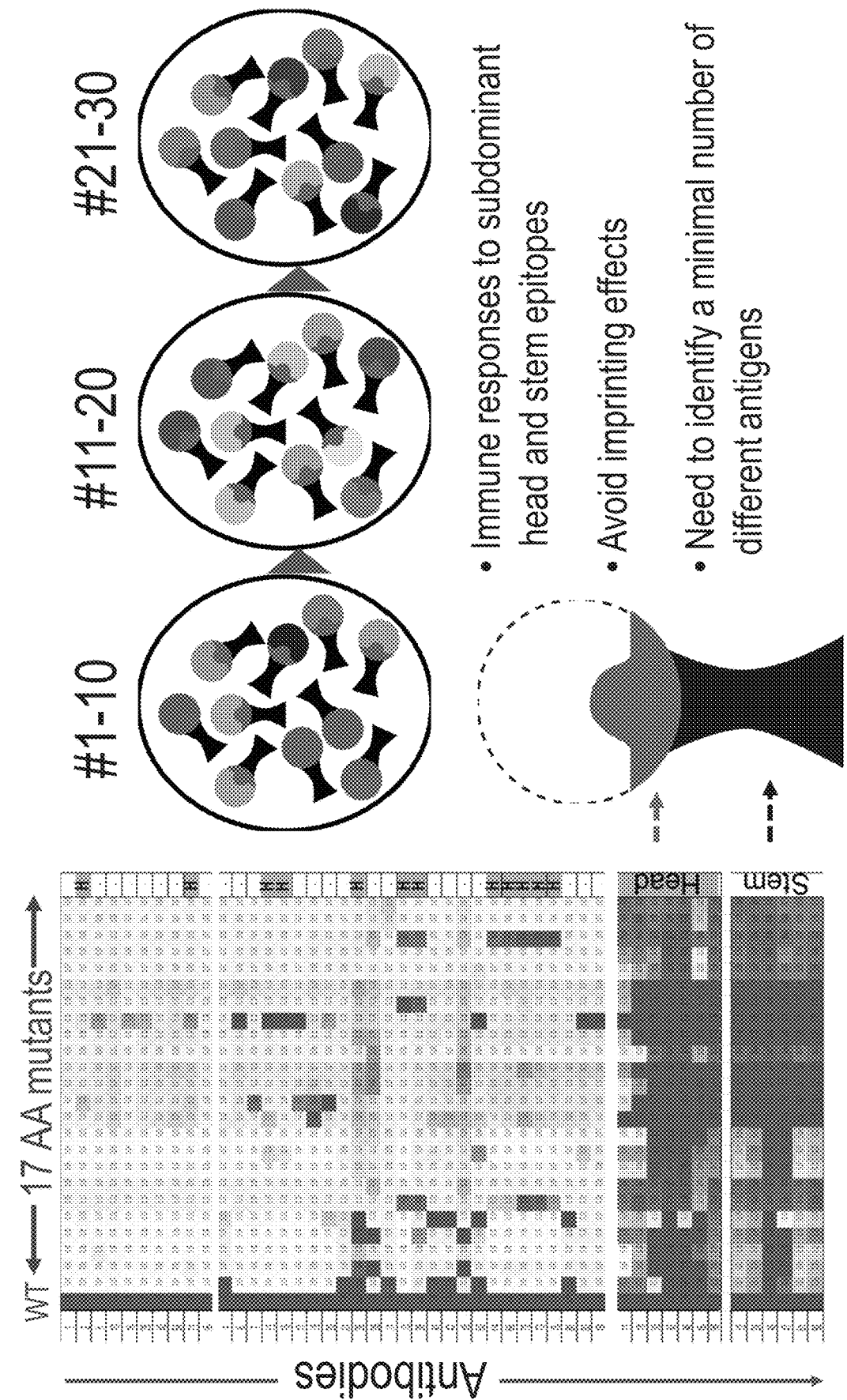
FIG. 16. Mixtures of H3 variants with substitutions in immunodominant epitope residues react with antibodies to sub-dominant epitopes.

Random mutations at 15 amino acid positions. Based on published and unpublished data, random mutations are introduced at the following 15 amino acid positions of HA, which have been shown or are suspected to affect the antigenicity of H3 HA (all amino acid position numbers refer to the 'mature' H3 HA, after removal of the signal peptide). 121, 131, 135, 138, 140, 142, 144, 145, 155, 156, 158, 159, 189, 193, and 212 (FIG. 3). These sites are primarily located in the highly variable, immunodominant antigenic head epitopes A (positions 131, 135, 138, 140, 142, 144, 145), B (positions 155, 156, 158, 159, 189, 193), and C (positions 121, 193), and include the seven amino acid positions at which most seasonal H3N2 cluster changes have occurred (e.g., positions 145, 155, 156, 158, 159, 189, and 193 (84)). Random mutations at the selected positions are introduced into the HA protein of A/California/7/2004 (CA04) virus, the prototype of the California 2004 (CA04) antigenic cluster of humans H3N2 viruses. This older strain was selected so that the protective efficacy of the ID-EpiMut CA04-based vaccines could be tested against recent human H3N2 influenza viruses.

Briefly, a chemically synthesized cDNA library possessing random mutations at the selected positions of CA04 HA is prepared, the cDNA library is PCR amplified, and cloned into an RNA polymerase I vector, resulting in a plasmid library.

Generation of virus libraries. The plasmid library of mutant HAs is used to generate a virus library in the genetic background of a high-yield A/Puerto Rico/8/34 (PR8) virus, which confers high virus titers in cultured cells (Ping et al., 2015). Specifically, w $10^6$ 293T cells (in 6-well plates) are transfected with 1 µg of the mutant HA plasmid library, with 0.1 µg each of the RNA polymerase I plasmids for the transcription of the remaining viral RNAs (all derived from high-yield PR8 virus), and with 0.1 µg each of polymerase protein expression plasmids for the polymerase and NP proteins. Forty-eight hours later, aliquots of supernatants are collected from transfected cells and plaque assays performed in MDCK cells to assess the titers of the virus library. As stated earlier, typically about ~$10^4$-$10^7$ pfu of mutant viruses per ml of cell culture supernatant is obtained. Libraries are amplified in AX-4 cells (MDCK cells overexpressing α2,6-linked sialic acids on the cell surface, to which human influenza viruses bind efficiently).

Selection of ID-EpiMut HA Variants with Immunodominant Head Epitopes that are Antigenically Distinct from Those of (Most) Influenza Viruses To increase the levels of antibody responses to immune-subdominant epitopes in the stem and head of HA, HA variants with non-naturally occurring immunodominant antigenic head epitopes are generated. To select such mutants, the virus library is incubated with mixtures of ferret sera raised against viruses of different antigenic clades, and with mixtures of human sera from donors of different age groups who have been exposed to different viruses and vaccines during their lifetime.

Specifically, the virus library is incubated with different concentrations of serum mixtures, and then plaque assays in AX-4 cells are performed. Virus plaques are picked from the highest serum concentration at which plaques are detected. Individual viruses are amplified in AX-4 cells and their HA genes sequenced. >100 individual HA genes are sequenced for each serum type (human or ferret) and serum concentration.

Viruses with amino acids that are not commonly found at the respective amino acid position (e.g., in <1% of sequences in the Influenza Research Database) are of particular interest. Highest priority is given to HAs with amino acids that have not been frequently detected at the respective position of any HA subtype (e.g., in <1% of sequences in the Influenza Research Database). For all mutants, the entire HA gene is sequenced to determine whether additional mutations emerged (outside of the targeted amino acid positions) that may have compensatory functions such as stabilizing effects on HA. The 100 ID-EpiMut HA variants with the least sequence homology to known influenza viruses at the targeted positions) are selected for further analysis (FIG. 5).

Reactivity of ID-EpiMut HA variants with H3 HA- and stem-specific mAbs

After isolating ID-EpiMut HA variants with diverse sequences in the immunodominant antigenic head epitopes, reactivity of these HA proteins is tested with a panel of H3 HA-specific Abs. A panel may include >100 antibodies (Yamayoshi et al., 2017; Epstein et al., 2002). The ability of these mAbs to neutralize representative human H3N2 influenza viruses of all of the major antigenic clades was tested (Table 2) and it was found that most of them neutralized only subsets of the test viruses, indicating that they react with the highly variable, immunodominant antigenic head epitopes A-E. Several of these mAbs, however, did neutralize viruses from most of the major antigenic clusters of human H3N2 viruses (Table 2). Based on competition studies with known stem-reacting mAbs, these mAbs were found to interact with the HA head.

specific antibody (Jackson Immuno-Research). TMB (3,3', 5,5'-Tetramethylbenzidine) solution is added for 5 min at room temperature before the reaction is stopped by the

TABLE 2

IC$_{50}$ values (μg/ml) of selected mAbs measured by micro-neutralization assay[1]

| | Antigenic Cluster | | | | | | | |
|---|---|---|---|---|---|---|---|---|
| Name | HK68 | EN72 | VI75 | TX77 | BK79 | SI87 | BE89 | BE92 |
| #1 | 25.00** | 25.00** | 12.50*** | 25.00 * | 12.50*** | 25.00 * | 12.50*** | 12.50*** |
| #2 | >50 | >50 | >50 | 6.25*** | 0.78**** | 0.39**** | 1.56**** | 1.56**** |
| #3 | >50 | >50 | 0.20**** | 3.13*** | 0.20**** | 0.20**** | >50 | 1.56**** |
| #4 | >50 | >50 | 25.00* | 12.50*** | 1.56**** | 12.50*** | 0.78**** | 3.13**** |
| #5 | 25.00** | >50 | 0.78**** | 1.56*** | 0.78**** | 1.56**** | >50 | 3.13**** |

| | Antigenic Cluster | | | | | | | |
|---|---|---|---|---|---|---|---|---|
| Name | WH95 | SY97 | FU02 | CA04 | WI05 | PE09 | TX12 | HK14 |
| #1 | 12.50& *** | 12.50*** | 25.00 * | >50 | 6.25*** | 12.50** | >50 | >50 |
| #2 | 3.13**** | 3.13**** | 12.50** | 12.50** | 12.50** | 3.13**** | 6.25**** | 12.50*** |
| #3 | 0.78**** | 0.20**** | 1.56**** | 0.20**** | 0.20**** | 0.20**** | 1.56**** | 1.56**** |
| #4 | 3.13**** | 6.25*** | 0.78**** | 6.25*** | 0.39**** | 6.25*** | >50 | 12.50*** |
| #5 | 3.13**** | 12.50** | 3.13**** | 6.25*** | 12.50** | 6.25*** | 6.25*** | 25.00 * |

[1]Shown are the IC50 values of the indicated mAbs with viruses representing different antigenic clusters of human H3N2 viruses (HK68, Hong Kong '68; EN72, England '72; VI75, Victoria '75; TX77, Texas '77; BK79, Bangkok '79; SI87, Sichuan '87; BE89, Beijing '89; BE92, Beijing '92; WH95, Wuhan '95; SY97, Sydney '97; FU02, Fujan '02; CA04, California '04; WI05, Wisconsin '05; PE09, Perth '09; TX12, Texas '12; HK14, Hong Kong '14. The *, , *, **** indicate the level of reactivity (that is, *, , *, **** indicate higher reactivity).

In addition, the reactivity of ID-EpiMut HAs to a panel of stem-reactive mAbs (see, Yamayoshi et al., 2017 and 2018) or synthesized based on the published sequence (Corti et al., 2011) (Table 3) were tested. These mAbs recognize HAs of group 2 (1417infC10), or of group 1 and 2 HAs.

TABLE 3

Reactivity of stem-reactive mAbs with HAs of the indicated subtypes

| | Group 1 | | Group 2 | | |
|---|---|---|---|---|---|
| mAbs | H1 | H5 | H3 | H7 | Reference |
| S9-1-10/5-1[1] | ✓ | ✓ | | ✓ | Yamayoshi et al., 2017 |
| 3352E69 | ✓ | | ✓ | ✓ | Yamayoshi et al., 2017 |
| 10-4-7/1 | ✓ | ✓ | ✓ | ✓ | Yamayoshi et al., 2017 |
| 4-8-6/4 | ✓ | ✓ | ✓ | ✓ | Yamayoshi et al., 2017 |
| 3381E12 | ✓ | ✓ | ✓ | ✓ | Yamayoshi et al., 2017 |
| 3381A11 | ✓ | ✓ | ✓ | ✓ | Yamayoshi et al., 2017 |
| 3352E71 | ✓ | ✓ | ✓ | ✓ | Yamayoshi et al., 2017 |
| 1417infE21[2] | ✓ | | ✓ | ✓ | Yamayoshi et al., 2018 |
| 1417infC10[3] | | | ✓ | ✓ | Yamayoshi et al., 2018 |
| FI6V3[1] | ✓ | ✓ | ✓ | ✓ | Corti et al., 2011 |

[1]Reacts with HAs of all 18 subtypes
[2]Reacts with H1, H5, H6, H8 (all group 1) & H3, H4, H7, H10, H14, H15 (all group 2) HAs
[3]Reacts with H3, H4, H7, H10, H14, H15 (all group 2) HAs Hemagglutination inhibition (HI) assays measure the ability of antibodies to inhibit HA binding to red blood cells. HI assays are frequently used to distinguish between antibodies that bind to the head (where the receptor-binding pocket is located that mediates binding to sialic acids on red blood cells) and antibodies that bind to the stem and do not interfere with hemagglutination. However, recent H3N2 viruses do not bind to commonly used red blood cells.

To test the reactivity of the selected 100 ID-EpiMut HA variants, their HA genes are cloned into a protein expression plasmid and transfected into 293T cells. Wild-type CA04 HA protein serves as a control. At 24 h post-transfection, the cells are fixed with 4% paraformaldehyde. The HA-expressing cells are incubated with mAbs (1 μg/ml) followed by a peroxidase-conjugated goat anti-human IgG, Fcγ Fragment-specific antibody (Jackson Immuno-Research). TMB (3,3', 5,5'-Tetramethylbenzidine) solution is added for 5 min at room temperature before the reaction is stopped by the addition of $H_2SO_4$. The optical density at 450 nm (OD450) is measured by using a VersaMax plate reader (Molecular Devices). The OD450 values of mock-transfected wells incubated with each mAb is subtracted as background.

The reactivity of the ID-EpiMut HA variants is compared with that of wild-type HA. Mutants that lose their reactivity with cluster-specific Abs (directed against highly variable, immunodominant antigenic head epitopes), but retain their reactivity with broadly-reactive H3-specific Abs and with stem-specific Abs (directed against conserved, immune-subdominant antigenic epitopes), are identified. Up to 50 ID-EpiMut HA proteins that fulfill these criteria (FIG. 5) are collected.

Example 3

Immunogenicity and protective efficacy of ID-EpiMut vaccines. Each of the variants produced by the method likely have a unique antigen to the immune system; by mixing them, the vaccine contains low amounts of each of the non-naturally occurring immunodominant antigenic head epitopes, but high amounts of the immune-subdominant epitopes (which are the same in all ID-EpiMut HAs). Such a vaccine elicits higher amounts of antibodies directed at the conserved immune-subdominant epitopes compared with a vaccine presenting only one wild-type HA (which is the current practice with influenza vaccines); the higher levels of antibodies to conserved immune-subdominant epitopes result in cross-protection.

Experimental Approach. Mouse antisera to individual and mixed ID-EpiMut HA variants is generated and tested for reactivity. Vaccination and challenge studies are conducted in mice and ferrets to assess whether mixtures of non-naturally occurring immunodominant epitopes dilute the responses to these epitopes and increase the levels of antibodies to immune-subdominant epitopes, resulting in more broadly protective immunity.

Generation of virus-like particles possessing individual ID-EpiMut HA variants. In addition to HA (the major influenza viral antigen), other influenza viral proteins including NA, NP, and the matrix (M1) and ion channel (M2) proteins contribute to viral antigenicity; in fact, immunity to NP and M1 are protective in the mouse model. To avoid any confounding effects from these proteins, ID-EpiMut HA variants are presented on VLPs of Ebola virus. Co-expression of Ebola virus VP40 and influenza virus HA results in the highly efficient generation of VLPs decorated with HA. Moreover, a 293T cell line that stably expresses VP40 may be employed for highly efficient VLP formation. VP40-expressing 293T cells are transfected with protein expression plasmids encoding each of the 50 ID-EpiMut HA variants. Two-to-three days later, cells are treated with bacterial neuraminidase to efficiently release the VLPs from the cells. The cell culture supernatant with the released VLPs is harvested, purified through a sucrose gradient, concentrated by ultracentrifugation, and the total protein yield measured by using the BCA assay (Thermo Scientific). The resulting 50 ID-EpiMut-HA/VP40 VLPs (each decorated with a single HA mutant) (FIG. 5) is used to immunize mice.

Generation of virus-like particles possessing multiple ID-EpiMut HA variants. In addition to VLPs decorated with a single ID-EpiMut HA variant, eight different ID-EpiMut-HA/VP40 VLPs (FIG. 5) are generated. Specifically, five ID-EpiMut-HANP40 VLPs are tested that are decorated with 10 ID-EpiMut HA variants each, two ID-EpiMut-HA/VP40 VLPs are tested that are decorated with all 25 ID-EpiMut HA variants each, and one ID-EpiMut-HA/VP40 VLP is tested that is decorated with all 50 ID-EpiMut HA variants (for the first two sets, ID-EpiMut HA mutants are randomly sorted into groups of 10 or 25, respectively). VP40-expressing 293T cells are cotransfected with the respective number of different protein expression plasmids expressing different ID-EpiMut HAs. The presentation of different HA mutants on the same VLP will likely reduce the B cell populations that are specific to one particular mutant.

Generation and characterization of mouse sera directed against ID-EpiMut-HA/VP40 VLPs. Mice (BALB/c female mice, Jackson Laboratories; three per group) are intramuscularly immunized with 10-20 μg of total protein of ID-EpiMut-HA/VP40 VLPs and two weeks later are intramuscularly boosted with the same amount of protein of ID-EpiMut-HA/VP40 VLPs. Three weeks after the second immunization, blood is collected.

The mouse sera is tested for reactivity against the following groups of HA proteins: (1) Human H3N2 virus HA proteins representing all of the major antigenic clades, derived from viruses that have not been amplified in embryonated chicken eggs (thus eliminating the risk of egg-adapting HA mutations that affect antigenicity); (2) ID-EpiMut HA variants; and (3) HA proteins representing several other HA subtypes, including H1, H5, and H7 (for each of these subtypes, a panel of HA proteins representing the major antigenic clades and sub-clades are used).

An ELISA is employed with purified HA protein using protocol to express secreted forms of HA that are stabilized by a trimerization motif ('foldon') (Stevens et al., 2004). The interaction of mouse sera with purified HA proteins is detected as described above. To assess the relative contributions of antibodies binding to highly variable, immunodominant antigenic head epitopes, conserved immune-subdominant antigenic stem epitopes, and conserved immune-subdominant antigenic head epitopes, competition assays are performed with human Abs known to bind to these epitopes. Controls include wild-type HA protein and antiserum raised against it, as well as antigenically distant influenza B virus HA protein and antiserum raised against it.

From the 50 ID-EpiMut-HA/VP40 VLPs decorated with one EpiMut HA, the top 30 candidates with the highest proportions of antibodies reactive against the conserved, immune-subdominant antigenic epitopes in the stem and head regions of HA are selected (FIG. 5).

For the eight ID-EpiMut-HA/VP40 VLPs decorated with multiple EpiMut HAs, candidates are eliminated if they do not elicit increased amounts of antibodies to immune-subdominant epitopes (compared to wild-type HA) (FIG. 5).

Immunization of mice with mixtures of ID-EpiMut-HA/VP40 VLPs

Immunization with mixtures of ID-EpiMut HAs with multiple mutations in the immunodominant antigenic head epitopes likely results in relatively low antibody responses to each of the unique, immunodominant antigens, while boosting responses to the shared epitopes (e.g., the conserved immune-subdominant epitopes in the HA stem and head). To assess this, w different vaccination strategies are tested in which mice (e.g., groups of five animals) are primed with mixtures of 10, 15, or 30 ID-EpiMut-HA/VP40 VLPs, each decorated with a single ID-EpiMut HA (Table 4a). Mice are unboosted, boosted with the same ID-EpiMut-HA/VP40 VLPs used for the prime immunization, or boosted with a different set of 10 or 15 ID-EpiMut-HA/VP40 VLPs.

Likewise, mice are primed with a single ID-EpiMut-HA/VP40 VLP decorated with multiple different mutants (Table 4b), and then mock-boost, boost with the same ID-EpiMut-HA/VP40 VLP, or boost with a different ID-EpiMut-HA/VP40 VLP (this does not apply for animals vaccinated with the ID-EpiMut-HA/VP40 VLP decorated with all 50 EpiMut HA mutants). In addition, controls are primed or primed and boosted with HA/VP40 VLPs decorated with the wild-type HA protein.

Sera is collected 28 days after the last immunization and tested for antibody levels to immune-subdominant antigenic epitopes as described above. Comparison of the different vaccination strategies reveals if two immunizations with the same mixture of ID-EpiMut-HA/VP40 VLPs increase the amount of antibodies to immune-subdominant epitopes compared with a single immunization. Comparison of the different vaccination strategies also reveals if a prime/boost regimen with different ID-EpiMut-HA/VP40 VLPs increases the amount of antibodies to immune-subdominant epitopes compared with a prime/boost regimen with the same ID-EpiMut-HA/VP40 VLPs. Moreover, comparisons of the different vaccination strategies reveal if one VLP decorated with multiple HA mutants (see Table 4b) elicits higher amounts of antibodies to immune-subdominant epitopes than multiple VLPs decorated with one HA mutant each (see Table 4a). The comparison of VLPs decorated with 10, 25, or 50 HA mutants also provides information on the number of different HAs needed to dilute immune response to the immune-dominant epitopes in the HA head.

If mixtures of ten ID-EpiMut HAs (provided from one or ten VLPs) dilute the immune response to the immunodominant epitopes, similar experiments are performed with mixtures of five or three ID-EpiMut HAs to determine the lowest number of different ID-EpiMut HAs needed for the dilution effect.

From the different vaccination regimen tested here, the top 10 are selected (e.g., those with the highest levels of antibodies to immune-subdominant epitopes) for protection studies in mice (FIG. 5).

TABLE 4a

Overview of vaccination strategies

| Vaccination Strategy | ID-EpiMut HA/VP40 VLPs (Prime) # | ID-Epi Mut HA/VP40 VLPs (Boost) # |
|---|---|---|
| VLPs decorated with Individual EpiMut HAs | 1-10 | None |
|  |  | 1-10 |
|  |  | 11-20 |
|  |  | 21-30 |
|  | 11-20 | None |
|  |  | 1-10 |
|  |  | 11-20 |
|  |  | 21-30 |
|  | 21-30 | None |
|  |  | 1-10 |
|  |  | 11-20 |
|  |  | 21-30 |
|  | 1-15 | None |
|  |  | 1-15 |
|  |  | 16-30 |
|  | 16-30 | None |
|  |  | 1-15 |
|  |  | 16-30 |
|  | 1-30 | None |
|  |  | 1-30 |

TABLE 4b

Overview of vaccination strategies (cont.)

| Vaccination Strategy | ID-EpiMut HA/VP40 VLPs (Prime) # | ID-EpiMut HA/VP40 VLPs (Boost) # |
|---|---|---|
| VLPs decorated with *multiple* EpiMut HAs | 1 VLP with ID-EpiMut HAs 1-10 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 11-20 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 21-30 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 31-40 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 41-50 | None |
|  |  | 1 VLP with ID-EpiMut HAs 1-10 |
|  |  | 1 VLP with ID-EpiMut HAs 11-20 |
|  |  | 1 VLP with ID-EpiMut HAs 21-30 |
|  |  | 1 VLP with ID-EpiMut HAs 31-40 |
|  |  | 1 VLP with ID-EpiMut HAs 41-50 |
|  | 1 VLP with ID-EpiMut HAs 1-25 | None |
|  |  | 1 VLP with ID-EpiMut HAs 1-25 |
|  |  | 1 VLP with ID-EpiMut HAs 26-50 |
|  | 1 VLP with ID-EpiMut HAs 26-50 | None |
|  |  | 1 VLP with ID-EpiMut HAs 1-25 |
|  |  | 1 VLP with ID-EpiMut HAs 26-50 |
|  | 1 VLP with ID-EpiMut HAs 1-50 | None |
|  |  | 1 VLP with ID-EpiMut HAs 1-50 |

Challenge Studies in Mice Vaccinated with ID-EpiMut-HA/VP40 VLPs

After establishing that mixtures of highly mutated immunodominant antigenic head epitopes dilute the immune responses to these epitopes and boost the antibody levels to conserved, immune-subdominant epitopes, it is determined whether the increased levels of antibodies to the immune-subdominant epitopes provide broader protection against seasonal human H3N2 viruses than the protection elicited by a wild-type virus-based vaccine.

For the top 10 vaccination regimen that elicit increased levels of antibodies to conserved, immune-subdominant epitopes, the protective efficacy of the antibodies raised to ID-EpiMut-HAs is evaluated. First, 48 mice each are vaccinated with the selected vaccination regimen. Recent human H3N2 influenza viruses do not replicate efficiently in mice. Mouse-adapted variants of CA04 (for homologous challenge) and of viruses representing the Perth 2009 (PE09), Victoria 2011 (VI11), and Hong Kong 2014 (HK14) antigenic clusters are generated for heterologous challenges, using established strategies for the generation of mouse-adapted viruses. To rule out effects of mouse-adapting mutations on antigenicity, the reactivity of wild-type and mouse-adapted viruses is compared with sera directed against wild-type HAs. If the mouse-adapted variants are antigenically similar to wild-type viruses, the four mouse-adapted viruses are used at a dose of $10^6$ pfu to challenge 12 vaccinated mice each. Four mice per challenge group are observed for weight loss; the remaining eight animals are euthanized on days 3 and 6 post-challenge (four animals per timepoint) to assess virus titers in the lungs and nasal turbiantes. Vaccination with ID-EpiMut-HAs elicits Abs that are more broadly protective than Abs elicited after vaccination with wild-type HA.

Immunogenicity of ID-EpiMut HA Influenza Vaccines in Ferrets

The top 3 vaccination regimen are tested for their immunogenicity in ferrets (FIG. 5). In ferrets, like humans, the contribution of the 'internal' influenza viral proteins is less pronounced than in mice. Therefore, the vaccination and challenge experiments in ferrets are carried out with influenza virus-based vaccine (e.g., viruses that possess the respective ID-EpiMut HAs are generated in the genetic background of PR8 virus). The recombinant viruses possessing ID-EpiMut HAs are inactivated with beta-propiolactone (an established procedure for the inactivation of influenza viruses) and the equivalent of 15 µg of HA protein is used for vaccination.

Protective Efficacy of ID-EpiMut HA Influenza Vaccines in Ferrets

Next, it is tested whether vaccination of ferrets with ID-EpiMut-HA influenza vaccine confers broader protection than that elicited by a vaccine based on wild-type HA. Ferrets (groups of 5) are immunized with the top 3 vaccination regimens (determined as stated above) (FIG. 5). Twenty-eight days after the last immunization, ferrets are intranasally infected with $10^6$ pfu of the homologous CA04 virus, or viruses representing the more recent Perth 2009 (PE09), Victoria 2011 (VI11), and Hong Kong 2014 (HK14) antigenic clusters (heterologous challenges). Starting one day after challenge, the infected animals are weighed every day and nasal wash samples collected every other day to determine virus titers. Vaccination with inactivated influenza vaccine possessing wild-type HA is expected to protect against challenge with the homologous CA04 virus, but provide incomplete protection against the heterologous viruses (which belong to different antigenic clusters). The finding that vaccination with ID-EpiMut HA influenza vaccine protects against infection with antigenic drift variants establishes the feasibility of the concept for universal influenza vaccines.

TABLE 5

Vaccination/challenge groups to test the broadly protective efficacy of EpiMut HA influenza vaccines

| Group | Influenza virus infections | Vaccination with ID-EpiMut HA influenza vaccine | Challenge |
|---|---|---|---|
| 1 | Sequential infection with | ID-EpiMut HA vaccine 1* | CA 04 (homol.) |
| 2 | | | PE09 (heterol.) |

TABLE 5-continued

Vaccination/challenge groups to test the broadly protective efficacy of EpiMut HA influenza vaccines

| Group | Influenza virus infections | Vaccination with ID-EpiMut HA influenza vaccine | Challenge |
|---|---|---|---|
| 3 | WU95, SY97, | | VI11 (heterol.) |
| 4 | and FU02 | | HK14 (heterol.) |
| 5 | viruses | ID-EpiMut HA | CA 04 (homol.) |
| 6 | | vaccine 2* | PE09 (heterol.) |
| 7 | | | VI11 (heterol.) |
| 8 | | | HK14 (heterol.) |
| 9 | | ID-EpiMut HA | CA 04 (homol.) |
| 10 | | vaccine 3* | PE09 (heterol.) |
| 11 | | | VI11 (heterol.) |
| 12 | | | HK14 (heterol.) |
| 13 | | Wt-HA vaccine | CA 04 (homol.) |
| 14 | | (single vaccination) | PE09 (heterol.) |
| 15 | | | VI11 (heterol.) |
| 16 | | | HK14 (heterol.) |
| 17 | | Wt-HA vaccine | CA 04 (homol.) |
| 18 | | (two vaccinations) | PE09 (heterol.) |
| 19 | | | VI11 (heterol.) |
| 20 | | | HK14 (heterol.) |

*Vaccines 1, 2, and 3 indicate the top 3 vaccination regimen based on the data obtained in C.2.3.

Five ferrets (4-6-month-old females) per group are immunized intramuscularly. Twenty-eight days after the last immunization, sera is collected and the reactivity of the sera tested as described above. Control animals are immunized with inactivated influenza vaccine possessing wild-type HA protein. Immunization with ID-EpiMut HA influenza vaccine elicits higher amounts of antibodies directed against conserved, immune-subdominant epitopes than vaccination with a vaccine possessing wild-type HA.

Protective Efficacy of ID-EpiMut HA Influenza Vaccines in Ferrets

Next, it is tested whether vaccination of ferrets with ID-EpiMut-HA influenza vaccine confers broader protection than that elicited by a vaccine based on wild-type HA. Ferrets (groups of 5) are immunized with the top 3 vaccination regimen (determined as stated above) (FIG. 5). Twenty-eight days after the last immunization, ferrets are intranasally infected with $10^6$ pfu of the homologous CA04 virus, or viruses representing the more recent Perth 2009 (PE09), Victoria 2011 (VI11), and Hong Kong 2014 (HK14) antigenic clusters (heterologous challenges). Starting one day after challenge, the infected animals are weighed every day and nasal wash samples collected every other day to determine virus titers. Vaccination with inactivated influenza vaccine possessing wild-type HA protects against challenge with the homologous CA04 virus, but provides incomplete protection against the heterologous viruses (which belong to different antigenic clusters). The finding that vaccination with ID-EpiMut HA influenza vaccine protects against infection with antigenic drift variants establishes that vaccine as a universal influenza vaccine.

Protective Efficacy of ID-EpiMut HA Influenza Vaccine in Ferrets Pre-Exposed to Human Influenza Viruses Humans are repeatedly exposed to influenza viruses through natural infection and/or vaccination. To mimic this exposure to multiple influenza viruses, ferrets are sequentially infected with seasonal human H3N2 viruses representing three past antigenic clusters: the Wuhan 1995 (WU95), Sydney 1997 (SY97), and Fujian 2002 (FU02) clusters (Table 5). Next, animals are vaccinated with each of the top three vaccination approaches. Twenty-eight days after the last immunization, serum samples are collected from vaccinated animals and the reactivity of the sera tested. Sera from ferrets vaccinated with ID-EpiMut HA influenza vaccine are more cross-reactive than those obtained from ferrets immunized with influenza vaccine possessing wild-type HA.

Next, the pre-exposed and vaccinated animals are intranasally infected with $10^6$ pfu of the homologous CA04 virus, or with the heterologous PE09, VI11, or HK14 viruses (5 animals per group, Table 5). As described previously, body weight measurements are carried out every day and nasal washes are collected every other day, starting on day 1 after challenge. ID-EpiMut HA influenza vaccine provides broader protection against viruses of different antigenic clusters than influenza vaccine based on wild-type HA.

In summary, the reactivity and neutralizing properties of mouse sera raised against ID-EpiMut HA variants show that these sera are more broadly reactive and neutralizing than sera raised to wild-type HA. Vaccination/challenge studies establish that the disclosed vaccine approach provides more broadly protective immunity than that afforded by current vaccines based on wild-type HAs.

Thus, mixtures of non-naturally occurring immunodominant head epitopes dilute the immune responses to these epitopes and refocus immune responses towards conserved, immune-subdominant epitopes in HA, thereby increasing the amounts of cross-protective antibodies, thereby providing universal influenza vaccines.

TABLE 6

TK/2 (H3) Mutants

| Name | Amino acid position | | | | | | | | | |
|---|---|---|---|---|---|---|---|---|---|---|
| | 121 | 131 | 135 | 138 | 140 | 142 | 144 | 145 | 155 | 156 |
| Tokyo 2 | N | T | T | A | I | R | S | S | T | H |
| TK/2-177 hCK-41_14 | . | . | M | S | F | H | . | P | . | M |
| TK/2-177 hCK-41_69 | . | . | M | S | F | H | . | P | . | M |
| TK/2-177 hCK-41_9 | . | . | M | S | F | H | . | P | . | M |
| TK/2-177 hCK-37_87 | A | R | G | S | R | L | D | P | . | N |
| TK/2-177 hCK-37_73 | E | K | . | T | P | D | R | M | Y | K |
| TK/2-177 hCK-37_84 | E | K | . | T | P | D | R | M | Y | K |
| TK/2-177 hCK-37_68 | E | L | N | S | K | K | A | P | F | S |
| TK/2-177 hCK-37_101 | E | S | S | . | T | F | G | A | F | A |
| TK/2-177 hCK-41_3 | F | M | G | S | . | E | M | P | F | S |
| TK/2-177 hCK-41_34 | F | M | G | S | . | E | M | P | F | S |
| TK/2-177 hCK-37_70-3 | F | M | G | S | . | E | M | P | F | S |
| TK/2-177 hCK-37_11 | F | R | N | . | T | N | I | N | Y | I |
| TK/2-177 hCK-37_19 | F | R | S | S | P | M | G | N | . | L |
| TK/2-177 hCK-37_10 | F | S | G | S | L | H | R | A | W | S |
| TK/2-177 hCK-37_1 | F | S | H | S | S | T | N | P | F | A |
| TK/2-177 hCK-37_98 | F | V | G | S | K | T | G | Q | I | R |
| TK/2-177 hCK-37_71 | F | Y | H | S | W | N | K | L | . | A |
| TK/2-177 hCK-37_90 | H | A | V | . | R | I | Q | P | Y | Q |
| TK/2-177 hCK-41_H50 | H | E | V | . | V | N | V | P | H | R |
| TK/2-177 hCK-37_70-2 | H | K | S | S | K | . | G | P | S | Q |
| TK/2-177 hCK-41_H96 | H | K | V | S | P | L | R | T | S | A |
| TK/2-177 hCK-37_12 | H | R | V | . | R | S | M | T | V | S |
| TK/2-177 hCK-37_16 | I | E | H | S | D | . | K | P | V | T |
| TK/2-177 hCK-37_74 2and3 | I | E | K | S | Y | T | G | N | V | R |
| TK/2-177 hCK-41_58 | I | L | S | S | D | Y | K | K | R | A |
| TK/2-177 hCK-37_81 | I | R | M | S | L | A | N | . | . | N |
| TK/2-177 hCK-37_102 | I | R | Q | S | N | A | M | P | . | K |
| TK/2-177 hCK-37_49 | K | N | . | . | H | N | M | P | F | R |
| TK/2-177 hCK-37_22-1 | L | . | G | . | M | D | K | . | I | R |
| TK/2-177 hCK-37_31 | L | . | G | . | M | D | K | . | I | R |
| TK/2-177 hCK-37_56 | L | . | G | . | M | D | K | . | I | R |
| TK/2-177 hCK-41_75 | L | . | G | . | M | D | K | . | I | R |
| TK/2-177 hCK-37_95 | L | . | G | . | M | D | K | . | I | R |
| TK/2-177 hCK-41_H48 | L | A | . | S | P | D | F | P | H | S |
| TK/2-177 hCK-41_H51 | L | A | . | S | P | D | F | P | H | S |
| TK/2-177 hCK-41_H58 | L | A | . | S | P | D | F | P | H | S |
| TK/2-177 hCK-37_64 | L | A | A | S | L | K | N | Y | . | S |
| TK/2-177 hCK-37_74-1 | L | A | A | S | L | K | N | Y | . | S |
| TK/2-177 hCK-41_79 | L | A | F | . | S | H | R | . | Y | A |
| TK/2-177 hCK-37_59 | L | I | . | S | L | I | G | N | . | . |
| TK/2-177 hCK-41_89 | L | L | D | S | S | . | G | P | H | A |
| TK/2-177 hCK-37_33 | L | L | R | S | L | . | R | E | H | S |
| TK/2-177 hCK-37_35 | L | S | Q | . | N | F | A | P | F | S |
| TK/2-177 hCK-37_39 | M | . | N | S | P | T | N | Q | F | S |
| TK/2-177 hCK-37_45 | M | . | V | S | M | G | V | P | H | V |
| TK/2-177 hCK-41_76 | M | N | . | S | G | E | E | E | Y | A |
| TK/2-177 hCK-41_21 | M | Q | A | S | T | N | . | R | F | V |
| TK/2-177 hCK-37_17-1 | R | G | S | S | L | S | I | P | K | A |
| TK/2-177 hCK-41_93 | R | L | V | S | A | G | R | A | S | S |
| TK/2-177 hCK-41_53 | R | L | V | S | A | K | M | P | . | A |
| TK/2-177 hCK-37_36 | R | N | H | S | R | G | M | M | . | A |
| TK/2-177 hCK-37_60 | R | N | H | S | R | G | M | M | . | A |
| TK/2-177 hCK-37_H5 | R | N | S | . | M | Q | Q | V | . | K |
| TK/2-177 hCK-37_96 | S | A | V | S | N | K | H | A | F | S |

TABLE 6-continued

TK/2 (H3) Mutants

| Name | | | | | | | | | | |
|---|---|---|---|---|---|---|---|---|---|---|
| TK/2-177 hCK-41_48 | S | G | R | S | R | N | . | N | W | S |
| TK/2-177 hCK-37_67 | S | H | V | S | . | Q | Q | W | . | L |
| TK/2-177 hCK-41_7 | S | K | S | S | Y | L | E | . | H | A |
| TK/2-177 hCK-37_37 | T | E | G | C | M | H | T | M | F | K |
| TK/2-177 hCK-37_28 | T | G | V | S | . | . | T | R | . | V | A |
| TK/2-177 hCK-41_54 | T | K | Q | S | N | G | K | Q | S | S |
| TK/2-177 hCK-37_40 | T | N | W | S | S | N | A | G | . | S |
| TK/2-177 hCK-37_86 | T | R | G | T | V | . | E | R | V | Q |
| TK/2-177 hCK-37_85 | T | V | A | S | K | I | G | V | . | R |
| TK/2-177 hCK-37_97 | T | V | K | S | K | I | G | V | . | R |
| TK/2-177 hCK-37_94 | V | ? | V | S | S | S | G | M | . | A |
| TK/2-177 hCK-37_17-2and3 | V | A | . | . | L | C | E | A | V | S |
| TK/2-177 hCK-41_4 | V | K | . | S | P | G | . | D | F | T |
| TK/2-177 hCK-37_5 | V | K | . | S | P | G | . | D | F | T |
| TK/2-177 hCK-37_42 | V | K | V | . | P | G | D | Y | . | S |
| TK/2-177 hCK-41_55 | V | K | V | S | Q | . | R | H | . | S |
| TK/2-177 hCK-37_57 | V | L | V | S | L | S | . | H | V | V |
| TK/2-177 hCK-41_78 | V | L | V | S | L | S | . | H | V | V |
| TK/2-177 hCK-37_2 | V | N | C | S | A | A | M | N | . | Q |
| TK/2-177 hCK-37_65 | V | N | C | S | A | A | M | N | . | Q |
| TK/2-177 hCK-41_51 | V | Q | . | S | K | T | K | R | W | K |
| TK/2-177 hCK-37_100 | V | R | . | . | S | G | I | R | . | W |
| TK/2-177 hCK-37_20 | V | R | G | S | C | V | K | F | . | A |
| TK/2-177 hCK-41_41 | V | R | K | S | P | E | . | K | V | M |
| TK/2-177 hCK-41_26 | W | K | . | S | H | Y | T | P | S | A |
| TK/2-177 hCK-41_38 | W | K | . | S | H | Y | T | P | S | A |
| TK/2-177 hCK-41_66 | W | K | . | S | H | Y | T | P | S | A |
| TK/2-177 hCK-37_22-3 | Y | K | S | S | K | M | N | P | . | M |
| TK/2-177 hCK-37_32 | Y | L | R | S | L | H | E | R | S | R |
| TK/2-177 hCK-41_50 | Y | L | R | S | L | H | E | R | S | R |
| TK/2-177 hCK-41_8 | Y | L | R | S | L | H | E | R | S | R |
| TK/2-177 hCK-41_52 | Y | L | R | S | M | A | H | Q | Y | A |
| TK/2-177 hCK-37_62 | Y | M | S | . | . | E | R | M | V | K |

| | Amino acid position | | | | | | | |
|---|---|---|---|---|---|---|---|---|
| Name | 157 | 158 | 171 | 189 | 193 | 212 | 225 | |
| Tokyo 2 | L | N | N | K | F | A | D | Genotype |
| TK/2-177 hCK-41_14 | S | G | D | R | S | R | . | 1 |
| TK/2-177 hCK-41_69 | S | G | D | R | S | R | . | |
| TK/2-177 hCK-41_9 | S | G | D | R | S | R | . | |
| TK/2-177 hCK-37_87 | D | A | Y | N | R | N | E | 2 |
| TK/2-177 hCK-37_73 | S | A | T | L | E | S | G | 3 |
| TK/2-177 hCK-37_84 | S | A | T | L | E | S | G | |
| TK/2-177 hCK-37_68 | T | S | Q | A | R | L | T | 4 |
| TK/2-177 hCK-37_101 | R | G | R | M | H | Q | . | 5 |
| TK/2-177 hCK-41_3 | Q | M | R | T | D | L | G | 6 |
| TK/2-177 hCK-41_34 | Q | M | R | T | D | L | G | |
| TK/2-177 hCK-37_70-3 | Q | M | R | T | D | L | G | |
| TK/2-177 hCK-37_11 | R | E | K | D | G | S | E | 7 |
| TK/2-177 hCK-37_19 | P | D | K | D | A | . | A | 8 |
| TK/2-177 hCK-37_10 | R | T | F | F | S | S | L | 9 |
| TK/2-177 hCK-37_1 | S | R | M | A | Q | S | C | 10 |
| TK/2-177 hCK-37_98 | S | T | L | N | S | I | R | 11 |
| TK/2-177 hCK-37_71 | . | P | S | E | R | T | R | 12 |
| TK/2-177 hCK-37_90 | S | R | V | S | R | S | . | 13 |
| TK/2-177 hCK-41_H50 | H | E | M | N | W | T | S | 14 |
| TK/2-177 hCK-37_70-2 | G | R | M | A | . | L | G | 15 |
| TK/2-177 hCK-41_H96 | W | D | R | S | A | H | A | 16 |
| TK/2-177 hCK-37_12 | S | S | R | N | N | S | G | 17 |
| TK/2-177 hCK-37_16 | R | K | S | R | S | W | G | 18 |
| TK/2-177 hCK-37_74 2and3 | R | G | F | R | D | F | S | 19 |
| TK/2-177 hCK-41_58 | R | . | P | N | A | T | R | 20 |
| TK/2-177 hCK-37_81 | R | V | V | S | R | G | . | 21 |
| TK/2-177 hCK-37_102 | H | L | L | H | S | T | K | |
| TK/2-177 hCK-37_49 | S | . | T | T | L | S | H | 23 |
| TK/2-177 hCK-37_22-1 | R | Q | M | E | G | T | R | 24 |
| TK/2-177 hCK-37_31 | R | Q | M | E | G | T | R | |
| TK/2-177 hCK-37_56 | R | Q | M | E | G | T | R | |
| TK/2-177 hCK-37_75 | R | Q | M | E | G | T | R | |
| TK/2-177 hCK-37_95 | R | Q | M | E | G | T | R | |
| TK/2-177 hCK-41_H48 | R | L | A | S | T | Q | Q | 25 |
| TK/2-177 hCK-41_H51 | R | L | A | S | T | Q | Q | |
| TK/2-177 hCK-41_H58 | R | L | A | S | T | Q | Q | |
| TK/2-177 hCK-37_64 | M | D | C | F | A | T | S | 26 |

TABLE 6-continued

| TK/2 (H3) Mutants | | | | | | | | |
|---|---|---|---|---|---|---|---|---|
| TK/2-177 hCK-37__74-1 | M | D | C | F | A | T | S | 27 |
| TK/2-177 hCK-41__79 | V | G | T | M | M | T | S | 28 |
| TK/2-177 hCK-37__59 | S | G | V | H | Q | T | L | 29 |
| TK/2-177 hCK-41__89 | Q | A | A | R | S | V | H | 30 |
| TK/2-177 hCK-37__33 | P | M | . | M | A | N | H | 31 |
| TK/2-177 hCK-37__35 | E | S | . | N | G | . | S | 32 |
| TK/2-177 hCK-37__39 | R | R | H | V | N | S | T | 33 |
| TK/2-177 hCK-37__45 | M | S | L | Y | K | S | S | 34 |
| TK/2-177 hCK-41__76 | R | E | R | M | T | H | G | 35 |
| TK/2-177 hCK-41__21 | S | R | . | D | S | L | T | 36 |
| TK/2-177 hCK-37__17-1 | A | A | S | I | H | F | R | 37 |
| TK/2-177 hCK-41__93 | Q | S | Y | D | . | S | R | 38 |
| TK/2-177 hCK-41__53 | S | L | E | T | L | S | M | 39 |
| TK/2-177 hCK-37__36 | S | L | F | S | T | V | C | |
| TK/2-177 hCK-37__60 | S | L | F | S | T | V | C | 40 |
| TK/2-177 hCK-37__H5 | F | R | M | E | S | W | ? | 41 |
| TK/2-177 hCK-37__96 | D | S | Q | E | A | Q | . | 42 |
| TK/2-177 hCK-41__48 | G | K | L | T | S | I | G | 43 |
| TK/2-177 hCK-37__67 | H | D | T | G | A | S | . | 44 |
| TK/2-177 hCK-41__7 | D | Q | G | . | A | R | S | 45 |
| TK/2-177 hCK-37__37 | P | R | E | R | S | V | G | 46 |
| TK/2-177 hCK-37__28 | N | V | K | S | D | H | T | 47 |
| TK/2-177 hCK-41__54 | D | E | L | T | W | I | S | 48 |
| TK/2-177 hCK-37__40 | A | L | L | N | H | S | S | 49 |
| TK/2-177 hCK-37__86 | R | G | S | A | G | M | S | 50 |
| TK/2-177 hCK-37__85 | S | L | L | V | K | V | G | |
| TK/2-177 hCK-37__97 | S | L | L | V | K | V | G | 51 |
| TK/2-177 hCK-37__94 | S | E | I | T | S | L | L | 52 |
| TK/2-177 hCK-37__17-2and3 | T | R | S | G | S | S | G | 53 |
| TK/2-177 hCK-41__4 | P | I | Y | N | Y | V | E | |
| TK/2-177 hCK-37__5 | P | I | Y | N | Y | V | E | 54 |
| TK/2-177 hCK-37__42 | W | K | R | Q | . | G | Q | 55 |
| TK/2-177 hCK-41__55 | T | S | R | L | N | . | L | 56 |
| TK/2-177 hCK-37__57 | S | K | E | S | H | T | R | |
| TK/2-177 hCK-41__78 | S | K | E | S | H | T | R | 57 |
| TK/2-177 hCK-37__2 | S | Q | T | R | N | V | R | |
| TK/2-177 hCK-37__65 | S | Q | T | R | N | V | R | 58 |
| TK/2-177 hCK-41__51 | G | H | R | E | Q | S | T | 59 |
| TK/2-177 hCK-37__100 | V | G | M | V | A | W | A | 60 |
| TK/2-177 hCK-37__20 | K | S | L | E | I | L | E | 61 |
| TK/2-177 hCK-41__41 | E | Q | H | R | S | Q | H | 62 |
| TK/2-177 hCK-41__26 | Q | E | A | R | A | ? | Q | |
| TK/2-177 hCK-41__38 | Q | E | A | R | A | T | Q | |
| TK/2-177 hCK-41__66 | Q | E | A | R | A | T | Q | 63 |
| TK/2-177 hCK-37__22-3 | ? | L | W | T | L | L | R | 64 |
| TK/2-177 hCK-37__32 | . | R | M | A | E | H | . | |
| TK/2-177 hCK-41__50 | . | R | M | A | E | H | . | |
| TK/2-177 hCK-41__8 | . | R | M | A | E | H | . | 65 |
| TK/2-177 hCK-41__52 | W | R | E | Q | R | V | W | 66 |
| TK/2-177 hCK-37__62 | . | G | S | S | D | F | A | |

REFERENCES

Andrews et al., *Sci. Transl. Med.*, 7:316ra192 (2015).
Belser et al., *J. Virol.*, 90:4647 (2016).
Bommakanti et al., *J. Virol.*, 86:13434 (2012).
Bommakanti et al., *Proc. Natl. Acad. Sci. USA*, 107:13701 (2010).
Chen et al., *J. Virol.*, 90:3789 (2016).
Clementi et al., *PLoS One*, 6: e28001 (2011).
Corti et al., *Science*, 3:850 (2011).
DiLillo et al., *J. Clin. Invest.*, 126:605 (2016).
Dreyfus et al., *Science*, 33:1343 (2012).
Ekiert et al., *Curr. Opin. Virol.*, 2:134 (2012).
Ekiert et al., *Nature*, 489:526 (2011).
Ekiert et al., *Science*, 324:246 (2009).
Ekiert et al., *Science*, 3:843 (2011).
Ellebedy et al., *Proc. Natl. Acad. Sci. USA*, 111:13133 (2014).
Epstein et al., *Emerg. Infect. Dis.*, 8:796 (2002).
Erbelding et al., *J. Infect. Dis.*,__,:_doi:10.1093/infdis/jiy103 (2018).
Fleury et al., *Nat. Struct. Biol.*, 5:119 (1998).
Friesen et al., *Proc. Natl. Acad. Sci. USA*, 1:445 (2014).
Fu et al., *Nat. Commun.*, 7:12780 (2016).
Goff et al., *PLoS One*, 8:e79194 (2013).
Graves et al., *Viroloy*, 126:106 (1983).
Halliley et al., *J. Infect. Dis.*, 212:1270 (2015).
Henry et al., *Cell Host Microbe*, 19:800 (2016).
Henry et al., *J. Clin. Invest.*, 125:1255 (2015).
Herfst et al., *Science*, 36:1534 (2012).
Hong et al., *J. Virol.*, 87:12471 (2013).
Iba et al., *J. Virol.*, 88:7130 (2014).
Imai et al., *Nature*, 486:420 (2012).
Impagliazzo et al., *Science*, 349:1301 (2015).
Joyce et al., *Cell*, 166:609 (2016).
Kallewaard et al., *Cell*, 166:596 (2016).
Koel et al., *Science*, 342:976 (2013).
Krammer et al., *Clin. Vaccine Immunol.*, 21:1153 (2014).
Krammer et al., *J. Virol.*, 86:10302 (2012).
Krammer et al., *J. Virol.*, 87:6542 (2013).
Krammer et al., *J. Virol.*, 88:2340 (2014).

Krammer et al., *J. Virol.*, 88:3432 (2014).
Krause et al., *J. Virol.*, 85:10905 (2011).
Krause et al., *J. Virol.*, 86:6334 (2012).
Lee et al., *Nat. Commun.*, 5:3614 (2014).
Lee et al., *Proc. Natl. Acad. Sci. USA*, 109:17040 (2012).
Li et al., *Nat. Microbiol.*, 1:16058 (2016).
Li et al., *Proc. Natl. Acad. Sci. USA*, 109:9047 (2012).
Liu et al., *J. Infect. Dis.*, 215:518 (2017).
Luo et al., *J. Virol. Methods*, 154:121 (2008).
Mallajosyula et al., *Front. Immunol.*, 6:329 (2015).
Mallajosyula et al., *Proc. Natl. Acad. Sci. USA*, 11:E2514 (2014).
Margine et al., *J. Virol.*, 87:10435 (2013).
Margine et al., *J. Virol.*, 87:4728 (2013).
Miller et al., *J. Infect. Dis.*, 207:98 (2009).
Nachbagauer et al., *J. Virol.*, 88:13260 (2014).
Nachbagauer et al., *J. Virol.*, 90:3268 (2015).
Nachbagauer et al., *MBio*, 7:e01996 (2016).
Nachbagauer et al., *NPJ Vaccines*, 1:e00018 (2016).
Nachbagauer et al., *NPJ Vaccines*, 2:26 (2017).
Nakamura et al., *Cell Host Microbe*, 14:93 (2013).
Neumann et al., *Proc. Natl. Acad. Sci. USA*, 96:9345 (1999).
Ohshima et al., *J. Virol.*, 85:11048 (2011).
Okuno et al., *J. Virol.*, 67:2552 (1993).
Pica et al., *Proc. Natl. Acad. Sci. USA*. 109:2573 (2012).
Ping et al., *Nat. Commun.*, 6:8148 (2015).
Ping et al., *Proc. Natl. Acad. Sci. USA*, 113:E8296 (2016).
Raymond et al., *Proc. Natl. Acad. Sci. USA*, 115:168 (2018).
Sakabe et al., *Virus Res.*, 158:124 (2009).
Sangster et al., *Clin. Vaccine Immunol.*, 20:867 (2009).
Schmidt et al., *Proc. Natl. Acad. Sci. USA*, 110:264 (2013).
Steel et al., *MBio*, 1:e00018 (2010).
Steinbruck et al., *J. Virol.*, 88:12123 (2014).
Stevens et al., *Science*, 303:1866 (2004).
Sui et al., *Nat. Struct. Mol. Biol.*, 16:265 (2009).
Sun et al., *MBio*, 4:e00230 (2013).
Sutton et al., *NPJ Vaccines*, 2:35 (2017).
Taft et al., *Nat. Commun.*, 6:7491 (2015).
Tan et al., *J. Virol.*, 86:6179 (2012).
Thomson et al., *Front. Immunol.*, 3:87 (2012).
Throsby et al., *PLoS One*, 3:e3942 (2008).
Tsibane et al., *PLoS Pathog.*, 8:e1003067 (2012).
Valkenburg et al., *Sci. Rep.*, 6:22666. (2016)
Watanabe et al., *Nature*, 501:551 (2013).
Whittle et al., *Proc. Natl. Acad. Sci. USA*, 108:14216 (2011).
Wiley et al., *Annu. Rev. Biochem.*, 56:365 (1987).
Wiley et al., *Nature*, 289:373 (1981).
Wohlbold et al., *Vaccine* 33:3314 (2015).
Wrammert et al., *J. Exp. Med.*, 208:181 (2009).
Wu et al., *Nat. Commun.*, 6:7708 (2015).
Xu et al., *Nat. Struct. Mol. Biol.*, _:_doi:10.1038/nsmb.2500 (2013).
Yamayoshi et al., *EBioMedicine*, 17:182 (2017).
Yamayoshi et al., *J. Infect.*, 76:177 (2018).
Yang et al., *PLoS One*, 9:e106660 (2014).
Yao et al., *Sci. Rep.*, 7:1545 (2017).
Yassine et al., *Nat. Med.*, 21:1065 (2015).
Yoshida et al., *PLoS Pathog.*, 5:e1000350 (2009).
Zhang et al., *Science*, 341:410 (2013).
Zhu et al., *Science* doi:10.1126/science.1239844 (2013).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method, comprising: providing a library prepared by introducing random mutations at a plurality of codons in one or more immune dominant epitopes in an isolated parental influenza virus nucleic acid molecule encoding an influenza virus hemagglutinin having at least two immune dominant epitopes, thereby providing a library of influenza virus nucleic acid molecules encoding a mutant influenza virus hemagglutinin; introducing the library into cells so as to provide a library of cells that express the mutant hemagglutinins; identifying a mutant hemagglutinin encoded by the library with a reduced number of the immune dominant epitopes relative to the parental hemagglutinin as a result of one or more substitutions and/or deletions at residues that form the one or more immune dominant epitopes; and combining two or more distinct nucleic acid molecules from the library encoding distinct mutant hemagglutinins.

2. The method of claim 1 wherein at least 5, 10, 15 or 20 codons, or any integer between 5 and 20, are mutated.

3. The method of claim 1 wherein the immune dominant epitope that is mutated corresponds to residues 121 to 146 in a H3 HA (site A), residues 156 to 196 in a H3 HA (site B), residues 50 to 57 or 275 to 279 in a H3 HA (site C), residue 164, residue 182 or residues 208 to 217 in a H3 HA (site D) or residues 62 to 83 in a H3 HA (site E).

4. The method of claim 1 wherein the cells are mammalian cells.

5. The method of claim 1 wherein the immune dominant epitope that is mutated is H1 HA and the mutant H1 HA has a substitution at two or more of positions 121, 131, 135, 138, 140, 142, 144, 145, 155, 156, 157, 158, 171, 189, 193, 212, or 225, or a deletion at one or more of positions 121, 131, 135, 138, 140, 142, 144, 145, 155, 156, 157, 158, 171, 189, 193, 212, or 225, based on H3 numbering, or a combination thereof.

6. A method to prepare an influenza virus encoding a mutant hemagglutinin that has fewer immune dominant epitopes relative to a parental influenza virus, comprising: introducing a mutation in a parental H1 HA nucleic acid molecule at two or more codons for residue 121, 131, 135, 138, 140, 142, 144, 145, 155, 156, 157, 158, 171, 189, 193, 212, or 225 based on H3 numbering, wherein the mutation encodes a residue that is not an immune dominant epitope residue in the parent H1 HA or introducing a mutation in a parental H1 HA nucleic acid molecule at two or more codons for residue 119, 123, 125, 126, 127, 129, 138, 140, 141, 151, 152, 153, 154, 155, 156, 185, or 189 based on H5 numbering, wherein the mutation encodes a residue that is not an immune dominant epitope residue in the parent H1 HA; and isolating or preparing one or more influenza viruses with the mutated H1 HA.

7. A composition comprising a plurality of isolated distinct influenza virus H3 or H5 hemagglutinin polypeptides, isolated RNAs encoding the H3 or H5 polypeptides or isolated vectors encoding the H3 or H5 polypeptides comprising a plurality of antigenically distinct residues relative to residues that form an immune dominant epitope in a parent virus, wherein each of the plurality of influenza viruses comprises substitutions at two or more of positions 121, 131, 135, 138, 140, 142, 144, 145, 155, 156, 157, 158, 171, 189, 193, 212, or 225, or one or more deletions of positions 121, 131, 135, 138, 140, 142, 144, 145, 155, 156, 157, 158, 171, 189, 193, 212, or 225, in H3, or any combination thereof, relative to the parent virus H3 hemagglutinin; or wherein each of the plurality of influenza viruses comprises a substitution at two or more of positions 119, 123, 125, 126, 127, 129, 138, 140, 141, 151, 152, 153, 154, 155, 156, 185, or 189, or a deletion in one or more of positions 119, 123, 125, 126, 127, 129, 138, 140, 141, 151, 152, 153, 154, 155, 156, 185, or 189, in H5, or any combination thereof, relative to the parent virus H5 hemagglutinin;

a composition comprising a plurality of isolated distinct influenza virus H1 hemagglutinin polypeptides, isolated RNAs encoding the H1 polypeptides or isolated vectors encoding the H1 polypeptides comprising a plurality of antigenically distinct residues relative to residues that form an immune dominant epitope in a parent virus, wherein each of the plurality of influenza viruses comprises substitutions in H1 at two or more of positions 121, 131, 135, 138, 140, 142, 144, 145, 155, 156, 157, 158, 171, 189, 193, 212, or 225, or one or more deletions in H1 of positions 121, 131, 135, 138, 140, 142, 144, 145, 155, 156, 157, 158, 171, 189, 193, 212, or 225, based on H3 numbering, or any combination thereof, relative to the parent virus H1 hemagglutinin; or wherein each of the plurality of influenza viruses comprises a substitution in H1 at two or more of positions 119, 123, 125, 126, 127, 129, 138, 140, 141, 151, 152, 153, 154, 155, 156, 185, or 189, or a deletion in H1 in one or more of positions 119, 123, 125, 126, 127, 129, 138, 140, 141, 151, 152, 153, 154, 155, 156, 185, or 189, based on H5 numbering, or any combination thereof, relative to the parent virus H1 hemagglutinin;

a composition comprising a plurality of recombinant viruses or virus-like particles comprising distinct influenza virus H3 or H5 hemagglutinin polypeptides comprising a plurality of antigenically distinct residues relative to residues that form an immune dominant epitope in a parent virus, wherein each of the plurality of influenza viruses comprises substitutions at two or more of positions 121, 131, 135, 138, 140, 142, 144, 145, 155, 156, 157, 158, 171, 189, 193, 212, or 225, or one or more deletions of positions 121, 131, 135, 138, 140, 142, 144, 145, 155, 156, 157, 158, 171, 189, 193, 212, or 225, in H3, or any combination thereof, relative to the parent virus H3 hemagglutinin; or wherein each of the plurality of influenza viruses comprises a substitution at two or more of positions 119, 123, 125, 126, 127, 129, 138, 140, 141, 151, 152, 153, 154, 155, 156, 185, or 189, or a deletion in one or more of positions 119, 123, 125, 126, 127, 129, 138, 140, 141, 151, 152, 153, 154, 155, 156, 185, or 189, in H5, or any combination thereof, relative to the parent virus H5 hemagglutinin, wherein the recombinant virus is not an influenza virus; or a composition comprising a plurality of recombinant viruses or virus-like particles comprising distinct influenza virus H1 hemagglutinin comprising a plurality of antigenically distinct residues relative to residues that form an immune dominant epitope in a parent virus, wherein each of the plurality of influenza viruses comprises substitutions in H1 at more than five of positions 121, 131, 135, 138, 140, 142, 144, 145, 155, 156, 157, 158, 171, 189, 193, 212, or 225, or one or more deletions in H1 of positions 121, 131, 135, 138, 140, 142, 144, 145, 155, 156, 157, 158, 171, 189, 193, 212, or 225, in based on H3 numbering, or any combination thereof, relative to the parent virus H3 hemagglutinin; or wherein each of the plurality of influenza viruses comprises a substitution in H1 at two or more of positions 119, 123, 125, 126, 127, 129, 138, 140, 141, 151, 152, 153, 154, 155, 156, 185, or 189, or a deletion in H1 in one or more of positions 119, 123, 125, 126, 127, 129, 138, 140, 141, 151, 152, 153, 154, 155, 156, 185, or 189, based on H5 numbering, or any combination thereof, relative to the parent virus H1 hemagglutinin.

8. The composition of claim 7 which has at least three, four or five distinct viruses with the substitutions.

9. The composition of claim 7 which has five to ten distinct viruses with the substitutions.

10. The composition of claim 7 which has ten to twenty distinct viruses with the substitutions.

11. The composition of claim 7 wherein each distinct virus has at least one to five substitutions in antigenic site A or site B.

12. The composition of claim 7 wherein each distinct virus has at least one to ten substitutions in antigenic sites A and B.

13. The composition of claim 7 wherein each distinct virus has altered binding to antibodies that bind the corresponding parental hemagglutinin.

14. A method to immunize an animal, comprising: administering an effective amount of a composition comprising a plurality of distinct isolated recombinant influenza viruses each encoding a H1 hemagglutinin comprising a plurality of antigenically distinct residues relative to residues that form an immune dominant epitope in a parent virus, wherein each of the plurality of influenza viruses comprises substitutions in H1 at two or more of positions 121, 131, 135, 138, 140, 142, 144, 145, 155, 156, 157, 158, 171, 189, 193, 212, or 225, or one or more deletions in H1 of positions 121, 131, 135, 138, 140, 142, 144, 145, 155, 156, 157, 158, 171, 189, 193, 212, or 225, based on H3 numbering, or any combination thereof, relative to the parent virus H1 hemagglutinin; or wherein each of the plurality of influenza viruses comprises a substitution in H1 at two or more of positions 119, 123, 125, 126, 127, 129, 138, 140, 141, 151, 152, 153, 154, 155, 156, 185, or 189, or a deletion in H1 in one or more of positions 119, 123, 125, 126, 127, 129, 138, 140, 141, 151, 152, 153, 154, 155, 156, 185, or 189, based on H5 numbering, or any combination thereof, relative to the parent virus H1 hemagglutinin to an animal.

* * * * *

SEQUENCE LISTING

```
Sequence total quantity: 51
SEQ ID NO: 1              moltype = AA  length = 329
FEATURE                   Location/Qualifiers
source                    1..329
                          mol_type = protein
                          organism = Influenza A
SEQUENCE: 1
QKLPGNDNST ATLCLGHHAV PNGTIVKTIT NDQIEVTNAT ELVQSSSTGG ICDSPHQILD   60
GENCTLIDAL LGDPQCDGFQ NKKWDLFVER SKAYSNCYPY DVPDYASLRS LVASSGTLEF  120
NNESFNWTGV TQNGTSSSCK RRSNNSFFSR LNWLTHLKFK YPALNVTMPN NEKFDKLYIW  180
GVHHPGTNND QISLYTQASG RITVSTKRSQ QTVIPNIGSR PRVRDIPSRI SIYWTIVKPG  240
DILLINSTGN LIAPRGYFKI RSGKSSIMRS DAPIGKCNSE CITPNGSIPN DKPFQNVNRI  300
TYGACPRYVK QNTLKLATGM RNVPEKQTR                                   329

SEQ ID NO: 2              moltype = AA  length = 567
FEATURE                   Location/Qualifiers
source                    1..567
                          mol_type = protein
                          organism = Influenza A
SEQUENCE: 2
MEKIVLLLAV ISLVKSDQIC IGYHANNSTK QVDTIMEKNV TVTHAQDILE KTHNGKLCDL   60
NGVKPLILKD CSVAGWLLGN PMCDEFIRVP EWSYIVERAN PANDLCYPGT LNDYEELKHL  120
LSRINHFEKT LIIPRSSWPN HETSLGVSAA CPYQGASSFF RNVVWLIKKN DAYPTIKISY  180
NNTNREDLLI LWGIHHSNNA AEQTNLYKNP DTYVSVGTST LNQRLVPKIA TRSQVNGQSG  240
RMDFFWTILK PNDAIHFESN GNFIAPEYAY KIVKKGDSTI MKSEMEYGHC NTKCQTPIGA  300
INSSMPFHNI HPLTIGECPK YVKSNKLVLA TGLRNSPLRE RRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPKYSEE AILKREEISG VKLESIGTYQ ILSIYSTVAS  540
SLALAIIVAG LSLWMCSNGS LQCRICI                                     567

SEQ ID NO: 3              moltype = AA  length = 564
FEATURE                   Location/Qualifiers
source                    1..564
```

-continued

```
                       mol_type = protein
                       organism = Influenza A
SEQUENCE: 3
MKANLLVLLC ALAAADADTI CIGYHANNST DTVDTVLEKN VTVTHSVNLL EDSHNGKLCR  60
LKGIAPLQLG KCNIAGWLLG NPECDPLLPV RSWSYIVETP NSENGICYPG DFIDYEELRE  120
QLSSVSSFER FEIFPKESSW PNHNTNGVTA ACSHEGKSSF YRNLLWLTEK EGSYPKLKNS  180
YVNKKGKEVL VLWGIHHPPN SKEQQNLYQN ENAYVSVVTS NYNRRFTPEI AERPKVRDQA  240
GRMNYYWTLL KPGDTIIFEA NGNLIAPMYA FALSRGFGSG IITSNASMHE CNTKCQTPLG  300
AINSSLPYQN IHPVTIGECP KYVRSAKLRM VTGLRNIPSI QSRGLFGAIA GFIEGGWTGM  360
IDGWYGYHHQ NEQGSGYAAD QKSTQNAING ITNKVNTVIE KMNIQFTAVG KEFNKLEKRM  420
ENLNKKVDDG FLDIWTYNAE LLVLLENERT LDFHDSNVKN LYEKVKSQLK NNAKEIGNGC  480
FEFYHKCDNE CMESVRNGTY DYPKYSEESK LNREKVDGVK LESMGIYQIL AIYSTVASSL  540
VLLVSLGAIS FWMCSNGSLQ CRIC                                         564

SEQ ID NO: 4           moltype = AA  length = 562
FEATURE                Location/Qualifiers
source                 1..562
                       mol_type = protein
                       organism = Influenza A
SEQUENCE: 4
MAIIYLILLF TAVRGDQICI GYHANNSTEK VDTILERNVT VTHAKDILEK THNGKLCKLN  60
GIPPLELGDC SIAGWLLGNP ECDRLLSVPE WSYIMEKENP RDGLCYPGSF NDYEELKHLL  120
SSVKHFEKVK ILPKDRWTQH TTTGGSRACA VSGNPSFFRN MVWLTEKGSN YPVAKGSYNN  180
TSGEQMLIIW GVHHPNDETE QRTLYQNVGT YVSVGTSTLN KRSTPEIATR PKVNGQGGRM  240
EFSWTLLDMW DTINFESTGN LIAPEYGFKI SKRGSSGIMK TEGTLENCET KCQTPLGAIN  300
TTLPFHNVHP LTIGECPKYV KSEKLVLATG LRNVPQIESR GLFGAIAGFI EGGWQGMVDG  360
WYGYHHSNDQ GSGYAADKES TQKAFDGITN KVNSVIEKMN TQFEAVGKEF SNLERRLENL  420
NKKMEDGFLD VWTYNAELLV LMENERTLDF HDSNVKNLYD KVRMQLRDNV KELGNGCFEF  480
YHKCDDECMN SVKNGTYDYP KYEEESKLNR NEIKGVKLSS MGVYQILAIY ATVAGSLSLA  540
IMMAGISFWM CSNGSLQCRI CI                                           562

SEQ ID NO: 5           moltype = AA  length = 562
FEATURE                Location/Qualifiers
source                 1..562
                       mol_type = protein
                       organism = Influenza A
SEQUENCE: 5
MAIIYLILLF TAVRGDQICI GYHANNSTEK VDTILERNVT VTHAKDILEK THNGKLCKLN  60
GIPPLELGDC SIAGWLLGNP ECDRLLSVPE WSYIMEKENP RDGLCYPGSF NDYEELKHLL  120
SSVKHFEKVK ILPKDRWTQH TTTGGSRACA VSGNPSFFRN MVWLTEKGSN YPVAKGSYNN  180
TSGEQMLIIW GVHHPNDETE QRTLYQNVGT YVSVGTSTLN KRSTPEIATR PKVNGQGGRM  240
EFSWTLLDMW DTINFESTGN LIAPEYGFKI SKRGSSGIMK TEGTLENCET KCQTPLGAIN  300
TTLPFHNVHP LTIGECPKYV KSEKLVLATG LRNVPQIESR GLFGAIAGFI EGGWQGMVDG  360
WYGYHHSNDQ GSGYAADKES TQKAFDGITN KVNSVIEKMN TQFEAVGKEF SNLERRLENL  420
NKKMEDGFLD VWTYNAELLV LMENERTLDF HDSNVKNLYD KVRMQLRDNV KELGNGCFEF  480
YHKCDDECMN SVKNGTYDYP KYEEESKLNR NEIKGVKLSS MGVYQILAIY ATVAGSLSLA  540
IMMAGISFWM CSNGSLQCRI CI                                           562

SEQ ID NO: 6           moltype = AA  length = 512
FEATURE                Location/Qualifiers
source                 1..512
                       mol_type = protein
                       organism = Influenza A
SEQUENCE: 6
QKLPGNDNST ATLCLGHHAV PNGTIVKTIT NDQIEVTNAT ELVQSSSTGG ICDSPHQILD  60
GENCTLIDAL LGDPQCDGFQ NKKWDLFVER SKAYSNCYPY DVPDYASLRS LVASSGTLEF  120
NNESFNWTGV TQNGTSSACK RRSNNSFFSR LNWLTHLKFK YPALNVTMPN NEKFDKLYIW  180
GVHHPGTNND QISLYAQASG RITVSTKRSQ QTVIPNIGSR PRVRDIPSRI SIYWTIVKPG  240
DILLINSTGN LIAPRGYFKI RSGKSSIMRS DAPIGKCNSE CITPNGSIPN DKPFQNVNRI  300
TYGACPRYVK QNTLKLATGM RNVPEKQTRG IFGAIAGFIE NGWEGMVDGW YGFRHQNSEG  360
IGQAADLKST QAAINQINGK LNRLIGKTNE KFHQIEKEFS EVEGRIQDLE KYVEDTKIDL  420
WSYNAELLVA LENQHTIDLT DSEMNKLFER TKKQLRENAE DMGNGCFKIY HKCDNACIGS  480
IRNGTYDHDV YRDEALNNRF QIKGVELKSG YK                                512

SEQ ID NO: 7           moltype = AA  length = 512
FEATURE                Location/Qualifiers
source                 1..512
                       mol_type = protein
                       organism = Influenza A
SEQUENCE: 7
QKLPGNDNST ATLCLGHHAV PNGTIVKTIT NDQIEVTNAT ELVQSSSTGG ICDSPHQILD  60
GENCTLIDAL LGDPQCDGFQ NKKWDLFVER SKAYSNCYPY DVPDYASLRS LVASSGTLEF  120
NNESFNWTGV TQNGTSSSCK RRSNNSFFSR LNWLTHLKFK YPALNVTMPN NEKFDKLYIW  180
GVHHPGTNND QISLYTQASG RITVSTKRSQ QTVIPNIGSR PRVRDIPSRI SIYWTIVKPG  240
DILLINSTGN LIAPRGYFKI RSGKSSIMRS DAPIGKCNSE CITPNGSIPN DKPFQNVNRI  300
TYGACPRYVK QNTLKLATGM RNVPEKQTRG IFGAIAGFIE NGWEGMVDGW YGFRHQNSEG  360
IGQAADLKST QAAINQINGK LNRLIGKTNE KFHQIEKEFS EVEGRIQDLE KYVEDTKIDL  420
WSYNAELLVA LENQHTIDLT DSEMNKLFER TKKQLRENAE DMGNGCFKIY HKCDNACIGS  480
IRNGTYDHDV YRDEALNNRF QIKGVELKSG YK                                512
```

```
SEQ ID NO: 8              moltype = AA  length = 566
FEATURE                   Location/Qualifiers
source                    1..566
                          mol_type = protein
                          organism = Influenza A
SEQUENCE: 8
MKTIIALSCI LCLVFTQKIP GNDNSTATLC LGHHAVPNGT IVKTITNDRI EVTNATELVQ   60
NSSIGEICDS PHQILDGENC TLIDALLGDP QCDGFQNKKW DLFVERNKAY SNCYPYDVPD  120
YASLRSLVAS SGTLEFNNES FNWAGVTQNG TSSSCIRGSK SSFFSRLNWL THLNSKYPAL  180
NVTMPNNEQF DKLYIWGVHH PGTDKDQISL YAQSSGRITV STKRSQQAVI PNIGSRPRIR  240
DIPSRISIYW TIVKPGDILL INSTGNLIAP RGYFKIRSGK SSIMRSDAPI GKCKSECITP  300
NGSIPNDKPF QNVNRITYGA CPRYVKQSTL KLATGMRNVP ERQTRGIFGA IAGFIENGWE  360
GMVDGWYGFR HQNSEGRGQA ADLKSTQAAI DQINGKLNRL IGKTNEKFHQ IEKEFSEVEG  420
RIQDLEKYVE DTKIDLWSYN AELLVALENQ HTIDLTDSEM NKLFEKTKKQ LRENAEDMGN  480
GCFKIYHKCD NACIGSIRNG TYDHNVYRDE ALNNRFQIKG VELKSGYKDW ILWISFAISC  540
FLLCVALLGF IMWACQKGNI RCNICI                                      566

SEQ ID NO: 9              moltype = AA  length = 567
FEATURE                   Location/Qualifiers
source                    1..567
                          mol_type = protein
                          organism = Influenza A
SEQUENCE: 9
MEKIVLLLAV ISLVKSDQIC IGYHANNSTK QVDTIMEKNV TVTHAQDILE KTHNGKLCDL   60
NGVKPLILKD CSVAGWLLGN PMCDEFIRVP EWSYIVERAN PANDLCYPGT LNDYEELKHL  120
LSRINHFEKT LIIPRSSWPN HETSLGVSAA CPYQGASSFF RNVVWLIKKN DAYPTIKISY  180
NNTNREDLLI LWGIHHSNNA AEQTNLYKNP DTYVSVGTST LNQRLVPKIA TRSQVNGQSG  240
RMDFFWTILK PNDAIHFESN GNFIAPEYAY KIVKKGDSTI MKSEMEYGHC NTKCQTPIGA  300
INSSMPFHNI HPLTIGECPK YVKSNKLVLA TGLRNSPLRE RRRKRGLFGA IAGFIEGGWQ  360
GMVDGWYGYH HSNEQGSGYA ADKESTQKAI DGVTNKVNSI IDKMNTQFEA VGREFNNLER  420
RIENLNKKME DGFLDVWTYN AELLVLMENE RTLDFHDSNV KNLYDKVRLQ LRDNAKELGN  480
GCFEFYHKCD NECMESVRNG TYDYPKYSEE AILKREEISG VKLESIGTYQ ILSIYSTVAS  540
SLALAIIVAG LSLWMCSNGS LQCRICI                                     567

SEQ ID NO: 10             moltype = AA  length = 17
FEATURE                   Location/Qualifiers
source                    1..17
                          mol_type = protein
                          organism = synthetic construct
SEQUENCE: 10
NTTAIRSSTH LNNKFAD                                                 17

SEQ ID NO: 11             moltype = AA  length = 17
FEATURE                   Location/Qualifiers
source                    1..17
                          mol_type = protein
                          organism = synthetic construct
SEQUENCE: 11
YVVKWSGPVG VRDNZQK                                                 17

SEQ ID NO: 12             moltype = AA  length = 17
FEATURE                   Location/Qualifiers
source                    1..17
                          mol_type = protein
                          organism = synthetic construct
SEQUENCE: 12
MVGDFTDRCA NGREGNK                                                 17

SEQ ID NO: 13             moltype = AA  length = 17
FEATURE                   Location/Qualifiers
source                    1..17
                          mol_type = protein
                          organism = synthetic construct
SEQUENCE: 13
KRGAPDAGMT SPKDGLE                                                 17

SEQ ID NO: 14             moltype = AA  length = 17
FEATURE                   Location/Qualifiers
source                    1..17
                          mol_type = protein
                          organism = synthetic construct
SEQUENCE: 14
QRTKLNTPCP DRTAQVL                                                 17

SEQ ID NO: 15             moltype = AA  length = 17
FEATURE                   Location/Qualifiers
source                    1..17
                          mol_type = protein
```

```
                              -continued

SEQUENCE: 15
VRRFMNTWVA LHTISRP                                                        17

SEQ ID NO: 16            moltype = AA   length = 17
FEATURE                  Location/Qualifiers
source                   1..17
                         mol_type = protein
                         organism = synthetic construct
SEQUENCE: 16
VKVTHERRAS PVRRTIS                                                        17

SEQ ID NO: 17            moltype = AA   length = 17
FEATURE                  Location/Qualifiers
source                   1..17
                         mol_type = protein
                         organism = synthetic construct
SEQUENCE: 17
RVKWMGVPIG PVFTRRP                                                        17

SEQ ID NO: 18            moltype = AA   length = 17
FEATURE                  Location/Qualifiers
source                   1..17
                         mol_type = protein
                         organism = synthetic construct
SEQUENCE: 18
TGLRCSGRYP LQTFART                                                        17

SEQ ID NO: 19            moltype = AA   length = 17
FEATURE                  Location/Qualifiers
source                   1..17
                         mol_type = protein
                         organism = synthetic construct
SEQUENCE: 19
ITNKTYDSRS SSFAQGC                                                        17

SEQ ID NO: 20            moltype = AA   length = 17
FEATURE                  Location/Qualifiers
source                   1..17
                         mol_type = protein
                         organism = synthetic construct
SEQUENCE: 20
VMLKTGAWQS RLQLRRE                                                        17

SEQ ID NO: 21            moltype = AA   length = 17
FEATURE                  Location/Qualifiers
source                   1..17
                         mol_type = protein
                         organism = synthetic construct
SEQUENCE: 21
AKSRNDGVRS RFTEAYG                                                        17

SEQ ID NO: 22            moltype = AA   length = 17
FEATURE                  Location/Qualifiers
source                   1..17
                         mol_type = protein
                         organism = synthetic construct
SEQUENCE: 22
VCNIKRPDAA GALAPSS                                                        17

SEQ ID NO: 23            moltype = AA   length = 17
FEATURE                  Location/Qualifiers
source                   1..17
                         mol_type = protein
                         organism = unidentified
SEQUENCE: 23
VCLLRFKTIP SPQNSTS                                                        17

SEQ ID NO: 24            moltype = AA   length = 17
FEATURE                  Location/Qualifiers
source                   1..17
                         mol_type = protein
                         organism = synthetic construct
SEQUENCE: 24
SSTKSQGSRP IKEPNVQ                                                        17

SEQ ID NO: 25            moltype = AA   length = 17
FEATURE                  Location/Qualifiers
source                   1..17
```

```
                         mol_type = protein
                         organism = synthetic construct
SEQUENCE: 25
VQVRREHSVT LRHLTMG                                                        17

SEQ ID NO: 26            moltype = AA  length = 17
FEATURE                  Location/Qualifiers
source                   1..17
                         mol_type = protein
                         organism = synthetic construct
SEQUENCE: 26
LRNTKTNSQK RFSFTVS                                                        17

SEQ ID NO: 27            moltype = AA  length = 17
FEATURE                  Location/Qualifiers
source                   1..17
                         mol_type = protein
                         organism = synthetic construct
SEQUENCE: 27
RRIVNGTRWP SPRSSVR                                                        17

SEQ ID NO: 28            moltype = AA  length = 17
FEATURE                  Location/Qualifiers
source                   1..17
                         mol_type = protein
                         organism = synthetic construct
SEQUENCE: 28
VRYKTAEQTL WGRYQMN                                                        17

SEQ ID NO: 29            moltype = AA  length = 16
FEATURE                  Location/Qualifiers
source                   1..16
                         mol_type = protein
                         organism = synthetic construct
SEQUENCE: 29
FDSKGNVKPT RRLSPS                                                         16

SEQ ID NO: 30            moltype = AA  length = 17
FEATURE                  Location/Qualifiers
source                   1..17
                         mol_type = protein
                         organism = unidentified
SEQUENCE: 30
SRKTNRAPQH MKFTNFC                                                        17

SEQ ID NO: 31            moltype = AA  length = 17
FEATURE                  Location/Qualifiers
source                   1..17
                         mol_type = protein
                         organism = synthetic construct
SEQUENCE: 31
FVWSMHQPQG RCTSEAY                                                        17

SEQ ID NO: 32            moltype = AA  length = 326
FEATURE                  Location/Qualifiers
source                   1..326
                         mol_type = protein
                         organism = Influenza A
SEQUENCE: 32
DTICIGYHAN NSTDTVDTVL EKNVTVTHSV NLLEDSHNGK LCLLKGIAPL QLGNCSVAGW          60
ILGNPECELL ISKESWSYIV ETPNPENGTC YPGYFADYEE LREQLSSVSS FERFEIFPKE         120
SSWPNHTVTG VSASCSHNGK SSFYRNLLWI TGKNGLYPNL SKSYVNNKEK EVLVLWGVHH         180
PPNIGNQRAL YHTENAYVSV VSSHYSRRFT PEIAKRPKVR DQEGRINYYW TLLEPGDTII         240
FEANGNLIAP WYAFALSRGF GSGIITSNAP MDECDAKCQT PQGAINSSLP FQNVHPVTIG         300
ECPKYVRSAK LRMVTGLRNI PSIQSR                                             326

SEQ ID NO: 33            moltype = AA  length = 327
FEATURE                  Location/Qualifiers
source                   1..327
                         mol_type = protein
                         organism = Influenza A
SEQUENCE: 33
DTLCIGYHAN NSTDTVDTVL EKNVTVTHSV NLLEDKHNGK LCKLRGVAPL HLGKCNIAGW          60
ILGNPECESL STASSWSYIV ETPSSDNGTC YPGDFIDYEE LREQLSSVSS FERFEIFPKT         120
SSWPNHDSNK GVTAACPHAG AKSFYKNLIW LVKKGNSYPK LSKSYINDKG KEVLVLWGIH         180
HPSTSADQQS LYQNADTYVF VGSSRYSKKF KPEIAIRPKV RDQEGRMNYY WTLVEPGDKI         240
TFEATGNLVV PRYAFAMERN AGSGIIISDT PVHDCNTTCQ TPKGAINTSL PFQNIHPITI         300
GKCPKYVKST KLRLATGLRN IPSIQSR                                            327
```

```
SEQ ID NO: 34             moltype = AA  length = 325
FEATURE                   Location/Qualifiers
source                    1..325
                          mol_type = protein
                          organism = Influenza A
SEQUENCE: 34
DQICIGYHAN NSTEKVDTIL ERNVTVTHAK DILEKTHNGK LCKLNGIPPL ELGDCSIAGW    60
LLGNPECDRL LSVPEWSYIM EKENPRDGLC YPGSFNDYEE LKHLLSSVKH FEKVKILPKD   120
RWTQHTTTGG SRACAVSGNP SFFRNMVWLT KKESNYPVAK GSYNNTSGEQ MLIIWGVHHP   180
NDETEQRTLY QNVGTYVSVG TSTLNKRSTP DIATRPKVNG LGSRMEFSWT LLDMWDTINF   240
ESTGNLIAPE YGFKISKRGS SGIMKTEGTL ENCETKCQTP LGAINTTLPF HNVHPLTIGE   300
CPKYVKSEKL VLATGLRNVP QIESR                                        325

SEQ ID NO: 35             moltype = AA  length = 326
FEATURE                   Location/Qualifiers
source                    1..326
                          mol_type = protein
                          organism = Influenza A
SEQUENCE: 35
DQICIGYHAN NSTEQVDTIM EKNVTVTHAQ DILEKAHNGK LCSLNGVKPL ILRDCSVAGW    60
LLGNPMCDEF LNVPEWSYIV EKDNPINGLC YPGDFNDYEE LKHLLSSTNH FEKIQIIPRS   120
SWSNHEASSG VSSACPYNGR SSFFRNVVWI IKKNNAYPTI KRSYNNTNQE DLLVLWGIHH   180
PNDAAEQTKL YQNPTTYVSV GTSTLNQRSV PEIATRPKVN GQSGRMEFFW TILKPNDAIN   240
FESNGNFIAP EYAYKIVKKG DSAIMKSGLE YGNCNTKCQT PMGAINSSMP FHNIHPLTIG   300
ECPKYVKSDR LVLATGLRNV PQRETR                                       326

SEQ ID NO: 36             moltype = AA  length = 329
FEATURE                   Location/Qualifiers
source                    1..329
                          mol_type = protein
                          organism = Influenza A
SEQUENCE: 36
DQICIGYHAN NSTEQVDTIM EKNVTVTHAQ DILEKTHNGK LCNLDGVKPL ILRDCSVAGW    60
LLGNPMCDEF LNVPEWSYIV EKINPANDLC YPGNFNDYEE LKHLLSRINH FEKIQIIPKN   120
SWSDHEASGV SSACPYQGRS SFFRNVVWLT KKDNAYPTIK RSYNNTNQED LLVLWGIHHP   180
NDAAEQTRLY QNPTTYISVG TSTLNQRLVP KIATRSKVNG QSGRMEFFWT ILKSNDAINF   240
ESNGNFIAPE NAYKIVKKGD STIMKSELEY GNCNTKCQTP IGAINSSMPF HNIHPLTIGE   300
CPKYVKSNRL VLATGLRNSP QRERRRKKR                                    329

SEQ ID NO: 37             moltype = AA  length = 329
FEATURE                   Location/Qualifiers
source                    1..329
                          mol_type = protein
                          organism = Influenza A
SEQUENCE: 37
DKICIGYHAN NSTTQVDTIL EKNVTVTHSV ELLENQKEER FCKIMNKSPL DLRECTIEGW    60
ILGNPKCDLL LGDQSWSYIV ERPTAQNGIC YPGALNEVEE LKALIGSGER VERFEMFPKS   120
TWAGVDTSSG VTNACPSYTI GSSFYRNLVW IIKTNSAAYP VIKGTYNNTG NQPILYFWGV   180
HHPPNTGVQD TLYGSGERYV RMGTDSMNFA KSPEIAERPV VNGQRGRIDY YWSVLKPGET   240
LNVESNGNLI APWYAYKFVS TNKKGAVFKS NLPIENCDAT CQTIAGVLRT NKTFQNVSPL   300
WIGECPKYVK SESLRLATGL RNIPQIKTR                                    329

SEQ ID NO: 38             moltype = AA  length = 328
FEATURE                   Location/Qualifiers
source                    1..328
                          mol_type = protein
                          organism = Influenza A
SEQUENCE: 38
YDRICIGYQS NNSTDTVNTL IEQNVPVTQT MELVETEKHP AYCNTDLGAP LELRDCKIEA    60
VIYGNPKCDI HLKDQGWSYI VERPSAPEGM CYPGSVENLE ELRFVFSSAA SYKRIRLFDY   120
SRWNVTRSGT SKACNASTGG QSFYRSINWL TKKKPDTYDF NEGAYVNNED GDIIFLWGIH   180
HPPDTKEQTT LYKNANTLSS VTTNTINRSF QPNIGPRPLV RGQQGRMDYY WGILKRGETL   240
KIRTNGNLIA PEFGYLLKGE SYGRIIQNED IPIGNCNTKC QTYAGAINSS KPFQNASRHY   300
MGECPKYVKK ASLRLAVGLR NTPSVEPR                                     328

SEQ ID NO: 39             moltype = AA  length = 320
FEATURE                   Location/Qualifiers
source                    1..320
                          mol_type = protein
                          organism = Influenza A
SEQUENCE: 39
DKICIGYQST NSTETVDTLT ETNVPVTHAK ELLHTEHNGM LCATNLGHPL ILDTCTIEGL    60
IYGNPSCDLL LGGREWSYIV ERPSAVNGMC YPGNVENLEE LRSLFSSASS YQRIQIFPDT   120
IWNVSYSGTS KACSDSFYRS MRWLTQKNNA YPIQDAQYTN NRGKSILFMW GINHPPTDTV   180
QTNLYTRTDT TSVTTEDINR TFKPVIGPRP PLVNGLHGRI DYYWSVLKPG QTLRVRSNGN   240
LIAPWYGHIL SGESHGRILK TDLNSGNCVV QCQTERGGLN TTLPFHNVSK YAFGNCPKYV   300
GVKSLKLAVG LRNVPARSSR                                              320

SEQ ID NO: 40             moltype = AA  length = 326
```

```
FEATURE                 Location/Qualifiers
source                  1..326
                        mol_type = protein
                        organism = Influenza A
SEQUENCE: 40
DEICIGYLSN NSTDKVDTII ENNVTVTSSV ELVETEHTGS FCSINGKQPI SLGDCSFAGW  60
ILGNPMCDEL IGKTSWSYIV EKPNPTNGIC YPGTLESEEE LRLKFSGVLE FNKFEVFTSN 120
GWGAVNSGVG VTAACKFGGS NSFFRNMVWL IHQSGTYPVI KRTFNNTKGR DVLIVWGIHH 180
PATLTEHQDL YKKDSSYVAV GSETYNRRFT PEINTRPRVN GQAGRMTFYW KIVKPGESIT 240
FESNGAFLAP RYAFEIVSVG NGKLFRSELN IESCSTKCQT EIGGINTNKS FHNVHRNTIG 300
DCPKYVNVKS LKLATGPRNV PAIASR                                     326

SEQ ID NO: 41           moltype = AA  length = 326
FEATURE                 Location/Qualifiers
source                  1..326
                        mol_type = protein
                        organism = Influenza A
SEQUENCE: 41
YDKICIGYQT NNSTETVNTL SEQNVPVTQV EELVHGGIDP ILCGTELGSP LVLDDCSLEG  60
LILGNPKCDL YLNGREWSYI VERPKEMEGV CYPGSIENQE ELRSLFSSIK KYERVKMFDF 120
TKWNVTYTGT SKACNNTSNQ GSFYRSMRWL TLKSGQFPVQ TDEYKNTRDS DIVFTWAIHH 180
PPTSDEQVKL YKNPDTLSSV TTDEINRSFK PNIGPRPLVR GQQGRMDYYW AVLKPGQTVK 240
IQTNGNLIAP EYGHLITGKS HGRILKNNLP MGQCVTECQL NEGVMNTSKP FQNTSKHYIG 300
KCPKYIPSGS LKLAIGLRNV PQVQDR                                     326

SEQ ID NO: 42           moltype = AA  length = 325
FEATURE                 Location/Qualifiers
source                  1..325
                        mol_type = protein
                        organism = Influenza A
SEQUENCE: 42
DRICVGYLST NSSERVDTLL ENGVPVTSSI DLIETNHTGT YCSLNGVSPV HLGDCSFEGW  60
IVGNPACTSN FGIREWSYLI EDPAAPHGLC YPGELNNNGE LRHLFSGIRS FSRTELIPPT 120
SWGEVLDGVT SACRDNTGTN SFYRNLVWFI KKNNRYPVIS KTYNNTTGRD VLVLWGIHHP 180
VSVDETKTLY VNSDPYTLVS TKSWSEKYKL ETGVRPGYNG QRSWMKIYWS LIHPGEMITF 240
ESNGGFLAPR YGYIIEEYGK GRIFQSRIRM SRCNTKCQTS VGGINTNRTF QNIDKNALGD 300
CPKYIKSGQL KLATGLRNVP AISNR                                      325

SEQ ID NO: 43           moltype = AA  length = 325
FEATURE                 Location/Qualifiers
source                  1..325
                        mol_type = protein
                        organism = Influenza A
SEQUENCE: 43
DKICIGYLSN NSSDTVDTLT ENGVPVTSSV DLVETNHTGT YCSLNGISPI HLGDCSFEGW  60
IVGNPSCATN INIREWSYLI EDPNAPNKLC YPGELDNNGE LRHLFSGVNS FSRTELINPS 120
KWGNVLDGVT ASCLDRGASS FYRNLVWVK QKIGEYPVVK GEYNNTTGRD VLVLWGIHHP 180
DTETTATNLY VNKNPYTLVS TKEWSKRYEL EIGTRIGDGQ RSWMKLYWHL MHPGERIMFE 240
SNGGLIAPRY GYIIEKYGTG TIFQSGVRMA KCNTKCQTSL GGINTNKTFQ NIERNALGDC 300
PKYIKSGQLK LATGLRNVPI PIGER                                      325

SEQ ID NO: 44           moltype = AA  length = 324
FEATURE                 Location/Qualifiers
source                  1..324
                        mol_type = protein
                        organism = Influenza A
SEQUENCE: 44
DRICIGYQAN QNNQTVNTLL EQNVPVTGAQ EILETNHNGK LCSLNGVPPL DLQSCTLAGW  60
LLGNPNCDNL LEAAEEWSYIK INENAPDDLC FPGNFENLQD LLLEMSGVQN FTKVKLFNPQ 120
SMTGVTTNNV DQTCPFEGKP SFYRNLNWIQ GNSGLPFNIE IKNPTSNPLL LLWGIHNTKD 180
AAQQRNLYGN DYSYTIFNFG EKSEEFRPDI GQRDEIKAHQ DRIDYYWGSL PAQSTLRIES 240
TGNLIAPEYG FYYKRKEGKG GLMKSKLPIS DCSTKCQTPL GALNSTLPFQ NVHQQTIGNC 300
PKYVKATSLM LATGLRNNPQ MEGR                                       324

SEQ ID NO: 45           moltype = AA  length = 325
FEATURE                 Location/Qualifiers
source                  1..325
                        mol_type = protein
                        organism = Influenza A
SEQUENCE: 45
DQICIGYHSN NSTQTVNTLL ESNVPVTSSH SILEKEHNGL LCKLKGKAPL DLIDCSLPAW  60
LMGNPKCDEL LTASEWAYIK EDPEPENGIC FPGDFDSLED LILLVSNTDH FRKEKIIDMT 120
RFSDVTTNNV DSACPYDTNG ASFYRNLNWV QQNKGKQLIF HYQNSENNLN LIIWGVHQTS 180
NAAEQNTYYG SQTGSTTITI GEETNTYPLV ISESSILNGH SDRINYFWGV VNPNQNAIGD 240
STGNFIWPEY GYFFQKTTNI SGIIKSSEKI SDCDTICQTK IGAINSTLPF QNIHQNAIGD 300
CPKYVKAQEL VLATGLRNNP IKETR                                      325

SEQ ID NO: 46           moltype = AA  length = 329
FEATURE                 Location/Qualifiers
```

```
source                    1..329
                          mol_type = protein
                          organism = Influenza A
SEQUENCE: 46
QDLPGNDNST ATLCLGHHAV PNGTLVKTIT DDQIEVTNAT ELVQSSSTGK ICNNPHRILD    60
GIDCTLIDAL LGDPHCDVFQ NETWDLFVER SKAFSNCYPY DVPDYASLRS LVASSGTLEF   120
ITEGFTWTGV TQNGGSNACK RGPGSGFFSR LNWLTKSGST YPVLNVTMPN NDNFDKLYIW   180
GIHHPSTNQE QTSLYVQASG RVTVSTRRSQ QTIIPNIGSR PWVRGLSSRI SIYWTIVKPG   240
DVLVINSNGN LIAPRGYFKM RTGKSSIMRS DAPIDTCISE CITPNGSIPN DKPFQNVNKI   300
TYGACPKYVK QNTLKLATGM RNVPEKQTR                                    329

SEQ ID NO: 47             moltype = AA   length = 327
FEATURE                   Location/Qualifiers
source                    1..327
                          mol_type = protein
                          organism = Influenza A
SEQUENCE: 47
QNYTGNPVIC LGHHAVSNGT MVKTLTDDQI EVVTAQELVE SQHLPELCPS PLRLVDGQTC    60
DIVNGALGSP GCDHLNGAEW DVFIERPTAV DTCYPFDVPD YQSLRSILAN NGKFEFIAEE   120
FQWNTVKQNG KSGACKRANV NDFFNRLNWL TKSDGNAYPL QNLTKVNNGD YARLYIWGVH   180
HPSTDTEQTN LYKNNPGRVT VSTQTSQTSV VPNIGSRPWV RGLSSRISFY WTIVEPGDLI   240
VFNTIGNLIA PRGHYKLNSQ KKSTILNTAV PIGSCVSKCH TDKGSISTTK PFQNISRISI   300
GDCPKYVKQG SLKLATGMRN IPEKATR                                      327

SEQ ID NO: 48             moltype = AA   length = 321
FEATURE                   Location/Qualifiers
source                    1..321
                          mol_type = protein
                          organism = Influenza A
SEQUENCE: 48
DKICLGHHAV SNGTKVNTLT ERGVEVVNAT ETVERTNVPR ICSKGKRTVD LGQCGLLGTI    60
TGPPQCDQFL EFSADLIIER REGSDVCYPG KFVNEEALRQ ILRESGGIDK ETMGFTYSGI   120
RTNGATSACR RSGSSFYAEM KWLLSNTDNA AFPPQMTKSYK NTRKDPALII WGIHHSGSTT  180
EQTKLYGSGN KLITVGSSNY QQSFVPSPGA RPQVNGQSGR IDFHWLMLNP NDTVTFSFNG   240
AFIAPDRASF LRGKSMGIQS SVQVDANCEG DCYHSGGTII SNLPFQNINS RAVGKCPRYV   300
KQESLMLATG MKNVPEIPKG R                                            321

SEQ ID NO: 49             moltype = AA   length = 324
FEATURE                   Location/Qualifiers
source                    1..324
                          mol_type = protein
                          organism = Influenza A
SEQUENCE: 49
LDKICLGHHA VANGTIVKTL TNEQEEVTNA TETVESTSLN RLCMKGRNHK DLGNCHPIGM    60
LIGTPACDLH LTGTWDTLIE RENAIAYCYP GATVNEEALR QKIMESGGIS KISTGFTYGS   120
SINSNSAGTTKA CMRNGGNSFY AELKWLVSKS KGQNFPQTTN TYRNTDTAEH IIMWGIHHPS  180
STQEKNDLYG TQSLSISVGS STYQNNFVPV VGARPQVNGQ SGRIDFHWTL VQPGDNITFS   240
HNGGLIAPSR VSKLIGRGLG IQSDAPIDNN CESKCFWRGG SINTRLPFQN LSPRTVGQCP   300
KYVNKKSLML ATGMRNVPEI MQGR                                         324

SEQ ID NO: 50             moltype = AA   length = 330
FEATURE                   Location/Qualifiers
source                    1..330
                          mol_type = protein
                          organism = Influenza A
SEQUENCE: 50
QITNGTTGNP IICLGHHAVE NGTSVKTLTD NHEVVSAKE LVETNHTDEL CPSPLKLVDG    60
QDCDLINGAL GSPGCDRLQD TTWDVFIERP TAVDTCYPFD VPDYQSLRSI LASSGSLEFI   120
AEQFTWNGVK VDGSSSACLR GGRNSFFSRL NWLTKATNGN YGPINVTKEN TGSYVRLYLW   180
GVHHPSSDNE QTDLYKVATG RVTVSTRSDQ ISIVPNIGSR PRVRNQSGRI SIYWTLVNPG   240
DSIIFNSIGN LIAPRGHYKI SKSTKSTVLK SDKRIGSCTS PCLTDKGSIQ SDKPFQNVSR   300
IAIGNCPKYV KQGSLMLATG MRNIPGKQAR                                   330

SEQ ID NO: 51             moltype = AA   length = 331
FEATURE                   Location/Qualifiers
source                    1..331
                          mol_type = protein
                          organism = Influenza A
SEQUENCE: 51
DKICLGHHAV ANGTKVNTLT EKGVEVVNAT ETVEITGINK VCTKGKKAVD LGSCGILGTI    60
IGPPQCDSHL KFKADLIIER RNSSDICYPG KFTNEEALRQ IIRESGGIDK EPMGFRYSGI   120
KTDGATSACK RTVSSFYSEM KWLLSSKANQ VFPQLNQTYR NNRKEPALIV WGVHHSSSLD   180
EQNKLYGAGN KLITVGSSKY QQSFSPSPGD RPKVNGQAGR IDFHWLMLDP GDTVTFTFNG   240
AFIAPDRATF LRSNAPSGVE YNGKSLGIQS DAQIDESCEG ECFYSGGTIN SPLPFQNIDS   300
WAVGRCPRYV KQSSLPLALG MKNVPEKIHT R                                 331
```